(12) United States Patent
Eaves et al.

(10) Patent No.: US 11,246,595 B2
(45) Date of Patent: Feb. 15, 2022

(54) MEDICAL DEVICE FOR APPLYING FORCE ON BIOLOGICAL TISSUE, OR THE LIKE

(71) Applicant: EMRGE, LLC, Atlanta, GA (US)

(72) Inventors: Felmont F. Eaves, Atlanta, GA (US); Gary W. Knight, Lebanon, OH (US)

(73) Assignee: EMRGE, LLC, Atlanta, GA (US)

(*) Notice: Subject to any disclaimer, the term of this patent is extended or adjusted under 35 U.S.C. 154(b) by 0 days.

(21) Appl. No.: 17/336,695

(22) Filed: Jun. 2, 2021

(65) Prior Publication Data
US 2021/0298741 A1 Sep. 30, 2021

Related U.S. Application Data

(63) Continuation of application No. PCT/US2020/054702, filed on Oct. 8, 2020.
(Continued)

(51) Int. Cl.
*A61B 17/08* (2006.01)
*A61B 17/04* (2006.01)
*A61B 17/00* (2006.01)

(52) U.S. Cl.
CPC ............ *A61B 17/08* (2013.01); *A61B 17/083* (2013.01); *A61B 17/085* (2013.01);
(Continued)

(58) Field of Classification Search
CPC ... A61B 17/0466; A61B 17/08; A61B 17/083; A61B 17/085; A61B 2017/0495;
(Continued)

(56) References Cited

U.S. PATENT DOCUMENTS

| 815,264 A | 3/1906 | Chambers |
|---|---|---|
| 1,248,450 A | 12/1917 | Burke |

(Continued)

FOREIGN PATENT DOCUMENTS

| AU | 2012236205 B2 | 8/2016 |
|---|---|---|
| AU | 2016262734 | 12/2016 |

(Continued)

OTHER PUBLICATIONS

Extended Search Report in related EP Application 12762897.2, dated May 27, 2015, 11 pages.
(Continued)

*Primary Examiner* — Robert A Lynch
(74) *Attorney, Agent, or Firm* — Additon, Pendleton & Witherspoon, P.A.

(57) ABSTRACT

A medical device for at least partially covering and applying force on tissue includes a body having a spanning structure and struts respectively connected to lateral portions of the spanning structure. Inner ends of the struts extend into an area over which the medial portion of the spanning structure extends. The medical device is reconfigurable between extended and retracted configurations. The inner ends of the struts are closer to one another in the retracted configuration than in the extended configuration. The inner ends of the struts are closer to the medial portion of the spanning structure in the retracted configuration than in the extended configuration. Each strut includes an engagement zone configured to engage and apply force on the tissue, at least while the medical device is in the retracted configuration. A web can be connected to the struts and span between the inner ends of the struts.

30 Claims, 99 Drawing Sheets

Related U.S. Application Data

(60) Provisional application No. 62/913,754, filed on Oct. 11, 2019.

(52) U.S. Cl.
CPC . *A61B 17/0466* (2013.01); *A61B 2017/00951* (2013.01); *A61B 2017/0495* (2013.01); *A61B 2017/0496* (2013.01); *A61B 2017/081* (2013.01)

(58) Field of Classification Search
CPC ...... A61B 2017/0496; A61B 2017/081; A61B 2017/00951
See application file for complete search history.

(56) References Cited

U.S. PATENT DOCUMENTS

| | | |
|---|---|---|
| 1,908,229 A | 5/1933 | Dyer |
| 2,254,620 A | 9/1941 | Miller |
| D134,810 S | 1/1943 | Tawdish |
| 2,341,121 A | 2/1944 | Schaaff |
| 2,371,978 A | 3/1945 | Perham |
| 2,421,193 A | 5/1947 | Gardner |
| 2,679,671 A | 6/1954 | Garber, Jr. |
| 2,912,735 A | 2/1957 | Johnson et al. |
| 3,014,483 A | 12/1961 | McCarthy |
| 3,068,870 A | 12/1962 | Levin |
| 3,082,773 A | 3/1963 | Renstrom et al. |
| 3,120,687 A | 2/1964 | Greening et al. |
| 3,487,836 A | 1/1970 | Niebel et al. |
| 3,625,220 A | 12/1971 | Engelsher |
| 3,695,271 A | 10/1972 | Chodorow |
| 3,831,608 A | 8/1974 | Kletschka et al. |
| 3,861,008 A | 1/1975 | Wannag |
| 4,011,639 A | 3/1977 | Koleske |
| 4,275,736 A | 6/1981 | Chodorow |
| D260,681 S | 9/1981 | Chodorow et al. |
| 4,506,669 A | 3/1985 | Blake, III |
| 4,539,990 A | 9/1985 | Stivala |
| 4,646,731 A | 3/1987 | Brower |
| 4,702,251 A | 10/1987 | Sheehan |
| D293,717 S | 1/1988 | Proulx et al. |
| 4,734,320 A | 3/1988 | Ohira et al. |
| 4,742,826 A | 5/1988 | McLorg |
| 4,815,468 A | 3/1989 | Annand |
| 4,825,866 A | 5/1989 | Pierce |
| 5,047,047 A * | 9/1991 | Yoon .................. A61B 17/085 606/216 |
| 5,127,412 A | 7/1992 | Cosmetto et al. |
| 5,176,703 A | 1/1993 | Peterson |
| 5,230,701 A | 7/1993 | Meyer et al. |
| 5,236,440 A * | 8/1993 | Hlavacek ........... A61B 17/0644 606/219 |
| 5,366,480 A | 11/1994 | Corriveau et al. |
| D354,134 S | 1/1995 | Tanaka |
| D359,144 S | 6/1995 | Healzer et al. |
| 5,489,083 A | 2/1996 | Rollor |
| 5,549,713 A | 8/1996 | Kim |
| 5,562,705 A | 10/1996 | Whiteford |
| 5,630,430 A | 5/1997 | Shultz et al. |
| 5,775,345 A | 7/1998 | Chou |
| D407,489 S | 3/1999 | Kalat |
| 5,947,917 A | 9/1999 | Carte et al. |
| 5,947,998 A | 9/1999 | Cartmell et al. |
| 6,176,868 B1 | 1/2001 | Detour |
| 6,196,228 B1 | 3/2001 | Kreitzer et al. |
| 6,559,350 B1 | 5/2003 | Tetreault et al. |
| 6,894,204 B2 | 5/2005 | Dunshee |
| D530,420 S | 10/2006 | Chesnin |
| 7,332,641 B2 | 2/2008 | Lebner et al. |
| 7,683,234 B2 | 3/2010 | Gurtner et al. |
| 8,157,839 B2 | 4/2012 | Riskin et al. |
| 8,183,428 B2 | 5/2012 | Gurtner et al. |
| 8,246,590 B2 | 8/2012 | Hu et al. |
| D667,167 S | 9/2012 | Stewart |
| D671,265 S | 11/2012 | Stewart |
| 8,323,313 B1 | 12/2012 | Belson et al. |
| D674,544 S | 1/2013 | Stewart |
| 8,395,011 B2 | 3/2013 | Zepeda et al. |
| 8,435,221 B2 | 5/2013 | Hu et al. |
| D683,860 S | 6/2013 | Quimby |
| D690,020 S | 9/2013 | Quimby |
| 8,562,576 B2 | 10/2013 | Hu et al. |
| 8,592,640 B2 | 11/2013 | Zepeda et al. |
| 8,674,164 B2 | 3/2014 | Zepeda et al. |
| 8,834,434 B2 | 9/2014 | Hu et al. |
| 8,915,942 B2 | 12/2014 | Zhang |
| 9,028,529 B2 | 5/2015 | Riskin et al. |
| 9,050,086 B2 | 6/2015 | Belson et al. |
| 9,089,328 B2 | 7/2015 | Belson et al. |
| 9,119,620 B2 | 9/2015 | Peterson et al. |
| D754,862 S | 4/2016 | Huff |
| 9,301,760 B2 | 4/2016 | Fox |
| 9,421,133 B2 | 8/2016 | Hu et al. |
| 9,492,171 B2 | 11/2016 | Petenaude |
| 9,517,163 B2 | 12/2016 | Goldman et al. |
| D780,317 S | 2/2017 | Vandervoort |
| 9,603,596 B2 | 3/2017 | Riskin et al. |
| 9,649,226 B2 | 5/2017 | Zepeda et al. |
| D790,072 S | 6/2017 | Hiebert |
| D811,609 S | 2/2018 | Huff |
| D815,747 S | 4/2018 | Kellock et al. |
| 9,974,532 B2 | 5/2018 | Baas et al. |
| 10,064,616 B2 | 9/2018 | Lear et al. |
| D831,220 S | 10/2018 | Chase et al. |
| 10,213,350 B2 | 2/2019 | Jackson et al. |
| 10,327,774 B2 | 6/2019 | Eaves |
| D862,695 S | 10/2019 | Eaves, III et al. |
| 10,426,479 B2 | 10/2019 | Vold et al. |
| 10,517,768 B2 | 12/2019 | Zepeda et al. |
| D876,641 S | 2/2020 | Eaves, III et al. |
| D876,653 S | 2/2020 | Heller |
| D918,400 S | 5/2021 | Ma |
| 2002/0111641 A1 | 8/2002 | Peterson et al. |
| 2003/0221700 A1 | 12/2003 | La Fauci |
| 2005/0080453 A1 | 4/2005 | Lebner |
| 2005/0193527 A1 | 9/2005 | Gould |
| 2006/0200198 A1 | 9/2006 | Riskin et al. |
| 2009/0125052 A1 | 5/2009 | Pinna et al. |
| 2009/0151128 A1 | 6/2009 | Gould |
| 2009/0240186 A1 | 9/2009 | Fang |
| 2009/0259203 A1 | 10/2009 | Hu et al. |
| 2010/0051046 A1 | 3/2010 | Stevenson et al. |
| 2010/0081983 A1 | 4/2010 | Zocher |
| 2010/0228287 A1 | 9/2010 | Jeekel |
| 2010/0236566 A1 | 9/2010 | Stachowski |
| 2010/0262126 A1 | 10/2010 | Hu et al. |
| 2011/0004173 A1 | 1/2011 | Hu et al. |
| 2011/0023906 A1 | 2/2011 | Tu |
| 2011/0040325 A1 | 2/2011 | Moehrle |
| 2011/0054547 A1 | 3/2011 | Anderson |
| 2011/0105963 A1 | 5/2011 | Hu et al. |
| 2011/0152738 A1 | 6/2011 | Zepeda et al. |
| 2012/0172779 A1 | 7/2012 | Spinelli et al. |
| 2012/0221044 A1 | 8/2012 | Archibald et al. |
| 2013/0150899 A1 | 6/2013 | Sixto, Jr. et al. |
| 2013/0178897 A1 | 7/2013 | Wu et al. |
| 2013/0282049 A1 | 10/2013 | Peterson et al. |
| 2014/0066943 A1 | 3/2014 | Sixto, Jr. et al. |
| 2014/0107597 A1 | 4/2014 | Hu et al. |
| 2014/0128819 A1 | 5/2014 | Eaves |
| 2014/0227483 A1 | 8/2014 | Eaves |
| 2014/0243901 A1 | 8/2014 | Mebarak et al. |
| 2014/0336701 A1 | 11/2014 | McLorg |
| 2015/0005722 A1 | 1/2015 | Hu et al. |
| 2015/0012037 A1 | 1/2015 | Goldman et al. |
| 2015/0112311 A1 | 4/2015 | Hammond et al. |
| 2015/0305739 A1 | 10/2015 | Rolandi et al. |
| 2016/0324693 A1 | 11/2016 | Hu et al. |
| 2017/0049630 A1 | 2/2017 | Goldman et al. |
| 2017/0071596 A1 | 3/2017 | Lear et al. |
| 2017/0333039 A1 | 11/2017 | Leung |
| 2018/0125492 A1 | 5/2018 | Eaves |

(56) References Cited

U.S. PATENT DOCUMENTS

| | | |
|---|---|---|
| 2018/0303483 A1 | 10/2018 | Zhang |
| 2018/0338757 A1 | 11/2018 | Lear et al. |
| 2018/0353335 A1 | 12/2018 | Walker |
| 2019/0038474 A1 | 2/2019 | Eaves |
| 2019/0133582 A1 | 5/2019 | Eaves et al. |
| 2019/0261989 A1 | 8/2019 | Eaves |

FOREIGN PATENT DOCUMENTS

| | | |
|---|---|---|
| CA | 2830918 A1 | 10/2012 |
| CN | 1889903 A | 1/2007 |
| CN | 101606856 | 12/2009 |
| CN | 101828939 B | 9/2010 |
| CN | 201683935 U | 12/2010 |
| CN | 103892877 A | 7/2014 |
| CN | 104755033 A | 7/2015 |
| CN | 105147344 A | 12/2015 |
| CN | 205144638 U | 4/2016 |
| CN | 103533900 A | 12/2016 |
| EP | 2691029 A2 | 2/2014 |
| FR | 419096 | 10/1910 |
| FR | 794710 | 2/1936 |
| JP | 2011-500170 A | 1/2011 |
| JP | 2014-516288 | 7/2014 |
| KR | 10-2009-0066415 A | 6/2009 |
| KR | 10-2014-0020993 | 2/2014 |
| TW | M340039 U | 9/2008 |
| WO | 02/26181 A1 | 4/2002 |
| WO | 2006/124671 A2 | 11/2006 |
| WO | 2009049232 A1 | 4/2009 |
| WO | 2011/019859 A2 | 2/2011 |
| WO | 2013188884 A1 | 6/2012 |
| WO | 2012/135735 | 10/2012 |
| WO | 2013/059600 | 4/2013 |
| WO | 2013/059600 A1 | 4/2013 |
| WO | 2018/075879 A1 | 4/2014 |
| WO | 2014/070922 A1 | 5/2014 |
| WO | 2016/0107897 A1 | 7/2016 |
| WO | 2017/079782 A1 | 5/2017 |
| WO | 2018/075879 | 4/2018 |
| WO | 2021/072021 A1 | 4/2021 |

OTHER PUBLICATIONS

Japanese Office Action in related JP Application No. 2014-502866, dated Dec. 10, 2015, Translation provided, 11 pages.
Chinese First Office Action in related CN Application No. 201280017051.4, dated Jun. 1, 2015, Translation provided, 13 pages.
Chinese Second Office Action in related CN Application No. 201280017051.4, dated Dec. 31, 2015, Translation provided, 8 pages.
Australian Patent Examination Report No. 1 in related Australian Patent Application No. 201226205, dated Aug. 28, 2015, 5 pages.
International Search Report and Written Opinion issued in commonly owned PCT/US2012/031638 dated Nov. 29, 2012; 10 pages.
Supplementary Partial European Search Report in commonly owned EP Application No. 12762897, dated Dec. 23, 2014, 7 pages.
Japanese Notice of Reasons for Rejection in related JP Application No. 2014-502866, dated Oct. 3, 2016; 9 pages.
Southmedic Inc., SutureSafe Instructions for Use, 2 pages [Downloaded Jul. 25, 2017 from http://dynamictissuesystems.com/wp-content/uploads/2015/09/IFU0251_E.pdf].
SutureSafe Inc., Product Brochure SutureSafe Support closed wounds and provide stability; 2 pages [Downloaded Jul. 25, 2017 from http://dynamictissuesystems.com/wp-content/uploads/2015/09/SutureSafe-SS-lr2.pdf].
Search Report in related PCT Application No. PCT/2018/057569, dated Feb. 2, 2018, pp. 1-6.
Written Opinion in related PCT Application No. PCT/2018/057569, dated Apr. 26, 2018, pp. 1-5.
International Preliminary Report on Patentability in commonly owned International Application No. PCT/US2017/057569, dated May 2, 2019, pp. 1-6.
Amazon, "Elastic Bandage Wrap Compression Tape", Review by Maria A. Dec. 18, 2017, <URL:https://www.amazon.com/Elastic-Bandage-Wrap-Compression-Tape/dp/B06XQ8BY8?th=1> (Year 2017) 12 pages.
Supplementary Partial European Search Report in related EP Application No. 12762897, dated Dec. 23, 2014, 7 pages.
Examination Report No. 1 in related Australian Application No. 2016262734, dated Jan. 14, 2019, 3 pages.
First Chinese Office Action in related CN Application No. 201611102500.1, dated Aug. 20, 2018, 21 pages (including English Translation).
Summons to attend oral proceedings in related European Application No. 12762897.2 dated Mar. 22, 2021, pp. 1-11.
Partial Supplementary European Search Report in related European Application No. 17861546.4 dated Apr. 22, 2020, pp. 1-12.
Search Report in related European Application No. 17861546.4 dated Jul. 31, 2020, pp. 1-10.
International Search Report and Written Opinion in counterpart International Application No. PCT/US20/54702 dated Mar. 11, 2021, pp. 1-28.
Ruckel, U.S. Pat. No. 765,793 issued Jul. 26, 1904, pp. 1-3.
Knott et al., "Curved bistable composite slit tubes with positive Gaussian curvature", University of Surrey, Guilford, United Kingdom, pp. 1-22.
Jiang et al., "Snapping of bistable, prestressed cylindrical shells", A Letters Journal Exploring, www.epljournal.org, Jun. 2018, EPL, 122 (2018) 64003, pp. 1-8.
Kebadze, et al., "Bistable prestressed shell structures", International Journal of Solids and Structures, www.elsevier.com/locate/ijsolstr, 41 (2004) pp. 2801-2820.
Kim et al., "Flytrap-inspired robot using structurally integrated actuation based on bistability and developable surface", Bioinspiration & Miomimetics, 9 (2014) 036004, pp. 1-15.
Seffen, "Morphing bistable orthotropic elliptical shallow shells", Proceedings of the Roayl Society, (2007) 463, 67-83, pp. 1-17.
Kyle Design, Hair Barrettes Made in France—Extra Large 4" Blank Metal, No date specified, https://www.kyledesigns.com/hair-barrettes-made-in-france-extra-large-4-blank-metal/ (Year: 0) 4 pages.

* cited by examiner

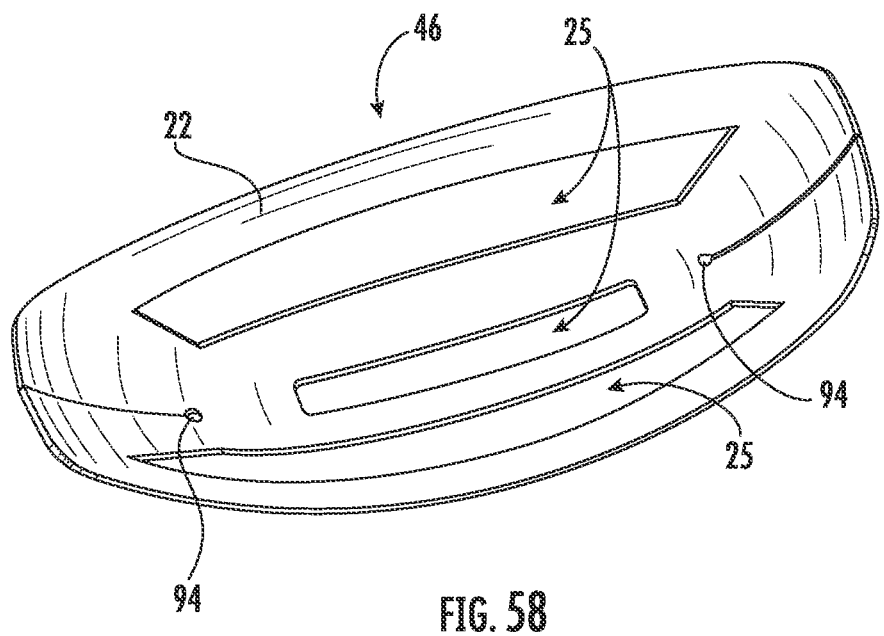
FIG. 58
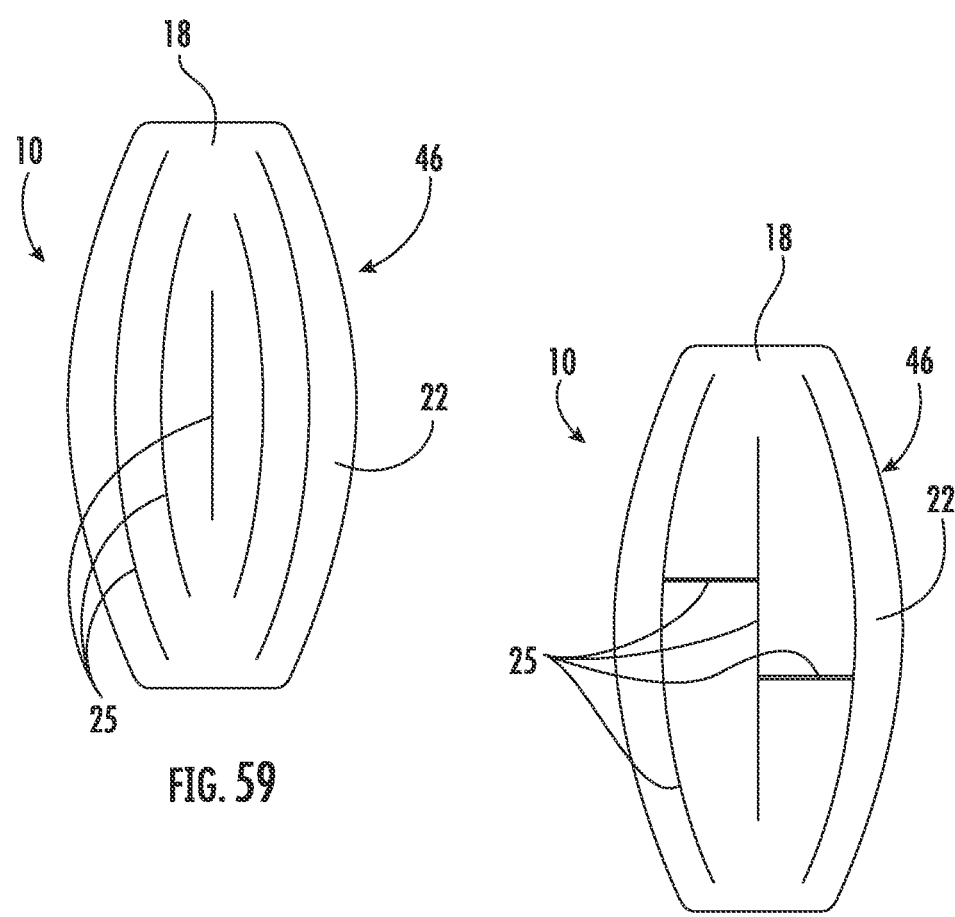
FIG. 59
FIG. 60

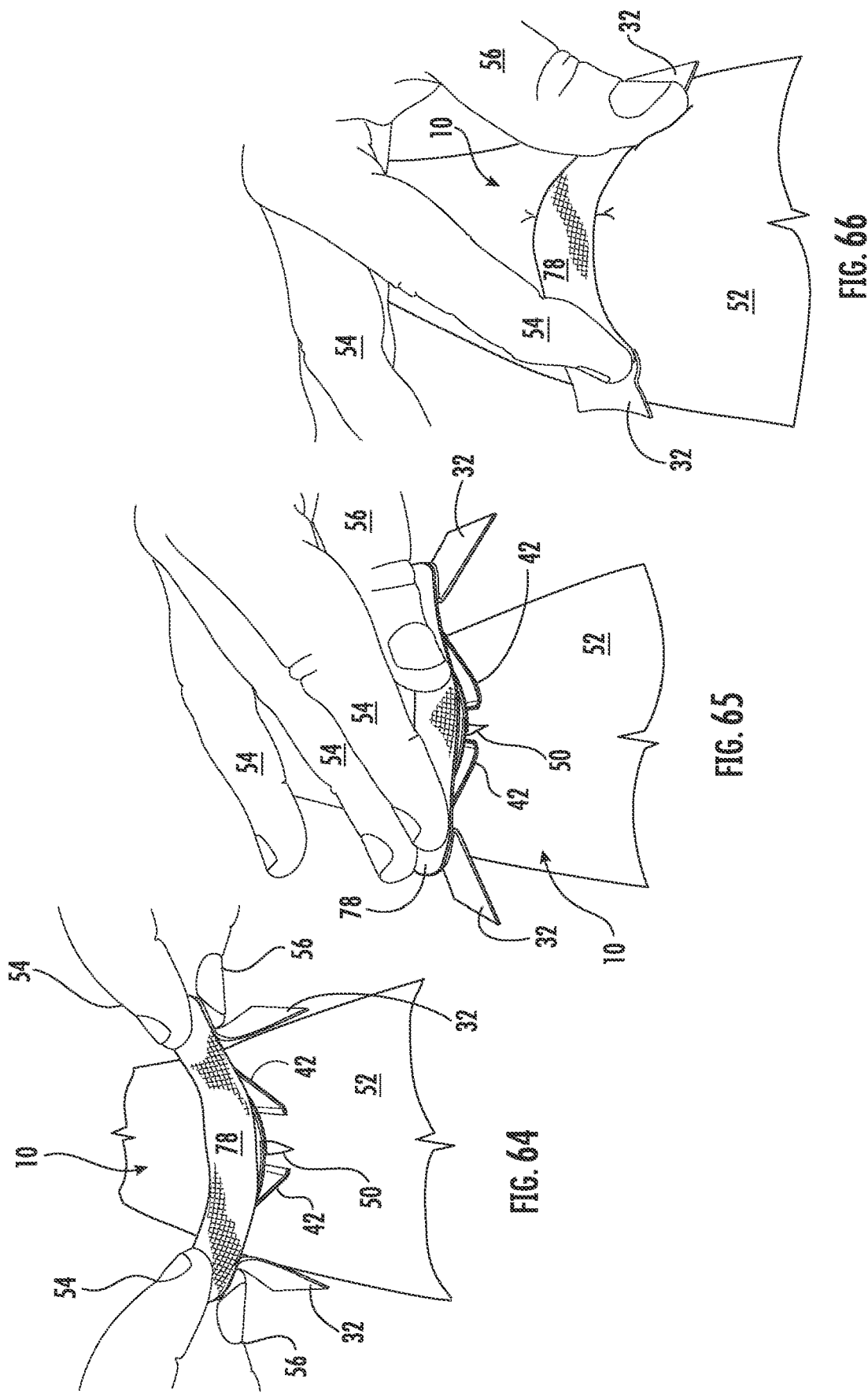

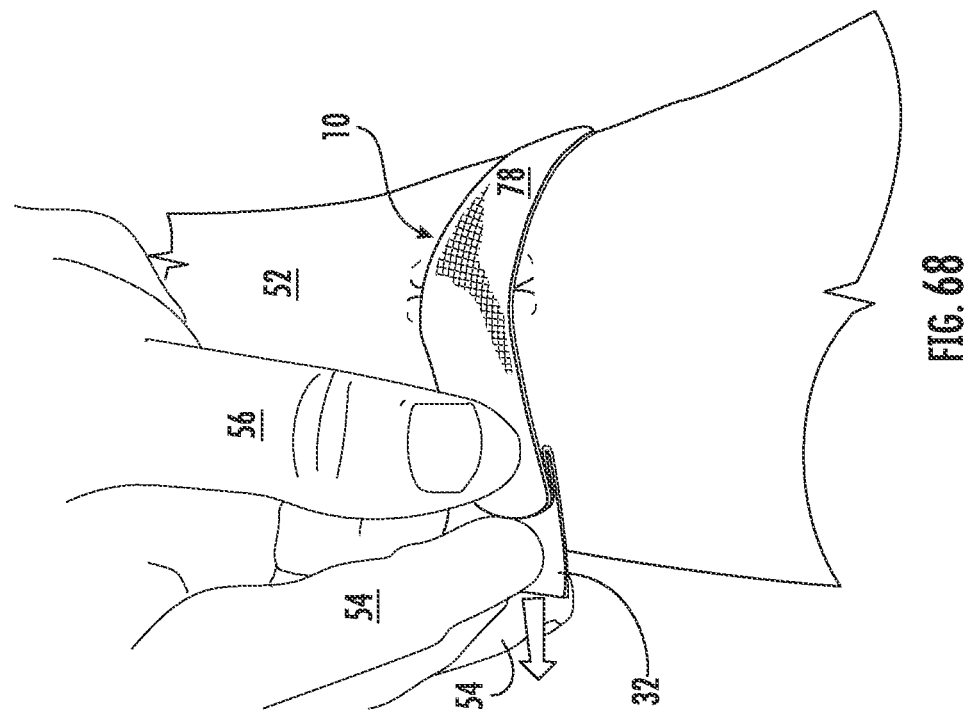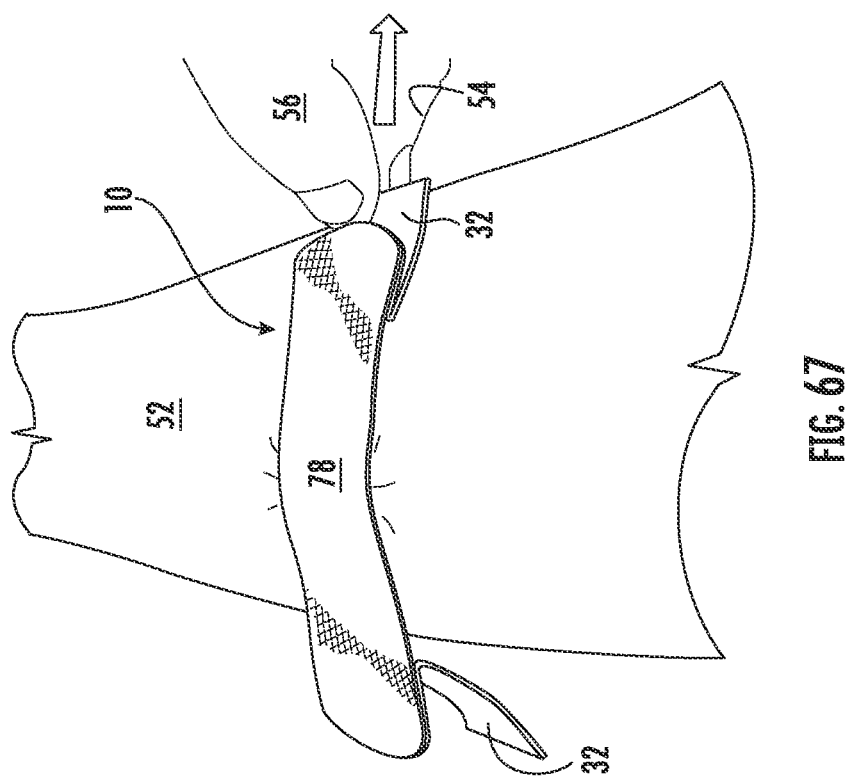

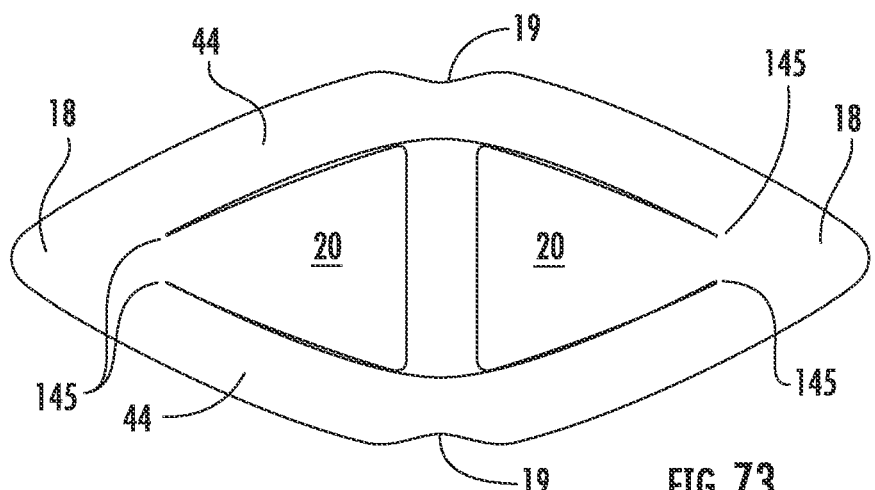
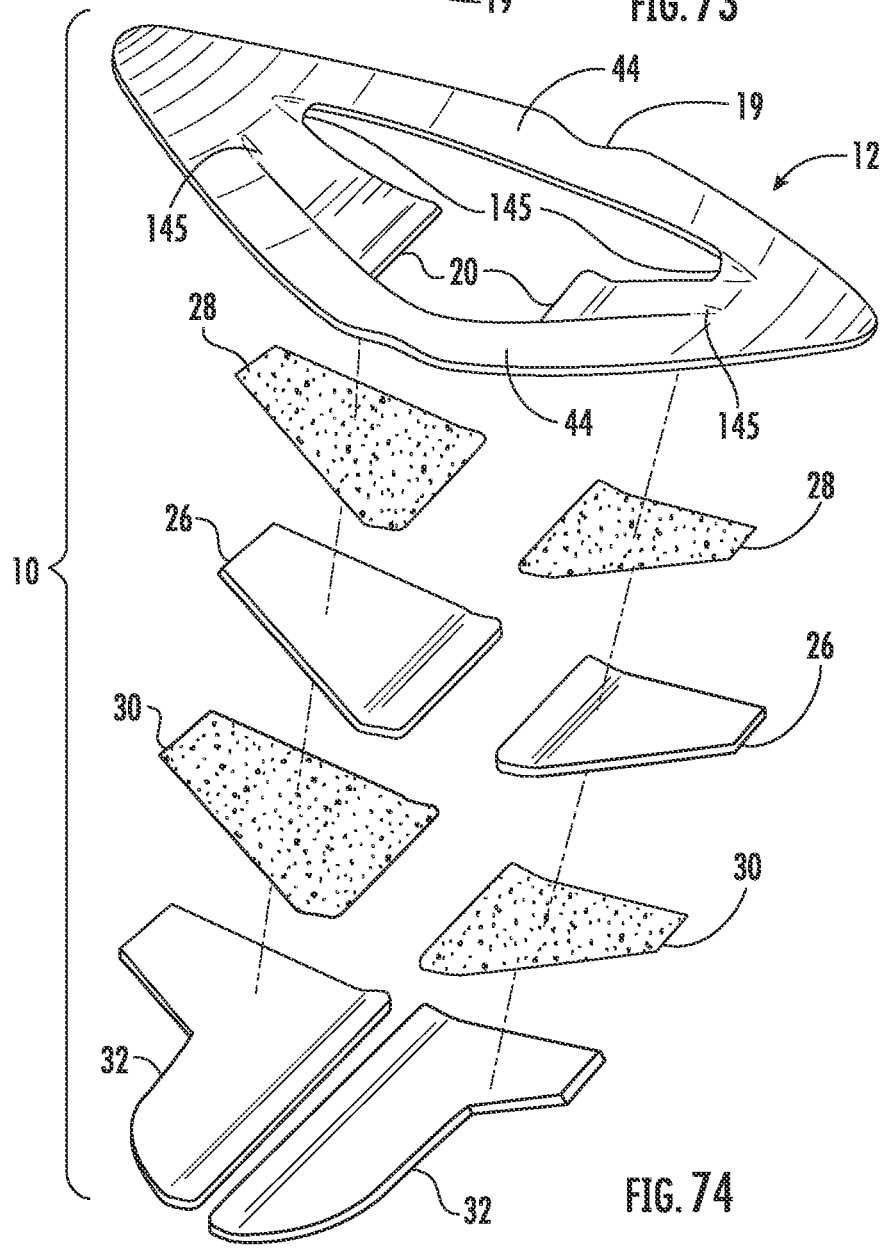

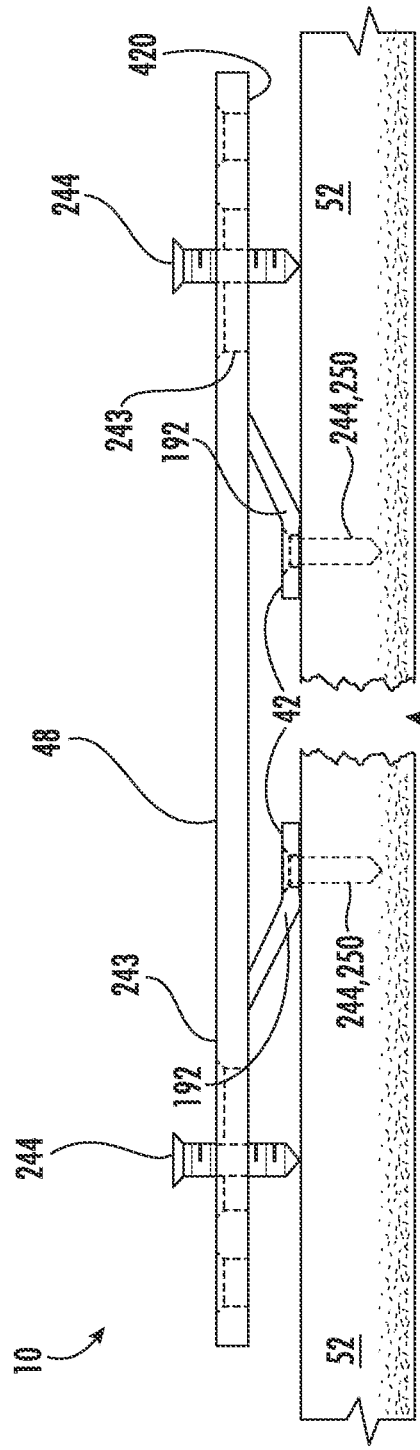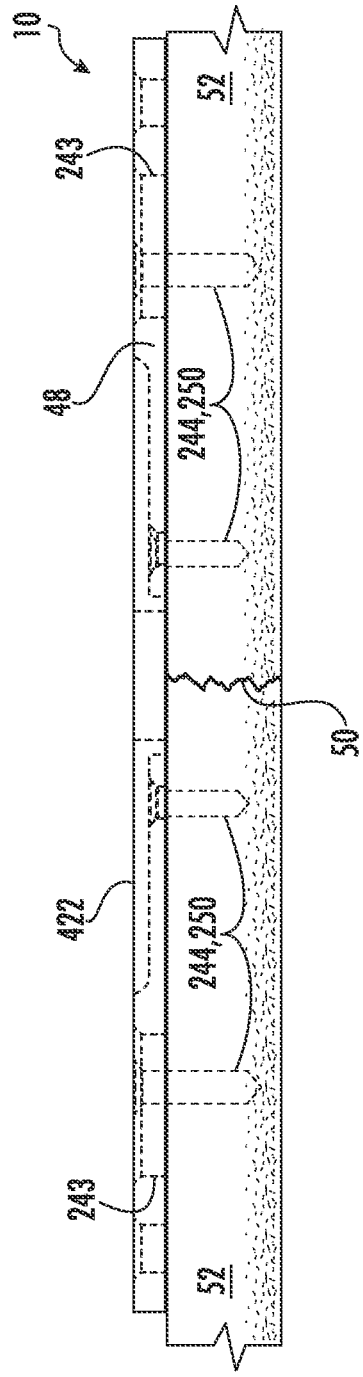

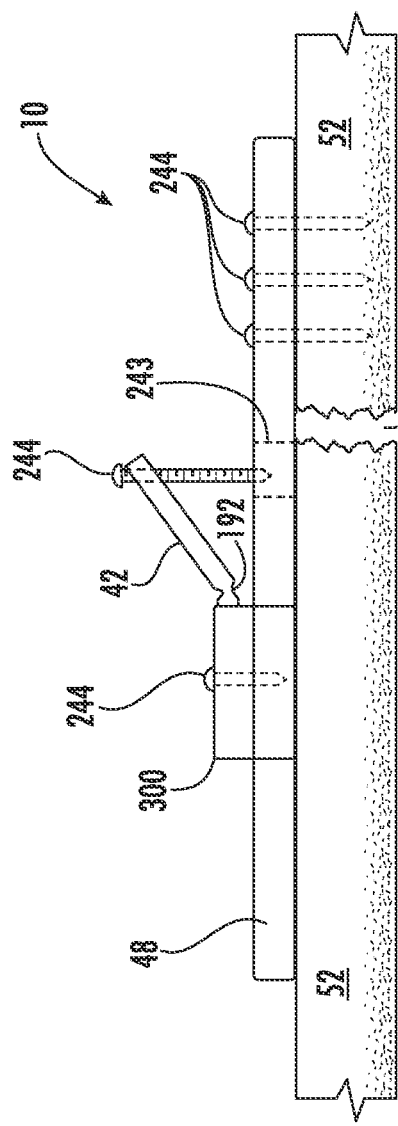
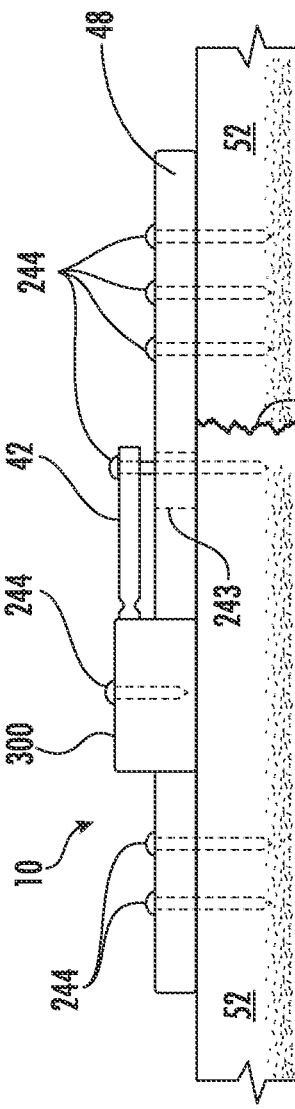

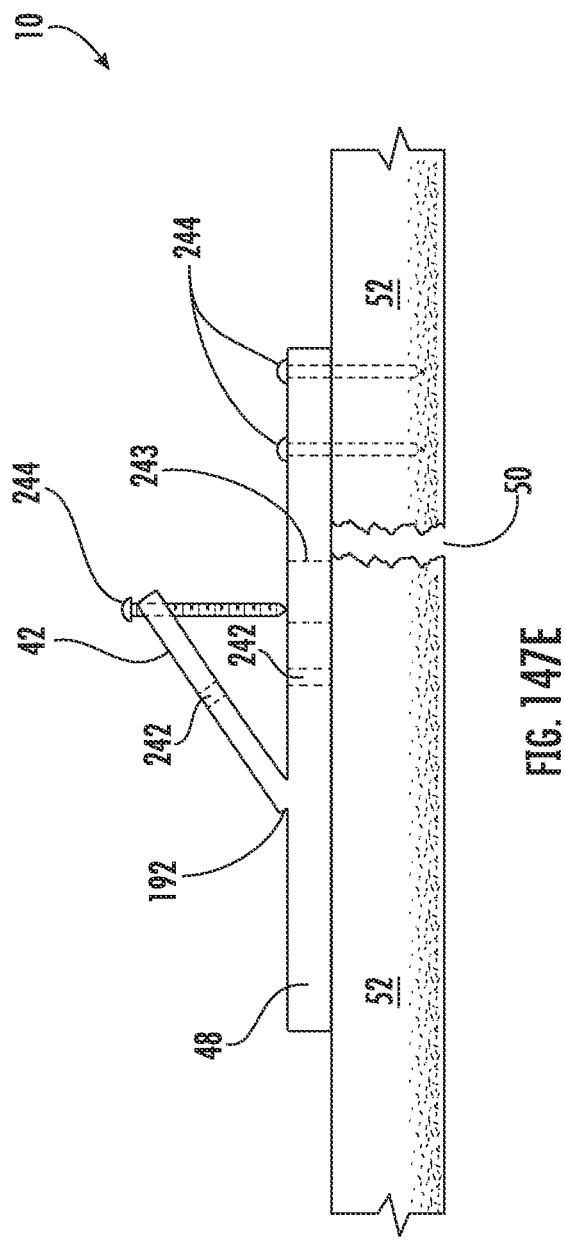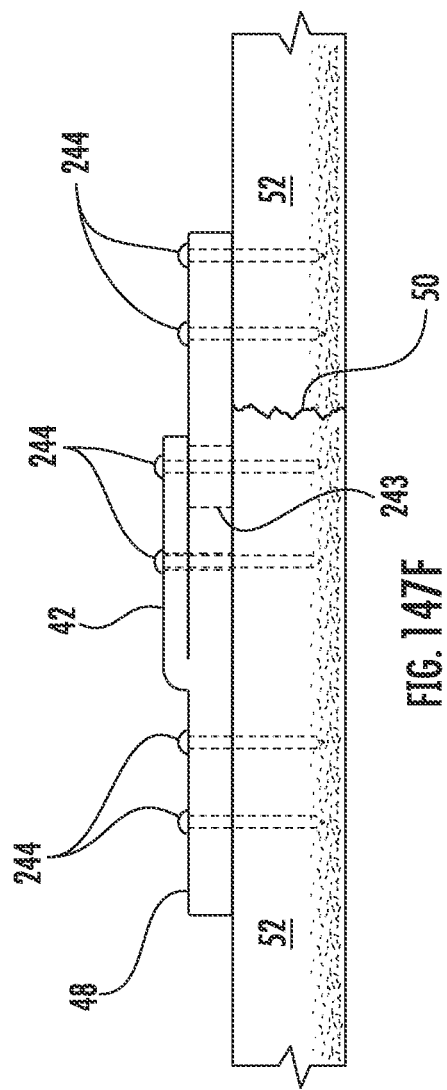

MEDICAL DEVICE FOR APPLYING FORCE ON BIOLOGICAL TISSUE, OR THE LIKE

CROSS-REFERENCE TO PRIORITY APPLICATIONS

The present application is a continuation of International Application No. PCT/US20/54702 filed Oct. 8, 2020, which claims the benefit of U.S. Provisional Patent Application No. 62/913,754, filed Oct. 11, 2019, and each of the above-referenced applications is incorporated herein by reference in its entirety.

FIELD OF THE INVENTION

The present invention generally relates to medical devices for at least partially covering wounds and/or scars, and, more particularly, to wound closure and/or reducing tension in wounds and/or scars.

BACKGROUND

Traditional methods of wound closure, wound support, wound dressings, and bandages typically do not adequately control wound tension, which is well known to be a primary stimulus of excess scar formation. In addition, tension reduction is known to decrease the size, discoloration, and poor appearance of scars when applied during the wound healing period.

Force modulating tissue bridges (see, e.g., International Publication Nos. WO 2012/135735 and WO 2018/075879) seek to allow wounds to be closed accurately, and further seek to provide simultaneous reduction of tension on closed wounds and scars in the healing phases. There is a desire for force modulating tissue bridges, and related devices, systems, and methods, that provide a new balance of properties.

SUMMARY

An aspect of this disclosure is the provision of a medical device for at least partially covering and applying force on tissue, wherein the medical device includes a body and a flexible web (e.g., sheet) connected to the body, and at least a portion of the web is configured to engage and apply force (e.g., everting forces) on the tissue. The body can include a spanning structure and struts respectively connected to lateral portions of the spanning structure. Inner ends of the struts can extend into an area over which the medial portion of the spanning structure extends. At least a portion of the web can span between the inner ends of the struts. The medical device typically is reconfigurable between extended and retracted configurations. The inner ends of the struts are typically closer to one another in the retracted configuration than in the extended configuration. The inner ends of the struts are typically closer to the medial portion of the spanning structure in the retracted configuration than in the extended configuration. Each strut typically includes an engagement zone configured to engage and apply force on the tissue, at least while the medical device is in the retracted configuration.

A wide variety of the medical devices are within the scope of this disclosure. For example, at least a portion of the web that is positioned between the inner ends of the struts can be omitted, the medical device can be biased toward the retracted configuration, the medical device can be solely biased toward the retracted configuration (e.g., monostable), the medical device can be multistable (e.g., biased toward both of the retracted and extended configurations), the medical device can include connecting mechanisms for at least partially retaining the medical device in its retracted configuration (e.g., for retaining the struts in their inner configurations), the medical device can include arrestation mechanisms for at least partially restricting the medical device from deforming past the extended configuration (e.g., for restricting outward movement of the struts), there can be a greater or lesser number of the struts, and/or the medical device can include guideway(s) configured to guide movement of the spanning structure and/or strut(s).

The foregoing summary provides a few brief examples and is not exhaustive, and the present invention is not limited to the foregoing examples. The foregoing examples, as well as other examples, are further explained in the following detailed description with reference to accompanying drawings.

BRIEF DESCRIPTION OF THE DRAWINGS

The drawings are provided as examples. The present invention may be embodied in many different forms and should not be construed as limited to the examples depicted in the drawings. The drawings may be schematic and may not be drawn to scale.

FIG. 58 is a top perspective view of a multistable spanning structure in accordance with another embodiment of this disclosure.

FIG. 59 is a top view of a multistable tissue bridge in accordance with another embodiment of this disclosure.

FIG. 60 is a top view of a multistable tissue bridge in accordance with another embodiment of this disclosure.

FIGS. 63 through 68 depict a sequence of steps of a method of applying the tissue bridge of FIG. 62 to a scar or wound in accordance with an embodiment of this disclosure.

FIG. 73 is an isolated top view of a multistable body in its extended stable equilibrium configuration, in accordance with an embodiment of this disclosure.

FIG. 74 is an exploded, top perspective view of an embodiment of a multistable tissue bridge including the multistable body of FIG. 73, wherein the body is its extended stable equilibrium configuration.

FIG. 86 is a schematic front view of an example of a multistable tissue bridge at least partially formed from steps including those described with reference to FIGS. 80 through 85, or the like.

FIGS. 136B and 136C depict a sequence of steps of a method of applying the tissue bridge of FIGS. 134 and 135 to a broken bone, in accordance with an embodiment of this disclosure.

FIG. 137 is a schematic top view of a tissue bridge in accordance with an embodiment of this disclosure.

FIG. 138 is a schematic cross-sectional view taken along line 138-138 of FIG. 137.

FIGS. 139 through 142 are front views that schematically depict a sequence of steps of a method of applying the tissue bridge of FIGS. 137 and 138 to a broken bone, in accordance with an embodiment of this disclosure.

FIGS. 143 through 147A depict other embodiments of tissue bridges.

FIG. 147B is an exploded, top perspective view of a multi-part tissue bridge including a spanning structure or plate and a strut-supporting body, in accordance with an embodiment of this disclosure.

Figure 147A:
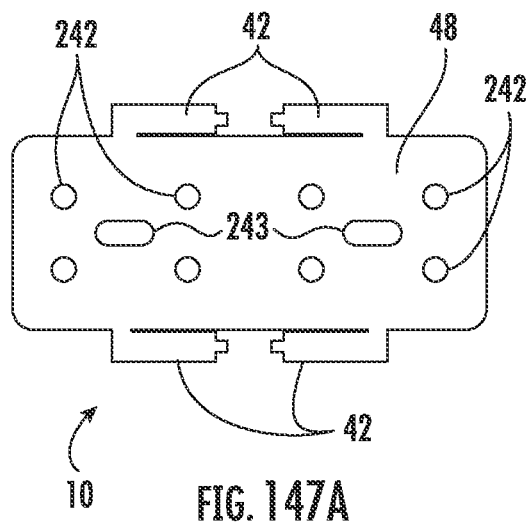
Figure 147B:
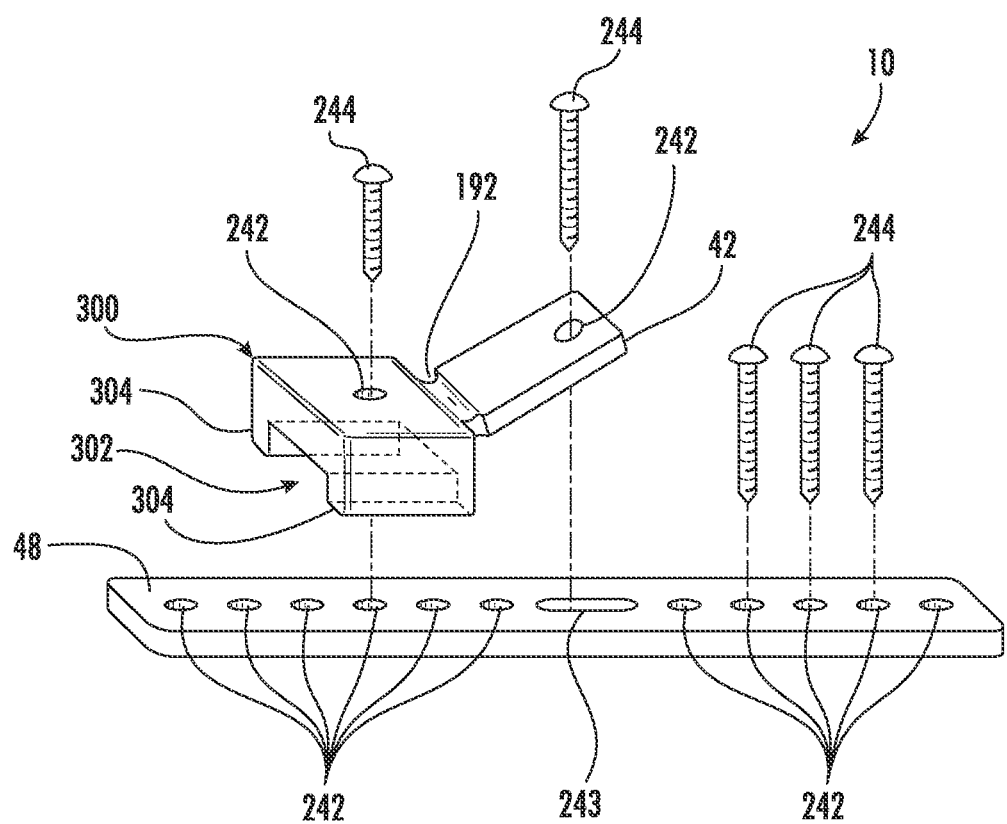

FIGS. 147C and 147D schematically depict an example of a sequence of steps of a method of applying the tissue bridge of FIG. 147B to bone.

FIGS. 147E and 147F schematically depict an example of a sequence of steps of a method of applying a tissue bridge to bone in accordance with another embodiment of this disclosure.

Figure 147G:
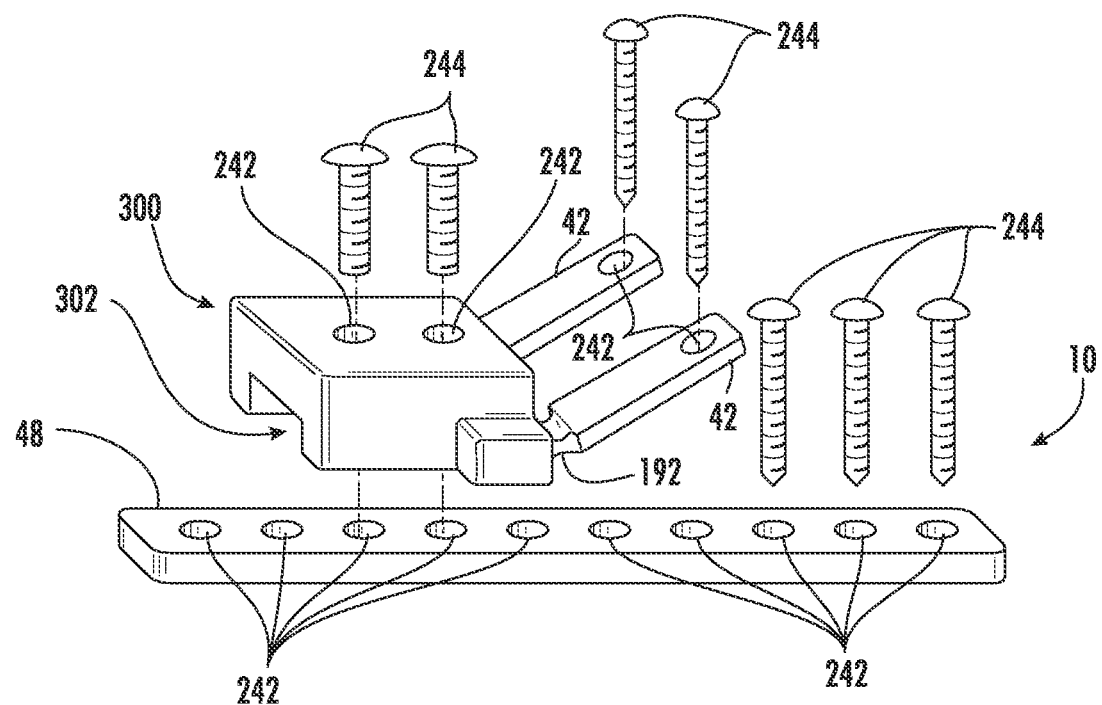

FIG. 147G is an exploded, top perspective view of a multi-part tissue bridge including a spanning structure or plate and a strut-supporting body, in accordance with an embodiment of this disclosure.

Figure 147H:
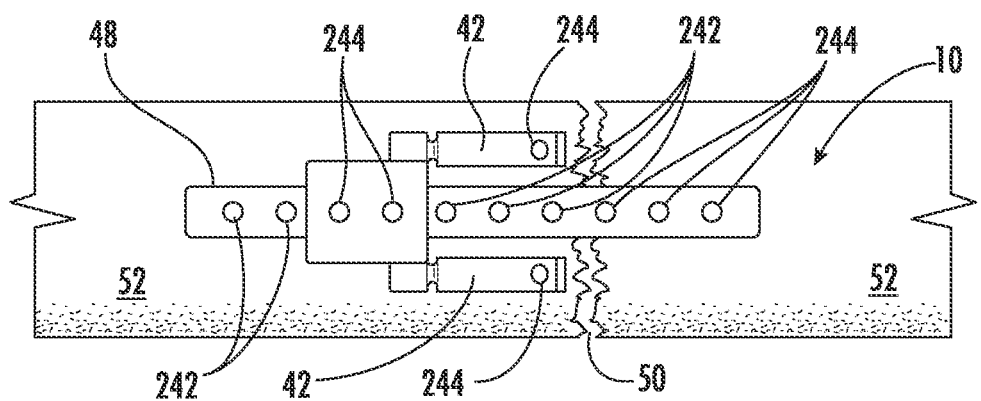
Figure 147I:
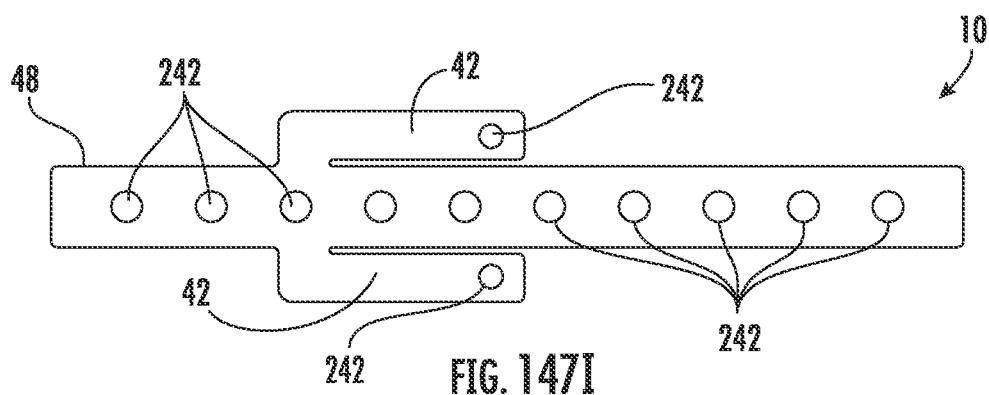
Figure 147J:
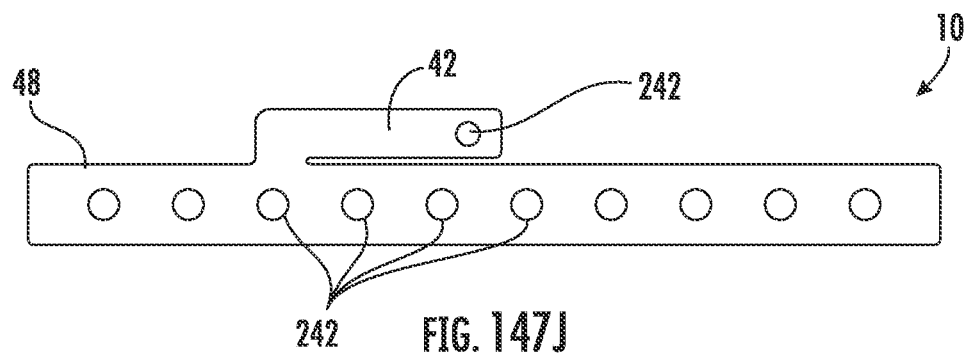
Figure 147K:
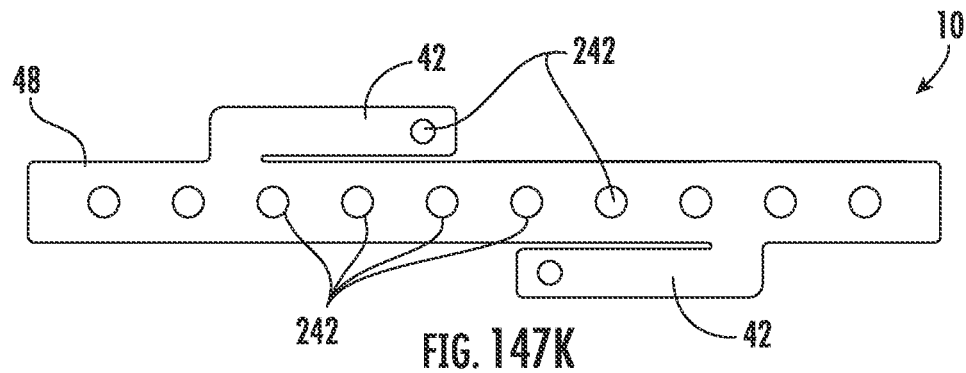
Figure 147L:
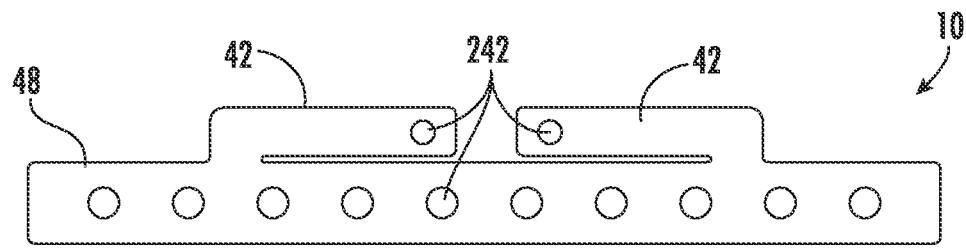
Figure 147M:
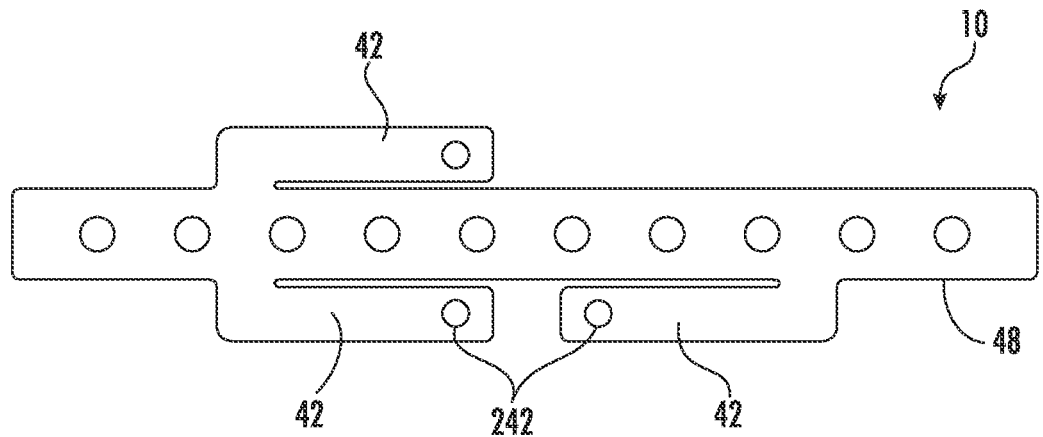
Figure 147N:
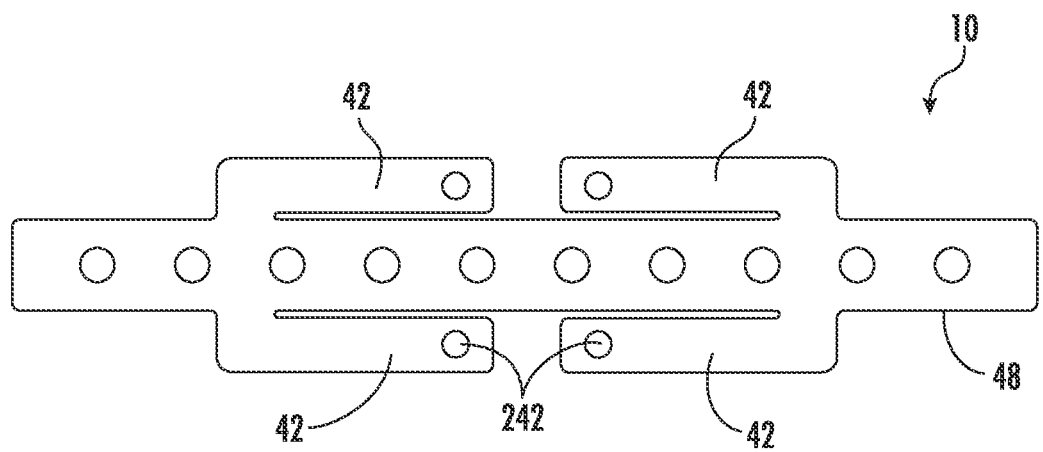
Figure 147O:
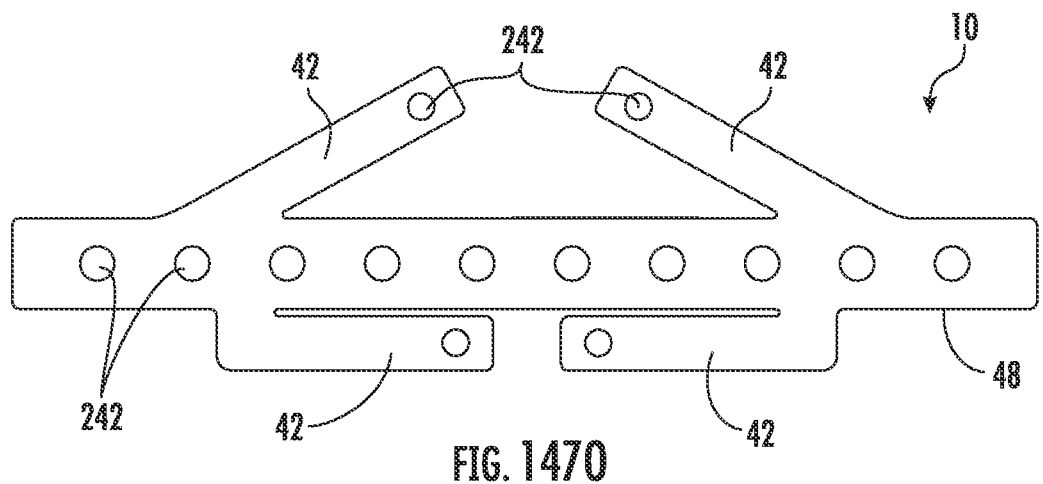

FIG. 147H is a top view that schematically depicts one of a sequence of steps of a method of applying the tissue bridge of FIG. 147G to a broken bone, in accordance with an embodiment of this disclosure.

FIGS. 147I through 147P depict other embodiments of tissue bridges.

Figure 147P:
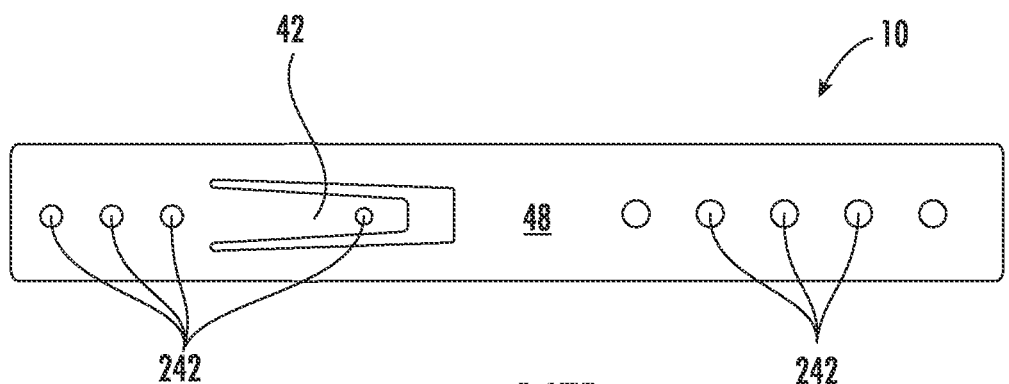
Figure 147Q:
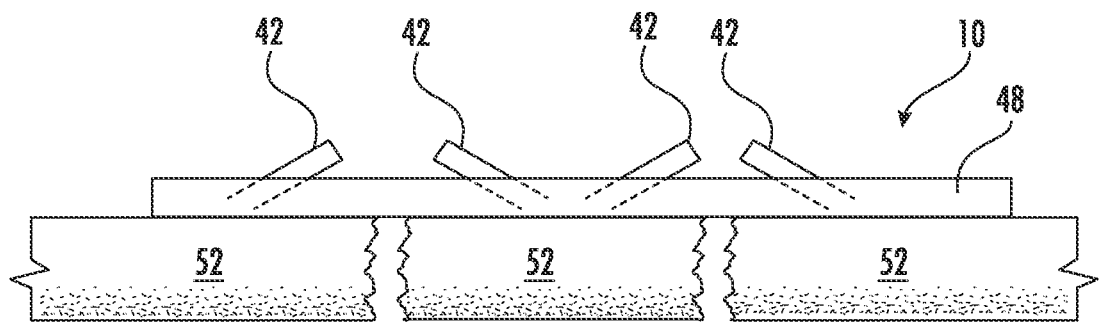

FIG. 147Q schematically depicts another example of a tissue bridge mounted on bone, in accordance with another embodiment.

Figure 147R:
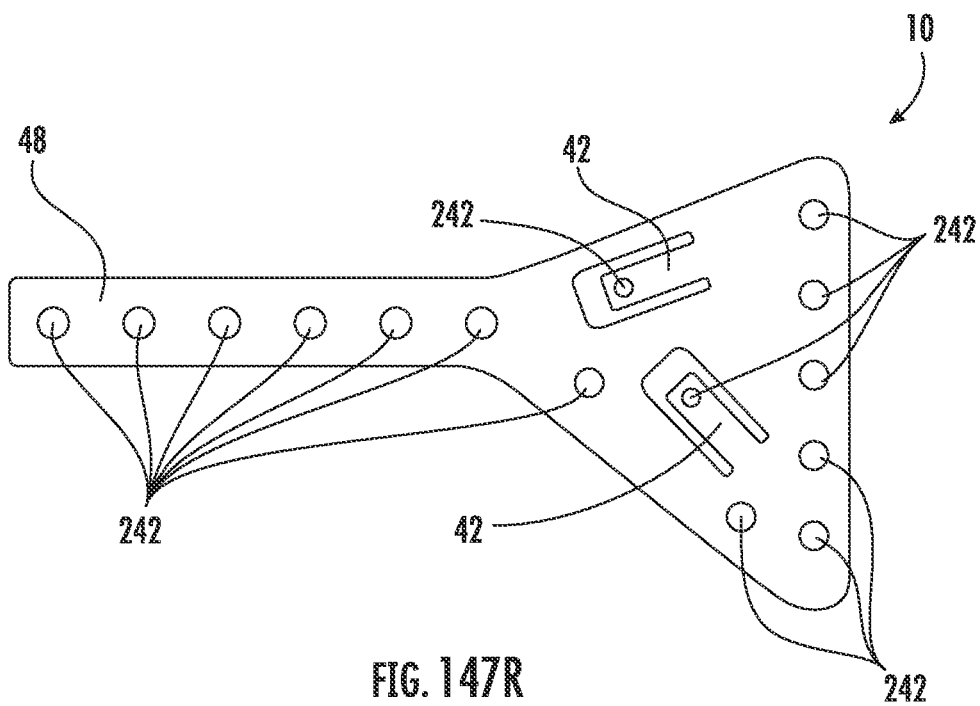
Figure 147S:
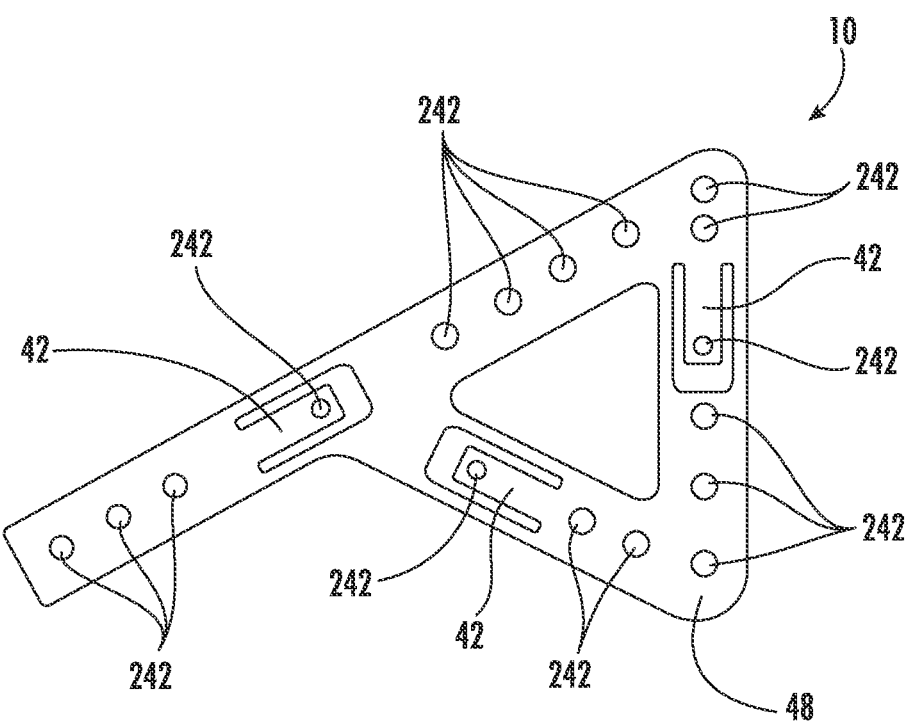
Figure 147T:
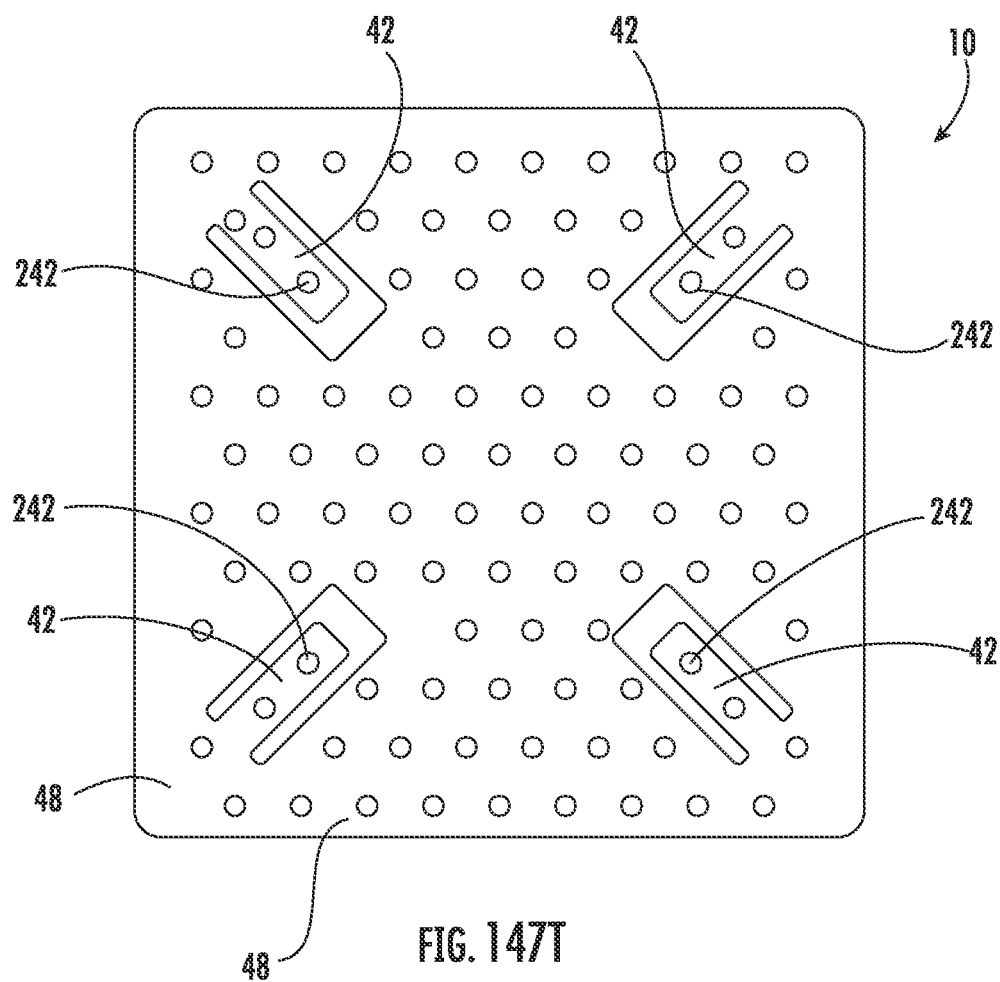

FIGS. 147R through 147T depict other embodiments of tissue bridges.

Figure 147U:
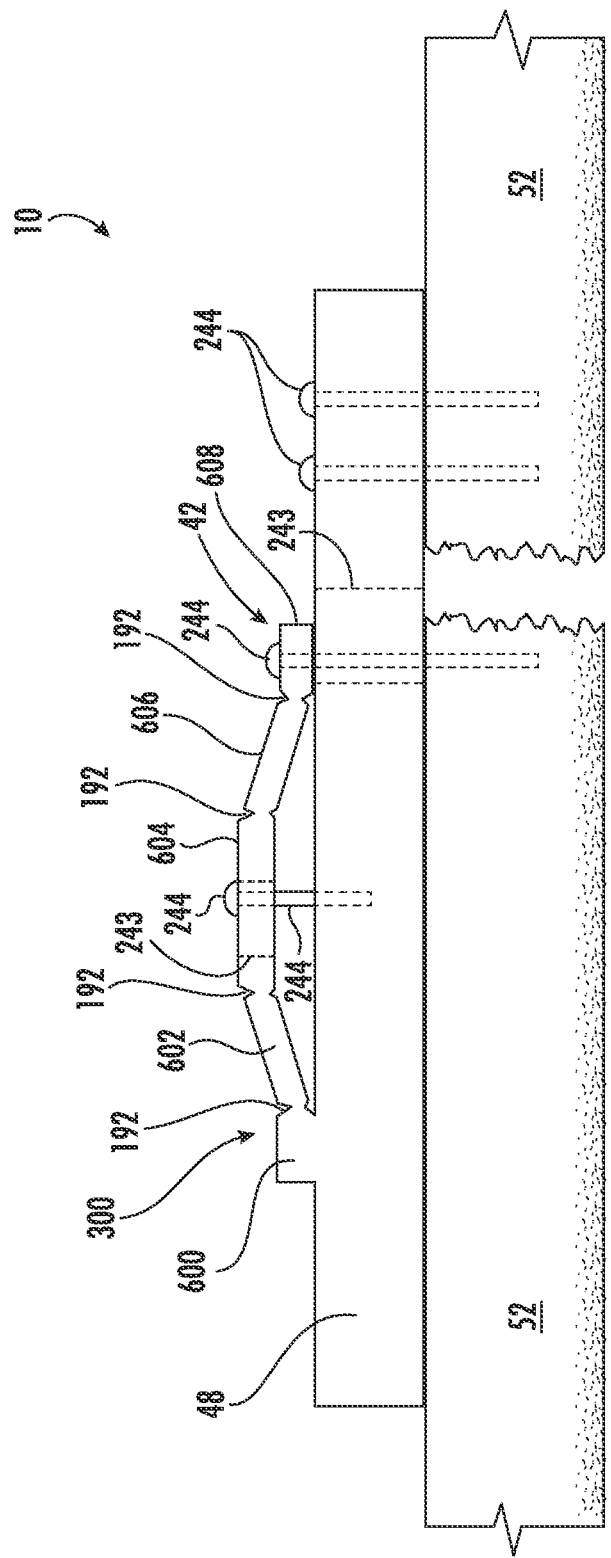
Figure 147V:
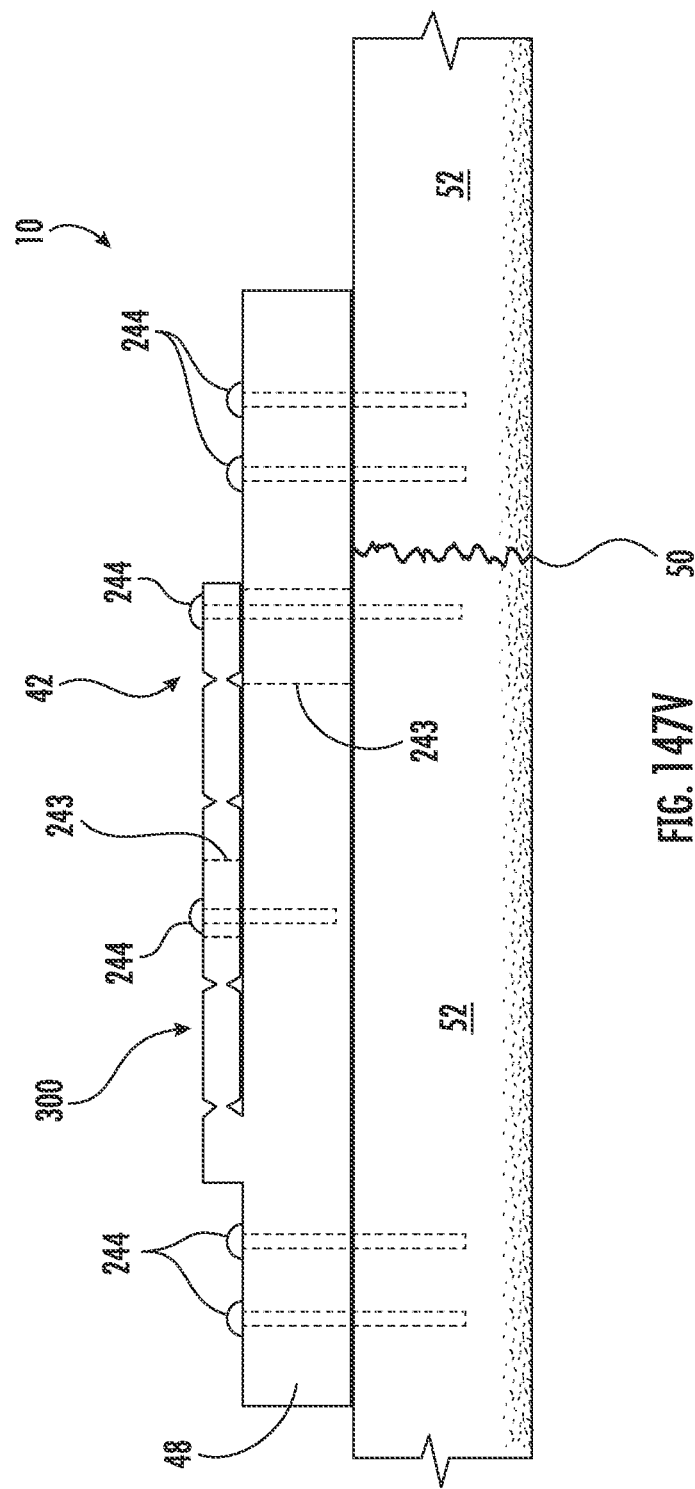

FIGS. 147U and 147V schematically depict an example of a sequence of steps of a method of applying a tissue bridge to bone in accordance with another embodiment of this disclosure.

Figure 148:
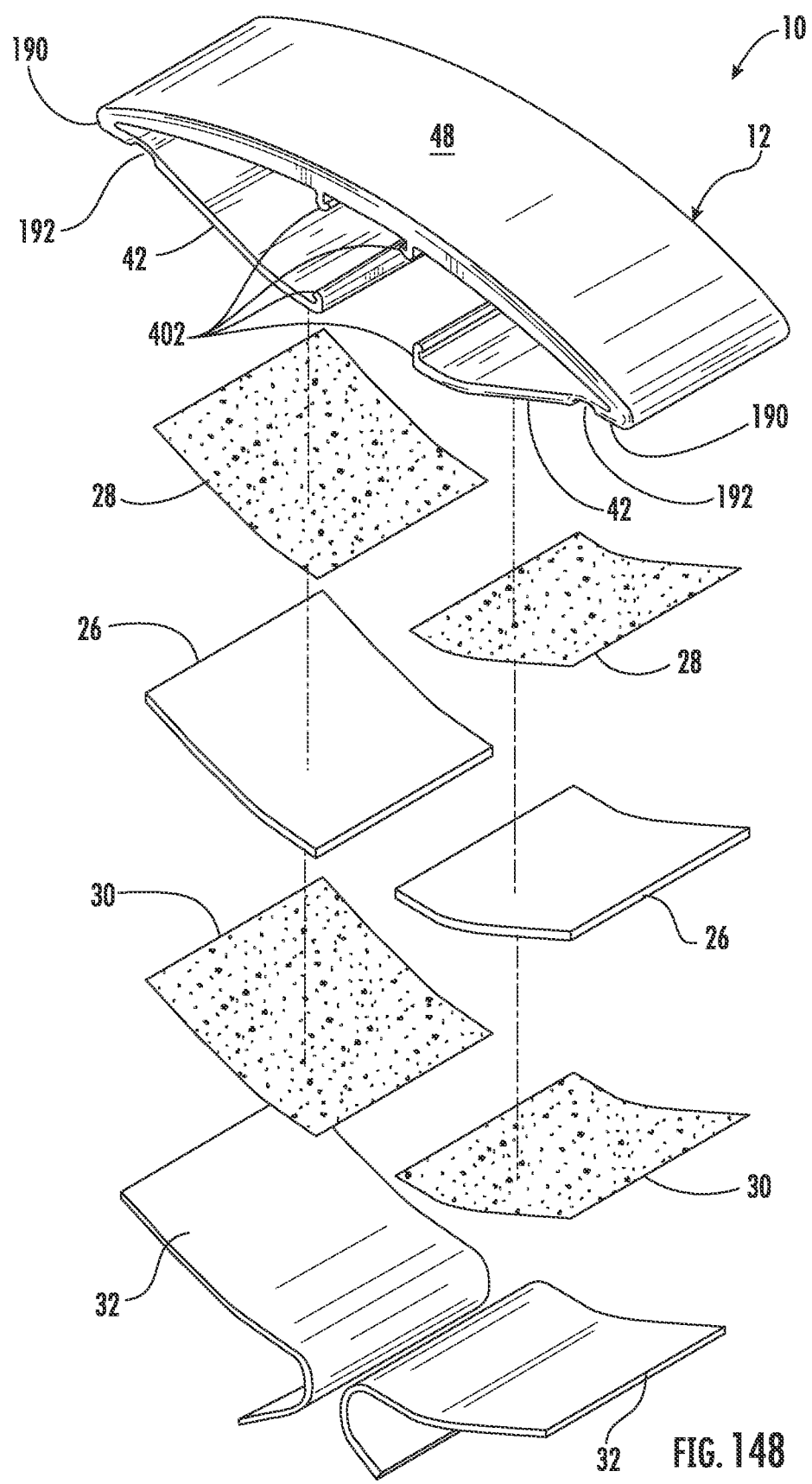

FIG. 148 is an exploded, top perspective view of another embodiment of a tissue bridge in its extended configuration.

Figure 149:
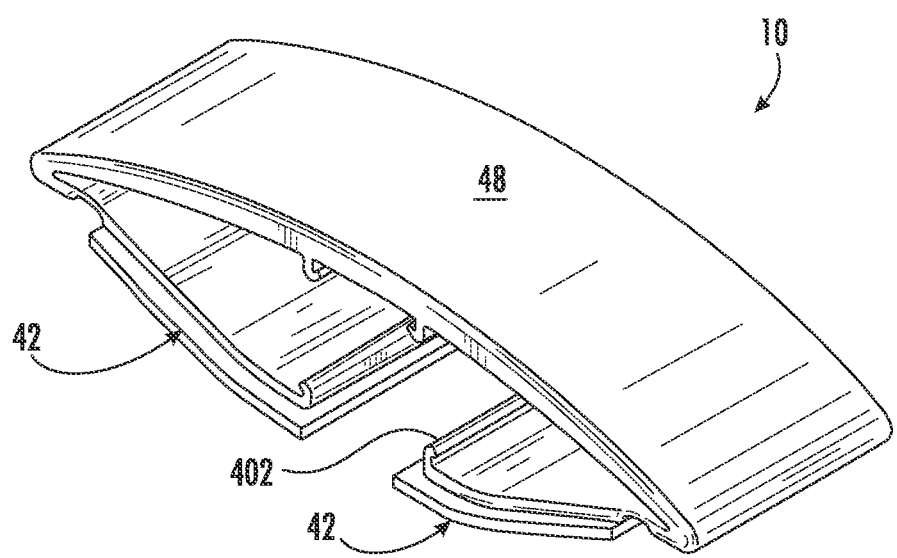

FIG. 149 is an assembled, top perspective view of the tissue bridge of FIG. 147 in its extended configuration, wherein outer release liners are not shown.

Figure 150:
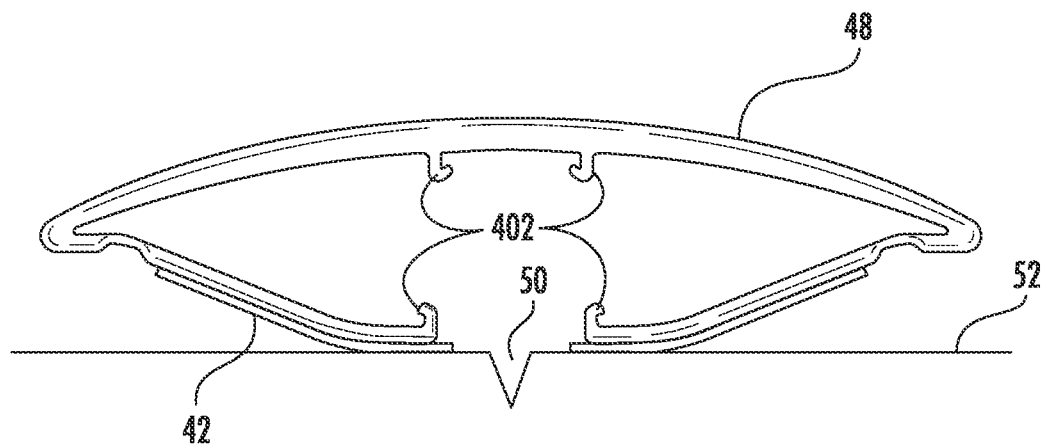
Figure 151:
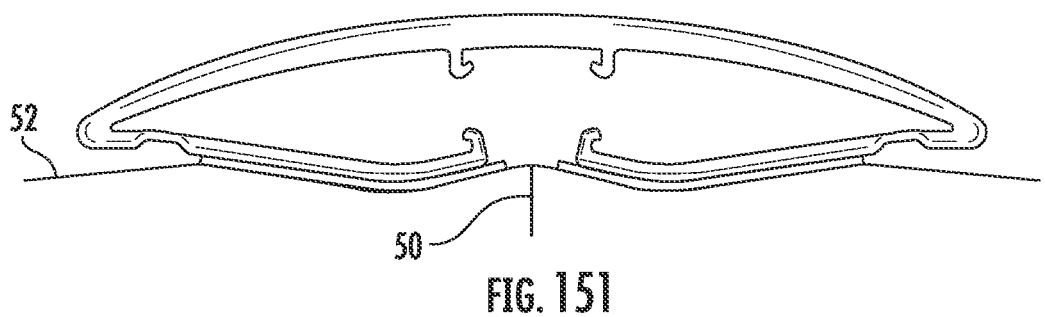
Figure 152:
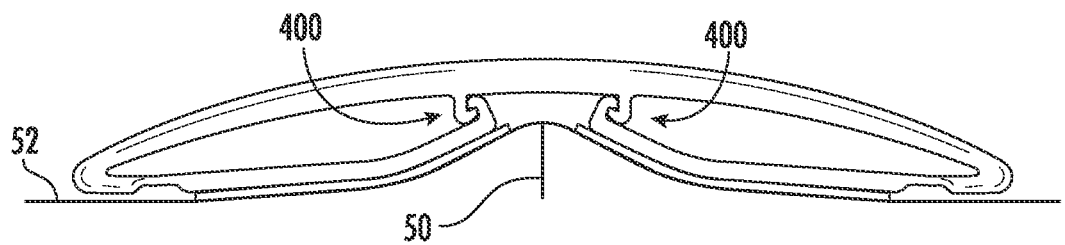

FIGS. 150 through 152 are front views that schematically depict an example of a sequence of steps of a method of applying the tissue bridge of FIG. 149 to wounded tissue.

Figure 153:
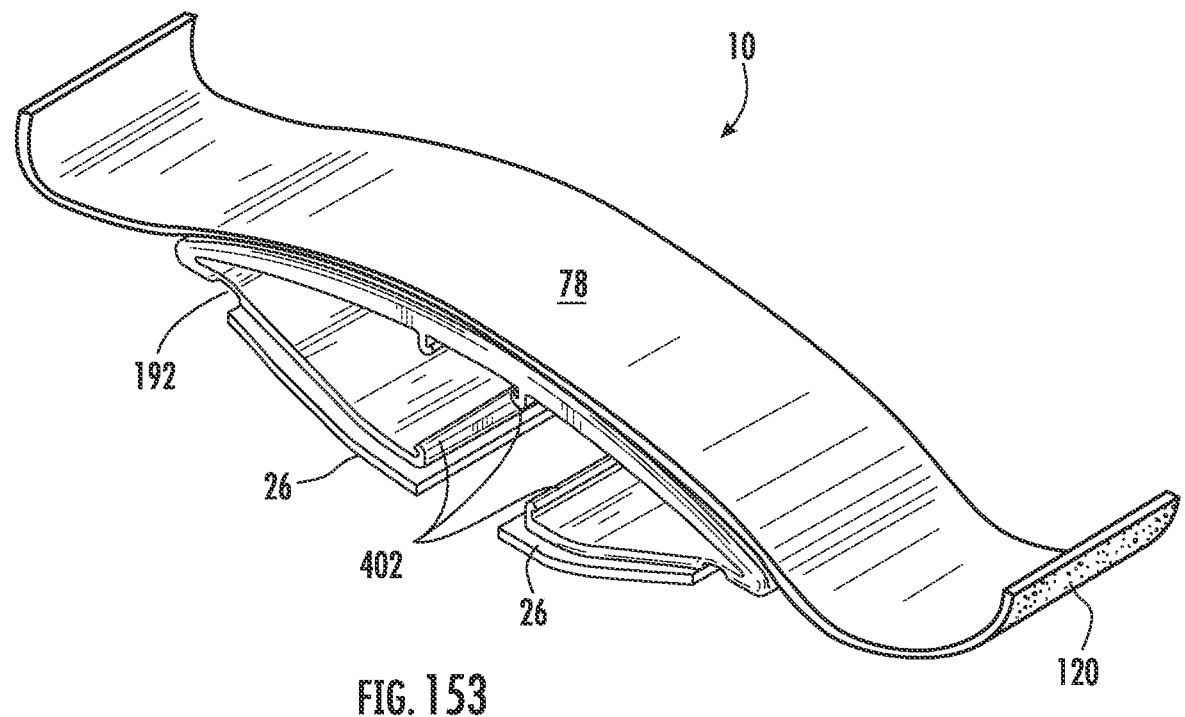

FIG. 153 schematically depicts an example of a version of the tissue bridge of FIG. 149 that includes an adhesive-backed cover sheet.

Figure 154:
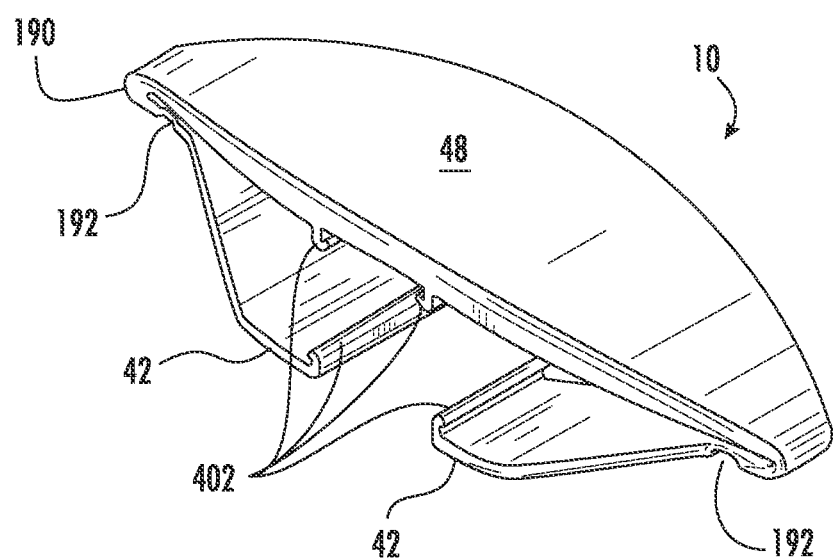

FIG. 154 depicts an example of a variation to the tissue bridge of FIG. 149.

Figure 155:
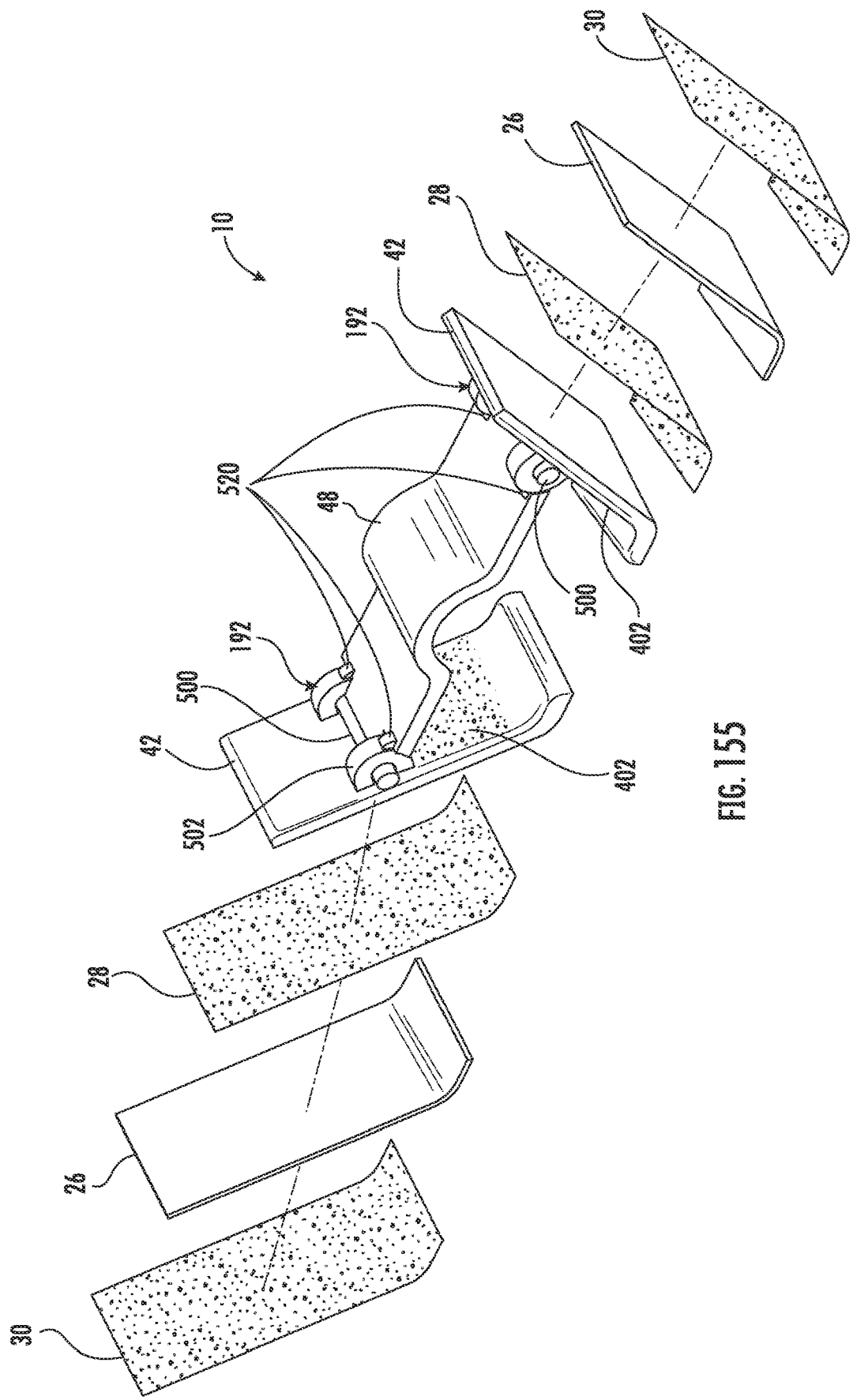

FIG. 155 is a partially exploded, top perspective view of another embodiment of a tissue bridge in its extended configuration, wherein outer release liners are not shown.

Figure 156:
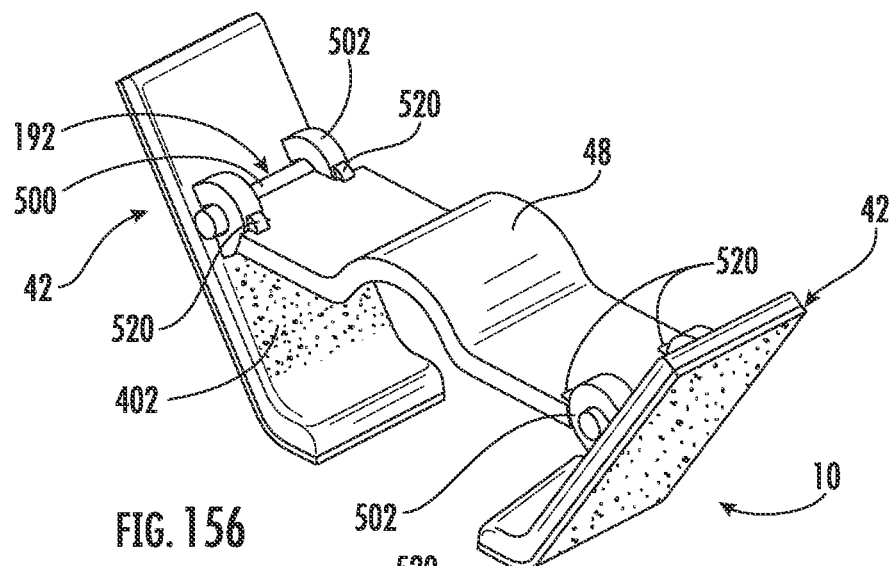

FIG. 156 is an assembled, top perspective view of the tissue bridge of FIG. 155 in its extended configuration.

Figure 157:
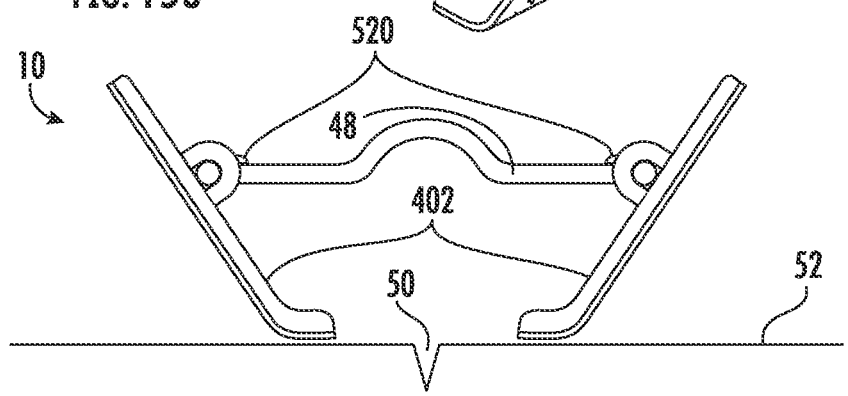
Figure 158:
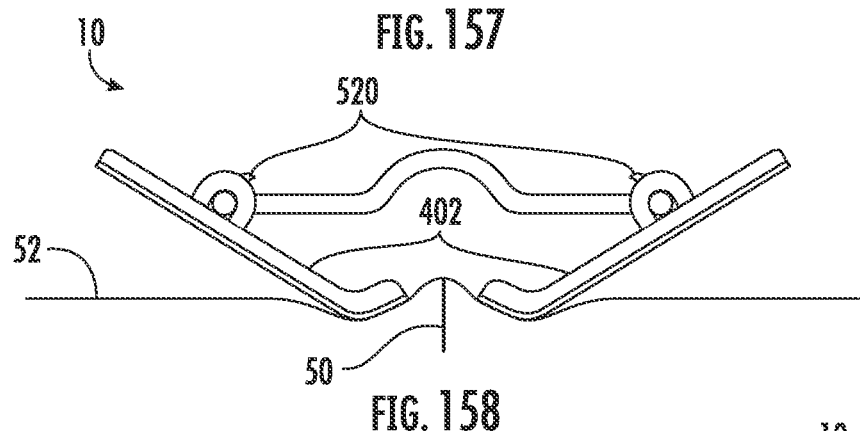
Figure 159:
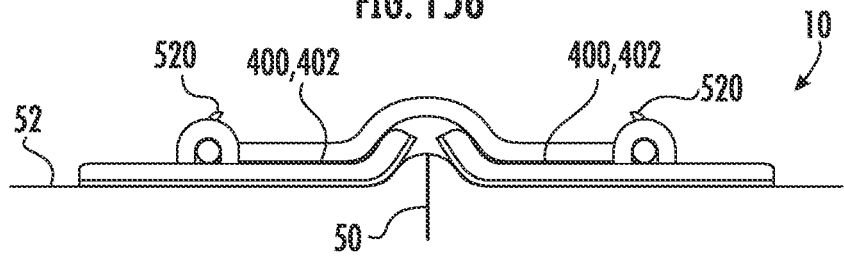

FIGS. 157 through 159 are front views that schematically depict an example of a sequence of steps of a method of applying the tissue bridge of FIG. 156 to wounded tissue.

Figure 160:
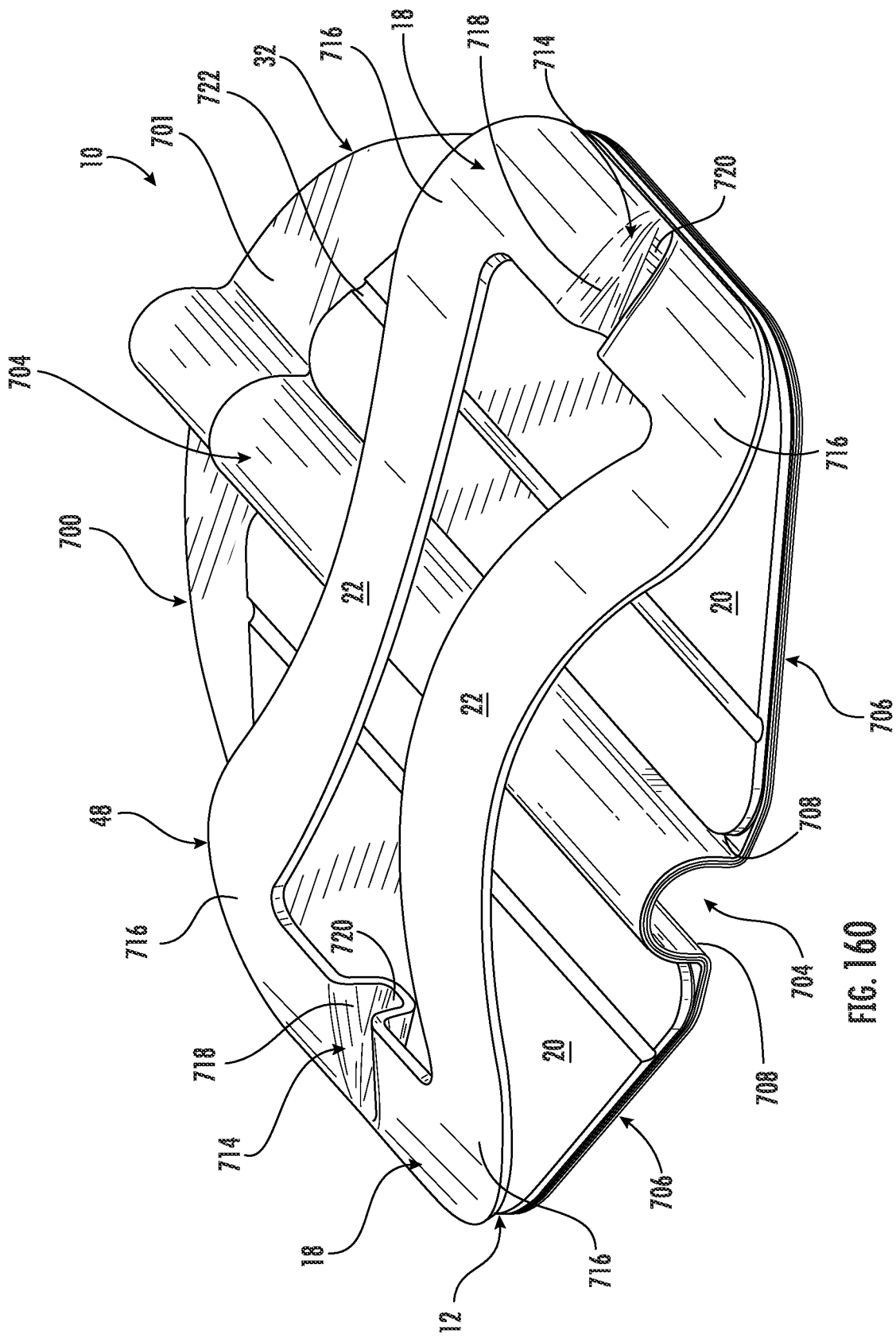

FIG. 160 is a top perspective view of a tissue bridge in its retracted stable configuration, in accordance with an embodiment of this disclosure.

Figure 161:
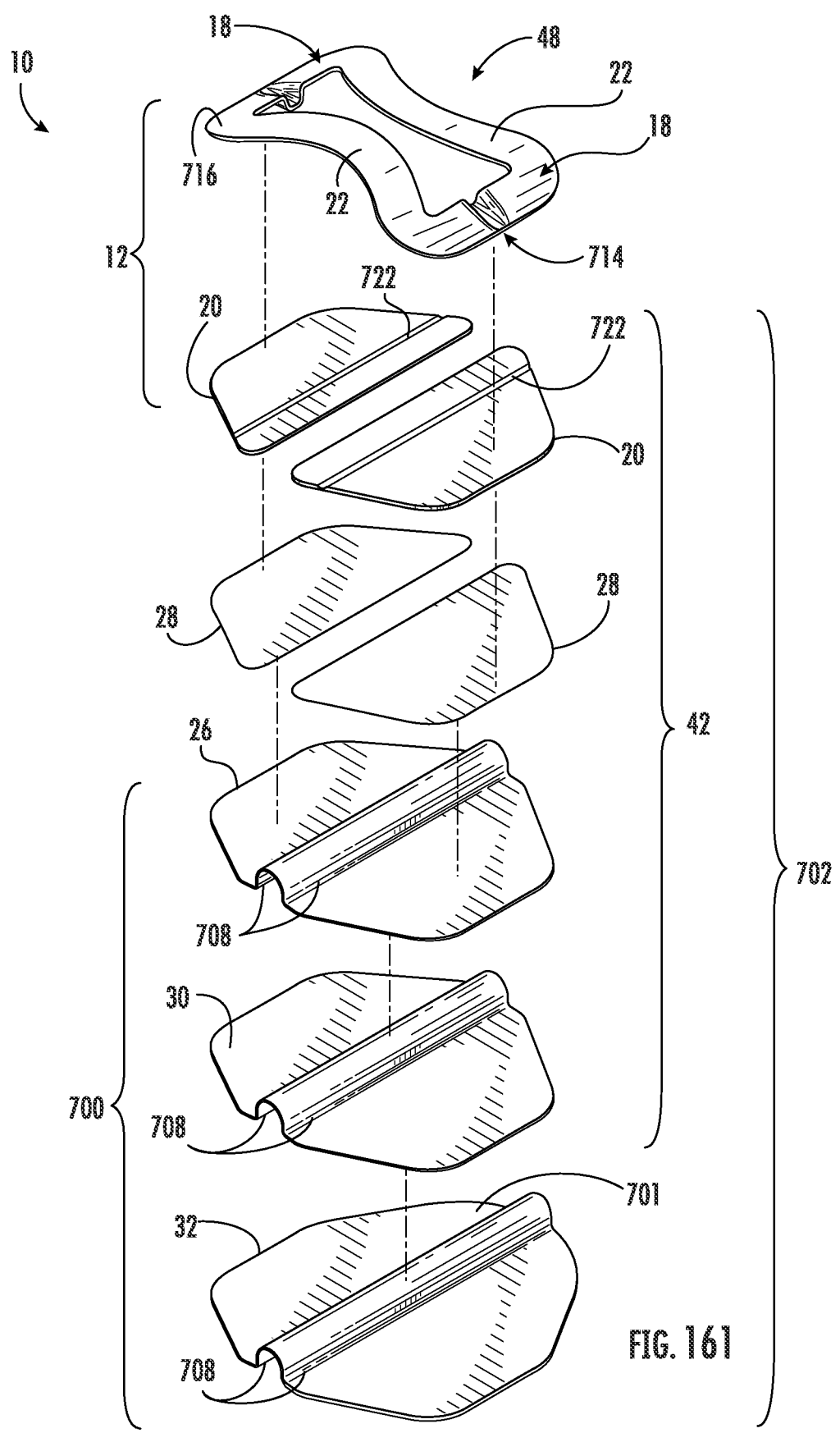

FIG. 161 is a top perspective, exploded view of the tissue bridge of FIG. 160 in its retracted stable equilibrium configuration.

Figure 162:
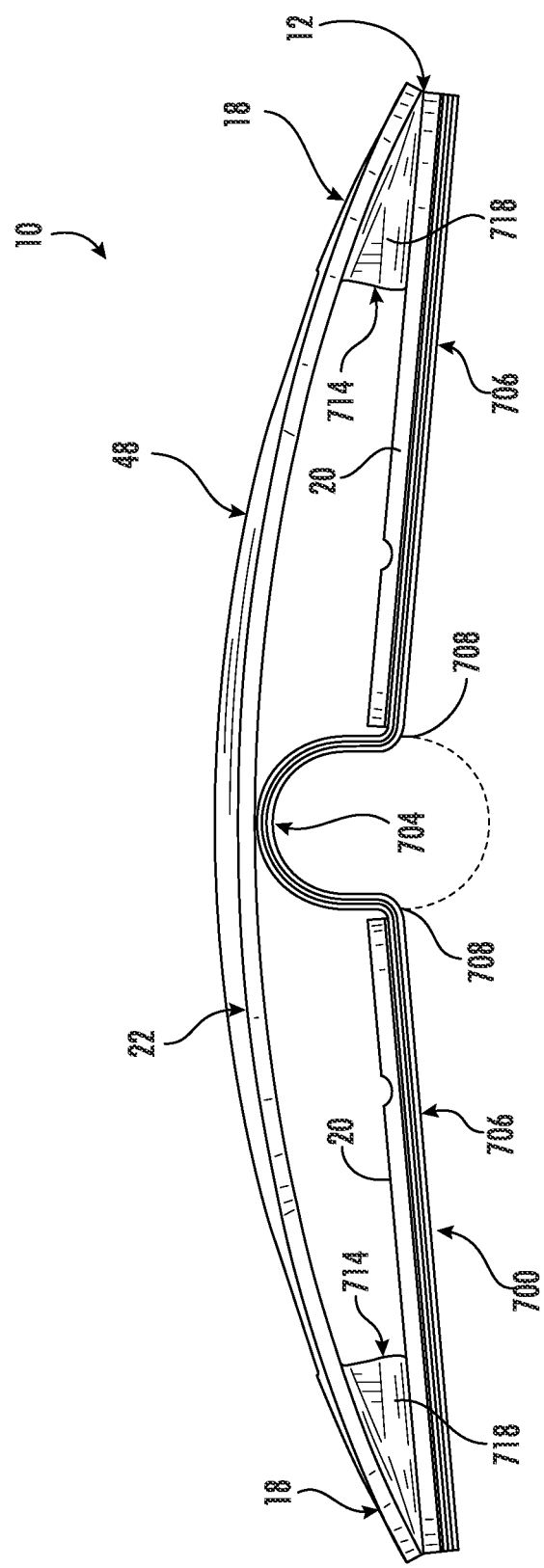

FIG. 162 is a front view of the configuration of FIG. 160.

Figure 163:
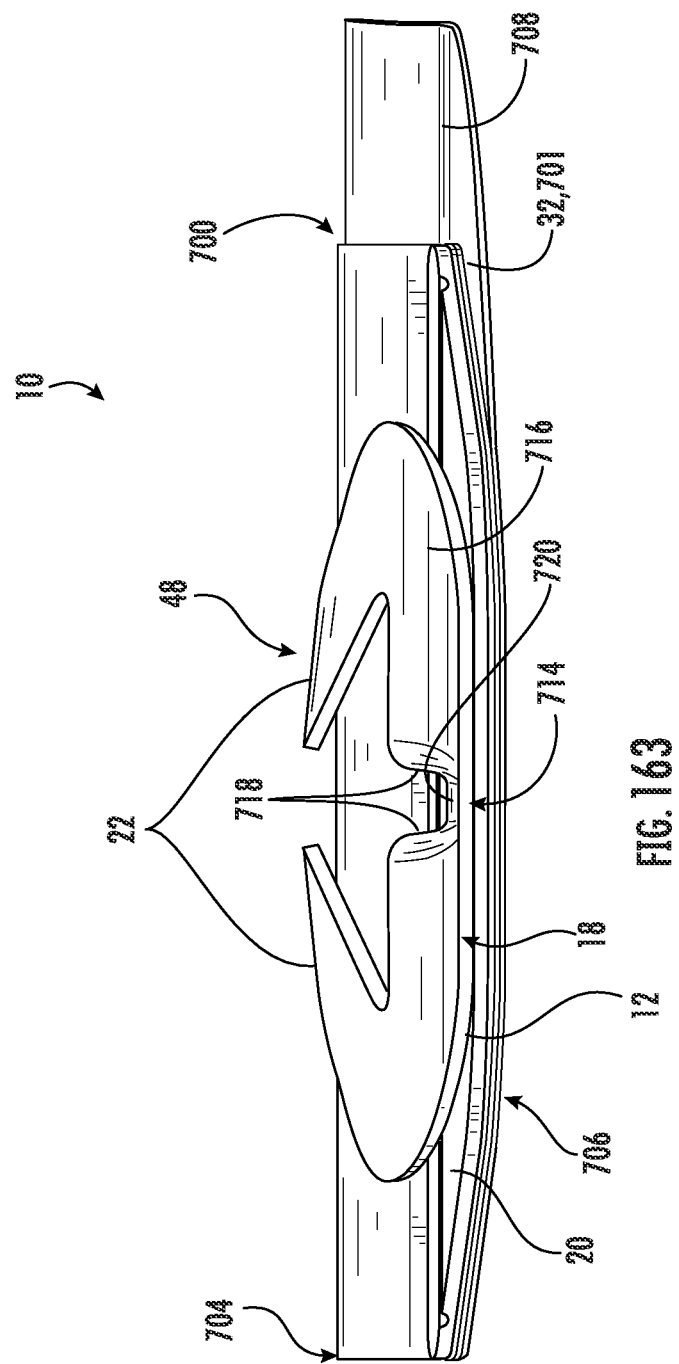

FIG. 163 is a right view of the configuration of FIG. 160.

Figure 164:
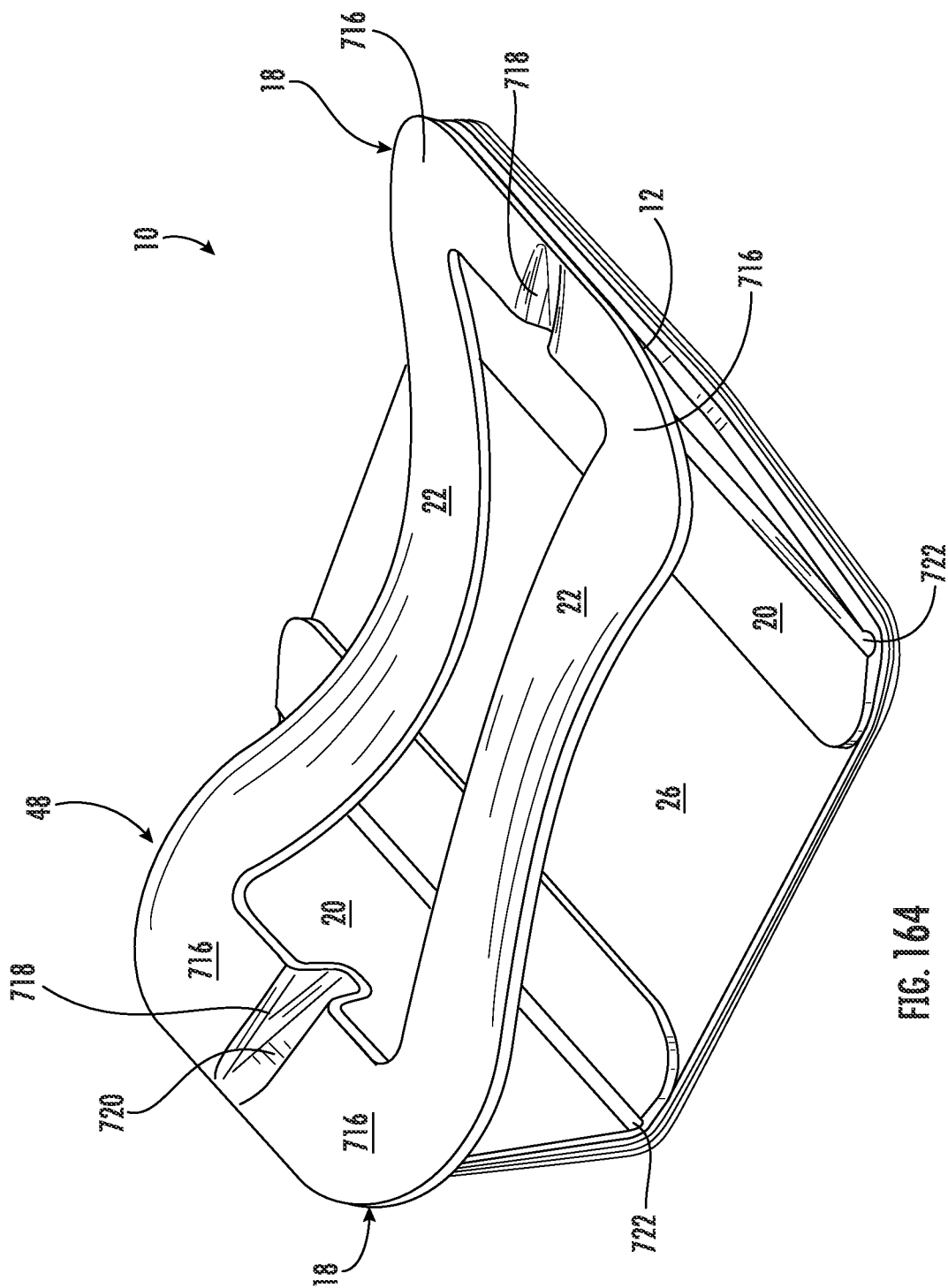

FIG. 164 is a top perspective view of the tissue bridge of FIG. 160 in an extended configuration.

Figure 165:
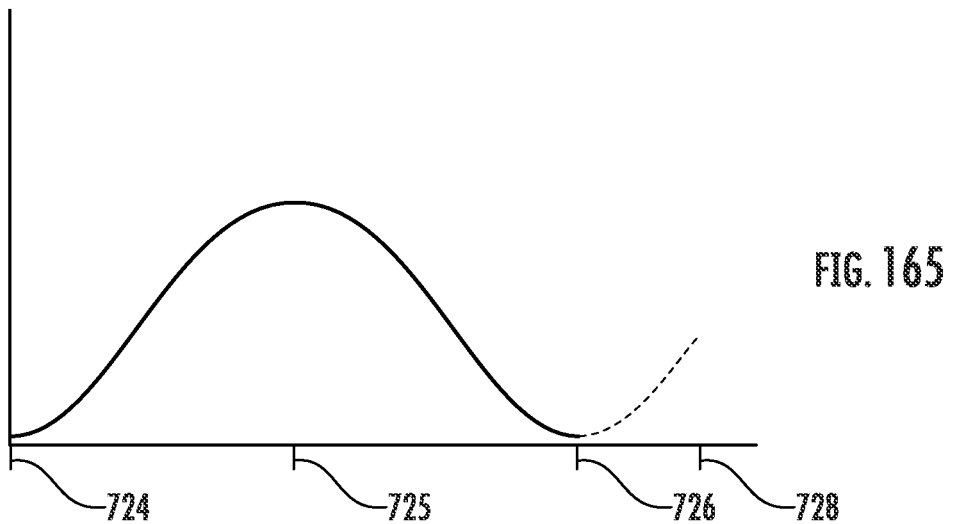
Figure 166:
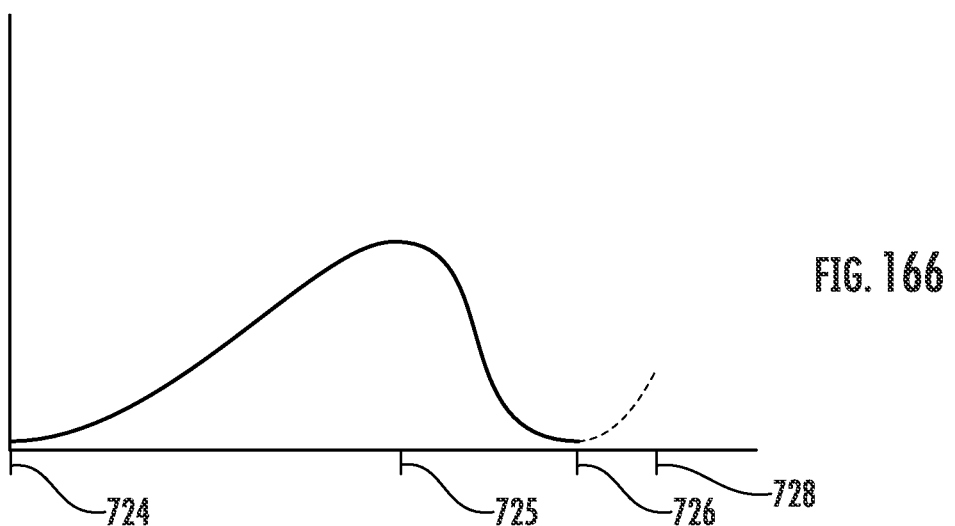
Figure 167:
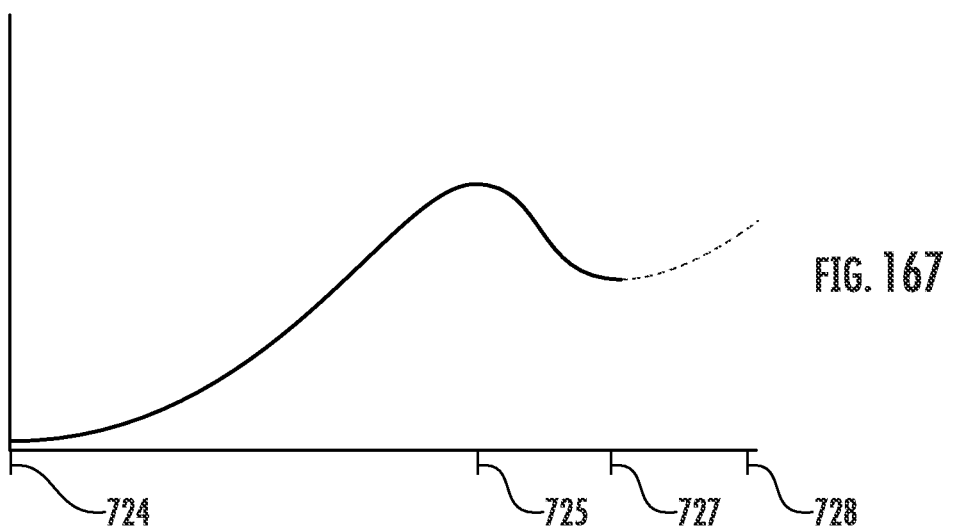

FIGS. 165-167 are graphs that respectively identify characteristics of examples of symmetrically bistable and asymmetrically bistable versions of the tissue bridge of FIG. 160.

Figure 168:
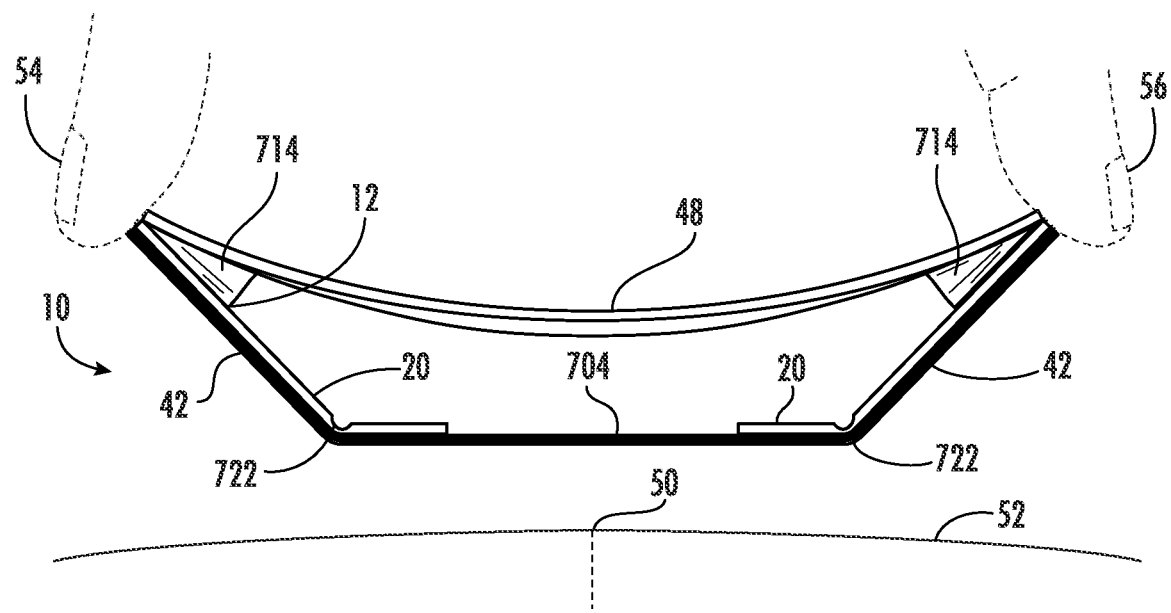
Figure 169:
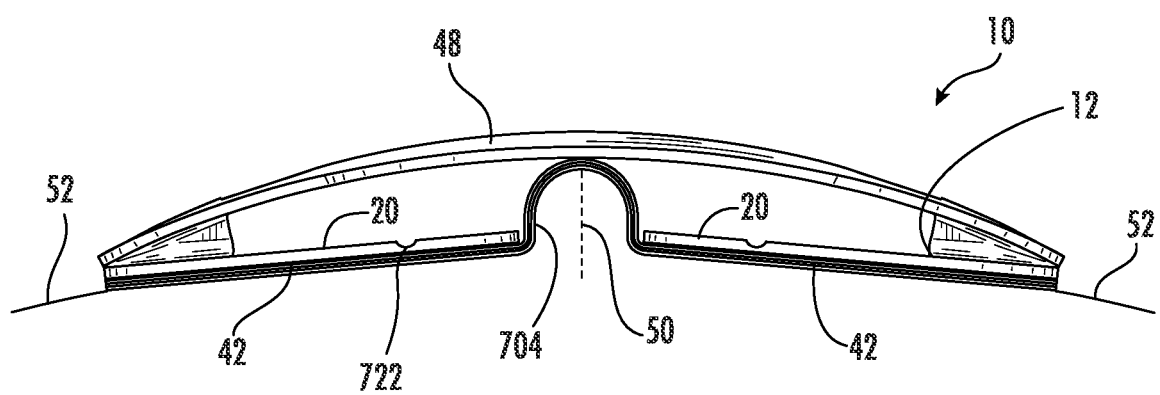

FIGS. 168 and 169 are front views that schematically depict an example of a portion of a sequence of steps of a method of applying the tissue bridge of FIG. 160 to wounded tissue (e.g., skin) after removal of an outer release liner.

Figure 170:
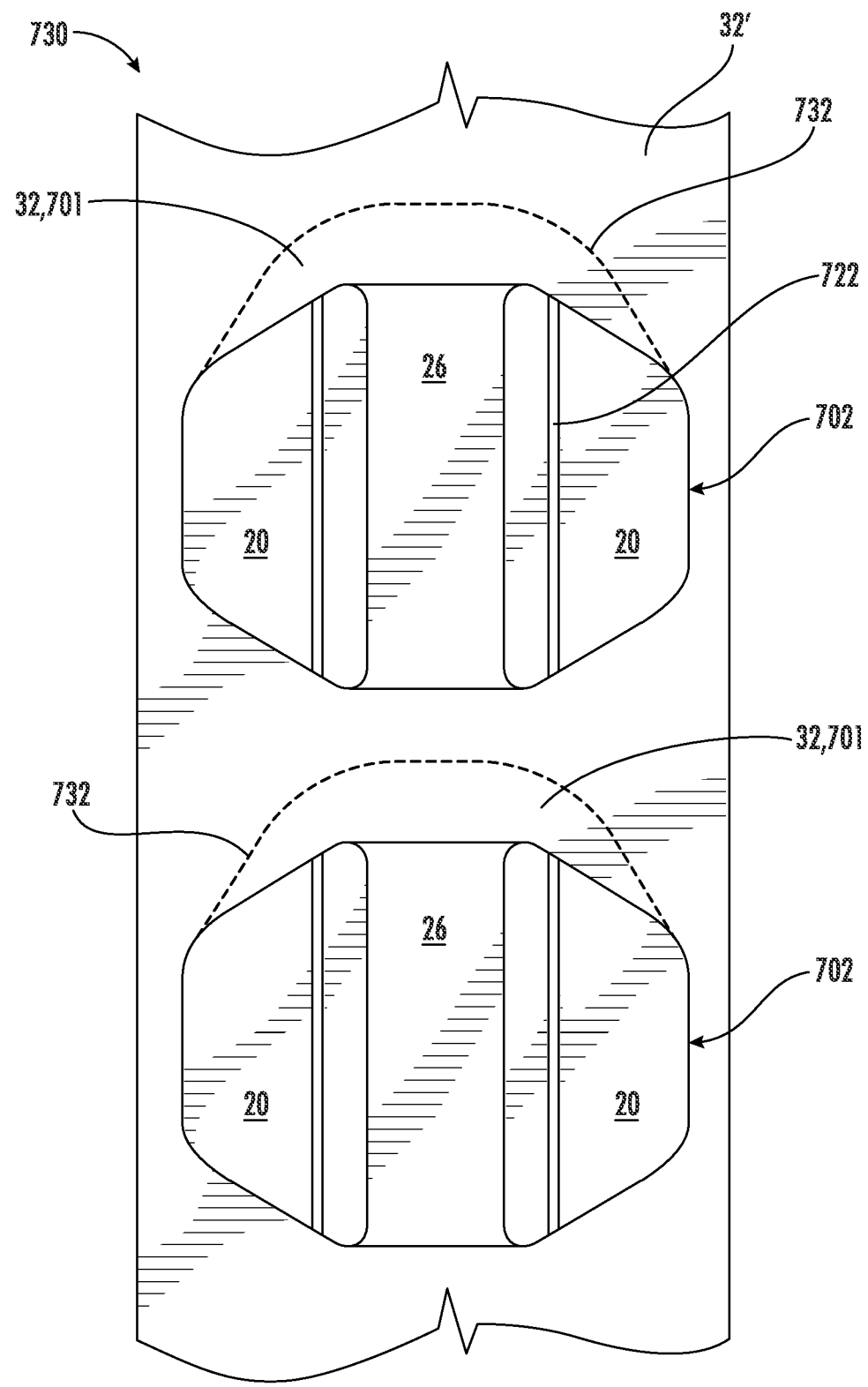
Figure 173:
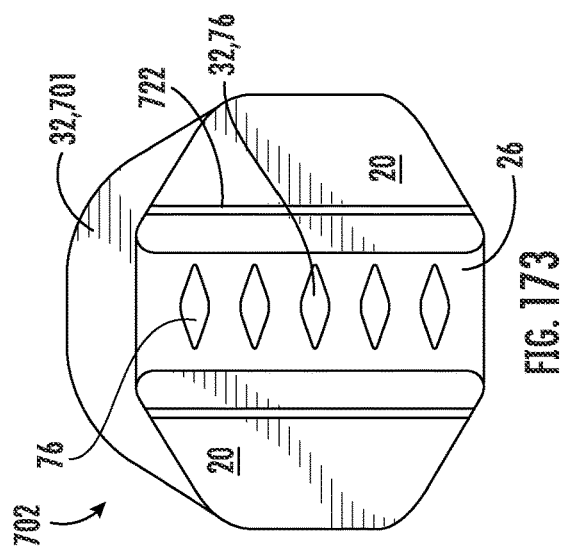

FIG. 170 is a top view of a portion of a flat multilayer precursor web including two flat subassemblies of tissue bridges of the type depicted in FIG. 160, in accordance with an embodiment of this disclosure.

FIGS. 171 through 177 each depict an isolated top plan view of a flat tissue bridge subassembly similar to the subassembly of the type depicted in FIG. 160, and similar to the subassemblies of FIG. 170, except for including differently configured disruptions, in accordance with other embodiments of this disclosure.

Figure 177:
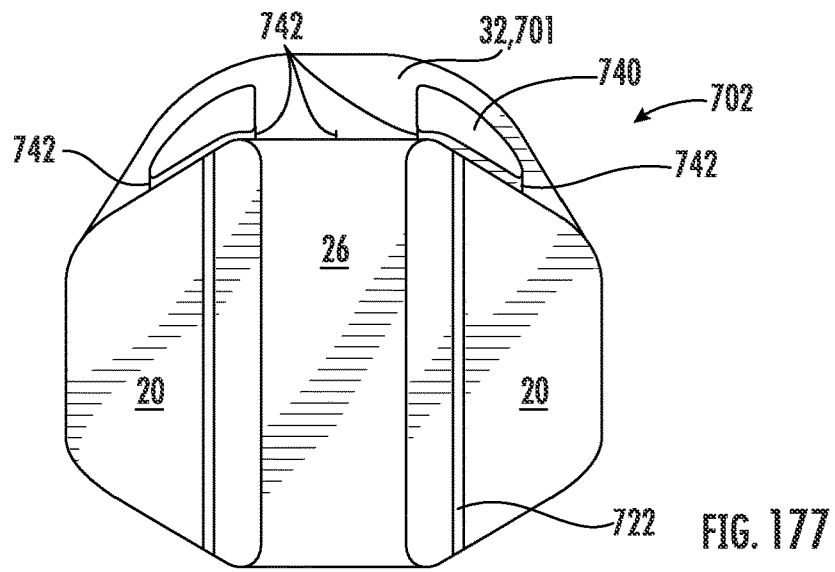
Figure 178:
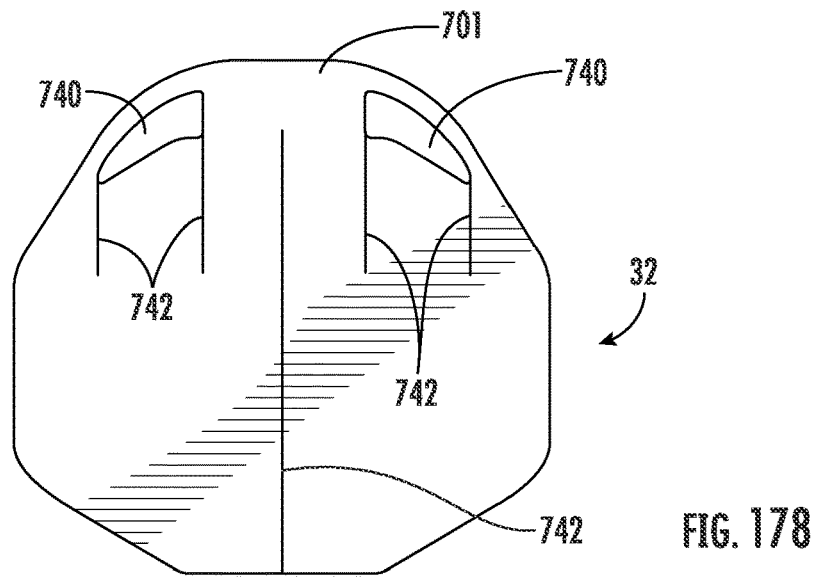

FIG. 178 is an isolated top plan view of a flat release liner of the subassembly of FIG. 177.

Figure 179:
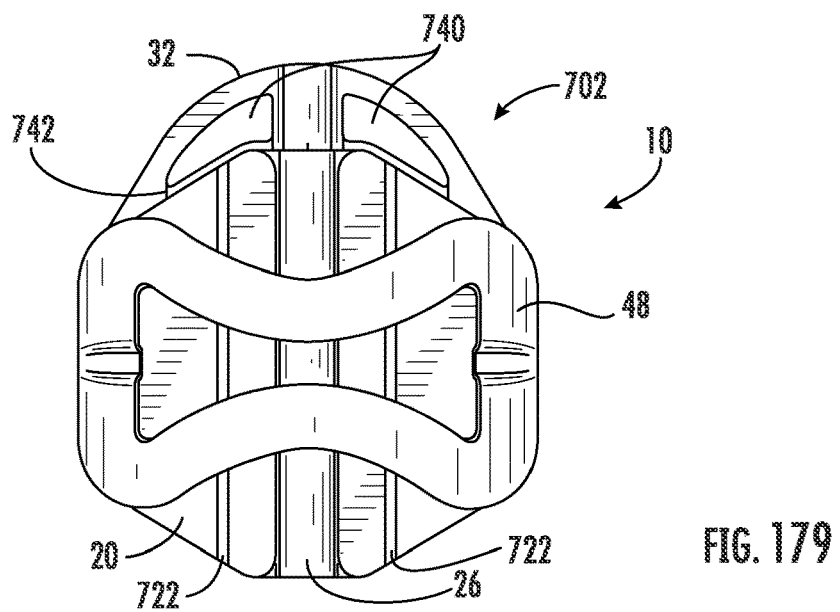

FIG. 179 is a top view of a tissue bridge including the subassembly of FIG. 177, wherein the tissue bridge is in its retracted stable equilibrium configuration, in accordance with an embodiment of this disclosure.

DETAILED DESCRIPTION

Examples of embodiments are disclosed in the following. The present invention may, however, be embodied in many different forms and should not be construed as limited to the embodiments set forth herein. For example, features disclosed as part of one embodiment can be used in the context of another embodiment to yield a further embodiment. As another example of the breadth of this disclosure, it is within the scope of this disclosure for one or more of the terms "substantially," "about," "approximately," and/or the like, to qualify each of the adjectives and adverbs of the Detailed Description section of disclosure, as discussed in greater detail below.

Figure 1:
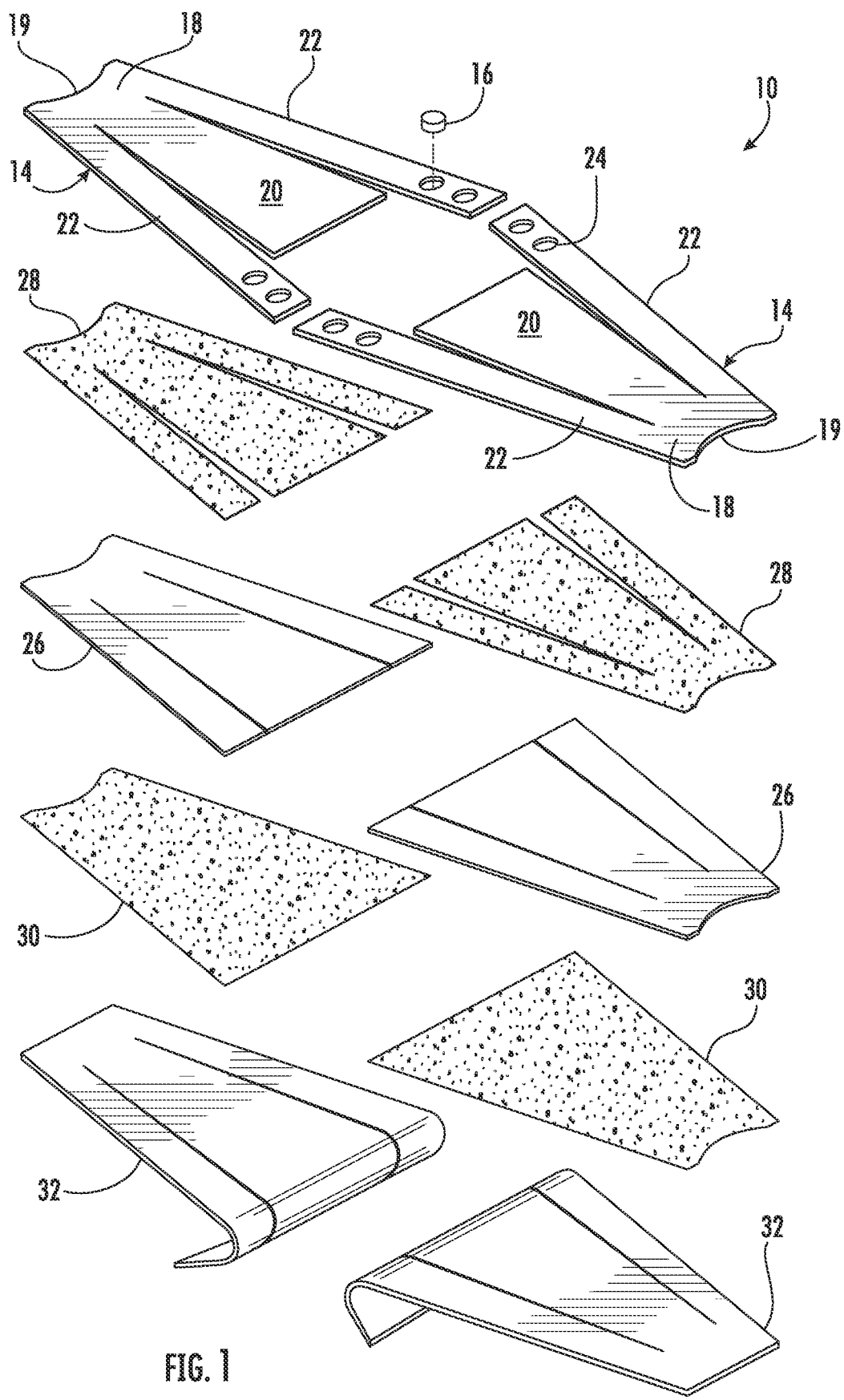
FIG. 1 is an exploded, top perspective view of a multistable medical device (e.g., force modulating tissue bridge) in accordance with a first embodiment of this disclosure.
Figure 3:
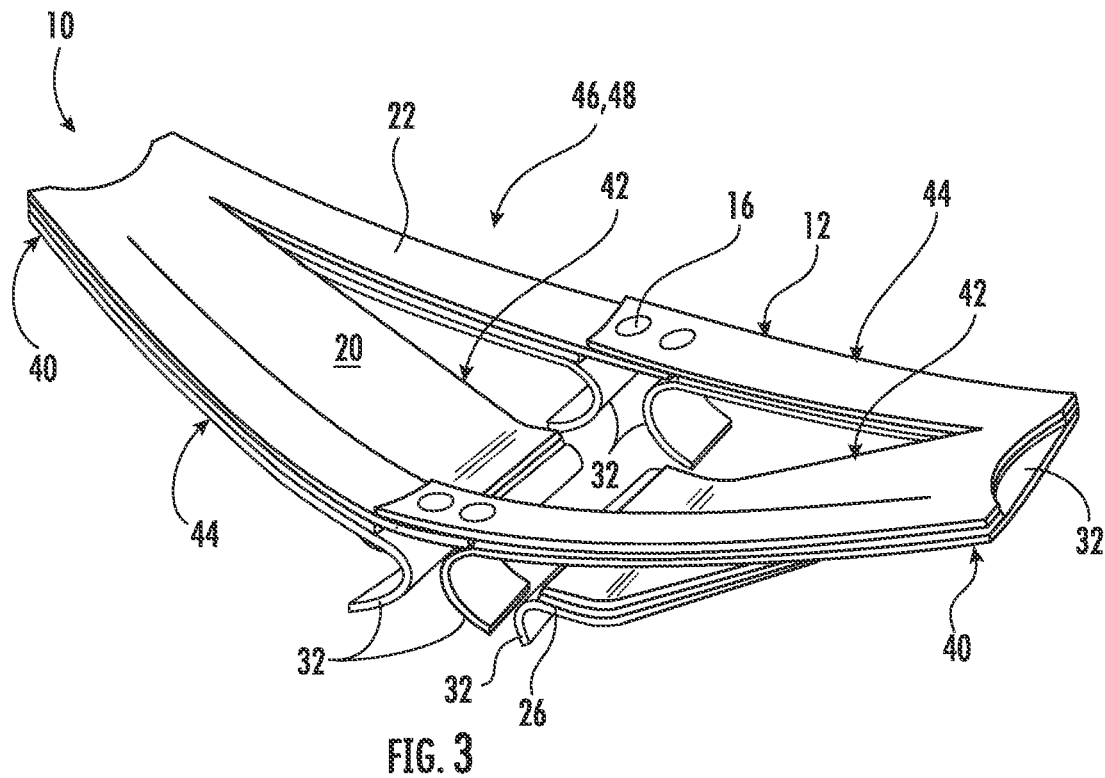
FIG. 3 is a top perspective view of the first embodiment tissue bridge in its extended stable equilibrium configuration.
Figure 4:
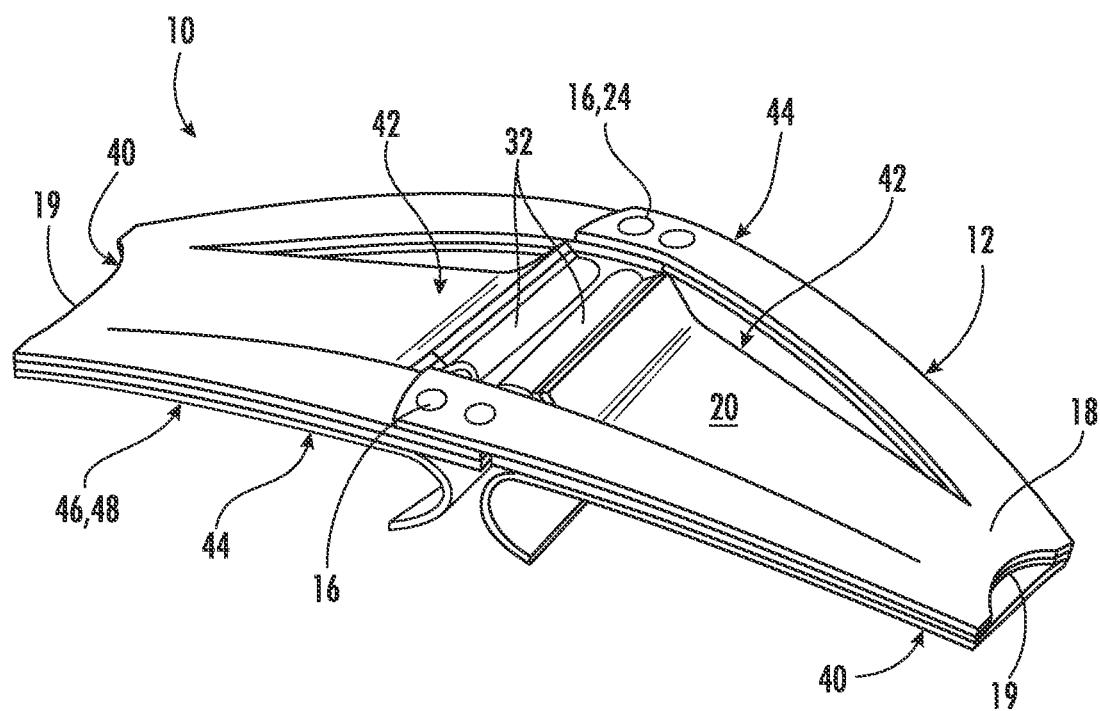
FIG. 4 is a schematic, top perspective view of the first embodiment tissue bridge in its retracted stable equilibrium configuration.

FIG. 1 is an exploded view of a flexible, multiconfigurable medical device 10 that is multistable (e.g., bistable), in accordance with a first embodiment of this disclosure. The medical device 10 may optionally be referred to as a force modulating tissue bridge, or simply tissue bridge. FIGS. 3 and 4 depict the assembled first embodiment tissue bridge 10 in its extended and retracted stable equilibrium configurations, respectively. In the following, first an example of a method of using the tissue bridge 10 is very briefly described, and thereafter the tissue bridge and other aspects of this disclosure are described in greater detail.

The tissue bridge 10 can be mounted to biological tissue such as, but not limited to, a surface of a patient's skin, for example the outer surface of the patient's epidermis. The tissue bridge 10 is typically mounted so that a central section of the tissue bridge extends across and at least partially covers a wound and/or scar. In the first embodiment, the tissue bridge 10 is in its extended stable equilibrium configuration (FIGS. 3, 9 and 10) at the beginning of being mounted on the patient. In an example, after being at least partially mounted, the tissue bridge 10 can automatically, biasedly reconfigure to, or proximate to, its retracted stable equilibrium configuration (FIGS. 4 and 13) in response to the tissue bridge being farther forced toward the tissue. In the first embodiment, the reconfiguring comprises elastic strain-induced bending. The reconfiguring between the extended and retracted stable equilibrium configurations seeks to, for example, reduce tension in the tissue, help close the wound, help inhibit wound reopening, and/or inhibit scar disfiguring (e.g., widening).

Referring to FIG. 1, the first embodiment tissue bridge 10 includes a flexible, multistable (e.g., symmetrically bistable or asymmetrically bistable) body 12 (FIG. 3) formed from two blanks 14 fastened together by mechanical fasteners 16 (e.g., pegs, rivets, split-pin fasteners, brad fasteners, snap fasteners) and/or other suitable fastening mechanisms, as will be discussed in greater detail below. Each blank 14 can include an end portion 18, at least one strut portion 20, and one or more links or side arm portions 22 extending from the end portion. In the first embodiment, the strut portion 20 includes a proximal end connected to the end portion 18, and a distal end opposite from the proximal end.

Figure 2:
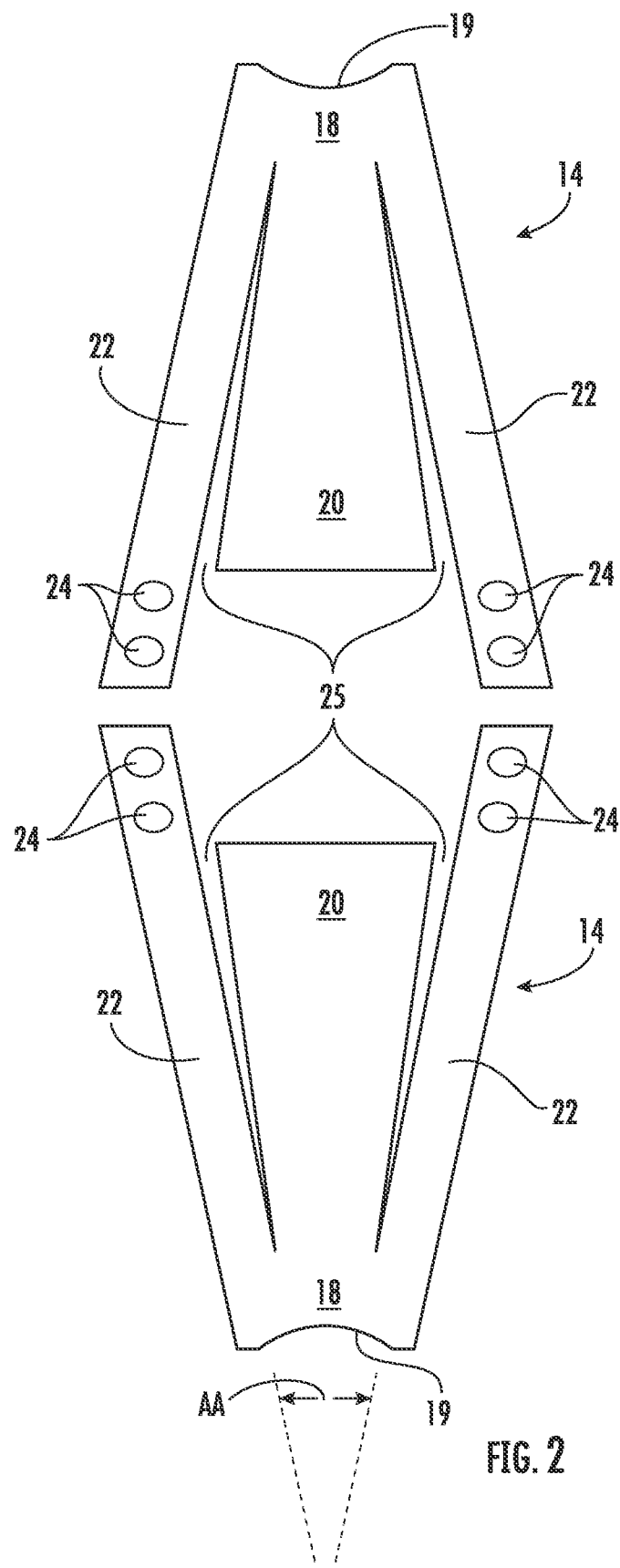
FIG. 2 is an exploded, isolated top view of blanks of the first embodiment tissue bridge.

Referring to FIG. 2, for each of the first embodiment blanks 14, its arm portions 22 extend away from the end portion 18 in a divergent manner to define an arm angle of divergence "AA" between the arm portions, as will be discussed in greater detail below. The body 12 can include or be formed from less or more than two blanks 14 of a variety of different configurations (e.g., a variety of arm angles of divergence or convergence AA are within the scope of this disclosure), as will be discussed in greater detail below.

Regarding connecting the blanks 14 to one another (e.g. connection zones of the blanks 14), one or more holes 24 can extend through distal end portions of the blank arm portions 22 for respectively receiving the peg fasteners 16 (FIGS. 1, 3 and 4) and/or other suitable fastening mechanisms can be utilized to respectively connect the arm portions to one another. In FIG. 1, a representative one of the four fasteners 16 is depicted, although there may be more or less of such fasteners and/or other fastening mechanisms.

Referring to FIG. 2, the outer end portions 18 can each include an inwardly recessed edge 19 configured for receiving the outer end portion of a finger or thumb of a user during installation, as will be discussed in greater detail below. The blanks 14 can be provided, for example, by die cutting them from appropriate webs or larger sheets of material, such as polymeric films or laminates (e.g., polyethylene, polyethylene terephthalate, or any other suitable materials), metallic sheets, alloys, and/or other suitable materials. The one or more strut portions 20 and one or more side arm portions 22 can be partially defined by cuts 25 (e.g., slits, holes, cutouts, and/or respective gaps) between adjacent portions of the blanks 14.

Referring to FIG. 1, the tissue bridge 10 can include one or more layers mounted to the blanks 14 or the body 12 (e.g., the body formed from the blanks or in any other suitable manner). In the first embodiment, the tissue bridge 10 includes several layers of material connected to the underside of the body 12. The layers can include, for example, carrier sheets 26, adhesive layers 28, 30, and outer release sheets or liners 32 (e.g., removable backings).

In the first embodiment, patient-contact structures comprise, consist essentially of, or consist of the carrier sheets 26 and the adhesive 30 being cooperatively configured so that the patient-contact structures can be used to attach the tissue bridge 10 to tissue (e.g., skin tissue) after removal of the one or more release liners 32. Accordingly and for ease of understanding, the carrier sheets 26 may be referred to as patient-contact carriers, and the adhesive 30 may be referred to as patient-contact adhesive 30.

More specifically regarding layers of the tissue bridge 10, the inner adhesive 28 can be between and fixedly connect the patient-contact carriers 26 to the body 12, and the patient-contact adhesive 30 can be on the outer sides of the patient-contact carriers 26 for attaching the tissue bridge 10 to tissue (e.g., a patient's skin), as will be discussed in greater detail below. One or more of the adhesive layers 28, 30 or sheets 26, 32 can include cuts (e.g., slits, holes, cutouts, and/or respective gaps) that are at least similar to and at least partially superposed with at least respective portions of the cuts 25 in the body 12.

One or more of the adhesive layers 28, 30 or sheets 26, 32, or portions thereof, can be omitted. For example, the patient-contact carriers 26 and the inner adhesive 28 can be omitted, so that the patient-contact adhesive 30 is mounted directly on (e.g., is in opposing face-to-face contact with) the body 12. As another example, at least some of, or all of, the portions of the patient-contact adhesive 30 and release liners 32 associated with the side arm portions 22 may be omitted. As a further example, the connection to tissue provided by the patient-contact adhesive 30 can be supplemented with or replaced by one or more suitable non-adhesive attachment mechanisms (e.g., pins, needles, sutures, staples, and/or the like).

At least partially reiterating from above, the drawings may not be drawn to scale. For example, in at least some of the drawings depicting exploded views (e.g., FIG. 1), the size of one or more of the adhesive layers 28, 30 and sheets 26, 32, or portions thereof, may be exaggerated as compared to the body 12.

The inner and outer sheets 26, 32 can be provided, for example, by die cutting them from appropriate webs or larger sheets of material. For example, the inner or patient-contact carriers 26 can be made of suitable fabric materials, cast materials, cast microporous polymeric sheet, polymeric films (e.g., polyurethane), padding, and/or other suitable materials (e.g., of the type from which skin-contact layers of bandages or other wound dressings are formed). The release liner 32 can be, for example, a paper or plastic-based film sheet coated with a release agent that is engaged against the patient-contact adhesive 30 so that the tissue bridge 10 is releasably mounted on the release liner. The inner adhesive 28 can comprise adhesive materials that are compatible with the materials being connected thereby. The patient-contact adhesive 30 can be, for example, a pressure-sensitive adhesive material of the type that is typically used as an adhesive backing for wearable medical devices, bandages, or other wound dressings. The patient-contact adhesive 30 can have a lower adhesive strength than the inner adhesive 28, such as when the tissue bridge 10 is to be removably mounted to tissue (e.g., a patient's skin). In other embodiments, for example wherein at least the multistable body 12 can function as an applicator of a wound covering, the inner adhesive 28 can have a lower adhesive strength as compared to one or more other adhesives (e.g., the patient-contact adhesive 30), as will be discussed in greater detail below.

FIGS. 3 and 4 respectively depict the assembled first embodiment tissue bridge 10 in its stable equilibrium configurations. These stable equilibrium configurations may be symmetrical or asymmetrical, as further discussed below. The first embodiment tissue bridge 10 includes lateral or end portions 40, one or more struts 42 (e.g., strut assemblies), and one or more arms 44. In the first embodiment, each strut 42 includes a proximal end connected to the respective tissue bridge end portion 40, and a distal end opposite from the proximal end.

The first embodiment tissue bridge's end portions 40, struts 42, and arms 44 respectively include the end portions 18, strut portions 20, and arm portions 22 of the blanks 14 and body 12, as well as corresponding portions of any of the sheets 26, 32 and adhesive layers 28, 30 that may be included in the tissue bridge. Whereas the tissue bridges 10 are sometimes described in the Detailed Description section as including two struts 42, it is within the scope of this disclosure for each of the tissue bridges to include any suitable number of struts, including, for example, one strut or more than two struts.

In FIGS. 3 and 4, the inner or distal end portions of the one or more struts 42 are angled or inclined relative to the central and outer or proximal end portions of the struts. The bends that define the inclination or angle of the distal end portions of the struts 42 can be provided, for example, by bending, thermoforming, stamping, and/or in any other suitable manner. Alternatively, the tissue bridges 10 can be formed, or at least partially formed, by injection molding, 3D printing, and/or in any other suitable manner. The bends that define the inclination or angle of the distal end portions of the struts 42 can be formed in response to tissue forces associated with the tissue bridge 10 being mounted on tissue 52 (see, e.g., FIG. 10), for example when the bend area includes at least one feature for helping to facilitate the bending. For example, a feature for helping to facilitate such bending of the distal end portion of a strut 42 can include at least one line of disruption (e.g., weakened areas, as formed by perforations or other suitable holes, kiss-cuts, score lines, areas of reduced thickness, and/or the like) along which bending may occur. Other features for helping to facilitate such bending of the distal end portion of a strut 42 may include at least one hinge, for example a living hinge, a hinge defined by malleable material, a hinge including a hinge pin and associated bearing structure(s), and/or other suitable features.

The assembling of the first embodiment body 12 and tissue bridge 10 includes causing relative movement between the inner or distal end portions of the arm portions 22 so that the arm inner end portions (e.g., the holes 24) respectively become superposed with one another in a plan view, and then fixedly fastening the superposed arm portions with one another. The superposed inner end portions of the arm portions 22 can be fixedly connected to one another using the peg fasteners 16, holes 24, adhesive material, heat sealing, welding, and/or any other suitable fastening mechanisms.

As an example of providing the multistability characteristics of the multistable body 12 and the tissue bridge 10, the blanks 14 are constructed of suitable flexible material, and the superpositioning and associated fastening of the inner end portions of the arm portions 22 decrease the angle of divergence AA (FIG. 2) between the arm portions 22 so that the tissue bridge has the stable equilibrium configurations depicted in FIGS. 3 and 4. Additionally, the first embodiment multistable body 12 and tissue bridge 10 have numerous unstable configurations between the stable equilibrium configurations depicted in FIGS. 3 and 4, as will be discussed in greater detail below.

Whereas in the first embodiment the connecting of the arm portions 22 and the providing of the multistability characteristics includes the superpositioning and connecting of respective portions of the arms 22, the connecting and providing of the multistability can be achieved in other suitable ways. For example, the connecting and providing of the multistability characteristics can include respectively joining the arm portions end-to-end (e.g., end-edge to end-edge) by way of suitable seams (e.g., welding (e.g., laser welding)), adhering (e.g., with adhesive and/or adhesive tape), injection molding (e.g., insert molding), or other suitable seaming together) and/or other suitable attachment mechanisms.

The first embodiment multistable body 12 functions as a substrate that carries the other components of the tissue bridge 10, and the tissue bridge is multistable (e.g., symmetrically bistable or asymmetrically bistable) by virtue of the multistability of the body 12. Alternatively, it is believed that any of the sheets 26, adhesive layers 28, 30, and/or other components that may be included in the tissue bridge 10 may be configured to contribute to or provide the multistable characteristics of the tissue bridge 10. The multistable body 12 and tissue bridge 10 of the first embodiment more specifically are bistable, so that they have the two stable equilibrium configurations depicted in FIGS. 3 and 4. As will be discussed in greater detail below, the multiple or bistable configurates may be altered in response to tissue forces associated with the tissue bridge 10 being mounted on tissue 52 (see, e.g., FIGS. 9-13).

FIGS. 3 and 4 respectively depict the bistable tissue bridge 10 in its extended stable equilibrium configuration (e.g., a first stable equilibrium configuration) and its retracted stable equilibrium configuration (e.g., a second stable equilibrium configuration). In the extended stable equilibrium configuration (FIG. 3), the inner or distal end portions of the one or more struts 42 extend (e.g., are inclined) outwardly (e.g., downwardly) away from the arms 44. In contrast, in the retracted configuration (FIG. 4), the one or more struts 42 are relatively retracted with respect to the arms 44, so that at least a portion of (e.g., the distal end portion of) at least one strut is closer to the arms. As another example of the retracted configuration, when the tissue bridge 10 includes a pair of struts that are opposite from one another, the struts 42 of the pair can be relatively retracted with respect to the arms 44 so that at least portions of (e.g., the distal end portions of) the struts are closer to one another.

In the first embodiment, the strut portions 20 of the body 12 are connected to one another by way of at least one flexible, multistable spanning structure 46 comprising, consisting essentially of, or consisting of the end and arm portions 18, 22 of the body 12. Similarly for the first embodiment tissue bridge 10, the struts 42 are connected to one another by way of at least one multistable spanning structure 48 comprising, consisting essentially of, or consisting of the end and arm portions 40, 44 of the tissue bridge 10. The spanning structures 46, 48 can each be described as including a medial or middle portion extending between lateral or end portions of the spanning structure.

In the first embodiment, a portion (e.g., core portion) of the tissue bridge 10 is multistable (e.g., essentially bistable), and other portions of the tissue bridge are connected to the core portion for moving with the core portion. In the first embodiment, the tissue bridge's multistable spanning structure 48, or more specifically the body's multistable spanning structure 46, is the core portion of the tissue bridge 10 that is multistable (e.g., essentially bistable). That is, the multistable spanning structures 46, 48 can be configured to provide the multistable (e.g., symmetrically bistable or asymmetrically bistable) behavior of the body 12 and tissue bridge 10, respectively. For example and as depicted in FIG. 3, the first embodiment multistable spanning structure 48 is in its concave-up stable equilibrium configuration (e.g., when the tissue bridge 10 is in the extended stable equilibrium configuration). For example, at least the arms 44 can form a central inverted arch when the multistable spanning structure 48 is in its concave-up stable equilibrium configuration (e.g., a first stable equilibrium configuration). In contrast and as depicted in FIG. 4, the first embodiment multistable spanning structure 48 is in its concave-down stable equilibrium configuration (e.g., a second stable equilibrium configuration) when the tissue bridge 10 is in the retracted stable equilibrium configuration. For example, at least the arms 44 can form a central arch when in their concave-down stable equilibrium configuration.

Figure 5:
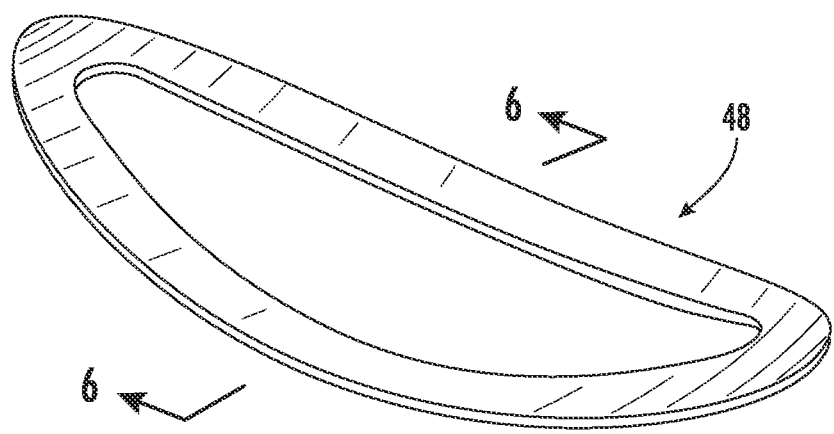
FIG. 5 is a schematic, isolated, top perspective view of a flexible, multistable spanning structure of the first embodiment tissue bridge, wherein the multistable spanning structure is in its concave-up stable equilibrium configuration.
Figure 6:
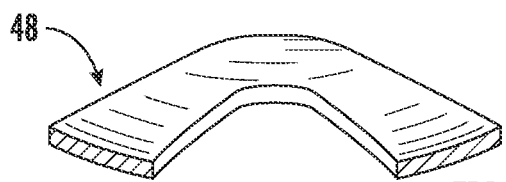
FIG. 6 is a cross-sectional view taken along line 6-6 of FIG. 5.
Figure 7:
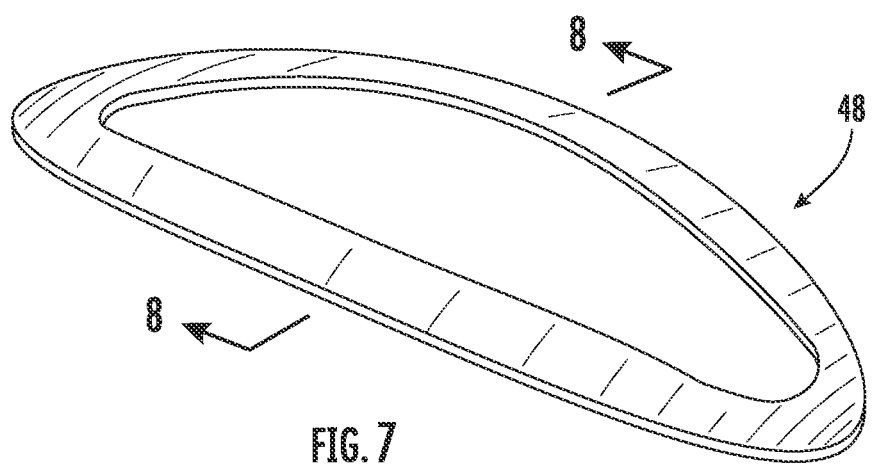
FIG. 7 is a schematic, isolated, top perspective view of the multistable spanning structure of the first embodiment tissue bridge, wherein the spanning structure is in its concave-down stable equilibrium configuration.
Figure 8:
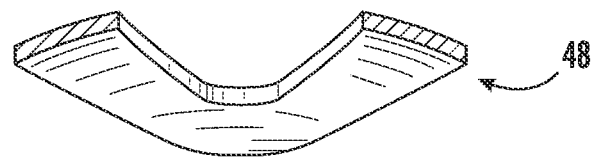
FIG. 8 is a cross-sectional view taken along line 8-8 of FIG. 7.

FIGS. 5 and 6 are isolated views that schematically depict the first embodiment multistable spanning structure 48 in the concave-up stable equilibrium configuration. As depicted in FIGS. 5 and 6, the concave-up stable equilibrium configuration defined by the multistable spanning structure 48 includes or defines both a length-wise arc and a width-wise arc (e.g., crosswise arcs and at least a portion of an inverted dome). As depicted in FIGS. 7 and 8, the concave-down stable equilibrium configuration defined by the multistable spanning structure 48 includes or defines both a length-wise arc and a width-wise arc (e.g., crosswise arcs and at least a portion of a dome). One or more of the subject curvatures can exist throughout the entire multistable spanning structure 48. Alternatively, it is believed that one or more of the subject curvatures may be present only in respective portions of the multistable spanning structure 48. Additionally, one or more of the subject curvatures can be modified (e.g., increased, decreased, and/or have a changed orientation) in order to alter the three-dimensional shape of the tissue bridge in its multistable (e.g. bistable) configurations.

As one example, the multistable spanning structure 48 can be symmetrically configured, for example so that the concave-up stable equilibrium configuration and concave-down stable equilibrium configuration are mirror images of one another. As another example, the multistable spanning structure 48 can be asymmetrically configured, for example so that the concave-up stable equilibrium configuration and concave-down stable equilibrium configuration are not mirror images of one another (e.g., in the concave-up and concave-down stable equilibrium configurations, corresponding portions of the spanning structure 48 can have different amounts of curvature from one another (e.g., can have radiuses of curvature that differ in magnitude from one another), or the like). As an example of the multistable spanning structure 48 being asymmetrically configured, one of the stable equilibrium configurations can be flatter than the other of the stable equilibrium configuration.

The multistable spanning structure 48 being symmetrically bistable, or the tissue bridge 10 being symmetrically bistable, can comprise it having a first stable equilibrium configuration in which it defines a first concavity having a radius of curvature (see, e.g., FIG. 5), and a second stable equilibrium configuration in which it defines a second concavity having a radius of curvature (see, e.g., FIG. 7), wherein the radius of curvature of the first concavity can be the same as, or about the same as, the radius of curvature of the second concavity. The multistable spanning structure 48 being asymmetrically bistable, or the tissue bridge 10 being asymmetrically bistable, can comprise it having a first stable equilibrium configuration in which it defines a first concavity having a radius of curvature (see, e.g., FIG. 5), and a second stable equilibrium configuration in which it defines a second concavity having a radius of curvature (see, e.g., FIG. 7), wherein the radius of curvature of the first concavity can differ from the radius of curvature of the second concavity.

In the first embodiment, the multistable spanning structure 48 has at least one unstable equilibrium configuration (e.g., a maximally unstable configuration) between its concave-up stable equilibrium configuration and concave-down stable equilibrium configuration. In this regard, the tissue bridge 10 is configured so that the multistable spanning structure's unstable equilibrium configuration, concave-up stable equilibrium configuration, and concave-down stable equilibrium configuration are respectively associated with the tissue bridge's unstable equilibrium configuration, extended stable equilibrium configuration, and retracted stable equilibrium configuration, as discussed in greater detail below.

Those of ordinary skill in the art will understand that directional references such as "up" and "down" are being used in the Detailed Description section of this disclosure for ease of understanding and may be described differently with respect to other directional frames of reference, for example as being directions that are opposite from one another. For example and in the first embodiment, the multistable spanning structure 48 can be described as having opposite first and second sides, wherein the first side is concave (e.g., substantially concave and/or otherwise suitably configured (e.g., curved)) in a first stable equilibrium configuration and convex (e.g., substantially convex and/or otherwise suitably configured (e.g., curved)) in a second stable equilibrium configuration, and wherein the second side is concave (e.g., substantially concave and/or otherwise suitably configured (e.g., curved)) in the second stable equilibrium configuration and convex (e.g., substantially convex and/or otherwise suitably configured (e.g., curved)) in the first stable equilibrium configuration.

Figure 9:
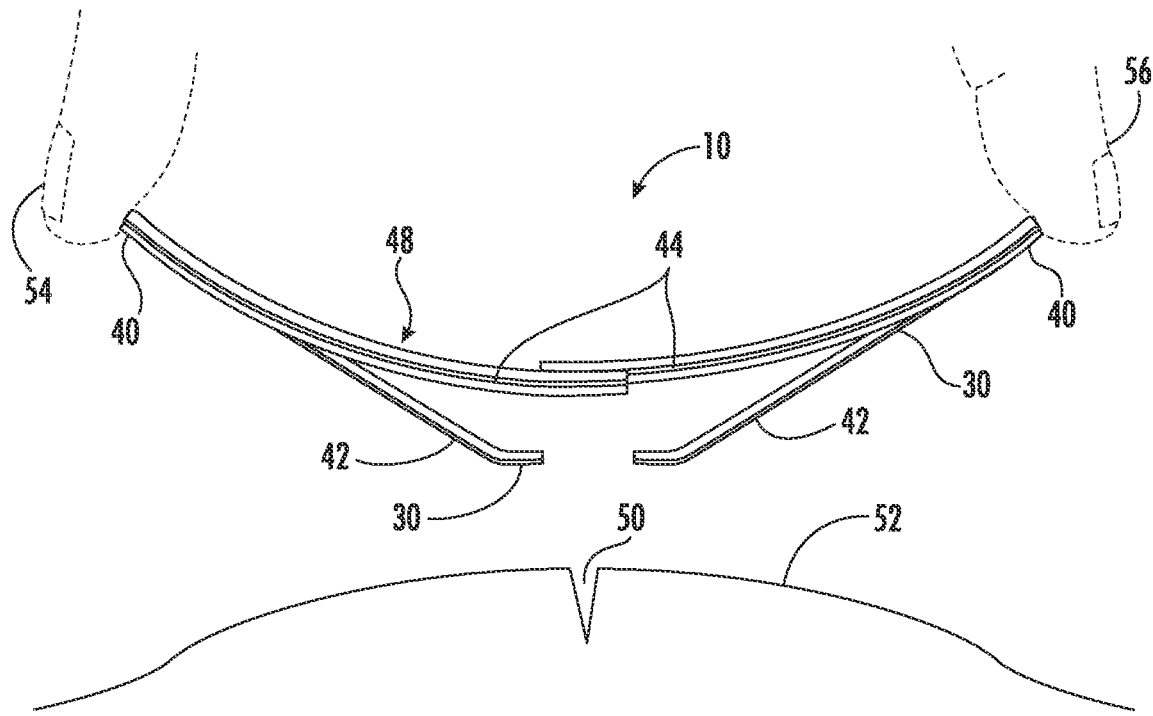
FIGS. 9 through 13 are front views that schematically depict an example of a sequence of steps of a method of applying the first embodiment tissue bridge to wounded tissue (e.g., skin) after removal of outer release liners.

In accordance with an example of a method of fabricating the first embodiment tissue bridges 10, they can be fully assembled, sterilized, and then be enclosed in packages that are provided to end users that open the packages and mount the tissue bridges on tissue 52 (see, e.g., FIG. 9). Each package can include one or more of the tissue bridges 10. For example, in a relatively compact package containing a plurality of the tissue bridges 10, the tissue bridges may be nested together in their retracted stable equilibrium configurations, in which case a user would typically reconfigure the tissue bridges into their extended stable equilibrium configurations before mounting them on tissue 52. Alternatively, the tissue bridges 10 can be packaged in their extended stable equilibrium configurations and/or partially assembled configurations, as will be discussed in greater detail below. The packaged tissue bridges 10 can be part of a kit, military pack, or the like, including one or more other items such as, for example, bandages, medical dressings, medical irrigation devices, wipes and/or liquids for use in sterilizing, gloves, and/or other suitable items.

FIGS. 9-13 schematically depict an example of a sequence of steps of a method of applying the first embodiment tissue bridge 10 to a scar or wound 50 after the release liners 32 have been removed. The tissue bridge 10 is in the extended stable equilibrium configuration in FIGS. 9 and 10; in unstable configurations in FIGS. 11 and 12; in the at least one unstable equilibrium configuration (e.g., a maximally unstable configuration) in FIG. 12; and in, or proximate, the retracted stable equilibrium configuration in FIG. 13.

Referring to FIG. 9, if the tissue bridge 10 is not yet in, or proximate, its extended stable equilibrium configuration, the tissue bridge can be manually reconfigured, for example, from its retracted stable equilibrium configuration to its extended stable equilibrium configuration. For example, the tissue bridge 10 can be manually reconfigured from its retracted stable equilibrium configuration to its extended stable equilibrium configuration by manually holding the tissue bridge 10 between a user's finger 54 (FIG. 9) and thumb 56 (FIG. 9), so that the finger and thumb are engaged against opposite ends of the tissue bridge and pulling upward, while another finger pushes downwardly on a medial portion of the spanning structure 48. As another example, the tissue bridge 10 can be manually reconfigured from its retracted stable equilibrium configuration to its extended stable equilibrium configuration by the user holding one end of the tissue bridge with one hand and holding the other end of the tissue bridge with their other hand, and then causing relative rotation between their hands in a manner that causes the tissue bridge to be reconfigured from its retracted stable equilibrium configuration to its extended stable equilibrium configuration. In either case, such reconfiguring can include manually bending the tissue bridge 10 from its retracted stable equilibrium configuration toward and then slightly past its maximally unstable equilibrium configuration, and then allowing the tissue bridge to automatically reconfigure (e.g., bend itself in response to its elastic potential energy) from adjacent its maximally unstable equilibrium configuration to its retracted stable equilibrium configuration.

Figure 10:
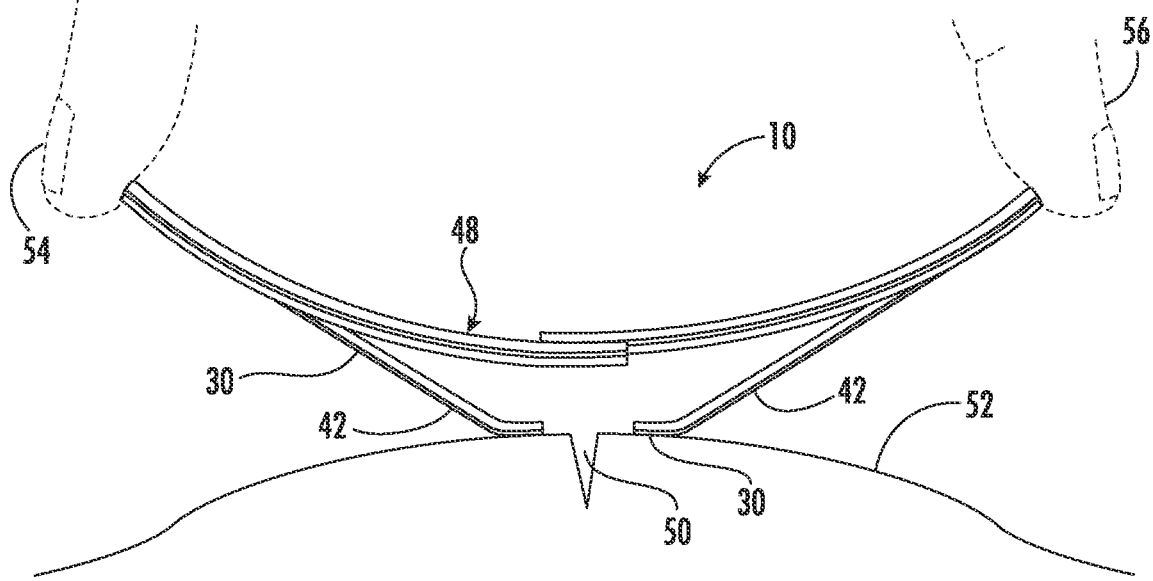

As depicted in FIG. 9, the tissue bridge 10 in, or proximate, its extended stable equilibrium configuration can be manually held between a user's finger 54 and thumb 56, or in any other suitable manner, so that the length of the tissue bridge extends crosswise to, or more specifically substantially perpendicular to, the length of a scar, cut, or wound 50 in a patient's tissue 52. Referring to FIG. 10, the patient-contact adhesive 30 (FIG. 1) on the lower or outer surfaces of the angled (e.g., inclined) inner or distal end portions of the one or more struts 42 (e.g., strut assemblies) can be engaged against the patient's tissue or skin 52 on either side of the scar, cut, or wound 50. The portions of the patient-contact adhesive 30 on the body's struts 20 can be referred to as engagement zones of the tissue bridge's struts 42. In addition to or as an alternative to the patient-contact adhesive 30 on the body's struts 20 being or defining the engagement zones, the engagement zones can comprise pins, needles, sutures, staples, barbs, prongs, and/or other suitable fastening mechanisms or the like.

Figure 11:
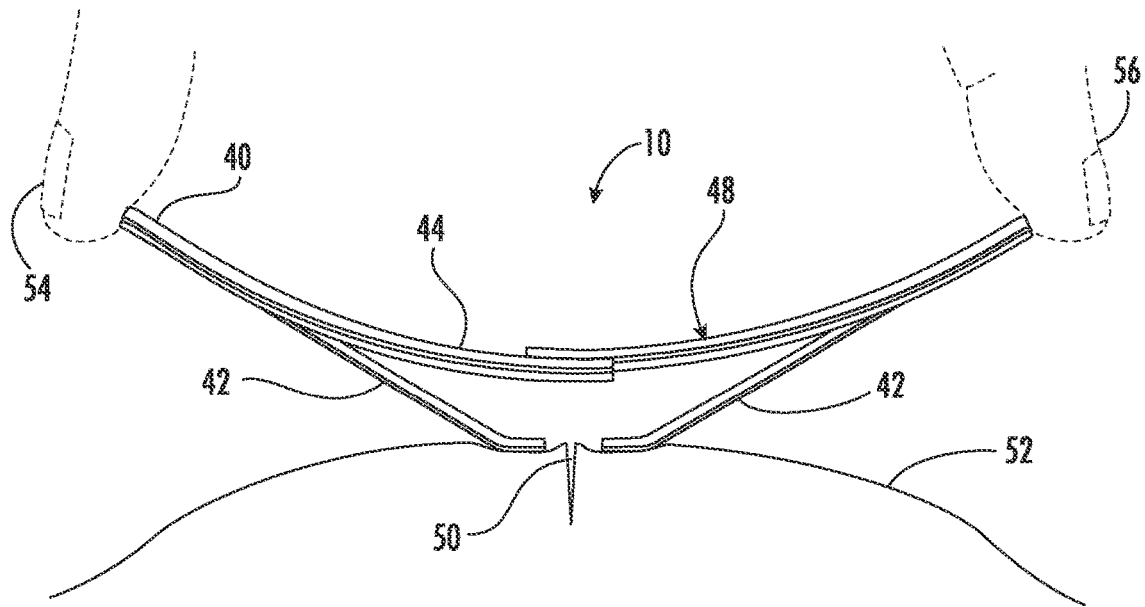
Figure 12:
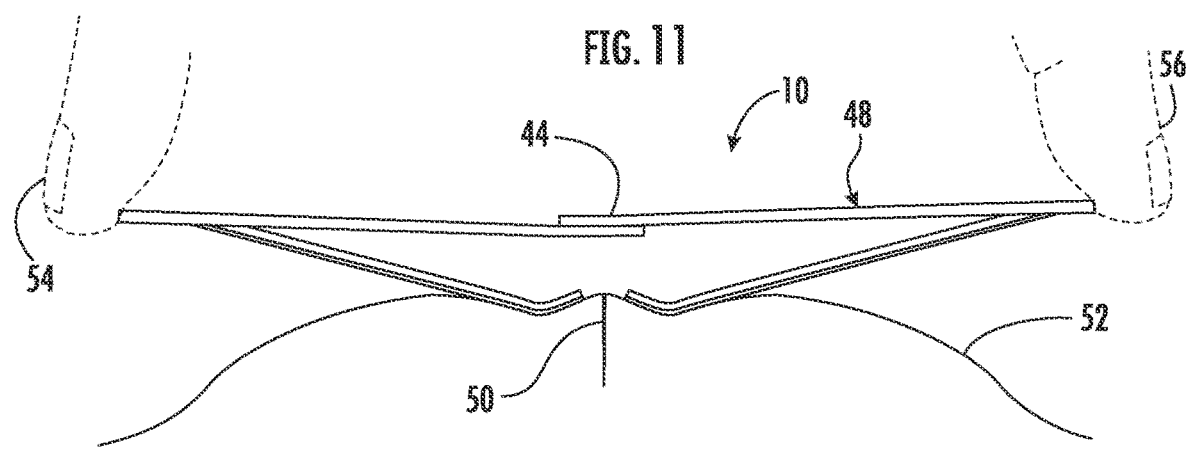

Referring to FIGS. 11 and 12, the tissue bridge 10 can continue to be manually forced or pushed closer to the tissue 52 so that the inner portions of the one or more struts 42 become further adhered to the patient's tissue 52 by the patient-contact adhesive 30. The action forces applied by the user's finger 54 and thumb 56 at the recessed edges 19 (FIGS. 1 and 2) or other suitable locations on the spanning structure 48 urge the struts 42 against the tissue 52. The tissue 52 provides resisting or reaction forces so that the struts 42 apply reaction forces against respective portions of the spanning structure 48. In the first embodiment, the locations of the action and reaction forces on the spanning structure 48 are spaced apart. When sufficiently large, the action and reaction forces and resulting torque cause the tissue bridge 10 to reconfigure (e.g., bend) from its extended stable equilibrium configuration toward and past its intermediate or maximally unstable equilibrium configuration (e.g., FIG. 12). In an example, after the tissue bridge 10 is forced or pushed past its maximally unstable equilibrium configuration, the tissue bridge automatically transitions (e.g., bends itself due to its elastic potential energy) at least proximate to its retracted stable equilibrium configuration to further adhere the one or more struts 42, and optionally also the end portions 40 and arms 44, to the tissue 52. In the process, the struts 42 become closer together and push the portions of the tissue 52 to which they are adhered toward one another (e.g., which may evert the tissue adjacent the scar or wound 52).

With continued reference to FIGS. 9-13, the first embodiment multistable tissue bridge 10 is configured for at least partially covering a wound 50 and/or scar tissue, and reducing tension associated with the wound and/or scar tissue. The multistable spanning structure 46 can be configured to have a plurality of configurations including the unstable configurations (e.g., FIGS. 11 and 12) between the concave-up stable equilibrium configuration (e.g., FIGS. 3, 5, 9 and 10) and the concave-down stable equilibrium configuration (e.g., FIGS. 4, 7 and 13). In the first embodiment, the multistable spanning structure 46 is configured to be biased toward the concave-up stable equilibrium configuration (e.g., the first stable equilibrium configuration) when in a configuration between the intermediate or maximally unstable equilibrium configuration (e.g., FIG. 12) and the concave-up stable equilibrium configuration. Similarly, the first embodiment multistable spanning structure 46 is biased toward the concave-down stable equilibrium configuration (e.g., the second stable equilibrium configuration) when in a configuration between the intermediate or maximally unstable equilibrium configuration and the concave-down stable equilibrium configuration.

The first embodiment multistable spanning structure 46 and struts 42 are cooperatively configured so that at least the inner or distal end portions of the struts become closer to one another at least in response to the multistable spanning structure being transitioned from the concave-up stable equilibrium configuration to past the intermediate or maximally unstable equilibrium configuration and toward the concave-down stable equilibrium configuration. In the first embodiment, at least lower or outer surfaces of the distal end portions of the struts 42 include engagement or connection zones (e.g., adhesive material 30) configured to be engaged to and move respective portions of patient tissue 52 toward one another in response to the struts becoming closer to one another.

More specifically regarding the above-discussed method of applying the first embodiment tissue bridge 10 to tissue 52, there is a first series of unstable configurations between the extended stable equilibrium configuration and the intermediate or maximally unstable equilibrium configuration. Similarly, there is a second series of unstable configurations between the retracted stable equilibrium configuration and the intermediate or maximally unstable equilibrium configuration. It is believed that: (i) the degree to which the multistable spanning structure 48 defines the concave-up shape varies serially from a relatively maximally defined concave-up shape in the extended stable equilibrium configuration to a relatively minimally defined concave-up shape at the first series' unstable configuration adjacent intermediate or maximally unstable equilibrium configuration; (ii) the multistable spanning structure is flat (substantially flat) in the intermediate or maximally unstable equilibrium configuration; and (iii) the degree to which the multistable spanning structure defines the concave-down shape varies serially from a relatively maximally defined concave-down shape in the retracted stable equilibrium configuration to a relatively minimally defined concave-down shape at the second series' unstable configuration adjacent the intermediate or maximally unstable equilibrium configuration.

The first embodiment tissue bridge 10 can be transitioned from either of the stable equilibrium configurations to the intermediate or maximally unstable equilibrium configuration by manually, or otherwise suitably, applying force against the tissue bridge in a manner that seeks to flatten out the concavity of the multistable spanning structure 48, wherein increasing external force is required as concavity decreases so that a maximum external force is required to achieve the at least one unstable equilibrium configuration (e.g., a maximally unstable configuration). In contrast, the first embodiment tissue bridge 10 is configured to automatically biasedly transition from any of the first series of unstable configurations to the extended stable equilibrium without requiring the application of any external force to the tissue bridge. Similarly, the first embodiment tissue bridge 10 is configured to automatically biasedly transition from any of the second series of unstable configurations to the retracted stable equilibrium without requiring the application of any external force to the tissue bridge. As an alternative to directly manually applying force against the tissue bridge 10 in a manner that seeks to flatten out the concavity of the multistable spanning structure 48, the force for flattening out the concavity can be provided by way of fasteners (e.g., threaded fasteners such as screws and bolts) and tools (e.g., hand tools), as will be discussed in greater detail below.

Figure 13:
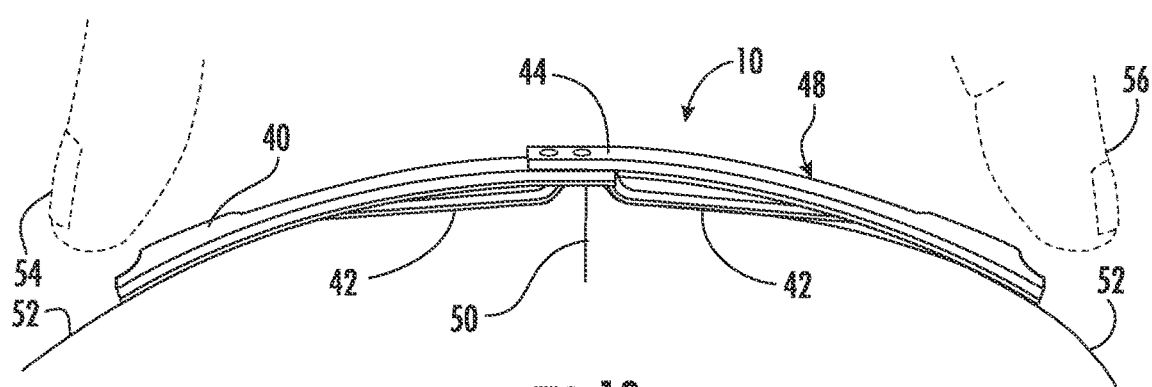

FIG. 12 depicts an example of an approximately maximally unstable intermediate configuration of at least the tissue bridge spanning structure 48. At least partially reiterating from above and as a further example, the first embodiment multistable spanning structure 48 is configured so that if the spanning structure is in an intermediate configuration between the configurations depicted in FIGS. 10 and 12, or the like, then the spanning structure would tend to return toward the configuration depicted in FIG. 10, or the like, if no, or minimal, external forces (e.g. digital pressure) were applied to the tissue bridge. Similarly, if the multistable spanning structure 48 is in an intermediate configuration between the configurations depicted in FIGS. 12 and 13, or the like, then the spanning structure would tend to change toward the configuration as shown in FIG. 13, or the like, if no, or minimal, external forces (e.g. digital pressure) were applied to the tissue bridge. The presence of tissue forces (e.g. tension or resistance to medial tissue advancement), adhesion forces (between the tissue bridge and the tissue to which it is applied), or other factors may alter the maximally unstable intermediate configuration and stable configurations (e.g., stable equilibrium configurations) of the tissue bridge.

Reiterating from above, FIG. 12 depicts an unstable equilibrium configuration of at least the tissue bridge spanning structure 48. In the example depicted in FIG. 12, the spanning structure is flat, substantially flat, planar, or substantially planar. It is believed that in other embodiments the spanning structure 48 may be curved (e.g., may not be flat, planar, or substantially planar) in its unstable equilibrium configuration At least partially reiterating from above, whereas the energy stored by the multistable spanning structure 48 is responsible for providing the multistability (e.g., bistability) of the tissue bridge 10 of the first embodiment, the other features (e.g., layers) of the tissue bridge that are carried by the multistable spanning structure can affect, for example, the overall stiffness, flexibility, and elasticity of the tissue bridge. Characteristics (e.g., stiffness, flexibility, and/or elasticity) of one or more of the various features of the tissue bridge 10 can be adjusted in a predetermined manner to tune the operability of (e.g., the multistability of) the tissue bridge. For example, as compared to one another, different parts of the same tissue bridge 10 can have different characteristics (e.g., different stiffness, flexibility, and/or elasticity resulting from different thicknesses or volumes, different construction materials, and/or different manufacturing techniques) to affect the operability of (e.g., the multistability of) the tissue bridge.

Similarly, the tissue upon which the tissue bridge 10 is mounted can affect, for example, the overall stiffness, flexibility, and elasticity of a system (e.g., combination) that includes both the tissue 52 and the tissue bridge 10. As a specific example, depending upon the configuration and properties of the tissue 52 upon which the tissue bridge 10 is mounted, the tissue bridge per se may not reach its retracted stable equilibrium configuration and remain in an unstable configuration of the tissue bridge when the system (e.g., the combination that includes both the tissue and the tissue bridge) is in a stable equilibrium configuration. Similarly, the configuration and properties of the tissue 52 upon which the tissue bridge 10 is being mounted can affect the intermediate or maximally unstable equilibrium configuration (e.g., may increase the amount of external force that is required to achieve the intermediate, maximally unstable equilibrium configuration of the system (e.g., the combination that includes both the tissue and the tissue bridge)). In accordance with one aspect of this disclosure, the tuning of the operability of the tissue bridge 10 can include taking into consideration the configuration and properties of the tissue to which the tissue bridge is to be mounted and adjusting the configuration and properties of the tissue bridge at least in view of that tissue.

Figure 14:
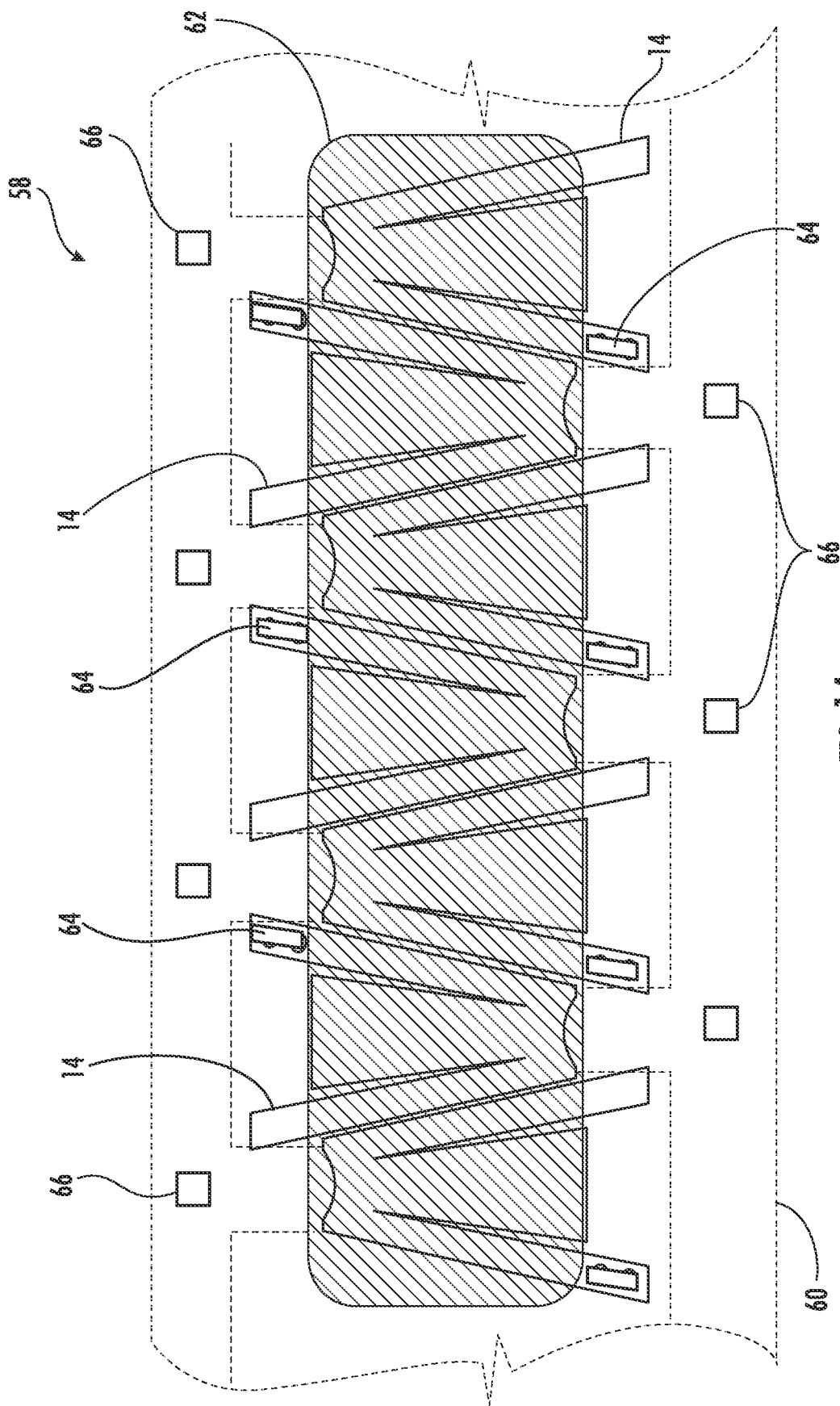
FIG. 14 is a schematic, top view of a multilayer precursor of multiple of the tissue bridges of FIG. 1, in accordance with an embodiment of this disclosure.
Figure 15:
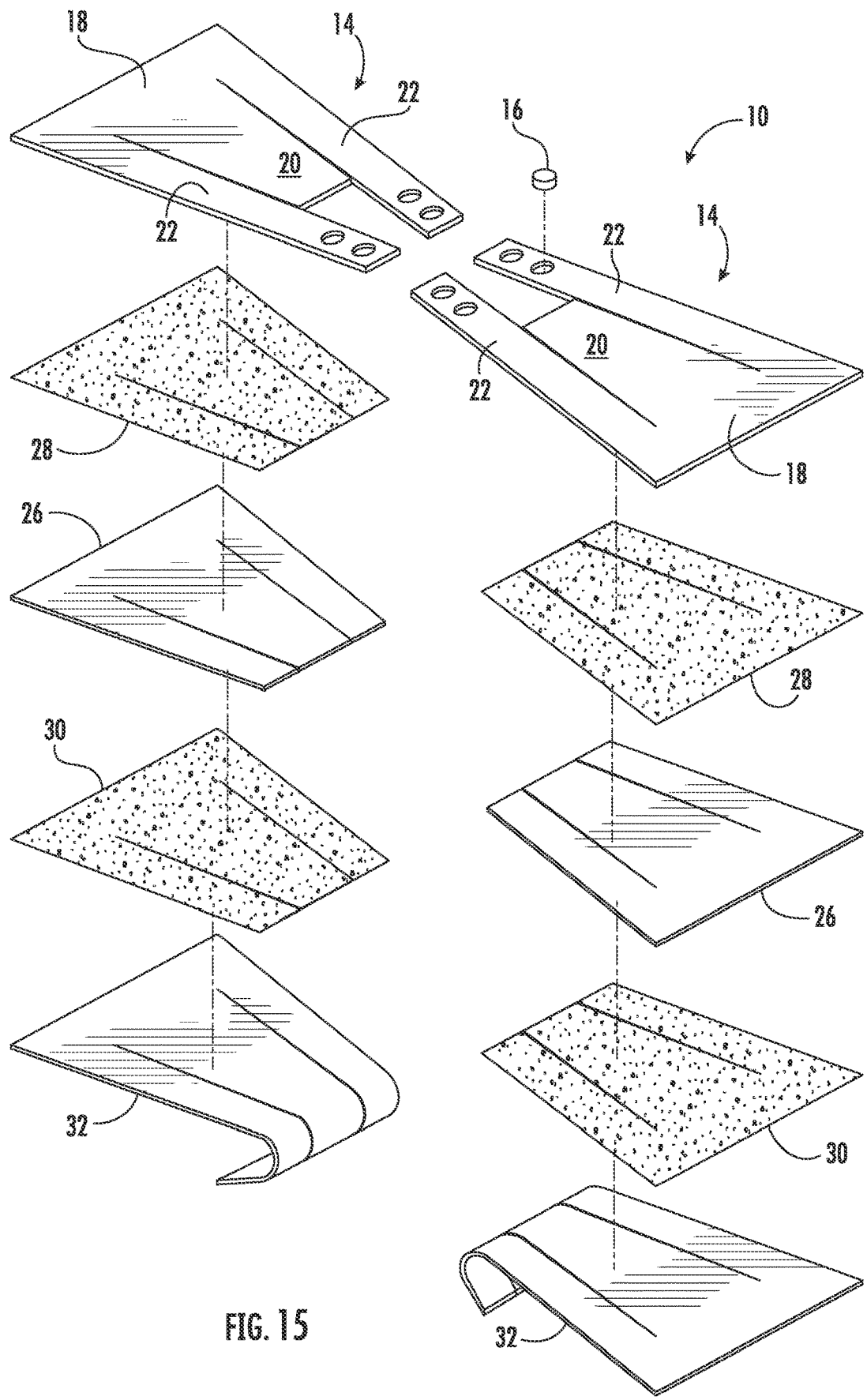
FIG. 15 is an exploded, top perspective view of a multistable tissue bridge in accordance with a second embodiment of this disclosure.
Figure 16:
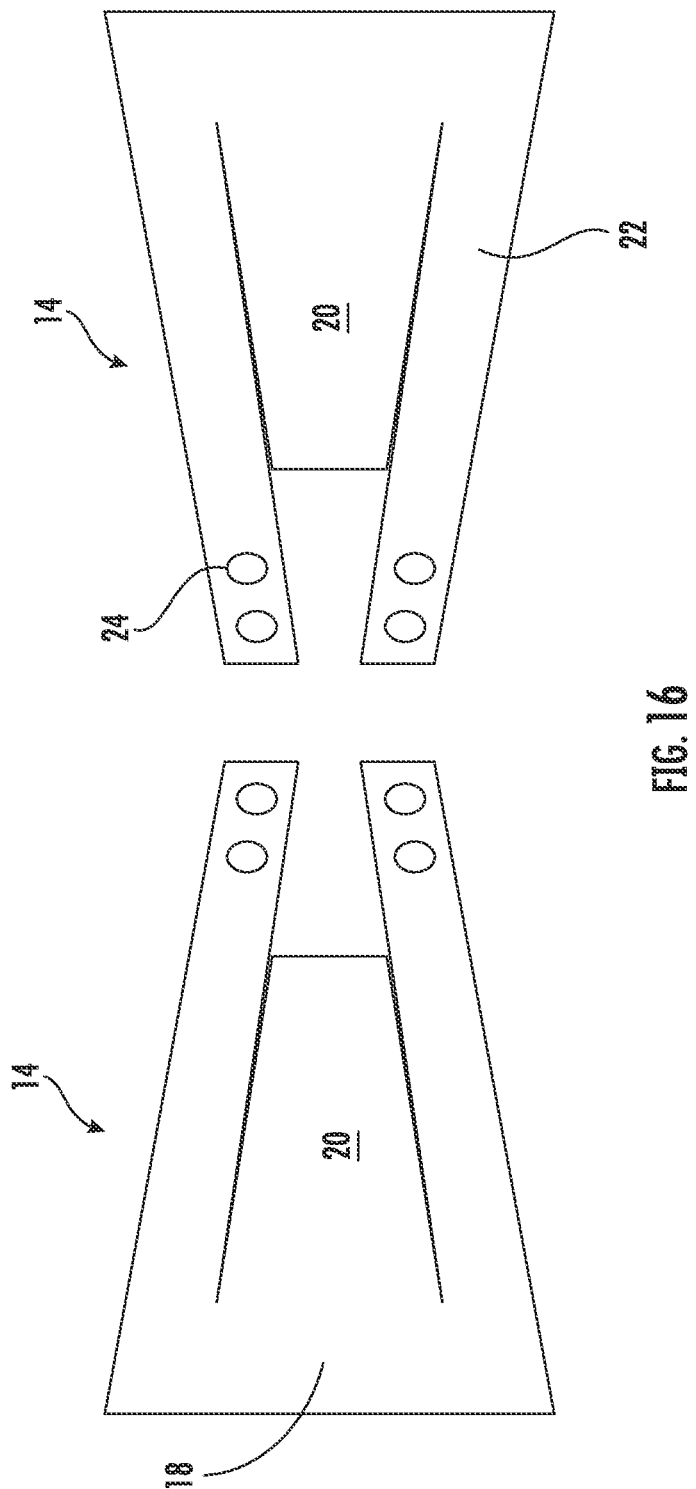
FIG. 16 is an exploded, isolated top view of the body-forming blanks depicted in FIG. 15.

FIG. 14 is a schematic view from above of a flat, multi-layer precursor 58 of multiple of the tissue bridges 10 (FIGS. 3 and 4), in accordance with an example of manufacturing for the first embodiment. In FIG. 14, the top layer of the multi-layer precursor 58 is in the form of several of the transparent blanks 14 (FIG. 2) arranged side-by-side. In FIG. 14, the lowest layer 60 of the multi-layer precursor 58 can be a precursor sheet 60 from which the outer release liners 32 (FIG. 1) can be cut. In FIG. 14, an intermediate layer 62 is schematically identified by cross hatching and is positioned between the upper blanks 14 and lowest layer 60. The intermediate layer 62 of the multi-layer precursor 58 can be a precursor sheet 62 from which the patient-contact carriers 26 (FIG. 1) are cut.

Also depicted in FIG. 14 are asperities 64 or other suitable features for facilitating or accommodating for welding, heat sealing, adhesive, and/or other suitable mechanisms for use in assembling the multistable bodies 12 (FIGS. 3 and 4) from pairs of the blanks 14. Also, registration features 66 (e.g., holes, eye marks, and/or other suitable registration features) can be included in the lower layer 60 and/or any other suitable layer of the precursor 58 for use in respectively aligning the blanks 14 with one another when assembling the multistable bodies 12. The asperities 64, registration features 66, and/or other suitable features associated with FIG. 14 can be utilized in other embodiments of this disclosure, for example embodiments in which each tissue bridge 10 is at least partially formed of less than two blanks or more than two blanks. Tissue bridges 10 can also be manufactured without incorporating blanks.

Whereas the tissue bridges 10, bodies 12, strut portions 20, struts 42 (e.g., strut assemblies), and/or multistable spanning structures 46, 48 are sometimes described in the Detailed Description section as being at least partially formed by erecting one or more blanks (see, e.g., blanks 14 of FIGS. 1 and 2), it is within the scope of this disclosure for each of the tissue bridges, bodies, strut portions, struts, and/or multistable spanning structures not to include one or more erected blanks. For example, it is within the scope of this disclosure for each of the tissue bridges 10 to be assembled in a manner that requires neither connecting together blanks nor connecting respective portions of a blank together. For example, the bodies 12 may be formed in any suitable manner, for example thermoforming, 3D printing, injection molding, or the like. For example, each body 12 can be an injection-molded or mechanically thermoformed, unitary (e.g., single-piece) article such that the strut portions 20, struts 42, and/or multistable spanning structures 46, 48 can be formed together as a single article from an injection-moldable or thermoformable material, or the like. As a further example, it is believed that when tissue bridges 10 are at least partially formed by thermoforming, temporary peelable release liners may be used during manufacture and/or at the time the tissue bridges are being applied to a patient. For example, the temporary peelable release liners may be used for indexing and/or orienting structures, and the thermoforming may occur after at least some of the layers have been adhered to the main substrate (e.g., polymeric film) to form a laminate. It is believed that the body 12 and/or tissue bridge 10 may be cut from the laminate at any suitable time (e.g., before, after, and/or during the thermoforming). Such temporary peelable release liners may be removed from the laminate, body 12, and/or tissue bridge 10 at any suitable time.

For ease of understanding, the blanks 14 may be described as, or alluded to as being, articles that are initially separately manufactured and thereafter converted into a multistable body 12 or tissue bridge 10. However, it is believed that the blanks 14 or a structure corresponding to the connected-together blanks can also be at least schematically illustrative of a structure that may be relatively temporarily present during a phase of thermoforming or another suitable manufacturing process that provides a multistable body 12 or tissue bridge 10.

The first embodiment (e.g., its structures and associated methods) and other embodiments (e.g., their structures and associated methods) disclosed in the following portion of the Detailed Description section can be alike, except for variations noted and variations that will be apparent to those of ordinary skill in the art. For example, FIGS. 15-18 depict features of a second embodiment of a multistable (e.g., symmetrically bistable or asymmetrically bistable) tissue bridge 10 that can be like the first embodiment multistable tissue bridge 10 (e.g., including both structures and associated methods) except, for example, in each blank 14 the arm portions 22 extend away from the end portion 18 in a convergent manner, to define an angle of convergence between the arm portions. In the second embodiment, the assembling of the tissue bridge 10 (e.g., superposing and connecting respective end portions of the arm portions 22) includes changing (e.g., decreasing) the angle of convergence between the arm portions 22 and, thus, causing deformation in the blanks 14 and formation of the multistable (e.g., symmetrically bistable or asymmetrically bistable) body 12. Alternatively, the superposing and connecting can be replaced by edge-to-edge connecting by way of one or more suitable seams (e.g., welding (e.g., laser welding)), adhering (e.g., with adhesive and/or adhesive tape), injection molding (e.g., insert molding), or other suitable seaming together) and/or other suitable attachment mechanisms.

The angle of divergence or the angle of convergence between arm portions 22, arms 44, or other suitable features of the tissue bridges 10 can be altered to be more acute or more obtuse in order to alter the three-dimensional shape of the tissue bridge in its multistable (e.g. bistable) configurations. For example, if the angle of divergence between the arms 22 of blanks 14 (either single piece or multi-piece) is increased compared to a reference embodiment, the resultant multistable (e.g. bistable) spanning section 46 can have, once assembled, a smaller radius in the extended (convex) stable equilibrium configuration and retracted (concave) stable equilibrium configuration. Similarly, if the angle of divergence is decreased compared to a reference embodiment, then, once assembled, the multistable (e.g. bistable) spanning section 46 can have a larger radius in the extended (convex) stable equilibrium configuration and retracted (concave) stable equilibrium configuration. If a blank has convergent angles, this relationship between angle changes and a reference blank is reversed. In addition, changing the angle of convergence or divergence can alter the force requirements to position the tissue bridge 10 in its maximally unstable intermediate configuration (e.g., unstable equilibrium configuration). For any given blank, given similar materials, thicknesses, and dimensions, with only the angle of convergence or divergence being altered, a greater angle of convergence or divergence will produce greater resistance—and therefore a greater force requirement to deform the tissue bridge 10 to the maximally unstable intermediate configuration—and similarly a lower angle of convergence or divergence will produce a lesser resistance—and therefore a lessor force requirement to deform the tissue bridge to the maximally unstable intermediate configuration, compared to a reference tissue bridge.

Figure 17:
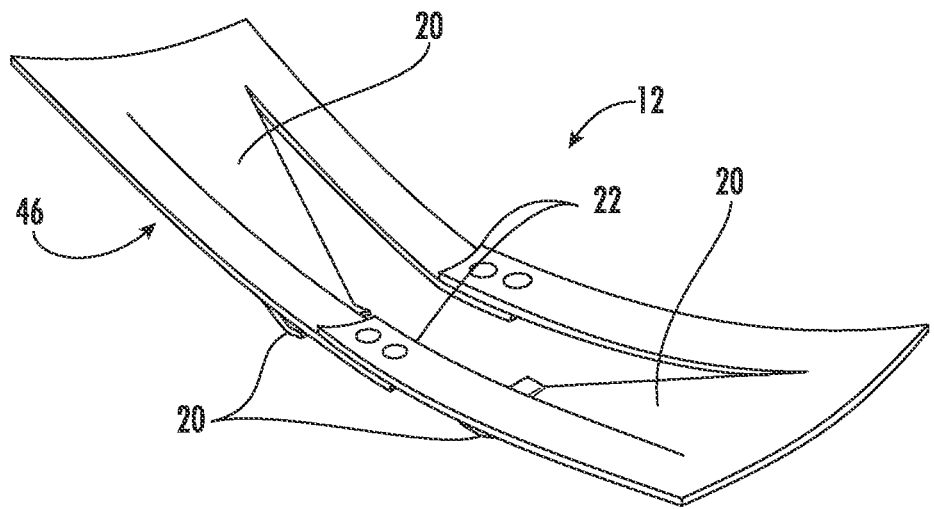
FIG. 17 is a top perspective view of a multistable body or tissue bridge formed from the blanks of FIG. 16 in its extended stable equilibrium configuration.
Figure 18:
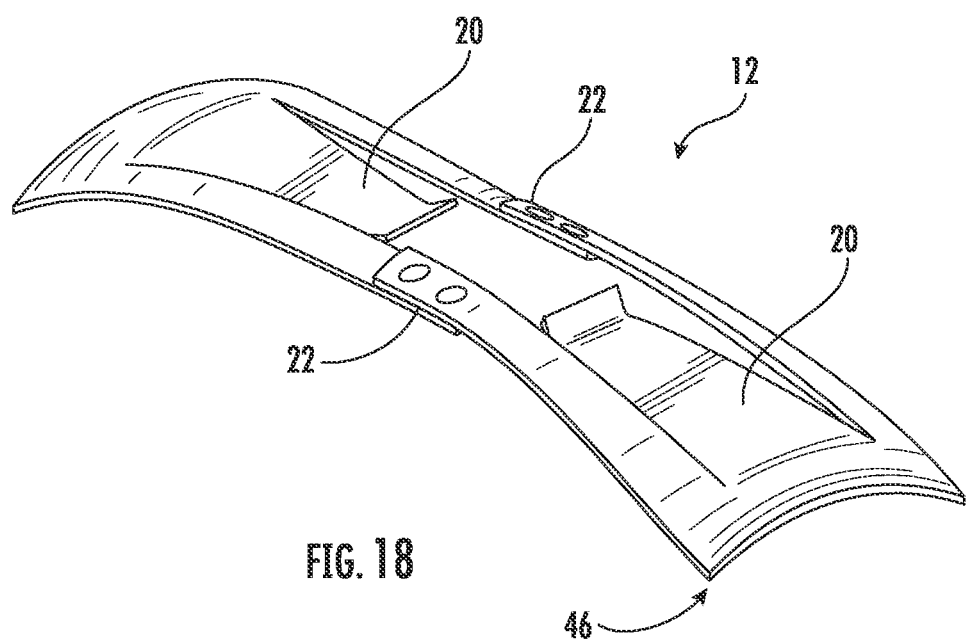
FIG. 18 is a top perspective view of the multistable body or tissue bridge of FIG. 17 in its retracted stable equilibrium configuration.
Figure 19:
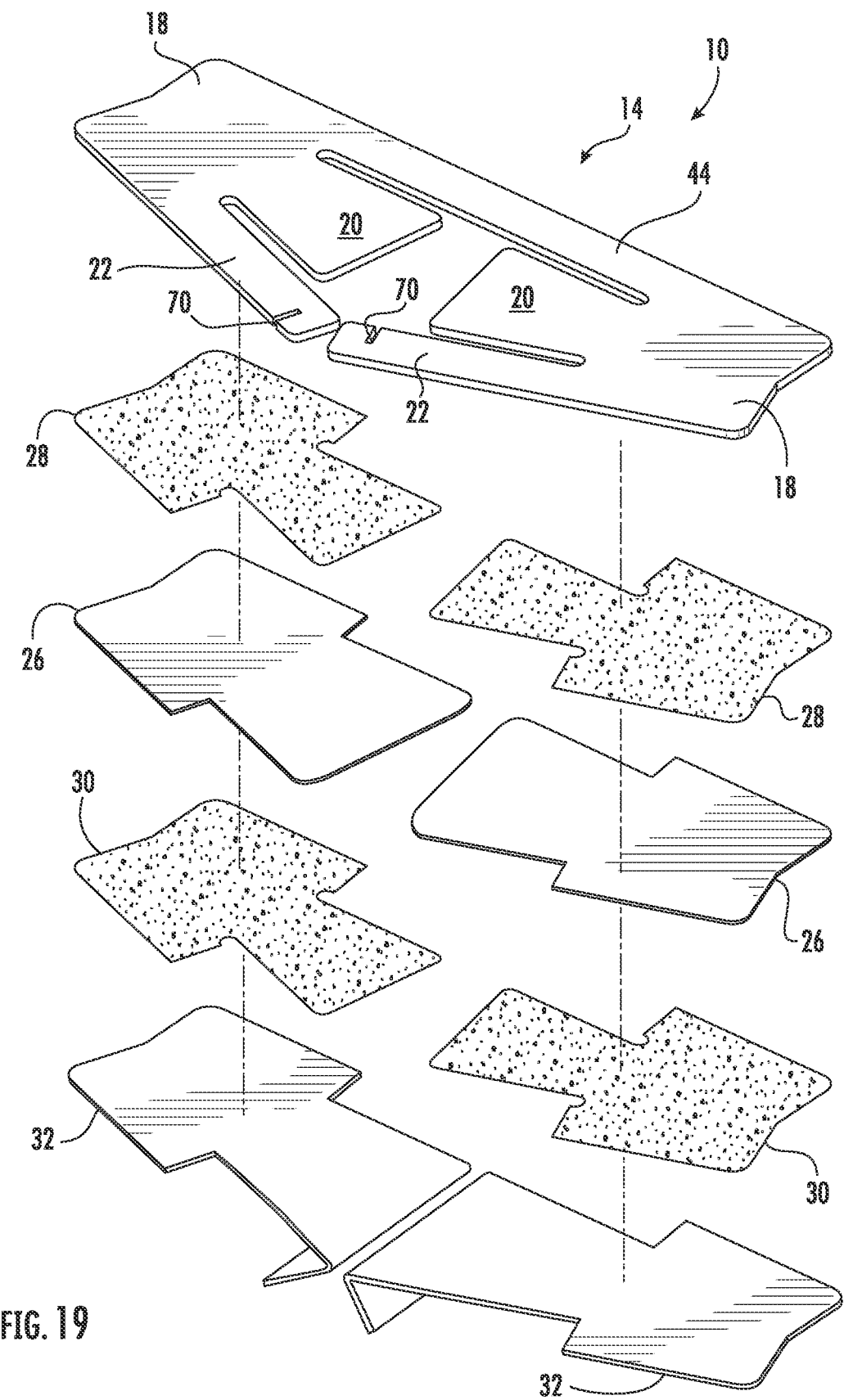
FIG. 19 is an exploded, top perspective view of a multistable tissue bridge in accordance with a third embodiment of this disclosure.

FIGS. 17 and 18 depict the second embodiment bistable body 12 in its extended stable equilibrium configuration and its retracted stable equilibrium configuration, respectively. In the extended stable equilibrium configuration (FIG. 17), the inner ends of the strut portions 20 extend outwardly (e.g., downwardly) away from the arm portions 22. In contrast, in the retracted stable equilibrium configuration (FIG. 18), the strut portions 20 are relatively retracted with respect to the arm portions 22, so that the inner or distal end portions of the struts are closer to one another. In the second embodiment, the strut portions 20 are connected to one another by way of at least one multistable spanning structure 46 including the end and arm portions 18, 22 of the blanks 14. In the second embodiment, the multistable spanning structure 46 is configured to provide the bistable behavior of the body 12 and tissue bridge 10. At least partially reiterating from above, rather than being formed from one or more blanks, the body 12 can be an injection-molded or mechanically thermoformed, unitary (e.g., single-piece) article such that the strut portions 20 and multistable spanning structures 46 can be formed together as a single article from an injection-moldable or thermoformable material, or the like. The bodies 12 and tissue bridges 10 can be formed from laminated structures.

FIGS. 19-26 depict features of a third embodiment of a multistable (e.g., symmetrically bistable or asymmetrically bistable) tissue bridge 10 that can be like the first and second embodiments (e.g., including both structures and associated methods) except, for example, only two arm portions 22 are superposed and connected to one another to form the multistable body. In the example depicted in FIGS. 19 and 20, one of the arms 44 is a single strip of material extending continuously between the body end portions 18, and the other of the arms 44 (FIGS. 24 and 25) is formed from at least two links or arm portions 22. The superpositioning and connecting together of the inner ends of the arm portions 22 can be facilitated by mating together connection zones including one or more pairs of oppositely oriented fastening slots 70 in the arm portions (see, e.g., FIGS. 24-26) and/or the arm portions 22 can be connected to one another using any other suitable mechanisms. Alternatively, the superposing and connecting can be replaced by edge-to-edge connecting by way of one or more suitable seams (e.g., welding (e.g., laser welding)), adhering (e.g., with adhesive and/or adhesive tape), injection molding (e.g., insert molding), or other suitable seaming together) and/or other suitable attachment mechanisms.

Figure 20:
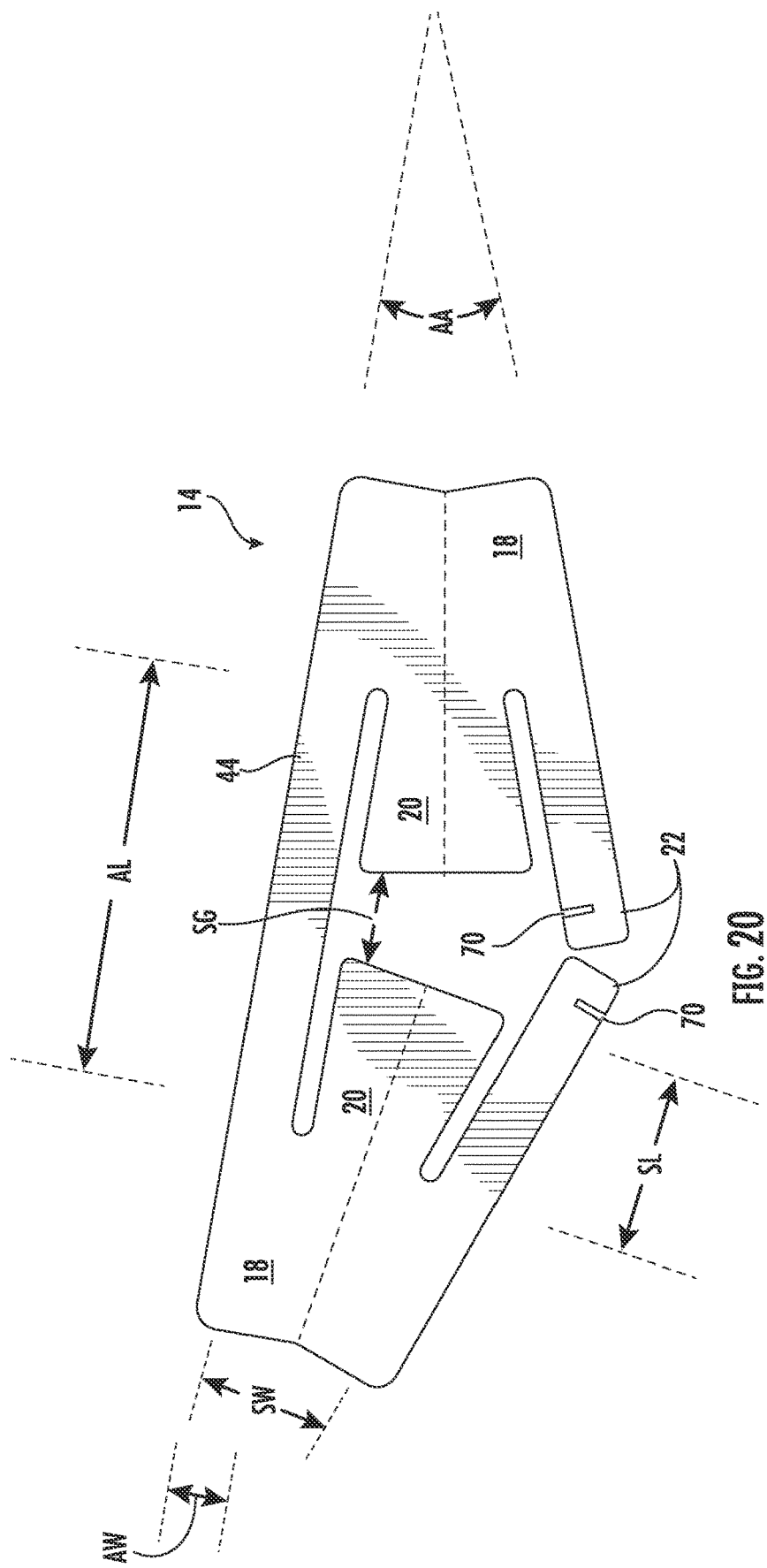
FIG. 20 is an isolated top view of the body-forming blank of FIG. 19.

Referring to FIG. 20, the arms 44 can have a length "AL", width "AW", and an angle of divergence "AA". The one or more struts 20 can have a width "SW" and a length "SL". A gap "SG" is typically defined between inner ends of the struts 20. One or more of the arm length "AL", arm width "AW", arm divergence angle "AA", strut width "SW", strut length "SL", strut gap "SG" and/or other suitable features of the tissue bridge 10 can be adjusted in a predetermined manner to tune the operability of (e.g., the multistability of) the tissue bridge. As another example, the configuration and manner in which respective portions of one or more blanks 14 are connected with one another to form the multistable body 12 can be adjusted in a predetermined manner to tune the operability of (e.g., the multistability of) the associated multistable body 12 and tissue bridge 10. The struts 20 and/or other features of the tissue bridge 10 may be asymmetrical.

Figure 21:
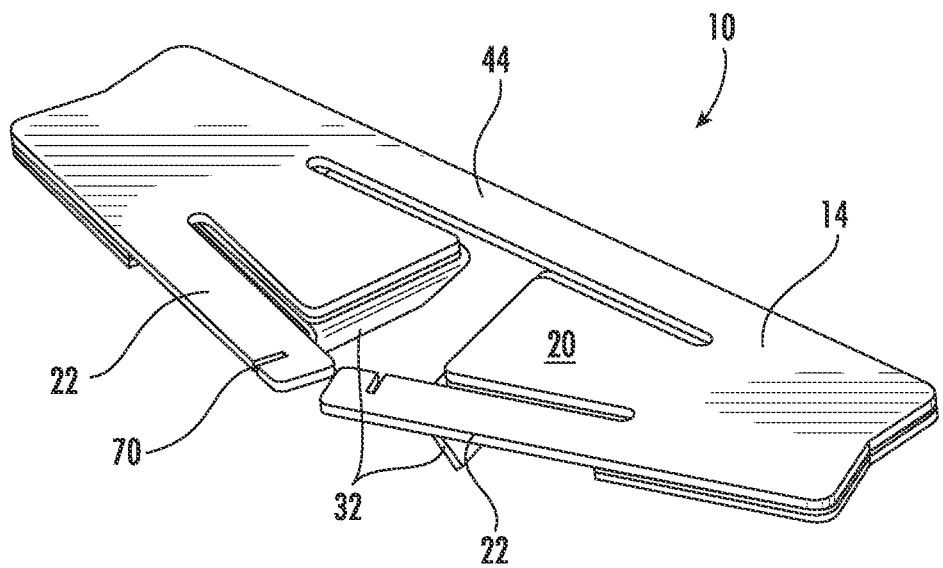
FIG. 21 is a partially assembled, top perspective view of the tissue bridge of FIG. 19.
Figure 22:
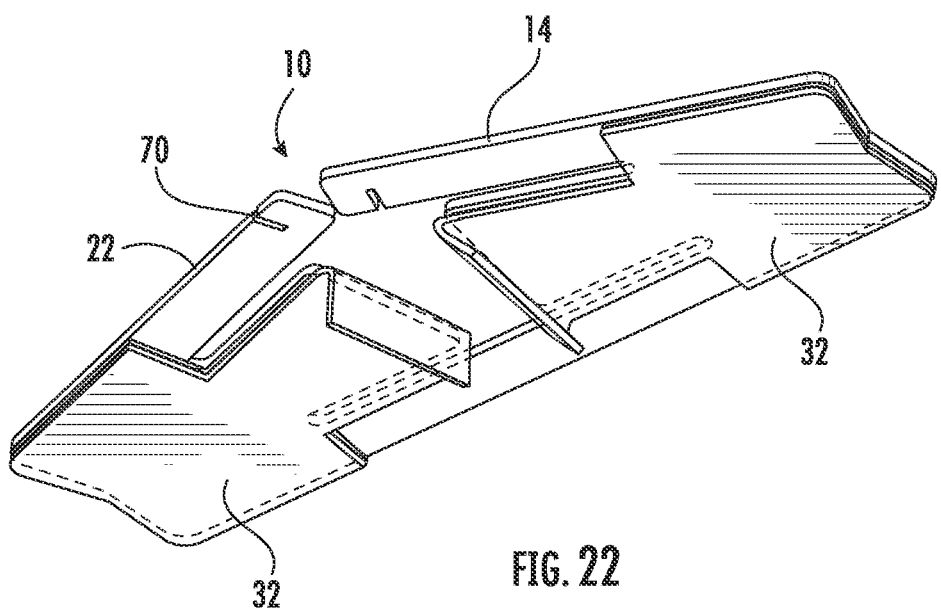
FIG. 22 is a schematic, bottom perspective view of the tissue bridge of FIG. 21.
Figure 23:
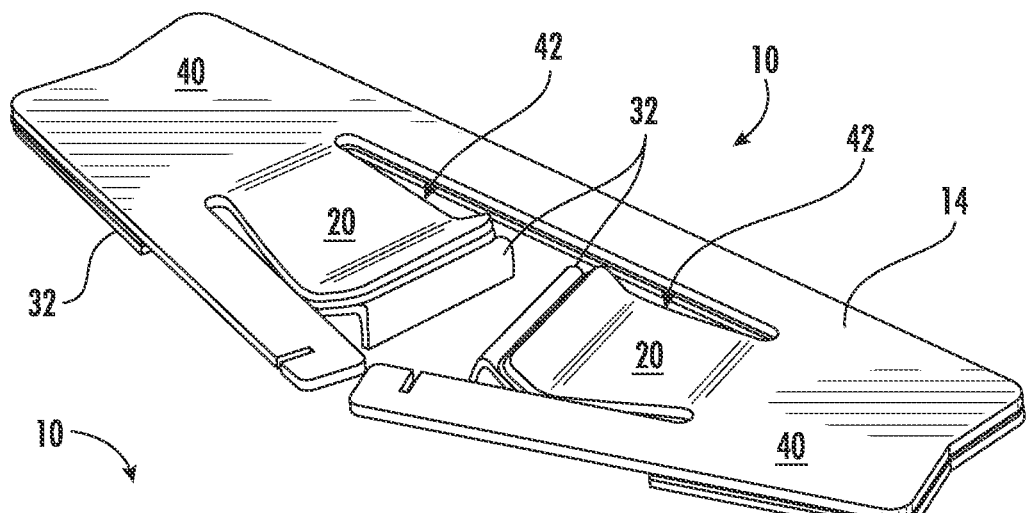
FIG. 23 depicts a version of the tissue bridge that is like the version depicted in FIGS. 21 and 22, except that portions of the struts are angled.

FIG. 23 depicts a version of the tissue bridge 10 that is like (e.g., including both structures and associated methods) the version depicted in FIGS. 21 and 22, except that one or more portions of the struts 42 (e.g., strut assemblies) are angled. For example, a tissue bridge 10 can be tuned by changing any one or more angles associated with the struts 42.

In FIG. 23, the inner or distal end portions of the struts 42 are angled or inclined relative to the central and outer or proximal end portions of the struts. Also in FIG. 23, the outer or proximal end portion of each strut 42 is bent or angled relative to the tissue bridge end portion 40 to which the strut is connected. The bends that define the angles associated with the struts 42 can be provided, for example, by bending, thermoforming, stamping, and/or in any other suitable manner. Alternatively, the tissue bridges 10 can be formed, or at least partially formed, by injection molding, 3D printing, and/or in any other suitable manner. At least partially reiterating from above, one or more of the bends that define the inclination or angle of the inner or distal end portions of the struts 42 can be formed in response to tissue forces associated with the tissue bridge 10 being mounted on tissue 52.

In accordance with an example of a method of fabricating the third embodiment tissue bridges 10, they can be substantially fully assembled, sterilized, and then be enclosed in packages that are provided to end users. After the end users open the packages, they can connect the inner ends of the arm portions 22 to one another as discussed above, or in any other suitable manner, and then mount the tissue bridges on tissue 52 (FIG. 9). Alternatively, the tissue bridges 10 can be fully assembled prior to packaging, as discussed above, for example, with reference to the first embodiment. Also and reiterating from above, rather than being formed from blank(s), the body 12 can be an injection-molded or mechanically thermoformed, unitary (e.g., single-piece) article such that the strut portions 20 and multistable spanning structures 46 can be formed together as a single article from an injection-moldable or thermoformable material, or the like. The bodies 12 and tissue bridges 10 can be formed from laminated structures.

Figure 24:
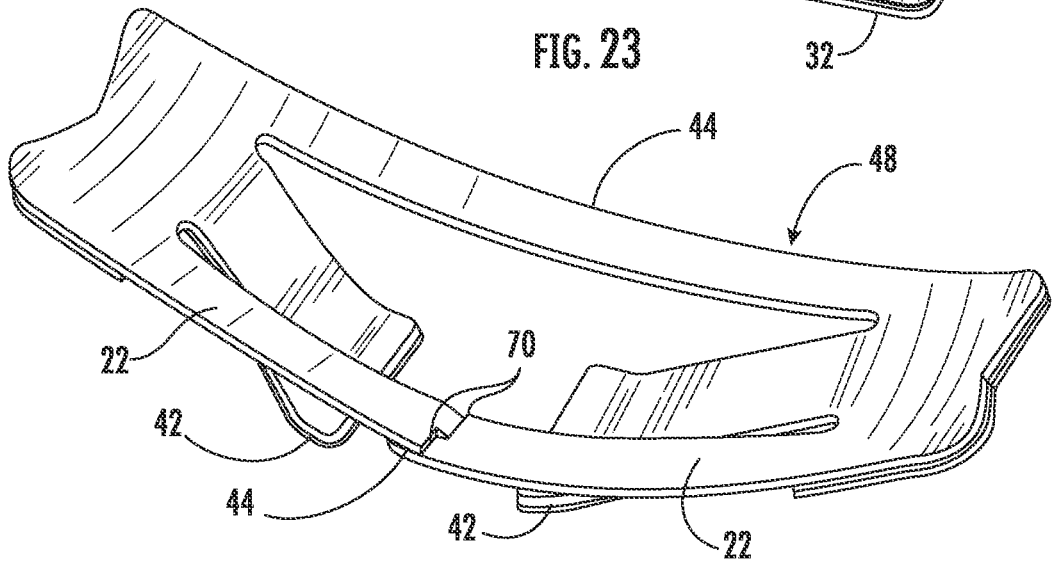
FIG. 24 is a top perspective view of the tissue bridge of FIG. 23 in its extended stable equilibrium configuration, wherein outer release liners are not shown.
Figure 25:
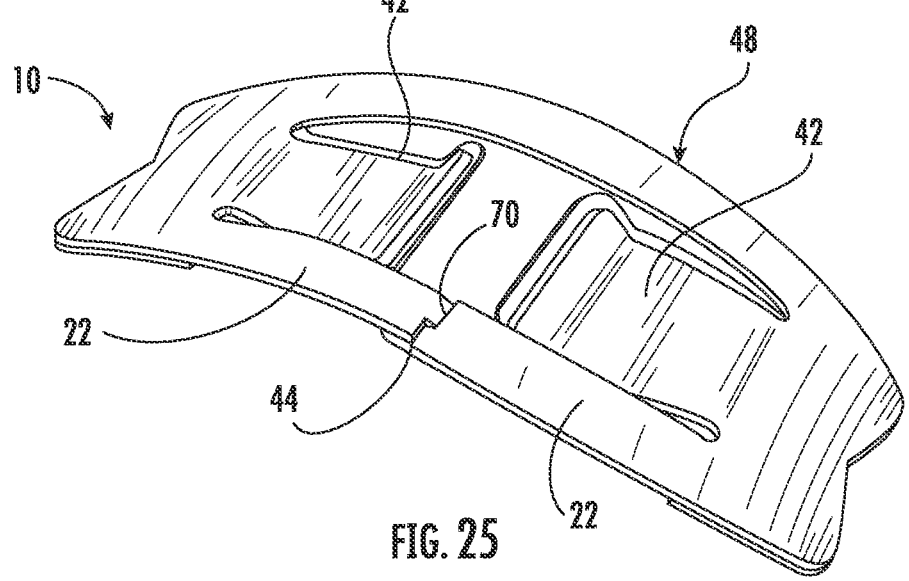
FIG. 25 is a top perspective view of the tissue bridge of FIG. 24 in its retracted stable equilibrium configuration.

FIG. 24 depicts the third embodiment multistable tissue bridge 10 in its extended stable equilibrium configuration, wherein the inner or distal end portions of the one or more struts 42 extend (e.g., are inclined) outwardly (e.g., downwardly) away from the arms 44, and the multistable spanning structure 48 is in its concave-up stable equilibrium configuration. FIG. 25 depicts the third embodiment tissue bridge 10 in its retracted stable equilibrium configuration, wherein the one or more struts 42 are relatively retracted with respect to the arms 44, and the multistable spanning structure 48 is in its concave-down stable equilibrium configuration.

Figure 26:
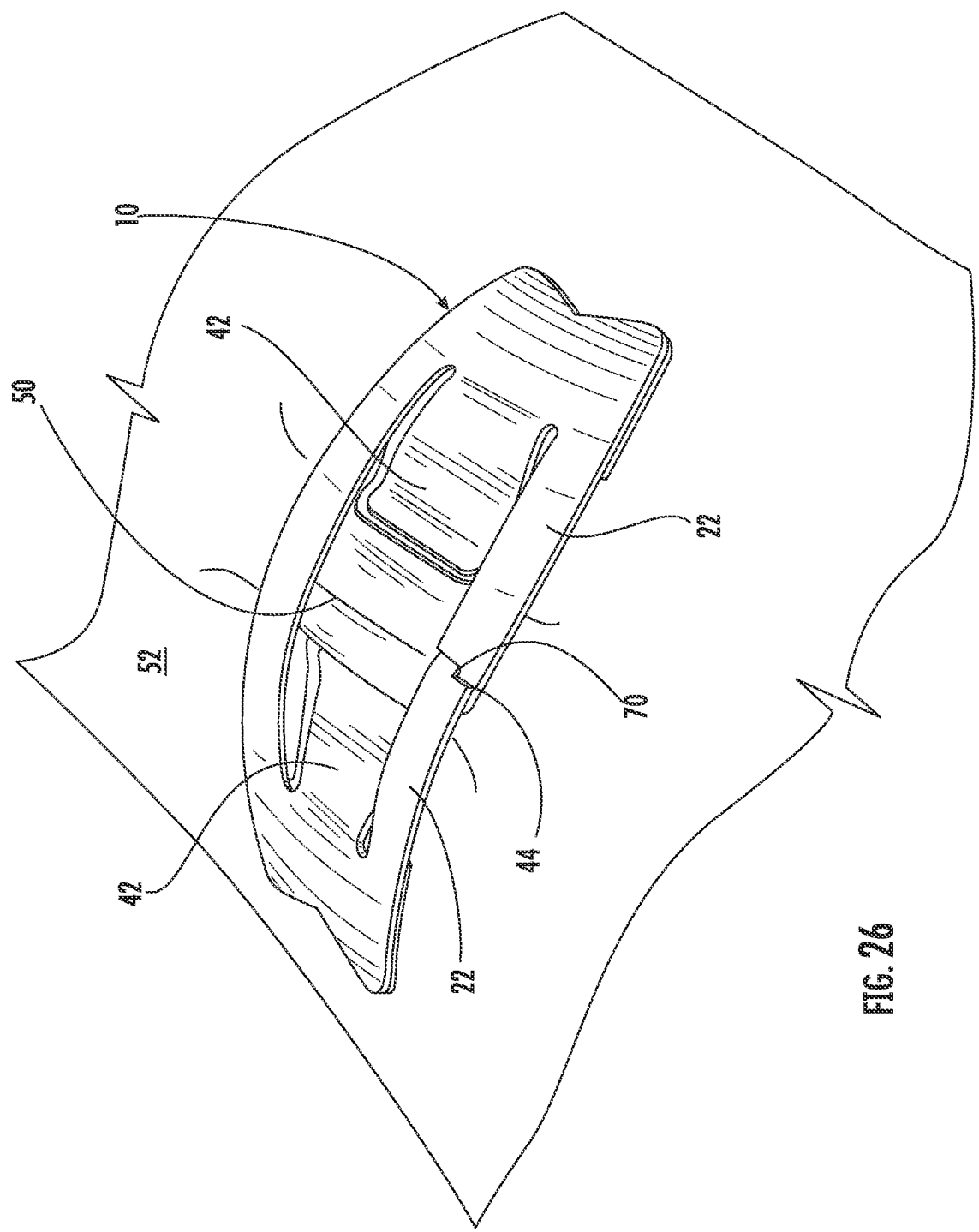
FIG. 26 is a top perspective view of the tissue bridge of FIG. 24 mounted on wounded tissue, in accordance with an embodiment of this disclosure.

FIG. 26 is a top perspective view of the third embodiment tissue bridge 10 in, or proximate, its retracted stable equilibrium configuration, wherein at least lower surfaces of the one or more struts 42 (e.g., strut assemblies) are adhered to and applying force against the patient's tissue 52 so that the wound 50 is at least partially closed and the wounded area of the patient is everted, in accordance with an embodiment of this disclosure. While the third embodiment tissue bridge 10 is in its extended stable equilibrium configuration, the tissue bridge can be forced or pushed against the tissue 52 so that the tissue bridge, tissue 52, and wound 50 become configured as schematically depicted in FIG. 26, wherein the tissue bridge can be secured to the tissue by way of the patient-contact adhesive 30 (see, e.g., FIG. 19) and/or any other suitable attachment mechanisms.

Figure 27:
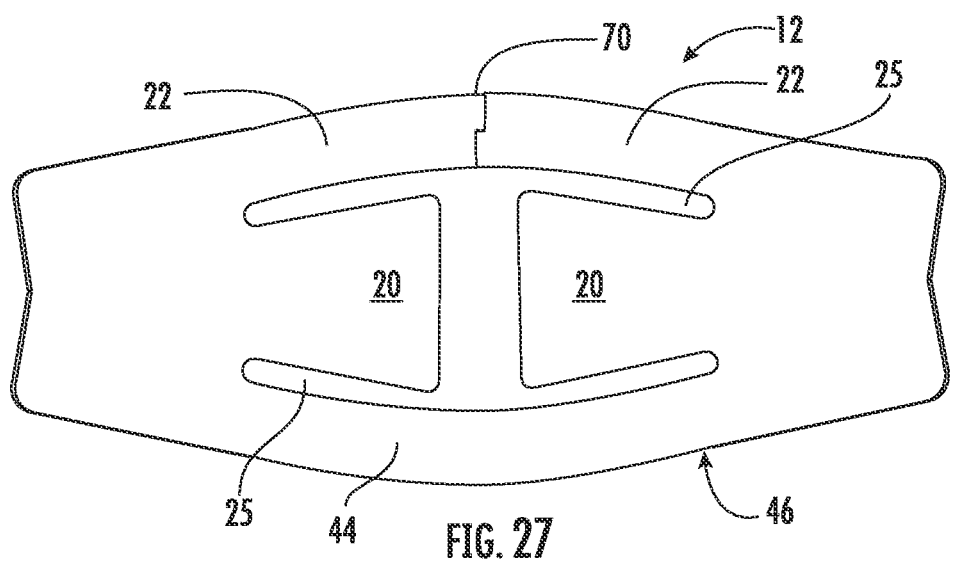
FIG. 27 is an isolated top view of the multistable body of the tissue bridge of FIG. 24, or a variation thereof.
Figure 28:
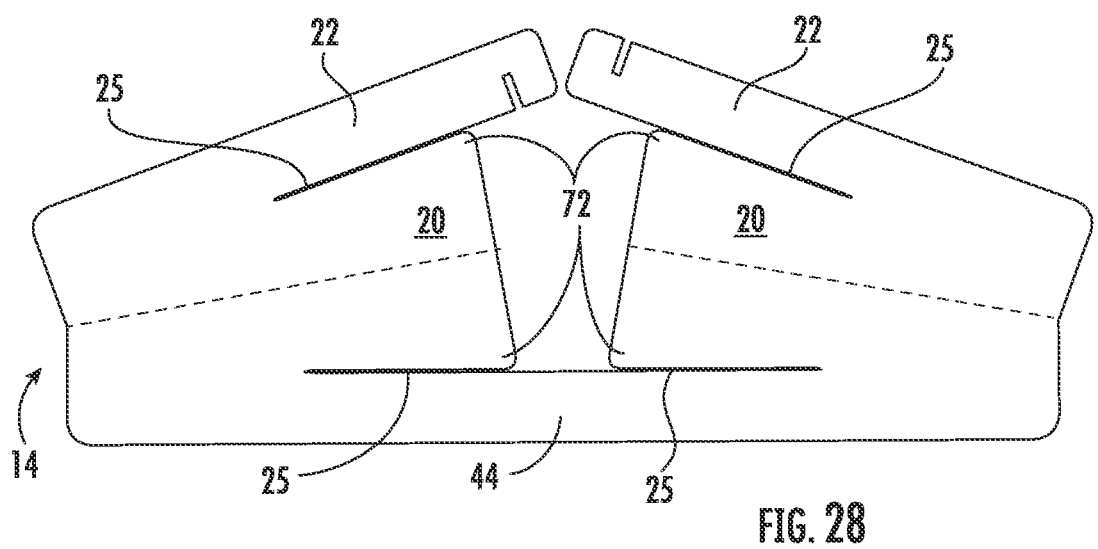
FIG. 28 is an isolated top view of a blank that is like the blank depicted in FIG. 20, except, for example, that the widths of cuts between the struts and arm portions are smaller in FIG. 28.
Figure 29:
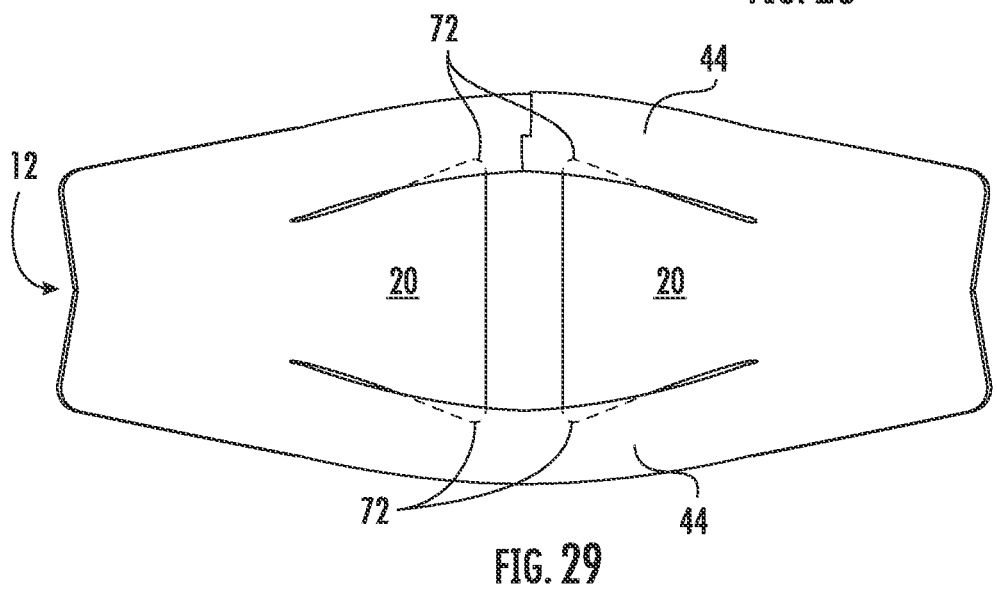
FIG. 29 is an isolated top view of a multistable body or tissue bridge formed from the blank of FIG. 28, wherein corners of the struts are hidden from view beneath the arms, and the hidden strut corners are schematically depicted by dashed lines.

FIG. 27 is an isolated top view of a version of the third embodiment multistable body 12 with its arm portions 22 connected to one another at least partially by way of the fastening slots 70. In the example of FIG. 27, the cuts 25 positioned between and at least partially defining the strut portions 20, arms 44, and arm portions 22 are wide enough so that, depending upon the angle of inclination of the strut portions 20 relative to the multistable spanning structure 46, the strut portions 20 may, in some situations, be able to pass upwardly into the gap between the arms when the tissue bridge transitions from the extended stable equilibrium configuration to the retracted stable equilibrium configuration. In contrast, in the example of FIG. 28, the cuts 25 positioned between and at least partially defining the strut portions 20, arms 44, and arm portions 22 may be narrow enough (e.g., may be in the form of slits or relatively narrow cuts) so that inner corners 72 of the strut portions 20 restrict the strut portions 20 from being able to pass upwardly into the gap between the arms when the tissue bridge transitions from the extended stable equilibrium configuration to the retracted stable equilibrium configuration. For example, FIG. 29 is a top view of a body 12 formed from the blank 14 of FIG. 28, wherein corners 72 of the struts 20 are hidden from view beneath the arms 44, and the hidden strut corners 72 are schematically depicted by dashed lines. Also and reiterating from above, rather than being formed from blank(s), the body 12 can be an injection-molded or mechanically thermoformed, unitary (e.g., single-piece) article such that the strut portions 20 and multistable spanning structures 46 can be formed together as a single article from an injection-moldable or thermoformable material, or the like. The bodies 12 and tissue bridges 10 can be formed from laminated structures and other suitable materials.

In addition to changing the gap between the arms 44 and struts 42 as discussed above, the widths of the gaps between the arms and struts and the corresponding gap between the arms can be altered by changing the angle of divergence or angle of convergence of the arm or arms, or changing the radius of the concavity of the assembled tissue bridge 10 in one or more of its multistable (e.g. bistable) states. A greater angle of divergence (e.g., if fabricated from a blank) or a lessor radius of concavity (e.g., if fabricated directly by another method such as thermoforming or injection molding) can produce a fully assembled/fabricated tissue bridge 10 with a relatively greater length ratio between the at least one strut 42 and the gap between the arms 44. Thus by altering either the gap between the struts 20 and the corresponding inner edge of the arm 44, by altering the relative divergence or convergence of the arms, or by altering the radius associated with the stable extended or retracted configurations, the relationship between the strut 20 and gap between the inner edge of the arms 44 can be altered. The resultant relationship may be that the strut width is less than the gap between the inner edges of the arms at a given point, that the width of the strut may be the same as the gap between the inner edges of the arms at a given point, and/or that the width of the strut may be greater than the gap between the inner edges of the arms at a given point. Depending on the configuration of the struts and arms, there may be different relationships between the strut and corresponding gap between the inner edges of the arms at different points along the length of the strut.

Figure 30:
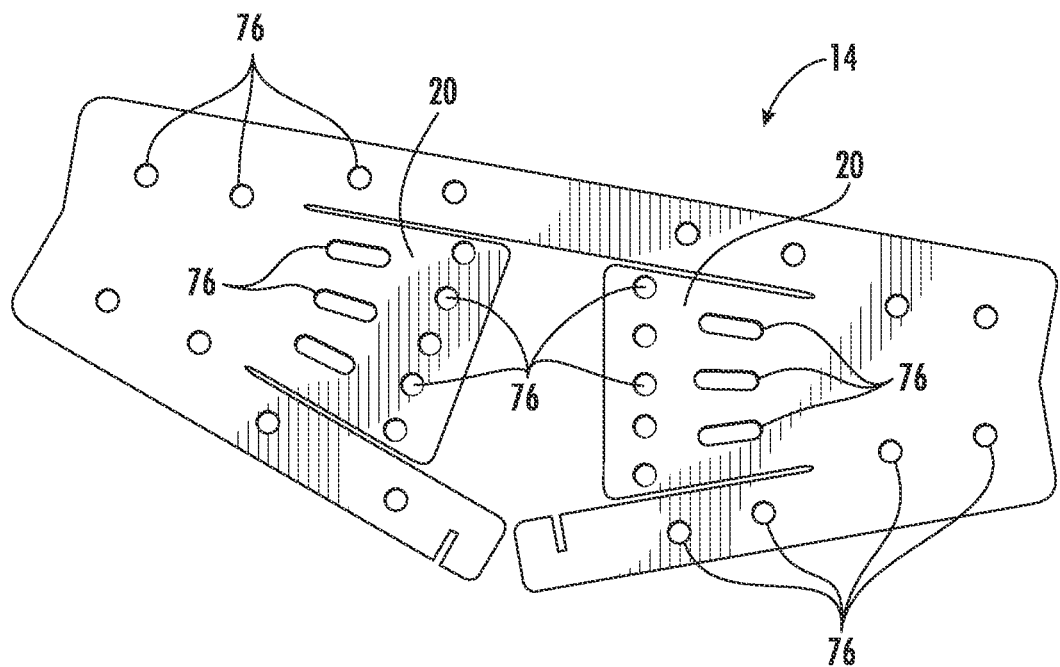
FIG. 30 is a top view of a blank that is similar to the blank of FIG. 28 except, for example, for the addition of holes.
Figure 31:
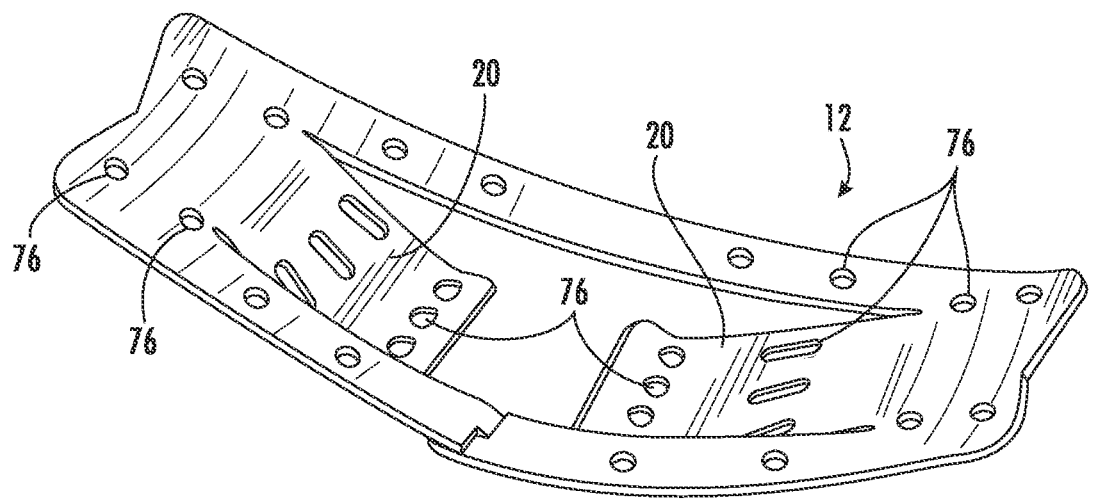
FIG. 31 is a top perspective view of a multistable body or tissue bridge formed from the blank of FIG. 30, wherein the body or tissue bridge is in its extended stable equilibrium configuration.

Referring to FIGS. 30 and 31, one or more holes 76 (e.g., circular holes, elongate holes, and/or any other suitable configured holes) can extend through respective portions of the blanks 14, bodies 12, and other structures of this disclosure. The holes 76 can be configured for providing ventilation, for allowing for the application of medicinal substances, for facilitating supplementary fixation (e.g., using pins, needles, sutures, staples, and/or the like), and/or for defining a line of disruption along which bending may occur, for example to at least partially facilitate the bending that defines the angle or inclination of the inner or distal end portions of the one or more struts 20. At least partially reiterating from above, the bending that defines the angle or inclination of the distal end portions of the one or more struts 20 may not occur until the tissue bridge 10 is mounted (e.g., in response to tissue forces associated with the tissue bridge 10 being mounted on tissue 52). As additional examples, one or more of the holes 76 can be used for fixation, either as part of a primary method of fixation (e.g. the patient-contact adhesive 30 may be omitted) or as part of a secondary, supplementary, or reinforcing method of fixation.

Figure 32:
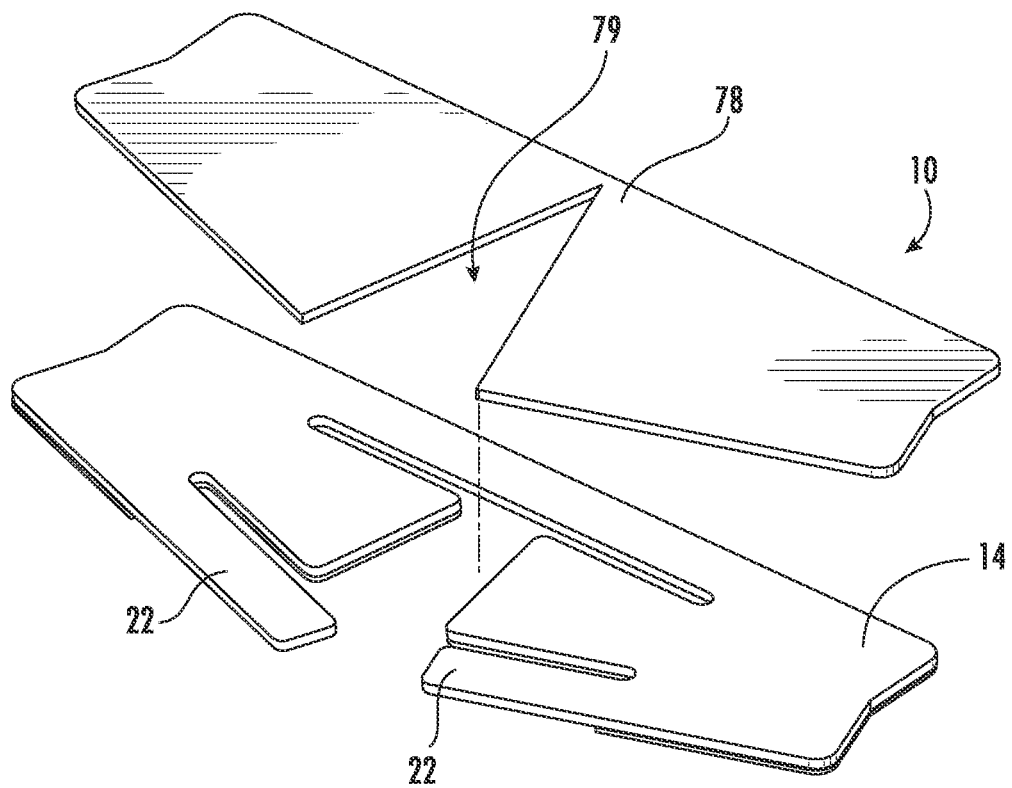
FIG. 32 is a partially exploded, top perspective view of a multistable tissue bridge including an upper cover sheet, in accordance with an embodiment of this disclosure.
Figure 33:
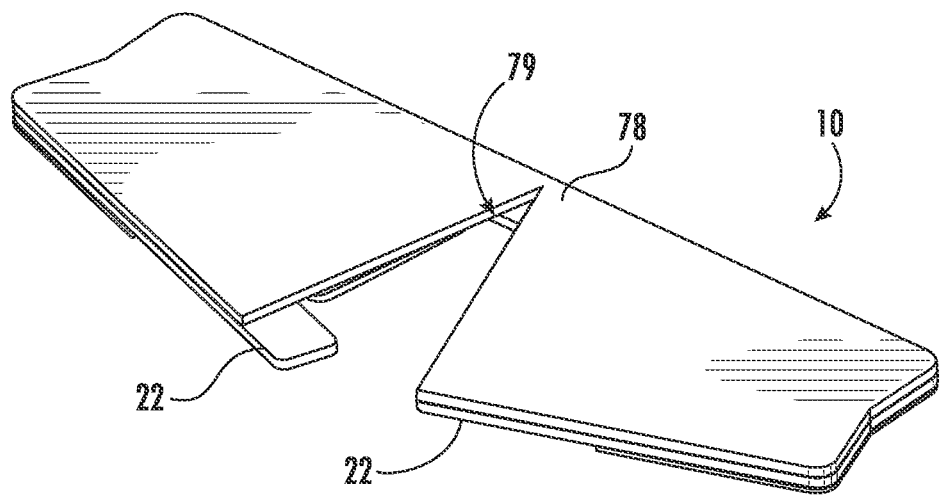
FIG. 33 depicts the tissue bridge of FIG. 32 in a further assembled configuration.
Figure 34:
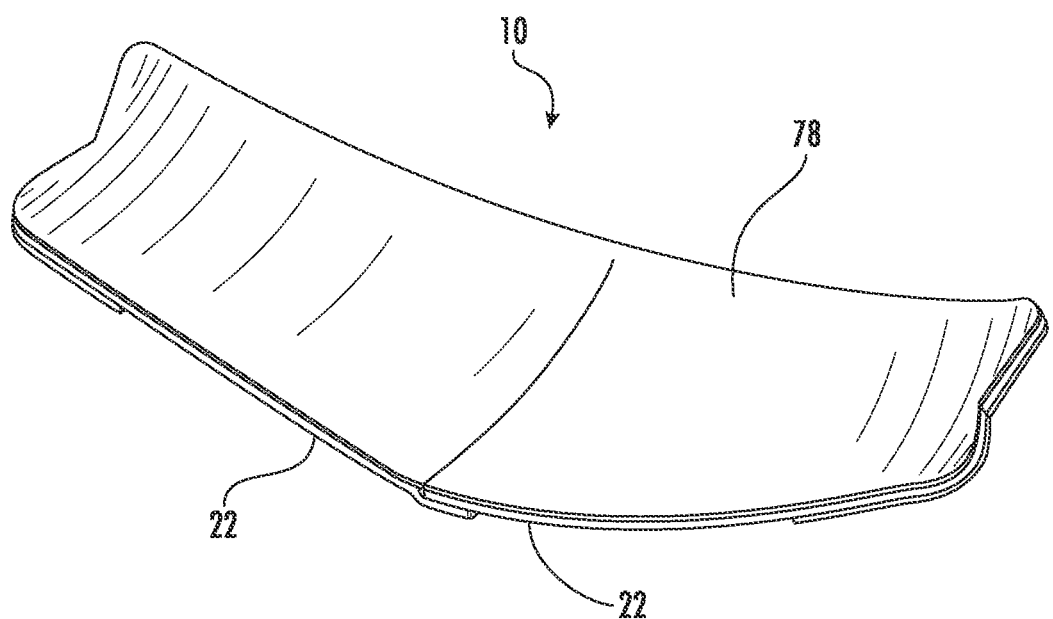
FIG. 34 is a top perspective view of the tissue bridge of FIG. 33 in its extended stable equilibrium configuration.

As depicted in FIGS. 32-34, and as will be discussed in greater detail below, one or more flexible webs or cover sheets 78 can be associated with or incorporated into one or more of the multistable tissue bridges 10 of this disclosure, for example by being mounted to the upper surface of one or more blanks 14, the multistable body 12, and/or the like through the use of an upper adhesive layer (see, e.g., upper adhesive layer 120 in FIG. 61) and/or other suitable attachment mechanism(s). In the example of FIGS. 32-33, the cover sheet 78 includes an opening or hole 79 (e.g., V-shaped hole). When the body 12 is formed by connecting the arm blank portions 22, adjacent edges of the cover sheet can come together to close the opening 79 previously defined between the adjacent edges of the cover sheet 78, for example as shown in FIG. 34.

At least partially reiterating from above, when arm blank portions 22 are present, they can be connected in any suitable manner. For example, inner end sections of the arm portions 22 can be superposed and connected (e.g., bonded) to one another by way of ultrasonic welding, laser welding, adhering, and/or in any other suitable manner. As another example, the cover sheet 78 and variations thereof can be mounted to the body 12 after the body has been fully formed into its concave-up or concave-down configuration. In this regard and reiterating from above, rather than being formed from blank(s), the body 12 can be an injection-molded or mechanically thermoformed, unitary (e.g., single-piece) article such that the strut portions 20 and multistable spanning structures 46 can be formed together as a single article from an injection-moldable or thermoformable material, or the like. The bodies 12 and tissue bridges 10 can be formed from laminated structures and other suitable materials. As will be discussed in greater detail below, the one or more struts 22 can be formed separately from the spanning structure 46, and thereafter the strut(s) can be mounted to the spanning structure.

Figure 35:
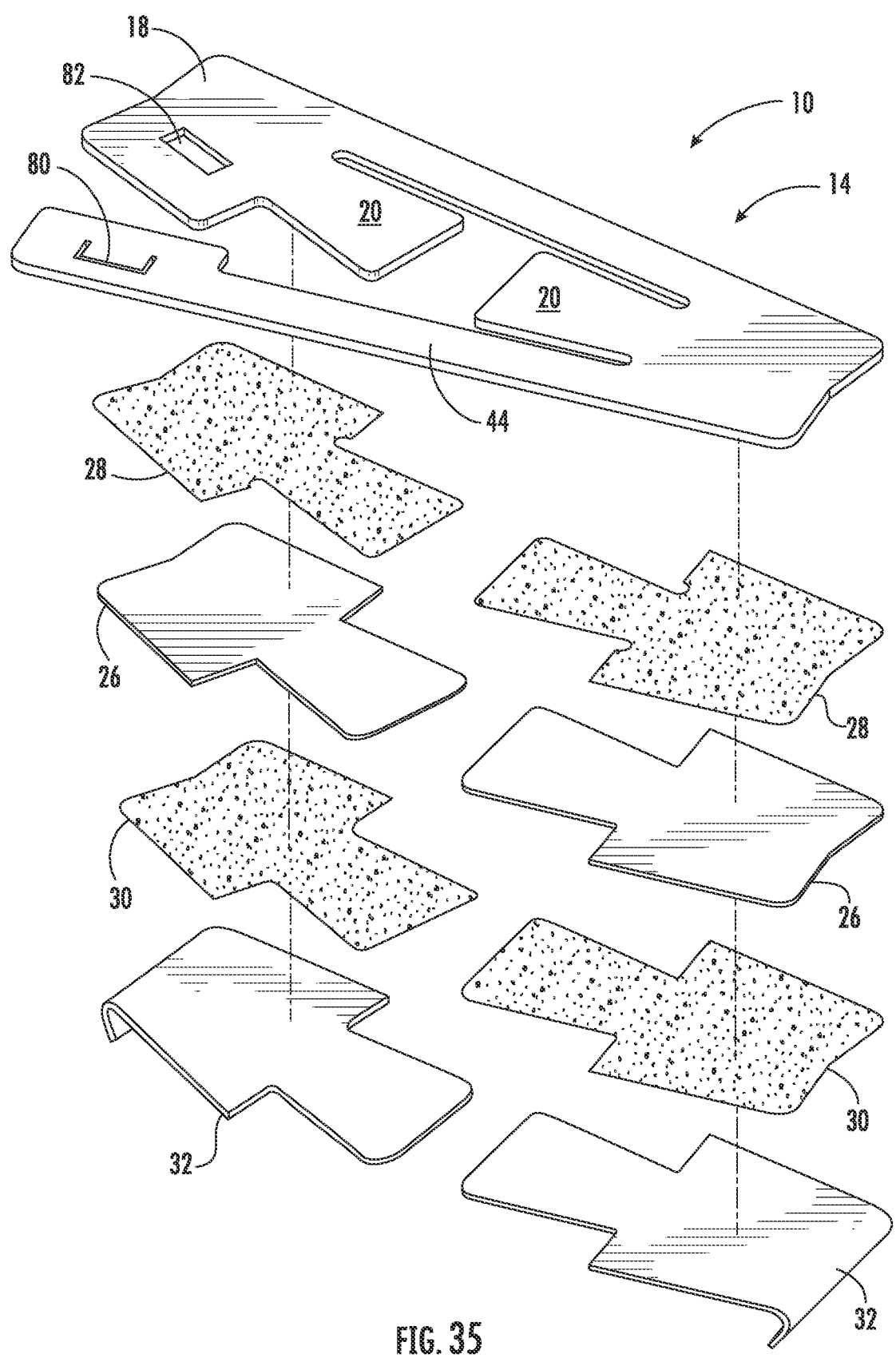
FIG. 35 is an exploded, top perspective view of a multistable tissue bridge in accordance with an embodiment of this disclosure.
Figure 36:
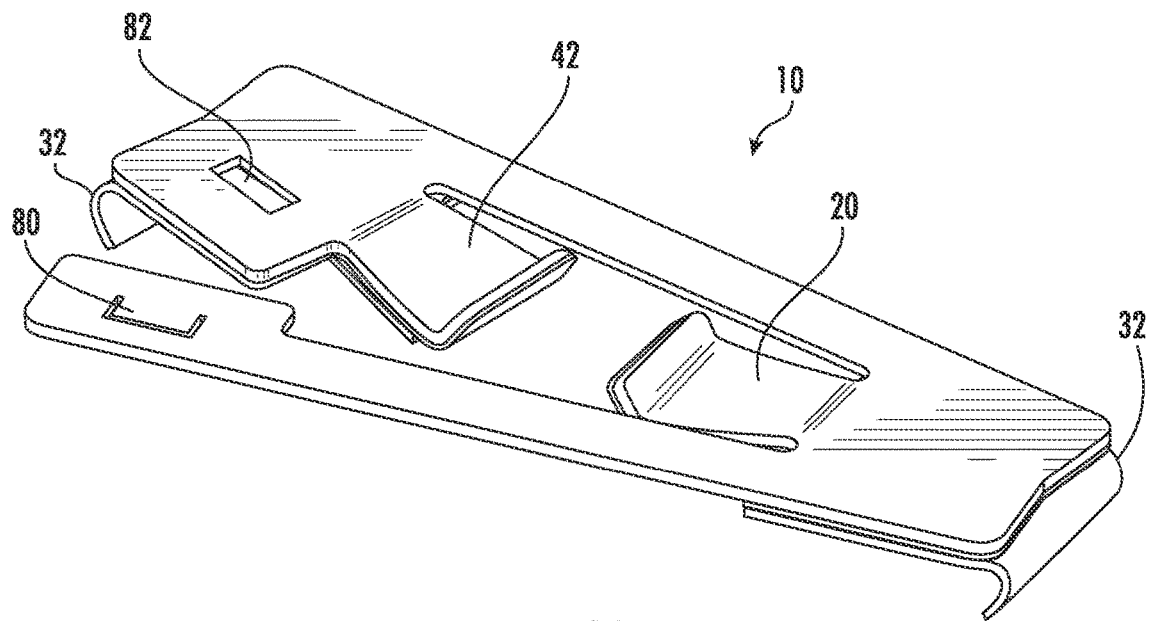
FIG. 36 is a partially assembled, top perspective view of the tissue bridge of FIG. 35, wherein portions of the struts are angled (e.g., inclined).
Figure 37:
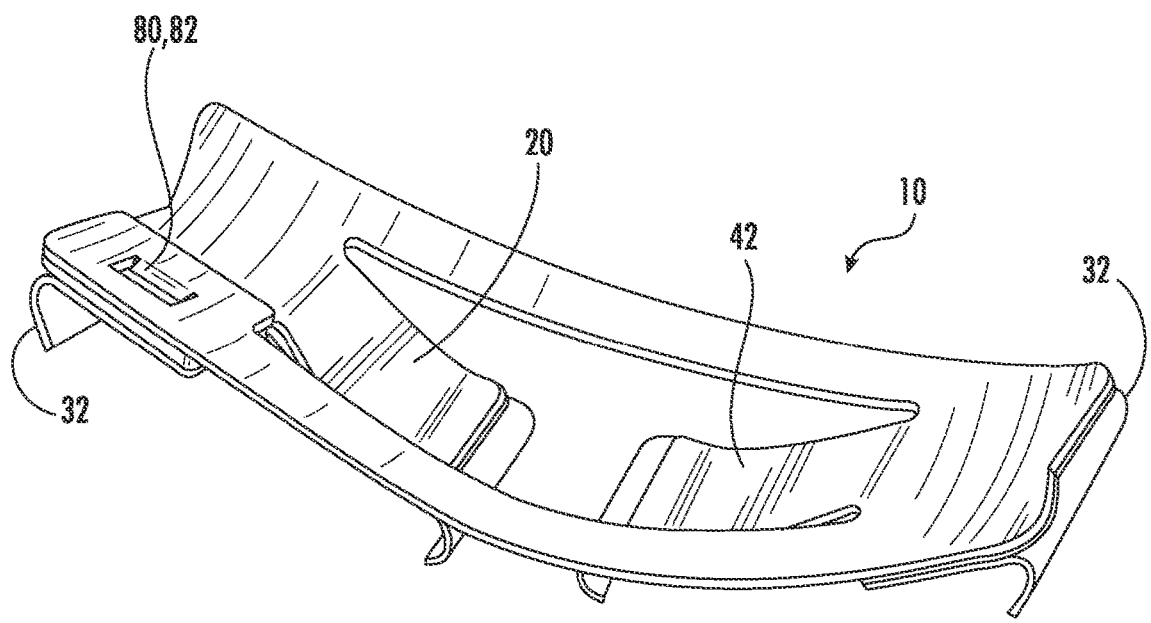
FIG. 37 is a top perspective view of the tissue bridge of FIG. 36 in its extended stable equilibrium configuration.

At least partially reiterating from above, erecting one or more blanks 14 to form the multistable body 12 of a multistable (e.g., symmetrically bistable or asymmetrically bistable) tissue bridge 10 can include superpositioning and connecting together at least one pair of arm portions 22. As a more general example, the erecting or assembling can include superpositioning and connecting together other suitable portions of the one or more blanks 14 or multistable spanning structures 46 at connection zones. Referring to FIGS. 35-37, such connecting can include connecting an end portion of an arm 44 to an end portion 18 by way of inserting a tab 80 into a hole or slot 82, and/or the arm 44 and the end portion 18 can be connected to one another using any other suitable mechanisms. Alternatively, the superposing and connecting can be replaced by edge-to-edge connecting by way of one or more suitable seams (e.g., welding (e.g., laser welding), adhering (e.g., with adhesive and/or adhesive tape), injection molding (e.g., insert molding), or other suitable seaming together) and/or other suitable attachment mechanisms.

Figure 38:
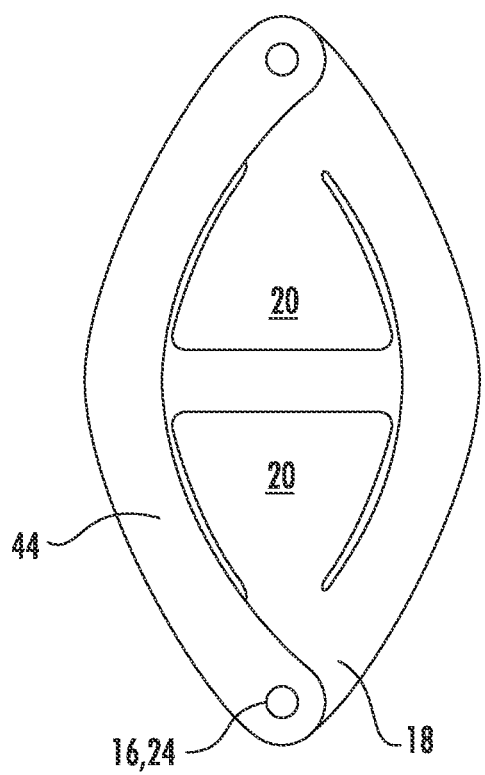
FIG. 38 is a schematic top view of a multistable body or tissue bridge in accordance with another embodiment of this disclosure.
Figure 39:
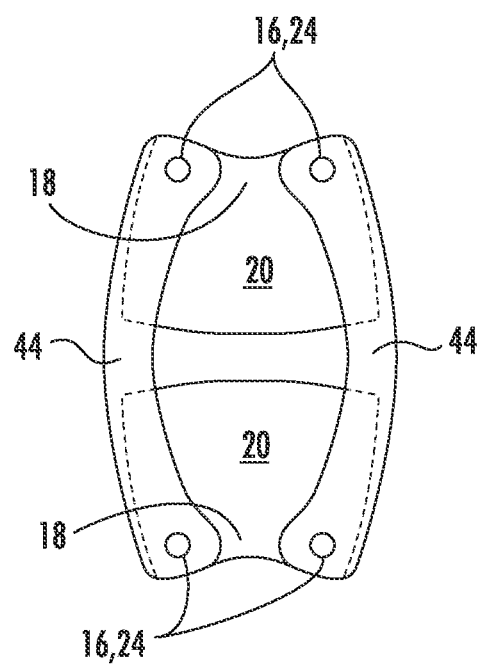
FIG. 39 is a top view of a multistable body or tissue bridge in accordance with another embodiment of this disclosure.

As another example of such connecting, FIG. 38 depicts that an end portion of an arm 44 can be connected to an end portion 18 by way of at least one hole 24 and at least one peg fastener 16. As a further example, FIG. 39 depicts that such connecting can include connecting end portions of arms 44 to end portions 18 by way of holes 24 and peg fasteners 16. Reiterating from above, the holes 24 and peg fasteners 16 can be supplemented with and/or replaced by any suitable connecting mechanisms. Also reiterating from above, rather than being formed from blank(s), the body 12 can be an injection-molded or mechanically thermoformed, unitary (e.g., single-piece) article such that the strut portions 20 and multistable spanning structures 46 can be formed together as a single article from an injection-moldable or thermoformable material, or the like. The bodies 12 and tissue bridges 10 can be formed from laminated structures and other suitable materials.

Figure 40:
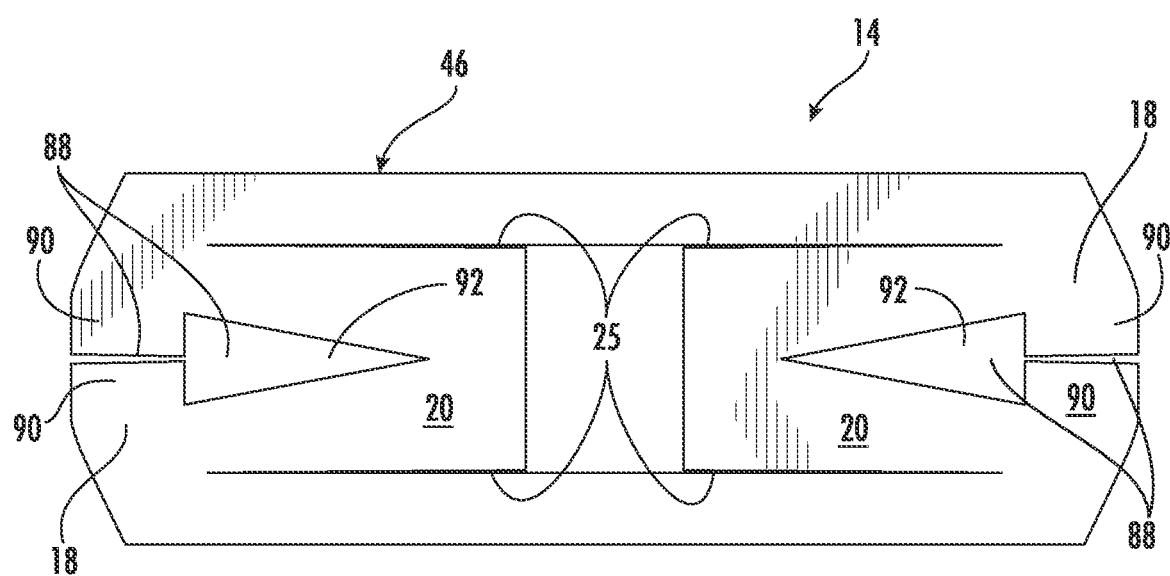
FIG. 40 is an isolated top view of a blank for being formed into or incorporated into a multistable tissue bridge in accordance with an embodiment of this disclosure.

Referring to FIGS. 40-45, the erecting of at least one blank 14 (FIG. 40) to form a multistable body 12 (FIGS. 41-45) of a multistable tissue bridge 10 can include superpositioning and connecting together other portions of the multistable spanning structures 46. Referring to FIG. 40, the end portions 18 and one or more strut portions 20 include cuts 88 (e.g., slits, holes, cutouts, and/or respective gaps) that define pairs of tabs 90 in the end portions and tapered holes 92 in the strut portions. The multistable body 12 of FIGS. 41-45 can be formed by causing relative movement between the adjacent tabs 90 so that they become superposed with one another. The superposed tabs 90 can be fixedly connected to one another using fasteners, adhesive material, heat sealing, welding, and/or any other suitable fastening mechanism. The configurations of the cuts 88, tabs 90, holes 92, and/or associated superpositioned portions can be adjusted in a predetermined manner to tune the operability of (e.g., the multistability of) the associated multistable body 12 and tissue bridge 10. Alternatively, the cuts 88 can be wider than depicted in the drawings and the superposing and connecting can be replaced by edge-to-edge connecting by way of one or more suitable seams (e.g., welding (e.g., laser welding), adhering (e.g., with adhesive and/or adhesive tape), injection molding (e.g., insert molding), or other suitable seaming together) and/or other suitable attachment mechanisms.

Figure 41:
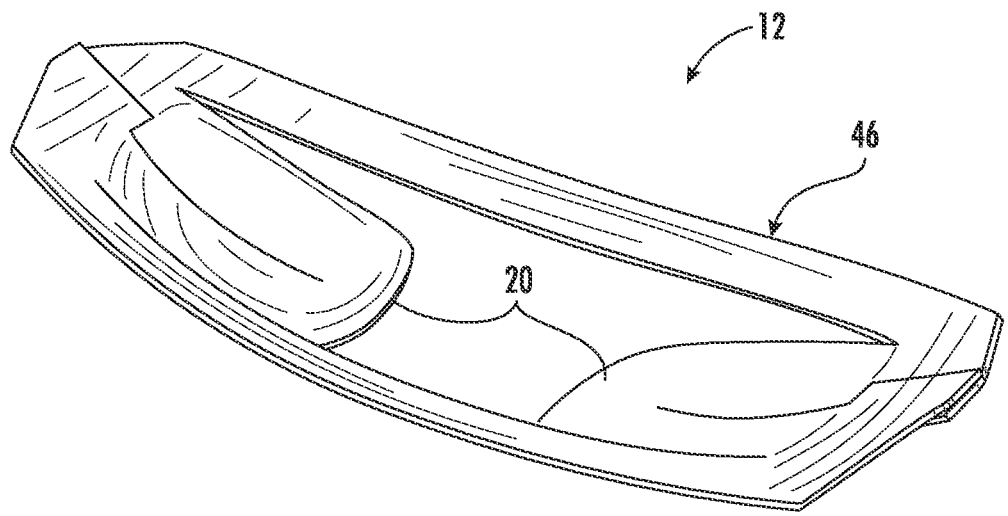
FIG. 41 is a top perspective view of a multistable body or tissue bridge formed from the blank of FIG. 40, wherein flexible, multistable strut portions of the body are in their concave-up stable equilibrium configurations, and the multistable spanning structure that connects the struts to one another is in its concave-up stable equilibrium configuration.
Figure 42:
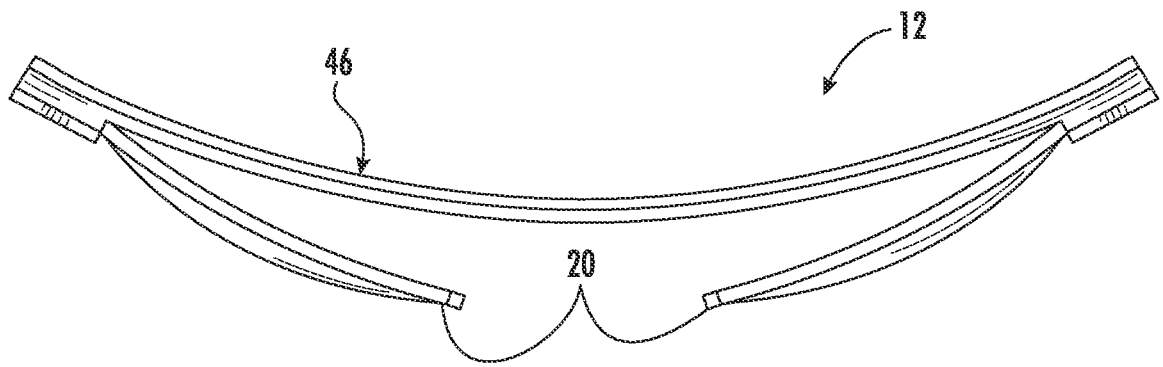
FIG. 42 is a front view of the configuration of FIG. 41.
Figure 43:
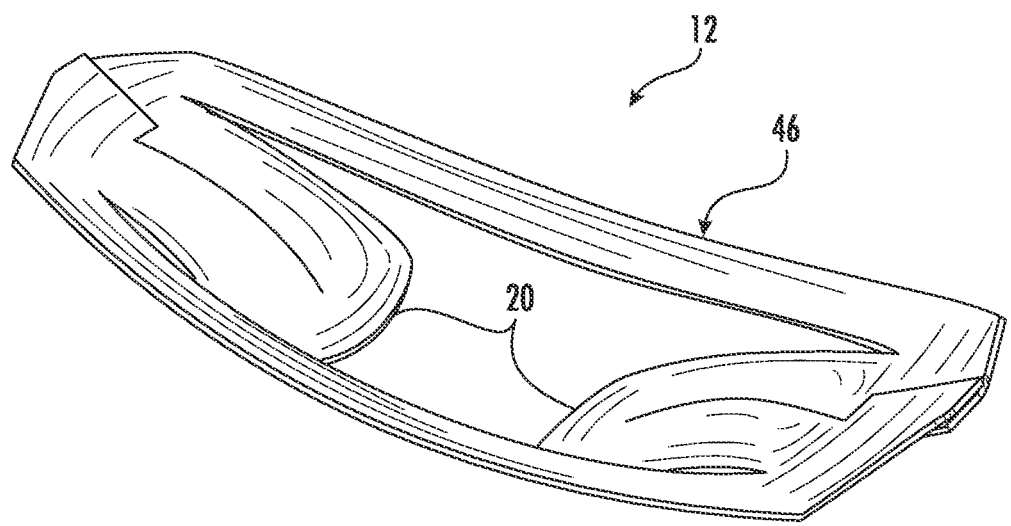
FIG. 43 is a top perspective view of the multistable body or tissue bridge formed from the blank of FIG. 40 in its extended stable equilibrium configuration, wherein the multistable spanning structure is in its concave-up stable equilibrium configuration, and the flexible, multistable struts are in their concave-down stable equilibrium configurations.
Figure 44:
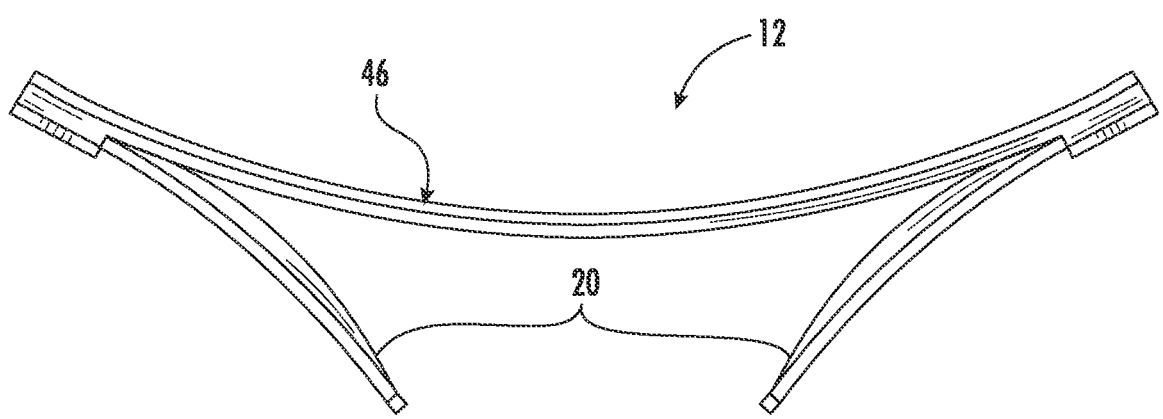
FIG. 44 is a front view of the configuration of FIG. 43.
Figure 45:
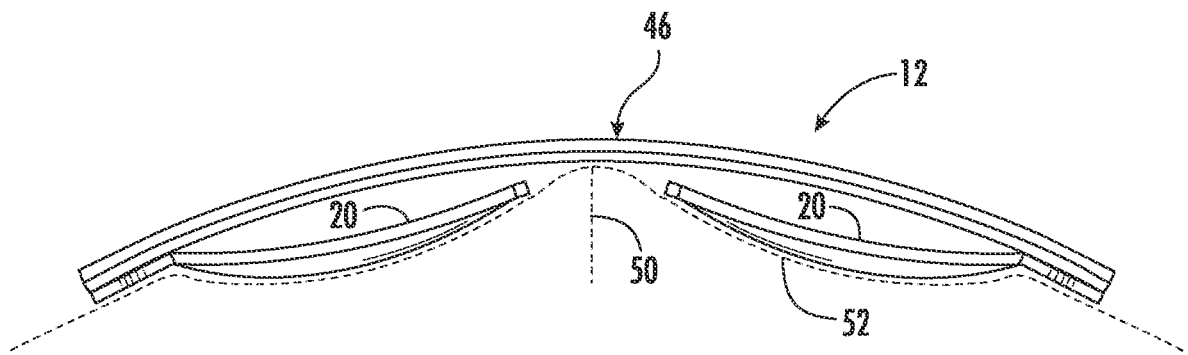
FIG. 45 is a front view of the multistable body or tissue bridge formed from the blank of FIG. 40 in its retracted stable equilibrium configuration, wherein an everted wound is schematically depicted with dashed lines, in accordance with an embodiment of this disclosure.

Different embodiments of the tissue bridge 10 can have multistable (e.g. bistable) structure/configurations in different sections of the device. As an example, in addition to or independent of a spanning structure 48 having such multistable (e.g. bistable) structure/configurations, the one or more struts 42 can have multistable (e.g. bistable) structure/configurations. For example, FIGS. 41 and 42 depict the multistable tissue bridge or body 12 formed from the blank 14 of FIG. 40 with the one or more struts 20 in their concave-up stable equilibrium configurations and the multistable spanning structure 46 in its concave-up stable equilibrium configuration. FIGS. 43 and 44 depict the multistable body 12 formed from the blank 14 of FIG. 40 in its extended stable equilibrium configuration, wherein the multistable spanning structure 46 is in its concave-up stable equilibrium configuration, and the one or more struts 20 are in their concave-down stable equilibrium configurations. FIG. 45 depicts the multistable body 12 formed from the blank of FIG. 40 in its retracted stable equilibrium configuration, wherein the multistable spanning structure 46 is in its concave-down stable equilibrium configuration, the one or more struts 20 are in their concave-up stable equilibrium configurations, and dashed lines schematically depict everted tissue 52 associated with a scar or wound 50.

Figure 46:
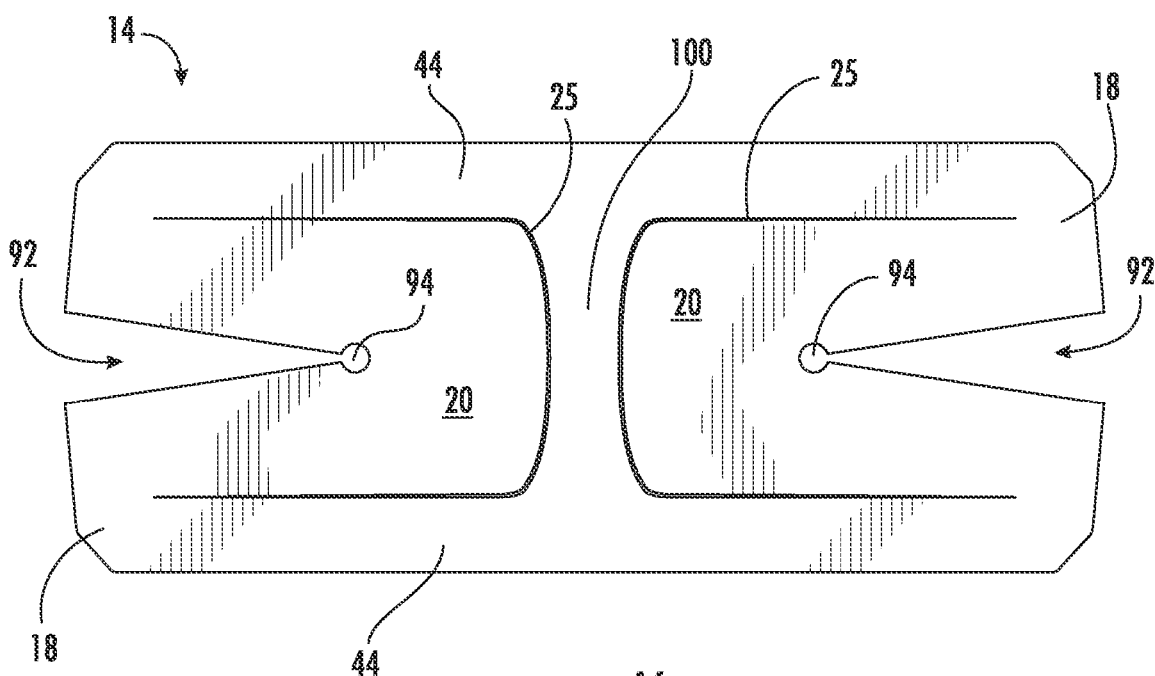
FIG. 46 is an isolated top view of a blank for being formed into or incorporated into a multistable tissue bridge in accordance with an embodiment of this disclosure.

As further examples for the above and below-discussed embodiments in which both the spanning structure 46 and at least one strut 20 have multistable (e.g. bistable) configurations, the shift or transition between the configurations of the different sections may occur independently, essentially contemporaneously, sequentially, and/or exclusively (e.g., one or more of the multistable (e.g. bistable) sections may remain in a single configuration). For example, in the embodiment shown in FIGS. 41-45, the multistable (e.g. bistable) spanning structure 46 may undergo transposition from its concave-up stable equilibrium configuration to its concave-down stable equilibrium configuration during the course of application of the tissue bridge 10 onto tissue, while one or both of the multistable (e.g. bistable) strut sections 20 may remain in either of their stable equilibrium configurations during the course of application, without change in configuration in relationship to itself FIGS. 46-50 depict an embodiment like the embodiment of FIGS. 40-45 (e.g., including both structures and associated methods), except for variations noted and variations that will be apparent to those of ordinary skill in the art. Referring to FIG. 46, the tapered holes 92 in the one or more struts 20 can extend through the end portions 18. The inner ends of the tapered holes 92 can terminate at circular hole portions 94 or other suitable features that seek to reduce strain in the material that forms the strut 20 when the blank 14 is erected and/or the tissue bridge 10 is in use. As depicted in FIGS. 46-50, the arms 44 can be connected by at least one crossmember 100 (e.g., a central spanning section). The erecting of the blank 14 (FIG. 46) to form the multistable body 12 (FIGS. 47-50) can include superpositioning and connecting together the margins of the blank 14 that are adjacent to, and extend along, the holes 92. Alternatively, the tapered holes 92 may be wider than depicted in the drawings and the superposing and connecting can be replaced by edge-to-edge connecting by way of one or more suitable seams (e.g., welding (e.g., laser welding), adhering (e.g., with adhesive and/or adhesive tape), injection molding (e.g., insert molding), or other suitable seaming together) and/or other suitable attachment mechanisms. A variety of differently configured blanks 14, struts 20, arms 44, holes 92, 94 and other features are within the scope of this disclosure. For example and at least partially reiterating from above, rather than being formed from blanks 14, the bodies 12, or variations thereof, may be formed through thermoforming, 3D printing, injection molding, or in any other suitable manner.

Figure 47:
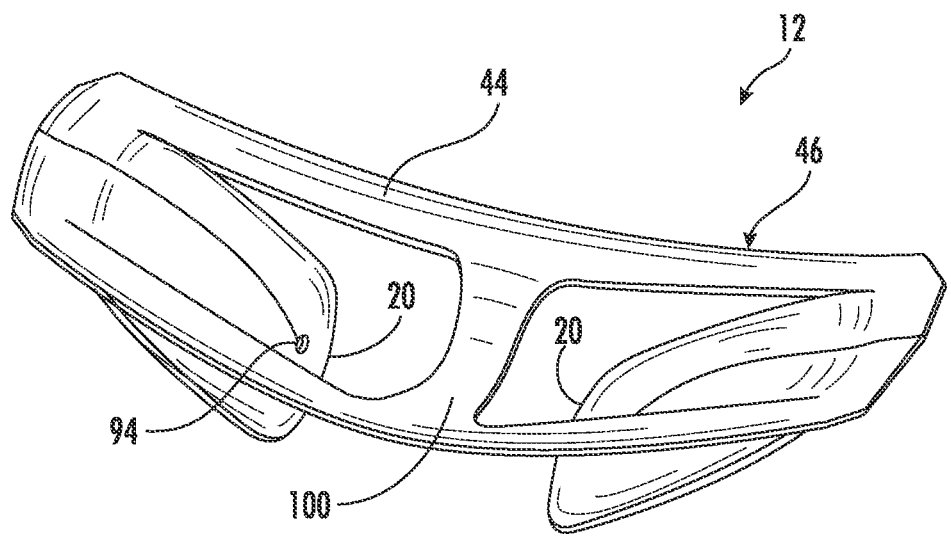
FIG. 47 is a top perspective view of a multistable body or tissue bridge formed from the blank of FIG. 46 in its extended stable equilibrium configuration.
Figure 48:
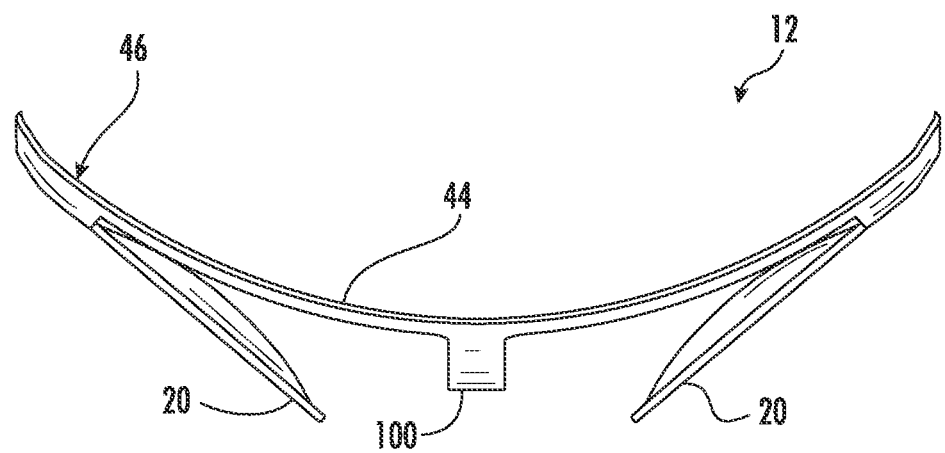
FIG. 48 is a front view of the configuration of FIG. 47.
Figure 49:
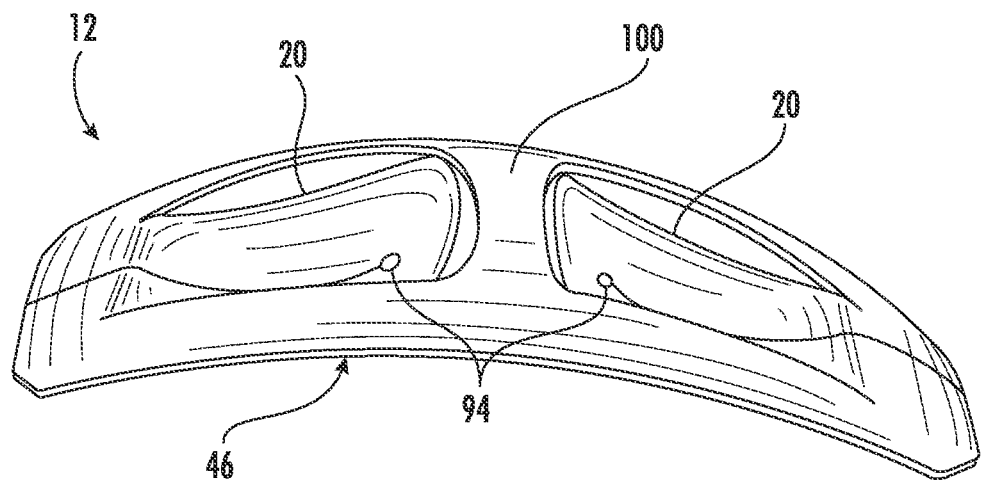
FIG. 49 is a top perspective view of a multistable body or tissue bridge formed from the blank of FIG. 46 in its retracted stable equilibrium configuration.
Figure 50:
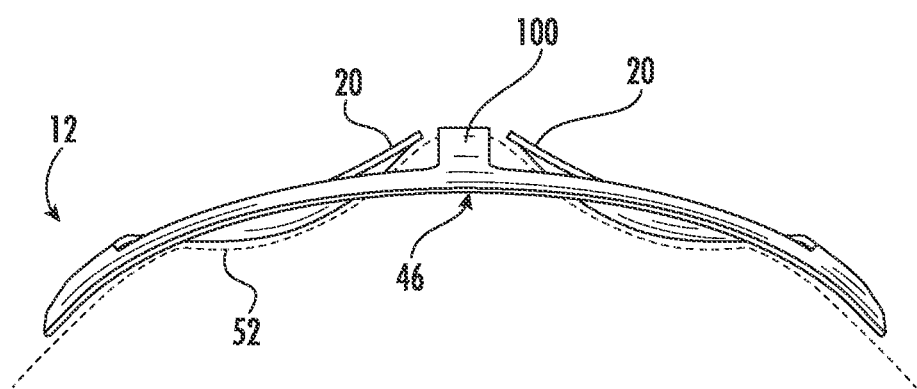
FIG. 50 is a front view of the configuration of FIG. 49, wherein an everted wound is schematically depicted with dashed lines.

FIGS. 47 and 48 depict the multistable tissue bridge or body 12 formed from the blank 14 of FIG. 46 in its extended stable equilibrium configuration, wherein the multistable spanning structure 46 is in its concave-up stable equilibrium configuration, and the one or more struts 20 are in their concave-down stable equilibrium configurations. FIGS. 49 and 50 depict the multistable body 12 formed from the blank of FIG. 46 in its retracted stable equilibrium configuration, wherein the multistable spanning structure 46 is in its concave-down stable equilibrium configuration, and the one or more struts 20 are in their concave-up stable equilibrium configurations. Dashed lines in FIG. 50 schematically depict everted tissue 52 associated with a scar or wound 50.

The spacer or crossmember 100 (FIGS. 47-50) can be configured to force apart central portions of the arms 44 in a manner that at least partially causes the spanning structure 46 to function as a multistable spanning structure. For example, the length, stiffness, and/or other characteristics of the crossmember 100, or the like, can be adjusted to tune the multistability, as will be discussed in greater detail below. As one example that can be best understood with reference to FIG. 46, the crossmember 100 can be enlarged to extend at least partially over, for example completely over, one or more of the strut portions 20, and the crossmember 100 can optionally further extend at least partially over, for example completely over, one or more of the end portions 18. The crossmember 100 can be configured to extend along and cover (e.g., at least partially cover) the underlying scar or wound 50 so that the crossmember at least partially protects the scar or wound 50 from external force. As another example, the crossmember 100 can have or otherwise provide a therapeutic environment for the scar or wound 50, for example by supporting a pad, silicone, and/or other suitable component for treating the wound/scar 50 (e.g., medicated, drug-eluting, wicking, and/or having other suitable characteristics).

Figure 51:
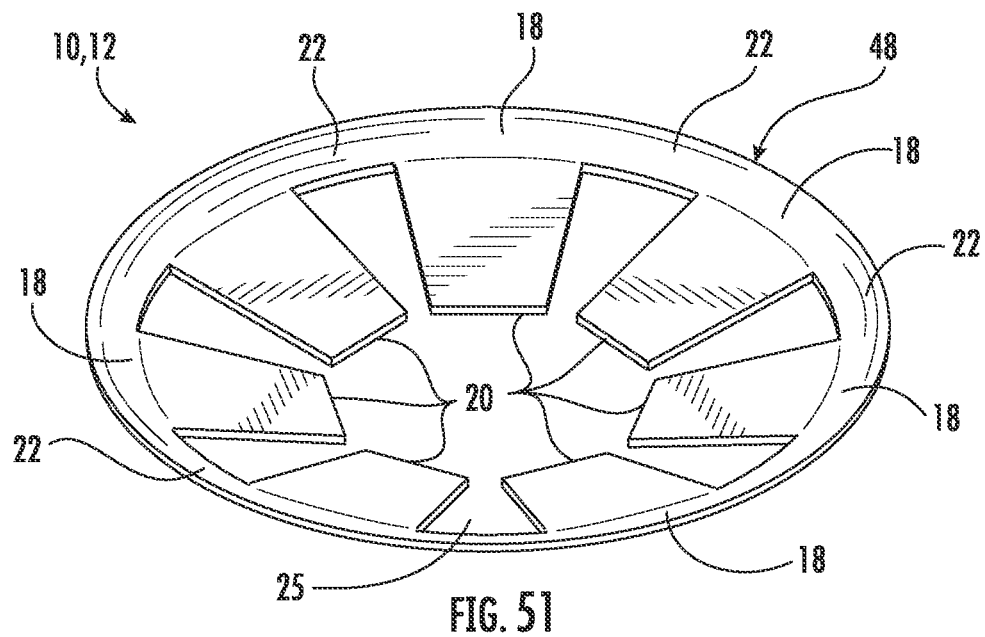
FIG. 51 is a top perspective view of a multistable body or tissue bridge in its extended stable equilibrium configuration, in accordance with another embodiment of this disclosure.
Figure 52:
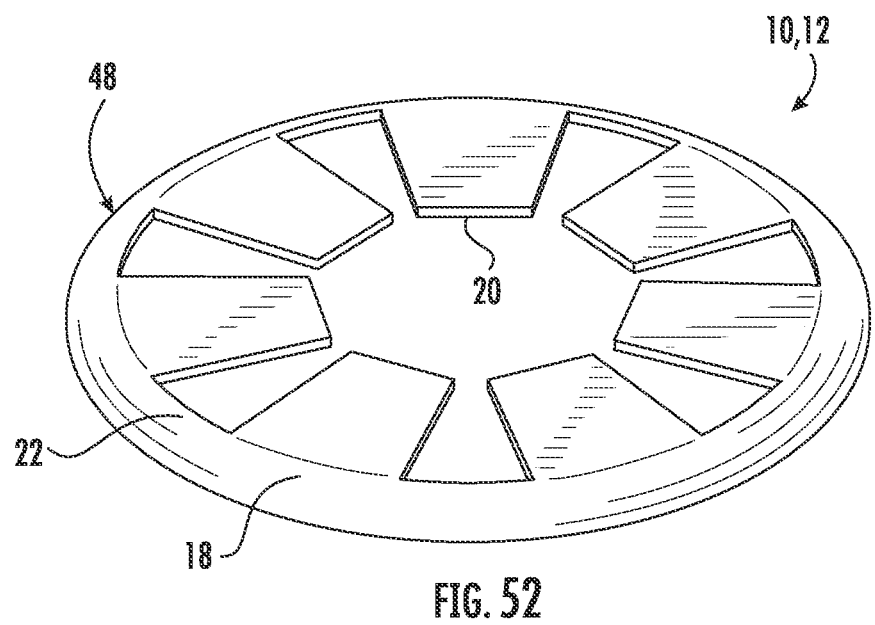
FIG. 52 is a top perspective view of the multistable body or tissue bridge of FIG. 51 in its retracted stable equilibrium configuration.

The blanks 14 and multistable bodies 12 can include any suitable number of the end portions 18, strut portions 20, arm portions 22, and/or cuts 25 (e.g., slits, holes, cutouts, and/or respective gaps) in any suitable configurations. In this regard and as one of numerous possible examples, FIGS. 51 and 52 depict a multistable (e.g., symmetrically bistable or asymmetrically bistable) body 12 or tissue bridge 10 in its extended and retracted stable equilibrium configurations, respectively. In the extended stable equilibrium configuration depicted in FIG. 51, the multistable spanning structure 48 is in its concave-up stable equilibrium configuration so that the multistable spanning structure 48 includes or defines crosswise arcs and at least a portion of an inverted dome (see, e.g., FIGS. 5 and 6). Also in the extended stable equilibrium configuration depicted in FIG. 51, the struts 42 are inclined downwardly. In the retracted stable equilibrium configuration depicted in FIG. 52, the multistable spanning structure 48 is in its concave-down stable equilibrium configuration so that the multistable spanning structure 48 includes or defines crosswise arcs and at least a portion of a dome (see, e.g., FIGS. 7 and 8).

In the example depicted in FIGS. 51 and 52, the multistable body 12 or tissue bridge is annular or more specifically circular, and the device can be characterized as including seven of each of the end portions 18, strut portions 20, and arm portions 22, although different overall shapes and numbers of features are within the scope of this disclosure. For example, the shapes and sizes of the multistable bodies 12, the shapes and sizes of one or more features of the multistable bodies (e.g., end portions 18, strut portions 20, and portions 22), and the numbers of one or more features can be adjusted in a predetermined manner to tune the operability of the multistable body 12 and associated tissue bridge 10.

In at least some of the above examples, the end portions 18, strut portions 20, and arm portions 22 are integral portions of one or more devices. Alternatively, the end portions 18, strut portions 20, and/or arm portions 22 can be formed separately from one another and thereafter be respectively mounted to one another. For example, the blank 14 depicted in FIG. 53 includes end portions 18 and arm portions 22 without including strut portions 20.

Figure 53:
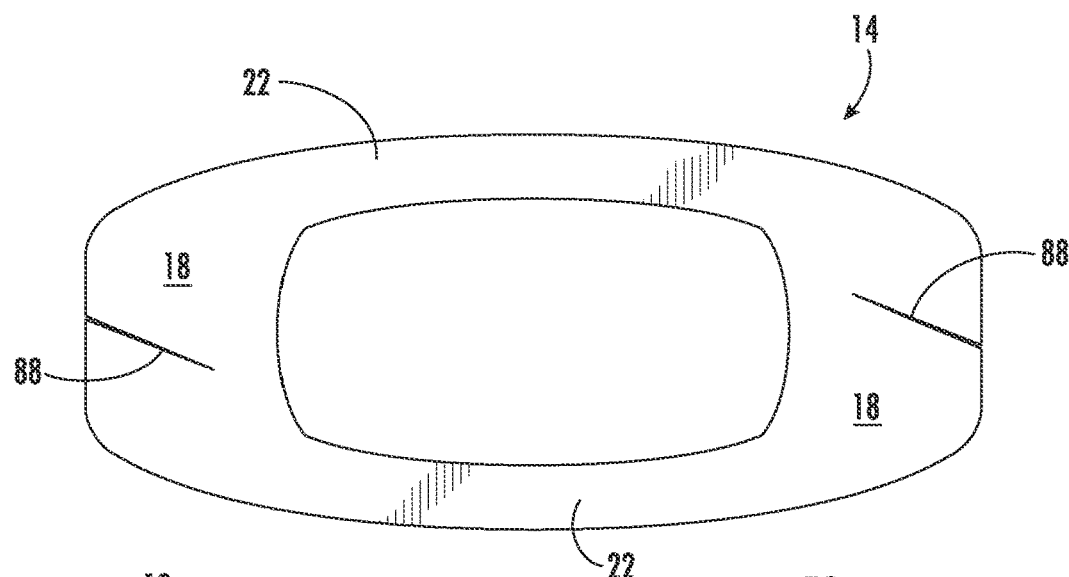
FIG. 53 is an isolated top view of a blank for being incorporated into a multistable tissue bridge in accordance with an embodiment of this disclosure.
Figure 54:
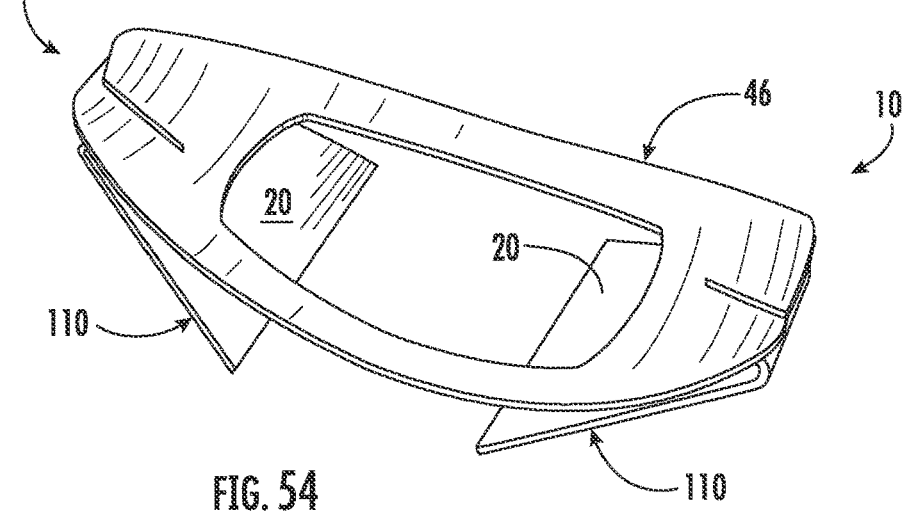
FIG. 54 is a top perspective view of a multistable body or tissue bridge including a multistable spanning structure formed from the blank of FIG. 53 and struts mounted to the spanning structure, in accordance with an embodiment of this disclosure.
Figure 55:
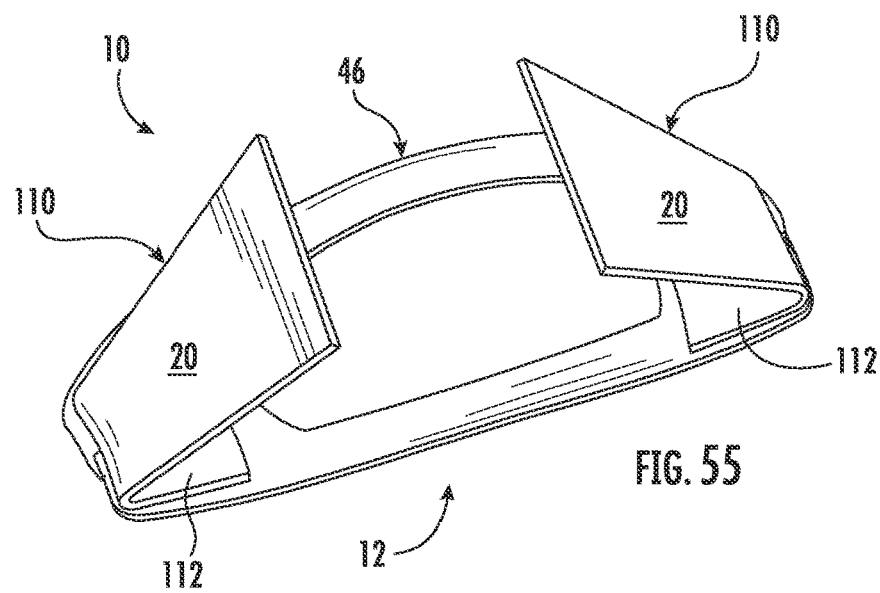
FIG. 55 is a bottom perspective view of the multistable body or tissue bridge of FIG. 54.

The blank of FIG. 53 can be erected to form the multistable spanning structure 46 of the multistable body 12 of FIGS. 54 and 55 by superpositioning and connecting together the margins of the blank 14 that are adjacent to, and extend along, the cuts 88 (e.g., slits) in the end portions 18. The multistable body 12 is in its extended stable equilibrium configuration in FIGS. 54 and 55. Alternatively, the cuts 88 can be wider than depicted in the drawings and the superposing and connecting can be replaced by edge-to-edge connecting by way of one or more suitable seams (e.g., welding (e.g., laser welding), adhering (e.g., with adhesive and/or adhesive tape), injection molding (e.g., insert molding), or other suitable seaming together) and/or other suitable attachment mechanisms. One or more strut assemblies 110 can be formed, for example, from blanks (not shown) including the strut portions 20 extending from mounting portions or tabs 112. The mounting tabs 112 or the like can be connected to the body end portions 18 using adhesive material, heat sealing, welding, and/or any other suitable fastening mechanism. The bend between the strut portions 20 and mounting tabs 112 can be formed, for example, by bending, thermoforming, stamping, or in any other suitable manner. The connecting of the mounting tabs 112 to the end portions 18 can occur simultaneously (e.g., substantially simultaneously) with (e.g., can facilitate or at least partially facilitate) the connecting together of the respective portions of the blank 14 that are adjacent to, and extend along, the cuts 88 in the end portions 18.

Reiterating from above, as compared to one another, different parts of the same tissue bridge 10 can have different characteristics (e.g., different stiffness, flexibility, and/or elasticity resulting from different thicknesses or volumes, different construction materials, and/or different manufacturing techniques) to affect the operability of (e.g., the multistability of) the tissue bridge. For example and referring to FIGS. 53-55, as compared to one another, the blank 14 and strut assemblies 110 can have different thicknesses (e.g., the blank 14 can be thinner than the blanks from which the strut assemblies 110 are formed, and the blank 14 and strut assemblies 110 can be formed of dissimilar materials (e.g., polycarbonate for the strut assemblies 110 and acrylonitrile butadiene styrene (ABS) for the blank 14). More generally, in a given tissue bridge 10, as compared to one another, the spanning structure 48 and struts 42 can have different thicknesses, can have different volumes, can be formed of dissimilar materials, and/or can be varied in other ways that affect the multistability of the tissue bridge.

Figure 56:
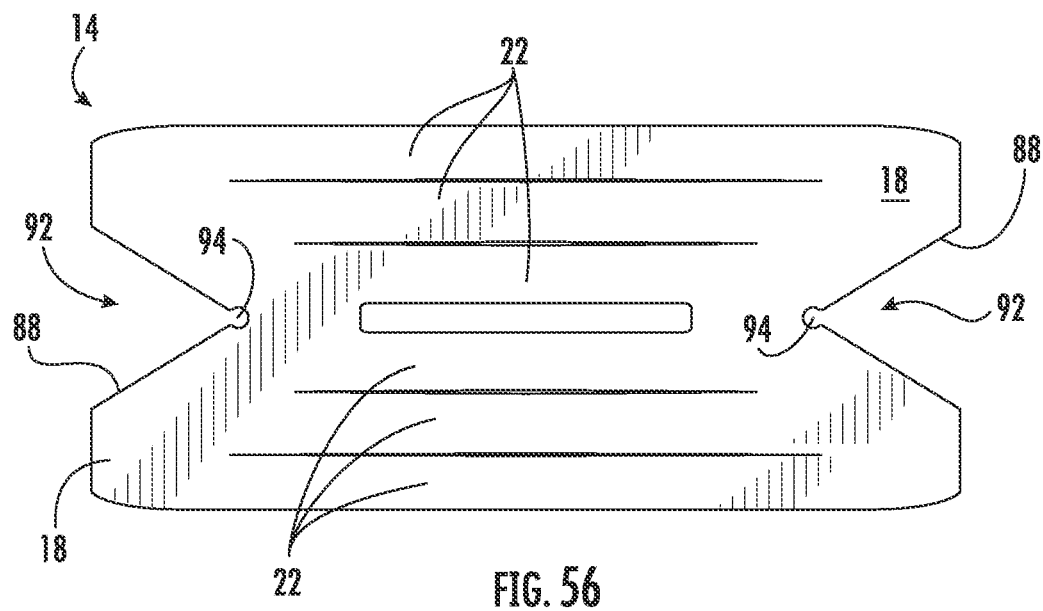
FIG. 56 is an isolated top view of a blank for being incorporated into a multistable tissue bridge in accordance with an embodiment of this disclosure.
Figure 57:
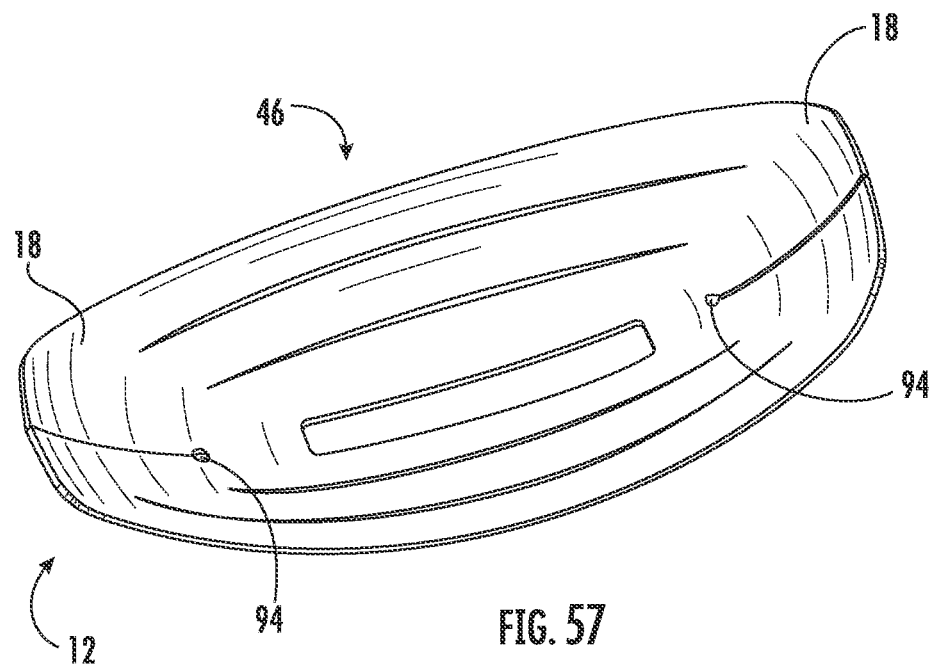
FIG. 57 is a top perspective view of a multistable spanning structure formed from the blank of FIG. 56.

FIG. 56 depicts another example of a blank 14 including end portions 18 and arm portions 22 without including strut portions 20. The blank of FIG. 56 can be erected to form the multistable spanning structure 46 of FIG. 57 by superpositioning and connecting together the margins of the blank 14 that are adjacent to, and extend along, the cuts 88 or holes 92 in the end portions 18. Alternatively, the superposing and connecting can be replaced by edge-to-edge connecting by way of one or more suitable seams (e.g., welding (e.g., laser welding), adhering (e.g., with adhesive and/or adhesive tape), injection molding (e.g., insert molding), or other suitable seaming together) and/or other suitable attachment mechanisms. The multistable spanning structure 46 of FIG. 57 is in its concave-up stable equilibrium configuration. One or more strut assemblies 110 (see, e.g., FIGS. 54 and 55) can be mounted to the body end portions 18 of FIG. 57, for example as discussed above.

FIG. 58 depicts a multistable spanning structure 46 similar to that of FIG. 57, with differently configured arms 22 and cuts or cutouts 25 configured for adjusting the operability of the multistable spanning structure. As other examples, FIGS. 59 and 60 respectively depict multistable tissue bridges 10 with differently configured end portions 18, arm portions 22, and cuts 25.

Figure 61:
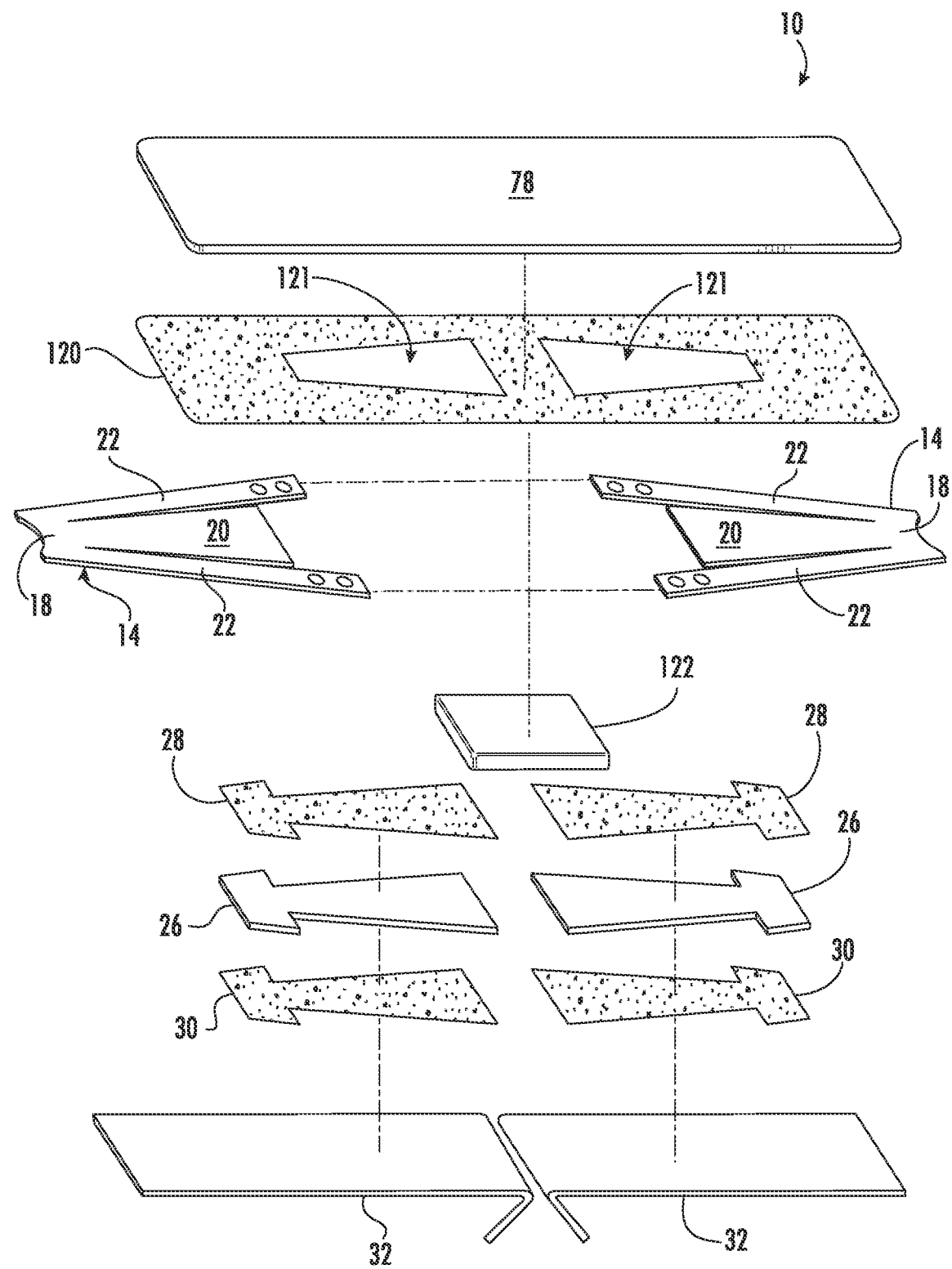
FIG. 61 is an exploded, top perspective view of another embodiment of a multistable tissue bridge including the first embodiment multistable body, or the like, and differently configured layers including, for example, a cover sheet.

FIG. 61 is an exploded, top perspective view of another embodiment of a multistable (e.g., symmetrically bistable or asymmetrically bistable) tissue bridge 10 that may include the first embodiment multistable body 12 and blanks 14, or the like, and an adhesive bandage, or the like. The adhesive bandage can include a flexible web or cover sheet 78 (e.g., polymer film, laminate, or bandage carrier material), upper adhesive layer 120, and pad 122 (e.g., gauze). The cover material 78 and upper adhesive 120, with or without a pad, can be generally in the form of, or can be, an adhesive bandage (e.g., in one example or version, the adhesive bandage can be conventional). The cover material 78 can be mounted by way of the upper adhesive 120 and/or other suitable fastening mechanism(s) to the upper surface of the multistable spanning structure 46 (e.g., end portions 18 and arm portions 22), so that the pad 122 is positioned in an opening or gap defined between the arms 22, 44. There can be voids or holes 121 in the upper adhesive 120 so that the strut portions 20 are not adhered to, and can move relative to, the cover sheet 78. As another example, the areas 121 can be portions of the adhesive 120 that have been rendered ineffective such that they cannot adhere to the strut portions 20. As a more specific example, the areas 121 can be schematically representative of one or more sheets or other suitable pieces of material that are adhered to the adhesive 120 and positioned between the adhesive 120 and the strut portions 20 in a manner that seeks to prevent the adhesive 120 from adhering to the strut portions 20, as will be discussed in greater detail below. As another example, the respective surfaces of the strut portions 20 can be at least partially coated with a substance to which the adhesive 120 will not adhere.

The cover material (e.g., carrier 78 and/or associated adhesive layer 120) can have various properties to vary the function of the tissue bridge 10. For example, the cover material can be waterproof, breathable, expandable, or have varied adhesive peel values, as may be required or desired for clinical use. Reiterating from above, rather than being formed from blank(s), the body 12 can be an injection-molded or mechanically thermoformed, unitary (e.g., single-piece) article such that the strut portions 20 and multistable spanning structure 46 can be formed together as a single article from an injection-moldable or thermoformable material, or the like. The bodies 12 and tissue bridges 10 can be formed from laminated structures and other suitable materials.

Figure 62:
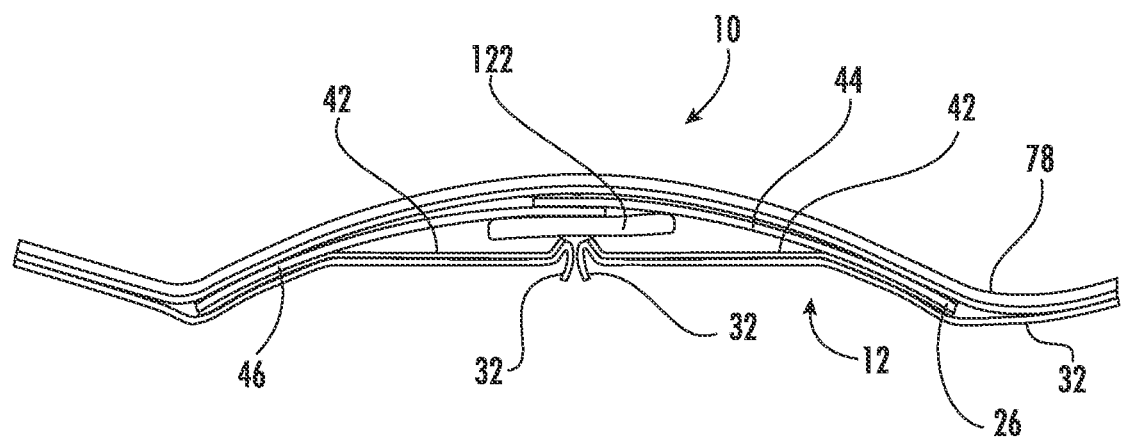
FIG. 62 is a front view of the tissue bridge of FIG. 61 in its retracted stable equilibrium configuration.

FIG. 62 depicts the tissue bridge 10 of FIG. 61 in its retracted stable equilibrium configuration. In the example depicted in FIG. 62, and referring also to FIG. 61, the opposite ends of the outer release liner 32, cover sheet 78, and upper adhesive layer 120 extend outwardly beyond the opposite ends of the multistable body 12, patient-contact carrier 26, inner adhesive 28, and patient-contact adhesive 30. The pad 122 may be omitted, the central portion of the upper adhesive layer 120 may be omitted, and/or at least central portions of the cover sheets 78 of this disclosure may be transparent or omitted (e.g., to define a "window" for facilitating venting and/or viewability of the scar or wound 50 (e.g., FIGS. 64 and 65)) after mounting the tissue bridge 10 to the tissue 52 adjacent the scar or wound.

Figure 63:
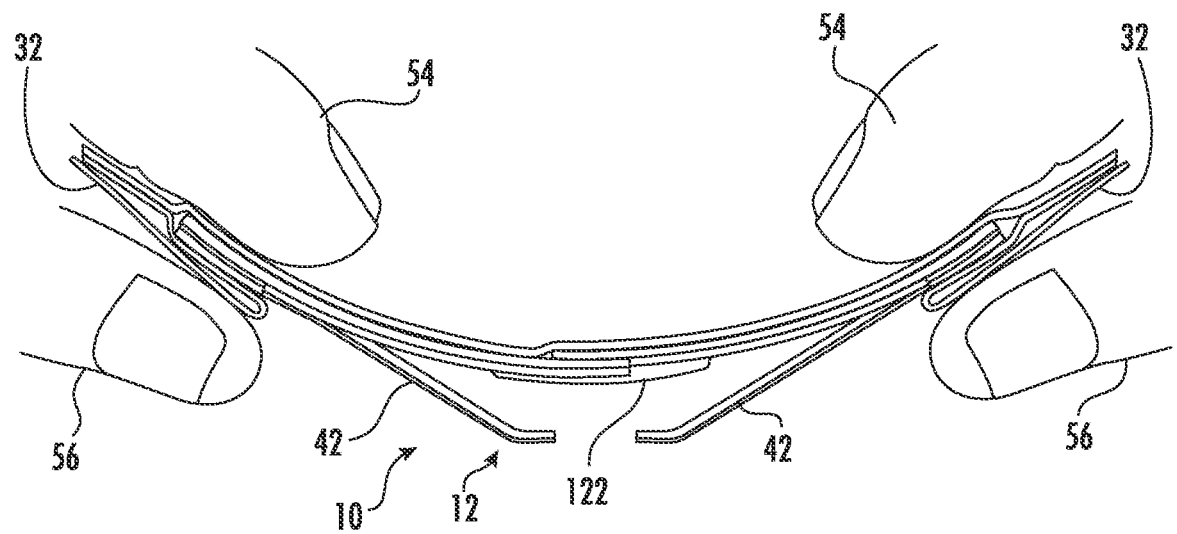

FIGS. 63-68 depict a sequence of steps of a method of applying the tissue bridge 10 of FIG. 62 to a scar or wound with a user's fingers 54 and thumbs 56, in accordance with an embodiment of this disclosure. In FIGS. 63 and 64, the tissue bridge 10 is in its extended stable equilibrium configuration. In FIG. 65, the tissue bridge 10 is in or proximate an intermediate or maximally unstable equilibrium configuration. In FIGS. 66-68 the tissue bridge 10 is in, or proximate, its retracted stable equilibrium configuration.

The central portions of the release liners 32 are shown in their partially removed configurations in FIGS. 63-66. Such partial removal of the release liners 32 seeks to prevent adherence or contamination of the patient-contact adhesive 30, e.g. by grasping fingers 54 and thumbs 56, as shown in FIGS. 63 and 64, or by a grasping instrument. The partial removal position of the release liners 32 can also prevent premature adherence of a lateral section of the patient-contact adhesive 30 to the skin 52, as shown in FIGS. 65 and 66. The partial removal of the release liners 32 can be aided by including in, or associating with, the release liners any one or more of tabs, loops, folds, varying-strength adhesive, textures, and/or release coatings. See, for example, U.S. Patent Application Publication Number 2014/0227483. FIGS. 67 and 68 schematically depict the release liners 32 being fully removed. Thereafter, the outer ends of the cover sheet 78 typically are pressed down.

At least partially reiterating from above, the tissue bridges 10, for example the tissue bridge depicted in FIG. 61, may not include patient-contact carriers 26 and inner adhesive 28, and other layers or features can be incorporated into the tissue bridges. For example, FIG. 69 depicts a multistable (e.g., symmetrically bistable or asymmetrically bistable) tissue bridge 10 similar to the tissue bridge of FIG. 61, except, for example, for omitting the patient-contact carrier 26 and inner adhesive 28, for including a differently configured (e.g., cross-shaped) pad 122, and further including one or more medicinal substances 130 (e.g., an elongate strip or bead of silicone, piece of silicone sheet, and/or the like) mounted to, or otherwise associated with, the pad 122.

Figure 69:
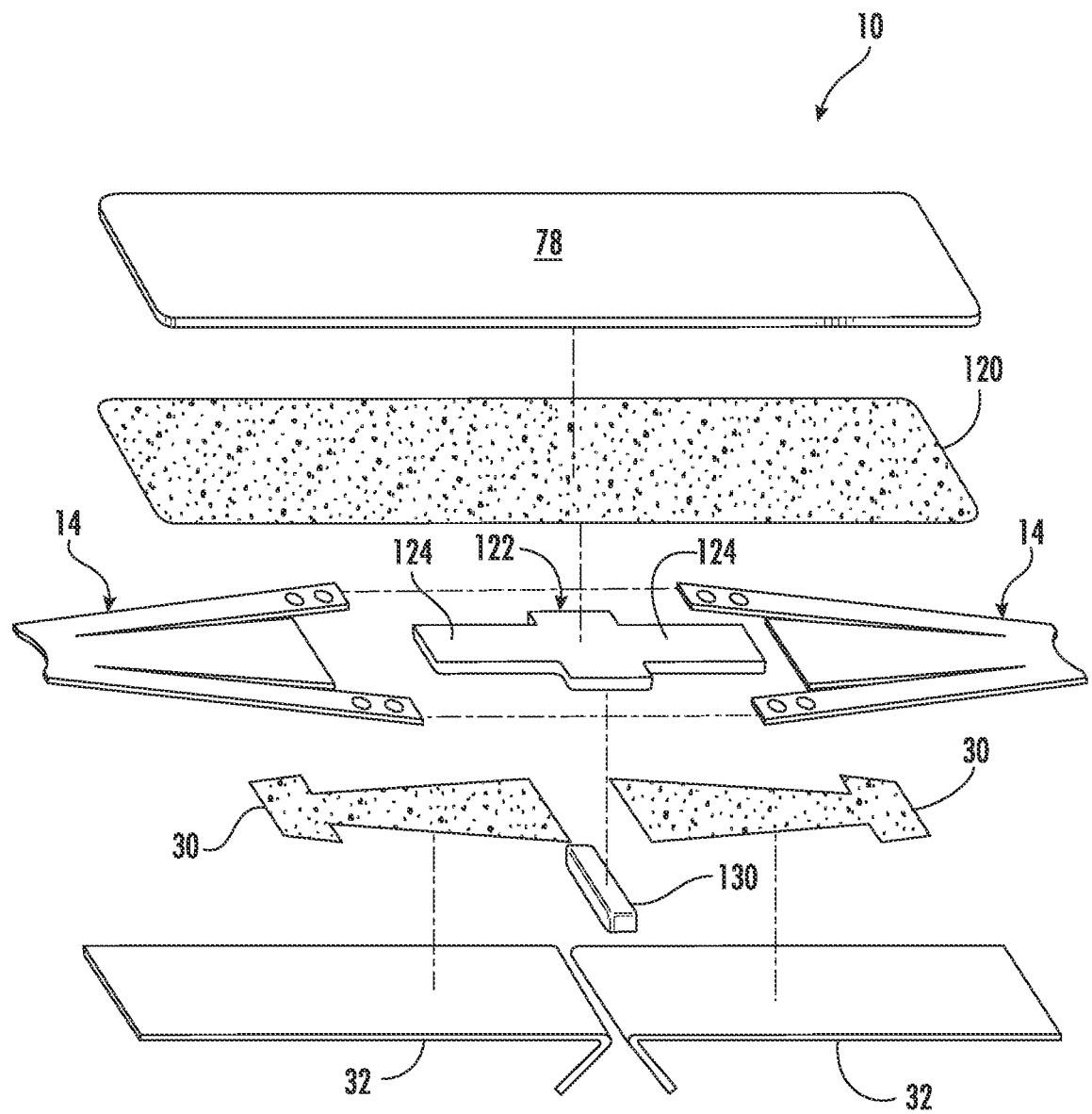
FIG. 69 is an exploded, top perspective view of an embodiment of a multistable tissue bridge having similarities to the embodiment of FIG. 62.
Figure 70:
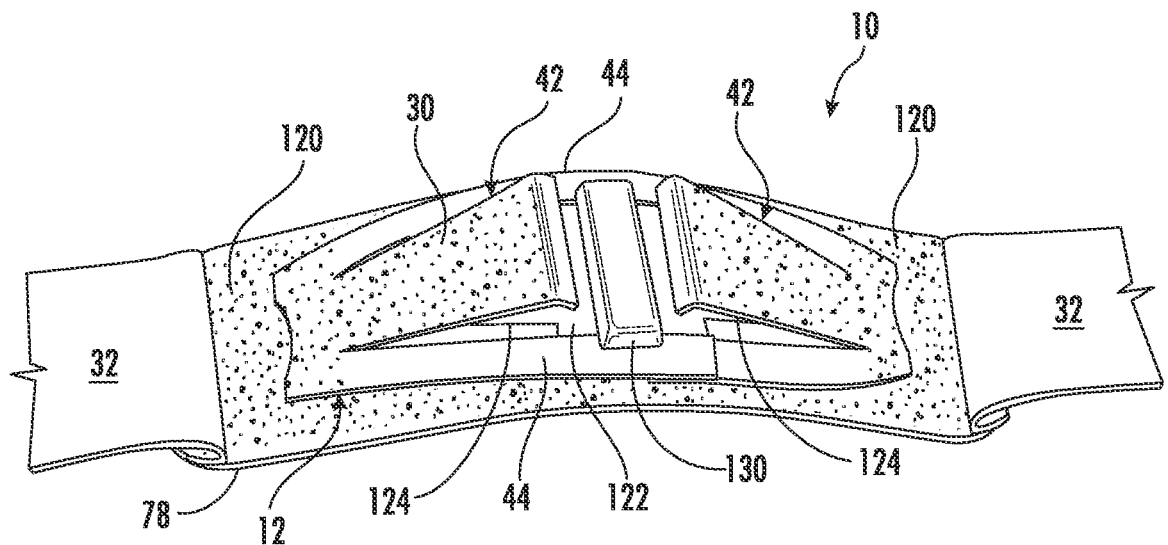
FIG. 70 is an assembled, bottom perspective view of the tissue bridge of FIG. 69, wherein the release liners have been partially pulled away from the reminder of the tissue bridge.

FIG. 70 is an assembled, bottom perspective view of the tissue bridge 10 of FIG. 69, wherein the release liners 32 have been partially pulled away. The pad 122 includes lateral extensions 124 configured for at least partially covering the struts 42, for example when the tissue bridge 10 is oriented so that the cover sheet 78 extends horizontally and is the uppermost layer of the tissue bridge. That is, for the example depicted in FIGS. 69 and 70, the pad lateral extensions 124 are positioned between the struts 42 and the adhesive layer 120, for example so that the struts 42 are not adhered to, and can move relative to, the cover sheet 78. In this regard, the pad lateral extensions 124 are an example of a material that is adhered to the adhesive 120 and positioned between the adhesive 120 and the strut portions 20 in a manner that seeks to prevent the adhesive 120 from adhering to the struts 42. The pad 122 can be constructed of a wicking material so that the pad lateral extensions 124 can carry moisture away from the scar or wound 50, if desired. The cover material (e.g., carrier 78 and/or associated adhesive layer 120) can have various properties to vary the function of the tissue bridge 10, e.g. can be waterproof, breathable, expandable, or have varied adhesive peel values, as required for clinical use.

Reiterating from above, rather than being formed from blank(s), the body 12 can be an injection-molded or mechanically thermoformed, unitary (e.g., single-piece) article such that the strut portions 20 and multistable spanning structures 46 can be formed together as a single article from an injection-moldable or thermoformable material, or the like. The bodies 12 and tissue bridges 10 can be formed from laminated structures and other suitable materials.

Figure 71:
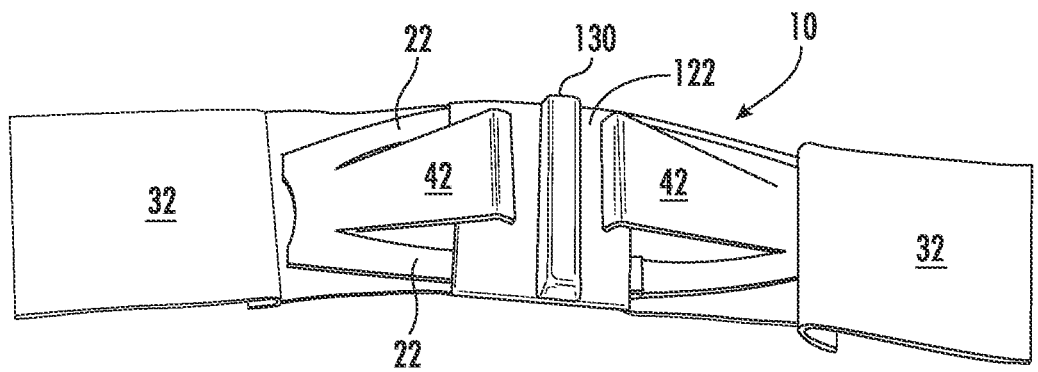
FIG. 71 is a bottom perspective view of an embodiment of a multistable tissue bridge having similarities to the embodiment of FIG. 70.

FIG. 71 is a bottom perspective view of an embodiment of a multistable (e.g., symmetrically bistable or asymmetrically bistable) tissue bridge 10 like the embodiment of FIG. 70 (e.g., including both structures and associated methods) except, for example, the pad 122 and silicone 130 or other suitable medicinal substance extend over the medial portions of the arms 22. When the tissue bridge 10 of FIG. 71 is mounted to a patient, the pad 122, silicone 130, and/or other suitable features can be positioned between the medial portions of the arms 22 and the patient's scar or wound 50 and associated tissue 52.

Figure 72:
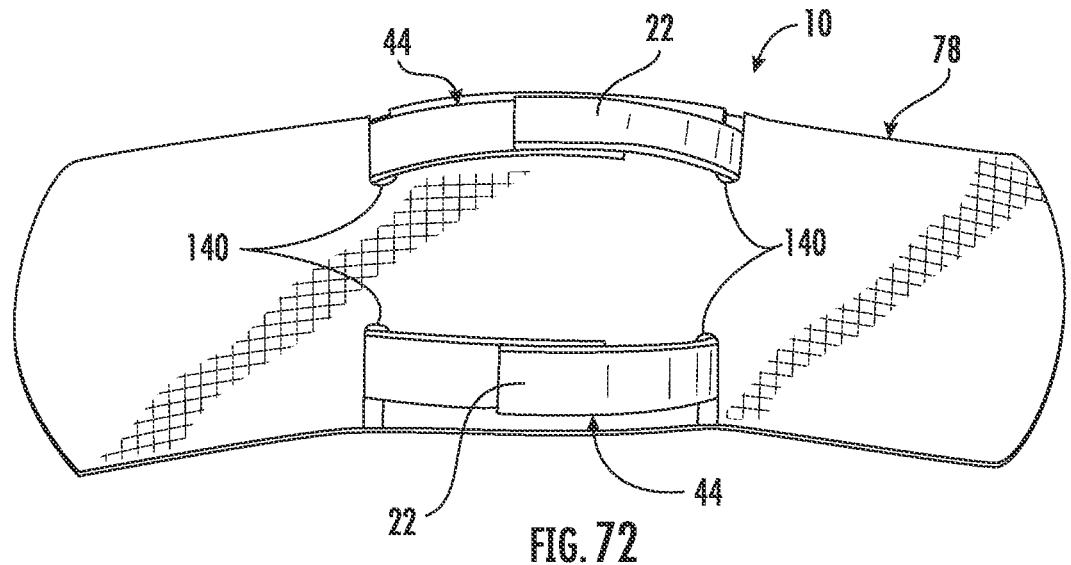
FIG. 72 is a top perspective view of an embodiment of a multistable tissue bridge having similarities to the embodiment of FIG. 69.

As another example like the embodiment of FIG. 70 (e.g., including both structures and associated methods), in the top view of FIG. 72, the arm portions 22 extend through holes 140 in the cover sheet 78 so that, in use, the cover sheet 78 is positioned between the medial portions of the arms 44 and the patient's scar or wound 50 and associated tissue 52. In addition to the holes 140 being open at opposite major surfaces of the cover sheet 78, each of the holes 140 (e.g., slots) can also extend to and be open at respective edges of the cover sheet, for example for streamlining insertion of the arm portions 22 or arms 44 into holes 140.

FIG. 73 is an isolated top view of an example of a flexible, multistable (e.g., symmetrically bistable or asymmetrically bistable) tissue bridge body 12 that can be at least partially manufactured, for example, by thermoforming. It is believed that the cuts that at least partially define features of the body 12 can be formed substantially during and/or after the thermoforming.

FIG. 74 is an exploded, top perspective view of a multistable (e.g., symmetrically bistable or asymmetrically bistable) tissue bridge 10 including the body of FIG. 73. It is believed that the manufacturing process for the tissue bridge 10 may include lamination/conversion of at least some of the layers of the tissue bridge prior to the thermoforming. As further examples, it is believed that the multistable body 12, as depicted in FIGS. 73 and 74, and which is part of the tissue bridge 10 of FIG. 74, can be fabricated by way of bending, thermoforming, stamping, and/or in any other suitable manner, either before the addition (e.g., by lamination or conversion) or after the addition of at least one additional layer of the tissue bridge (e.g. the inner adhesive 28, the patient-contact carrier 26, the patient-contact adhesive 30, and/or the release liner 32) and/or with the inclusion of additional layers (e.g., one or more temporary release liners).

As depicted in FIGS. 73-76, there can be four inclined webs 145 (e.g., draws, or draw portions resulting from the thermoforming) respectively connecting edges of the strut portions 20 to inner edges of the arms 44. The draw webs 145 can be positioned in the corners where the edges of the strut portions 20 join with the inner edges of the arms 44. The draw webs 145 can be configured to at least partially stabilize the relationship (e.g., any angle or bend) between the strut portions 20 and end portions 18 of the body 12. Characteristics (e.g., size, thickness, stiffness, flexibility, and/or elasticity) of the draw webs 145 can be adjusted in a predetermined manner to tune the operability of (e.g., the multistability of) the tissue bridge 10. Similarly, there can be more or less than four of the draw webs 145, and the number and/or other characteristics of the draw webs can be selected to tune the operability of (e.g., the multistability of, stiffness of, symmetry of, and/or asymmetry of) the tissue bridge 10.

Figure 75:
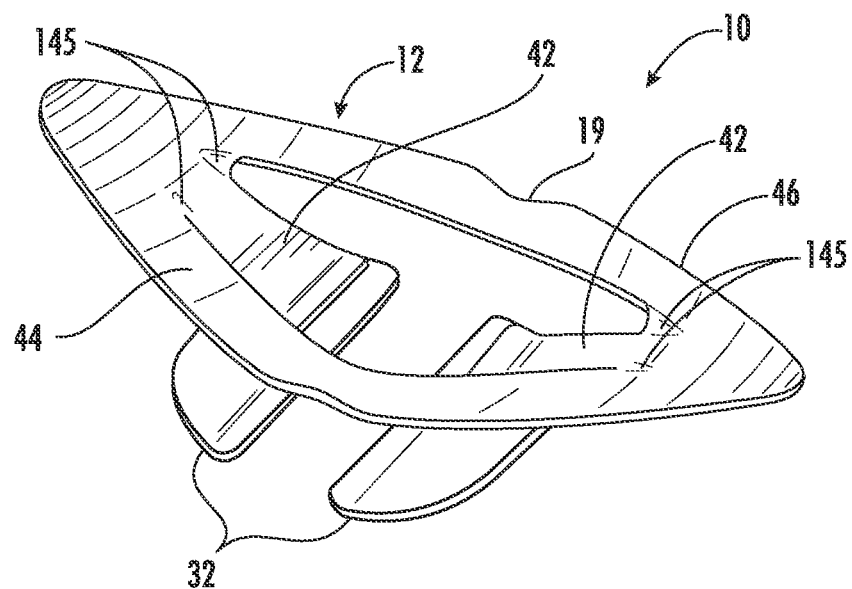
FIG. 75 is a top perspective view of the tissue bridge of FIG. 74 in its extended stable equilibrium configuration.
Figure 76:
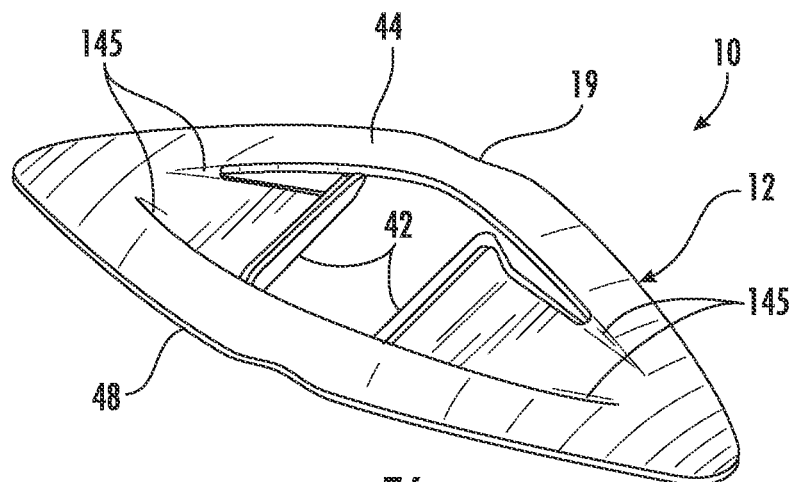
FIG. 76 is a top perspective view of the tissue bridge of FIG. 74 in its retracted stable equilibrium configuration, without release liners.
Figure 77:
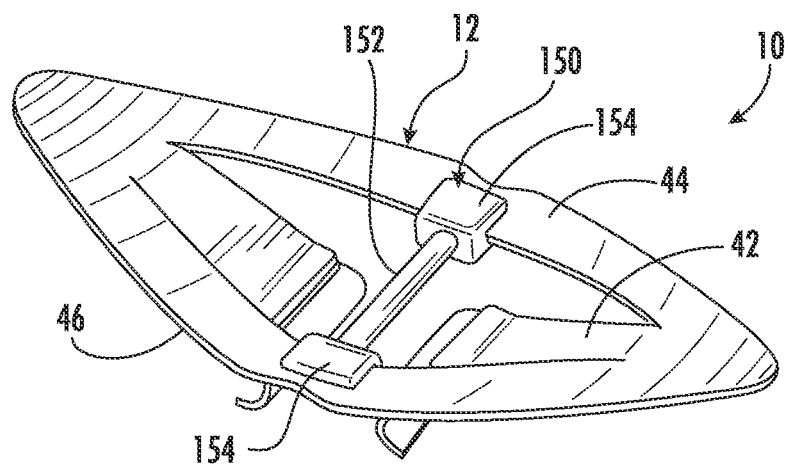
FIG. 77 is a top perspective view of a multistable tissue bridge, wherein the tissue bridge is in its extended stable equilibrium configuration and includes a spacer assembly configured to at least partially control the multistability, in accordance with an embodiment of this disclosure.
Figure 78:
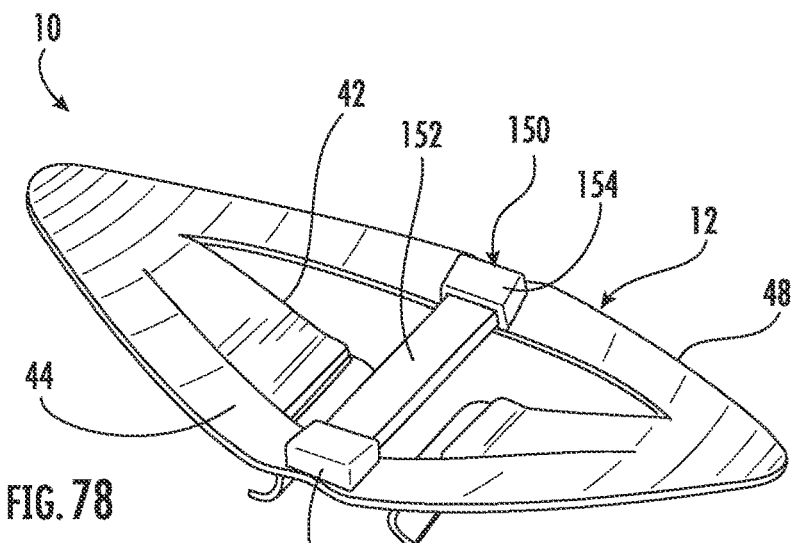
FIG. 78 is like FIG. 77, except for depicting another embodiment of a spacer assembly.

Referring to FIGS. 73-76, outer edges of medial portions of the arms 44 can include inwardly recessed edges 19 configured for receiving the outer end portion of a finger or thumb of a user during installation of the multistable tissue bridge 10. FIGS. 75 and 76 depict the tissue bridge of FIG. 74 in its stable equilibrium configurations. In FIG. 75 the tissue bridge 10 is in its extended stable equilibrium configuration, In FIG. 76 the tissue bridge 10 is in its retracted stable equilibrium configuration and the release liners 32 are not included.

Referring to FIGS. 77-79A, in addition to, or as an alternative to, forming a multistable body 12 or multistable spanning structure 46 by bending, thermoforming, stamping, or the like, central portions of the arms 44 of a flexible spanning structure 48 can be forced apart by a spacer assembly 150 in a manner that causes the spanning structure to function as a multistable spanning structure 48. For example, the length, stiffness, and/or other characteristics of a crossbar 152 of the spacer assembly 150, the configuration of end-holders 154 for the crossbar, and/or the position of the spacer assembly along the length of the body 10 or spanning structure 48 can be adjusted to tune the multistability.

Optionally, the crossbar 152 can be configured to be removable/replaceable while the rest of the tissue bridge 10 remains attached to tissue 52. Therefore, differently configured crossbars 152 can be substituted for one another in the spacer assembly 150 of the tissue bridge 10 while the tissue bridge remains attached to the tissue to tune the multistability tissue bridge (e.g., the forced applied to the tissue by the tissue bridge) while the tissue bridge remains attached to the tissue (e.g., to adjust the tissue bridge from a stronger, higher radius stable configuration to a lesser radius stable configuration, thus allowing the forces on the tissues to be adjusted post-application). As another example, the crossbar 152 can have or otherwise provide a therapeutic environment for the scar or wound 50, for example by supporting a pad, silicone, and/or other suitable component for treating the wound/scar 50 (e.g., medicated, drug-eluting, wicking, and/or having other suitable characteristics).

Figure 79A:
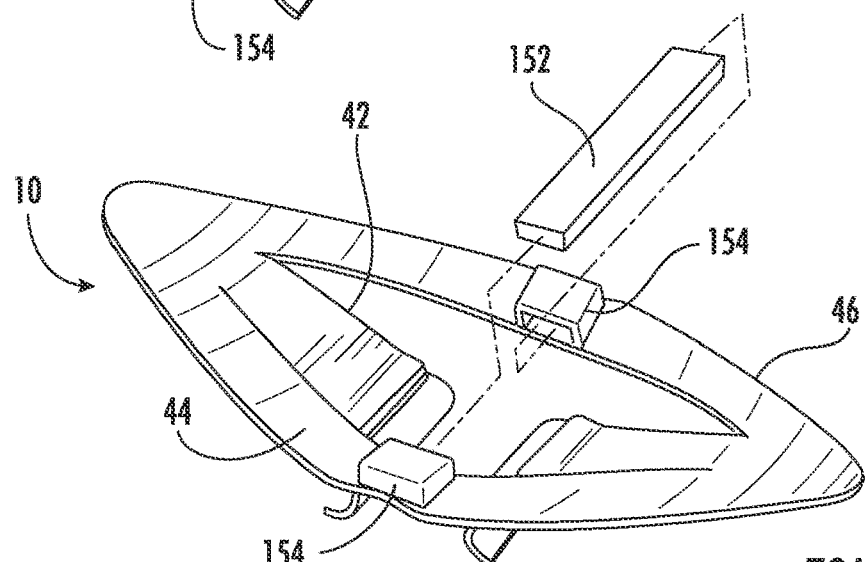
FIG. 79A depicts the tissue bridge of FIG. 78 in a partially exploded configuration.
Figure 79B:
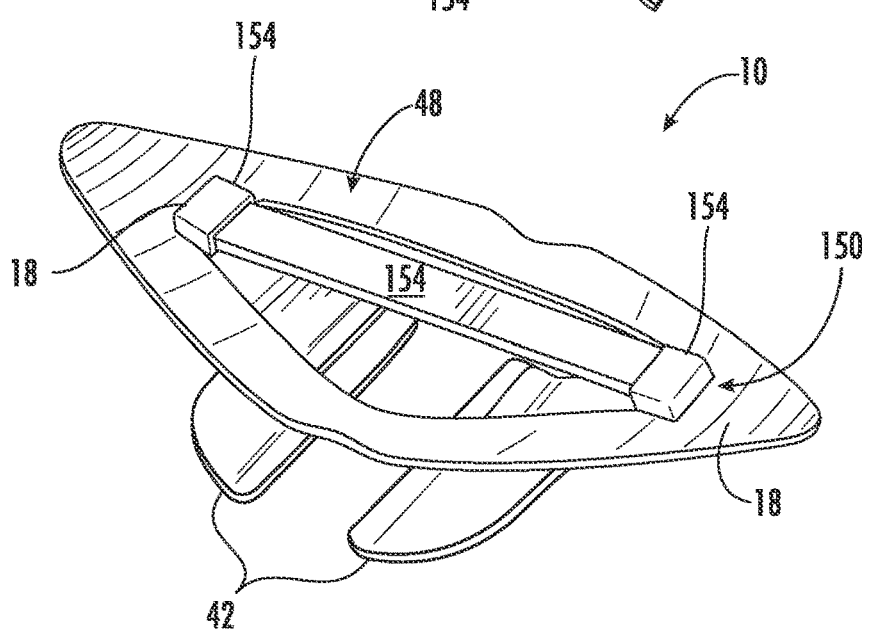
FIG. 79B is a top perspective view of a multistable tissue bridge, wherein the tissue bridge is in its extended stable equilibrium configuration and includes a spacer assembly configured to at least partially control the multistability, in accordance with an embodiment of this disclosure.

Referring to FIG. 79B, the spacer assembly 150 can be configured, as an example, to function as an arrestation mechanism. For example, the spacer assembly 150 can extend above and between the opposite ends 18 of the spanning structure 48, or in other suitable locations, to function as an arrestation mechanism for restricting how far the opposite ends 18 can move toward one another and, thus, for restricting how far the struts 42 can move away from one another, for example in a manner that seeks to restrict the tissue bridge 10 from being transitioned beyond, or too far beyond, a predetermined, desired extended configuration of the tissue bridge. The spacer assembly 150 can include a bar 152 having opposite ends respectively fitted into end-holders 154 that are respectively mounted to, or defined by, upper surfaces of the spanning structure's ends 18, or the spacer assembly can be in any other suitable configuration. For example, the length, stiffness, and/or other characteristics of the crossbar 152 of the spacer assembly 150, the configuration of end-holders 154 for the crossbar, and/or the position of the spacer assembly along the width of the spanning structure 48 can be adjusted to tune the multistability or other characteristics of the tissue bridge. For example, the spacer assembly 150 can be configured to function as an arrestation mechanism that restricts, for example, how far the struts 20 can move away from one another and, thus, at least partially defines the tissue bridge's extended configuration. A variety of differently configured arrestation mechanisms are within the scope of this disclosure, as further discussed below.

A variety of differently configured release liners 32 are within the scope of this disclosure. For example, FIGS. 74 and 75 depict release liners 32 with pull tabs protruding in a direction that differs from the protruding direction of the pull tabs of the release liners of FIGS. 77-79A. The pull tabs of the release liners 32 of the tissue bridges 10 can be configured in any suitable manner, including having pull tabs that protrude in any suitable configuration and direction for at least partially providing a mechanism by which a user can initiate removal of the release liners. As another example, whereas in some of the drawings of this disclosure the pull tab of the release liner 32 is depicted as extending from the reminder of the release liner at a gentle bow or curve, it may be more typical for the pull tab to extend from the reminder of the release liner at a sharper or more pronounced fold.

As further examples, each release liner 32 can be adhered to the tissue bridge 10 such that resistance to removal of the release liner varies at different zones of attachment between the release liner and the tissue bridge. The resistance variation may be achieved, for example, by employing tabs, loops, folds, varying-strength adhesive, textures, and/or release coatings. See, for example, U.S. Patent Application Publication Number 2014/0227483.

As other examples, one or more tissue bridges 10 can be releasably mounted to a single release liner 32, and some tissue bridges may not include or otherwise be associated with a release liner. For example, the container or packaging containing one or more tissue bridges 10 can have a surface to which the patient-contact adhesive 30 is releasably adhered, wherein the surface to which the patient-contact adhesive 30 is releasably adhered can be coated with a release agent configured so that the patient-contact adhesive 30 is relatively weakly (i.e., readily removably) adhered to the release agent.

Figure 80:
FIGS. 80 through 85 schematically depict a sequence of steps of a method of forming a tissue bridge having multiple multistable portions in accordance with an embodiment of this disclosure.
Figure 81:
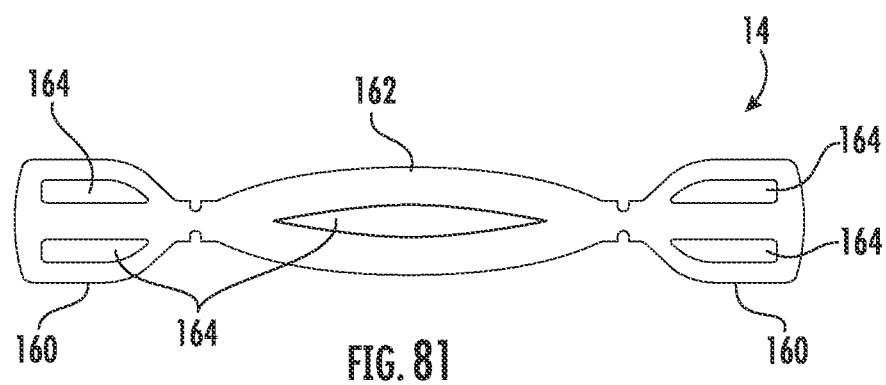

FIGS. 80-85 schematically depict a sequence of steps of a method of forming a multistable tissue bridge 10 that optionally has multiple multistable (e.g., symmetrically bistable or asymmetrically bistable) portions in accordance with an embodiment of this disclosure. FIG. 80 is a top view of a web or sheet of material, such as a polymeric film or laminate (e.g., polyethylene, polyethylene terephthalate, or any other suitable materials), a metallic sheet, alloy sheet, and/or other suitable materials, from which the blank 14 of FIG. 81 can be cut, stamped, or the like. The blank 14 includes strut precursors 160 connected to one another by multistable spanning structure 162, and holes 164 extending therethrough. Referring to the top perspective view of FIG. 82, one or more of, for example each of, the strut precursors 160 and multistable spanning structure 162 can be made upwardly concave by bending, thermoforming, stamping, and/or in any other suitable manner.

Figure 82:
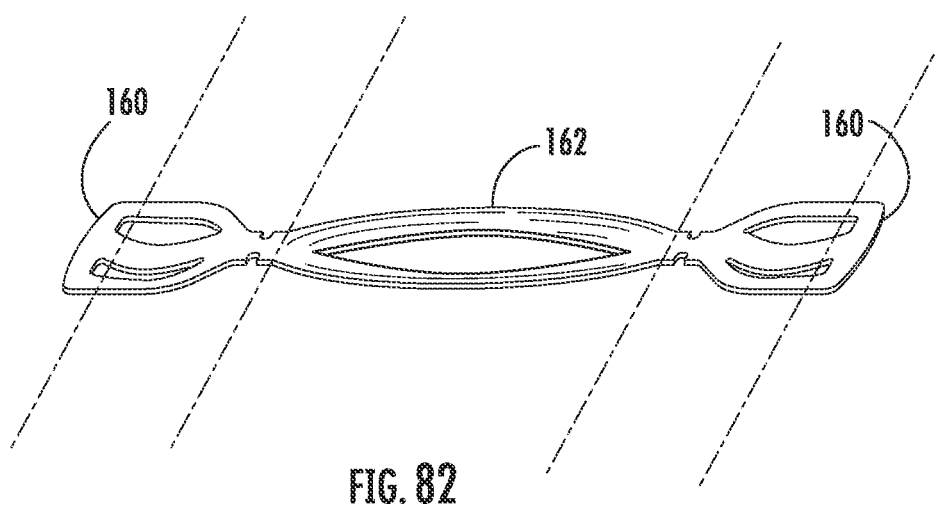
Figure 83:
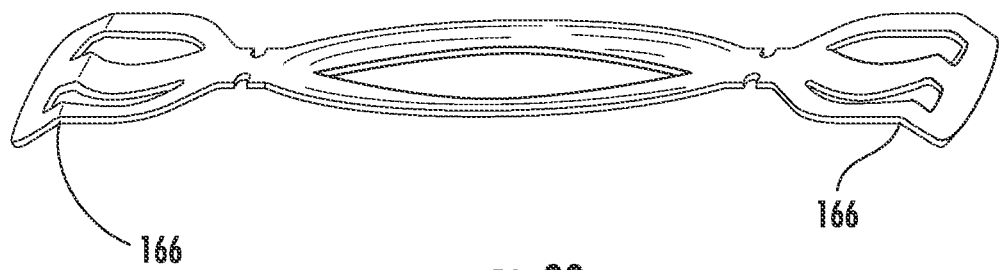
Figure 84:
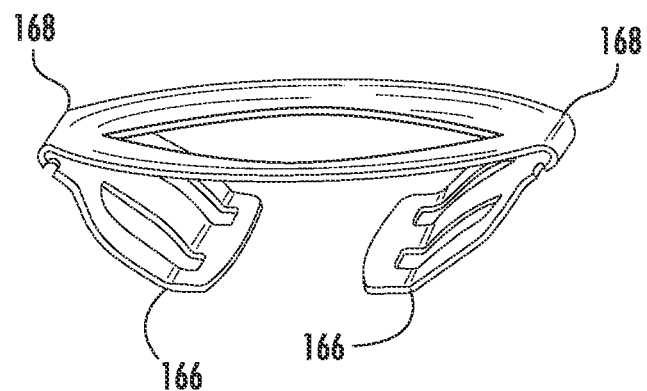
Figure 85:
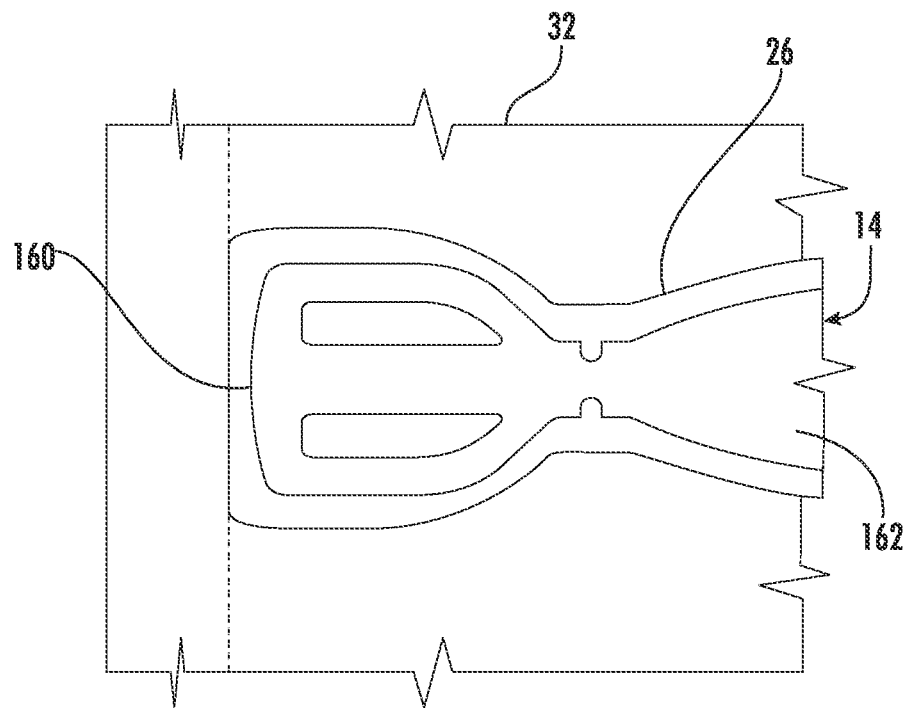
Figure 86:
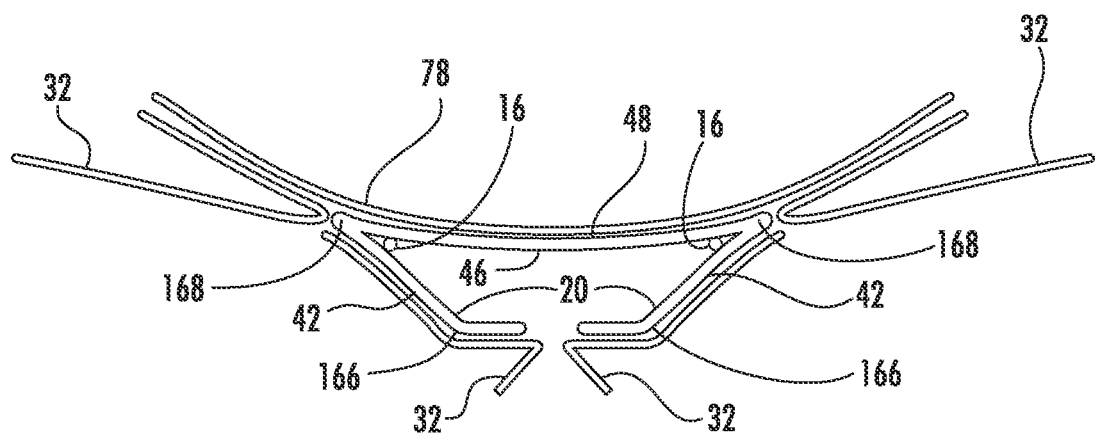

Further referring to FIG. 82, the blank 14 can be bent along lines schematically depicted as dashed lines. Referring to FIGS. 83, 84 and 86, bends 166 can be formed in the outer ends of the strut precursors 160, and bends 168 can be formed between the strut precursors 160 and multistable spanning structure 162, to further form the one or more strut portions 20 (FIG. 86) and the multistable spanning structure 46 (FIG. 86). FIG. 85 schematically depicts that one or more of the layers 26, 28, 30, 32, 78, 120 (see, e.g., FIGS. 1 and 61) can be incorporated into the tissue bridge 10 including the multistable body 12 formed from the blank 14 of FIG. 81.

FIG. 86 schematically depicts an example of a multistable tissue bridge 10 formed from steps including those described above with reference to FIGS. 80-85, or the like. FIG. 86 depicts the multistable (e.g., symmetrically bistable or asymmetrically bistable) tissue bridge 10 in its extended stable equilibrium configuration, wherein the multistable spanning structure 48 is in its concave-up stable equilibrium configuration, and the flexible, multistable (e.g., symmetrically bistable or asymmetrically bistable) struts 42 are in their concave-down stable equilibrium configurations. In the example of FIG. 86, pairs of release liners 32 are respectively attached to (i) the struts 42 (e.g., by way of patent-contact adhesive 30) and (ii) the end portions of the cover sheet 78 (e.g., by way of adhesive 120).

Referring back to FIG. 84, in one example the bends 168 can be provided by living hinges that are initially utilized to obtain the configuration depicted in FIG. 84. Thereafter, for each of the living hinges 168, one or more fastening mechanisms 16 (FIG. 86) can be associated with the hinge in a manner that disables the hinge by providing a fixed connection thereat or proximate there. The fastening mechanisms 16 can be snap fasteners that each include a protruding part that fits into a receptacle part to provide a press fit or interference fit connection, so that pivotability of the associated hinge 168 is disabled, and flexibility of respective portions of the tissue bridge 10 provide the biased characteristics of the tissue bridge. As an alternative to or in addition to the snap fastener features 16, other suitable features (e.g., pegs, rivets, split-pin fasteners, brad fasteners) may be included for transitioning the living hinge into a fixed connection point, or the like. The fastening mechanisms 16 can be positioned at any suitable positions along the lengths of the struts 42.

A method of applying the tissue bridge 10 of FIG. 86 to a scar or wound 50 is briefly described in the following, in accordance with an embodiment of this disclosure. The release liners 32 attached to struts 42 can be removed while the tissue bridge 10 is in, or proximate, its extended stable equilibrium configuration. The user can hold the tissue bridge 10 by way of the end portions of the cover sheet 78 that continue to be attached to respective release liners 32 in a manner that seeks to prevent adherence or contamination of the patient-contact adhesive 30, e.g. by grasping fingers and thumbs, or by a grasping instrument. Then, the patient-contact adhesive 30 on the struts 42 can be engaged against the tissue 52, and the tissue bridge 10 can continue to be forced closer to the tissue so that the tissue bridge 10 reconfigures to its retracted stable equilibrium configuration and is adhered to the tissue 52 by the patient-contact adhesive. Then, the release liners 32 attached to the end portions of the cover sheet 78 can be removed, and the end portions of the cover sheet can be adhered to the tissue 52 by way of the adhesive 120.

Reiterating from above, for ease of understanding at least some of the above-described blanks 14 may have been described as, or alluded to as being, an article that is initially separately manufactured and thereafter converted into a multistable body 12 or tissue bridge 10. However, it is believed that one or more blanks 14 may also be at least schematically illustrative of a structure that may be relatively temporarily present during a phase of thermoforming or another suitable manufacturing process that provides a multistable body 12 or tissue bridge 10.

Figure 87:
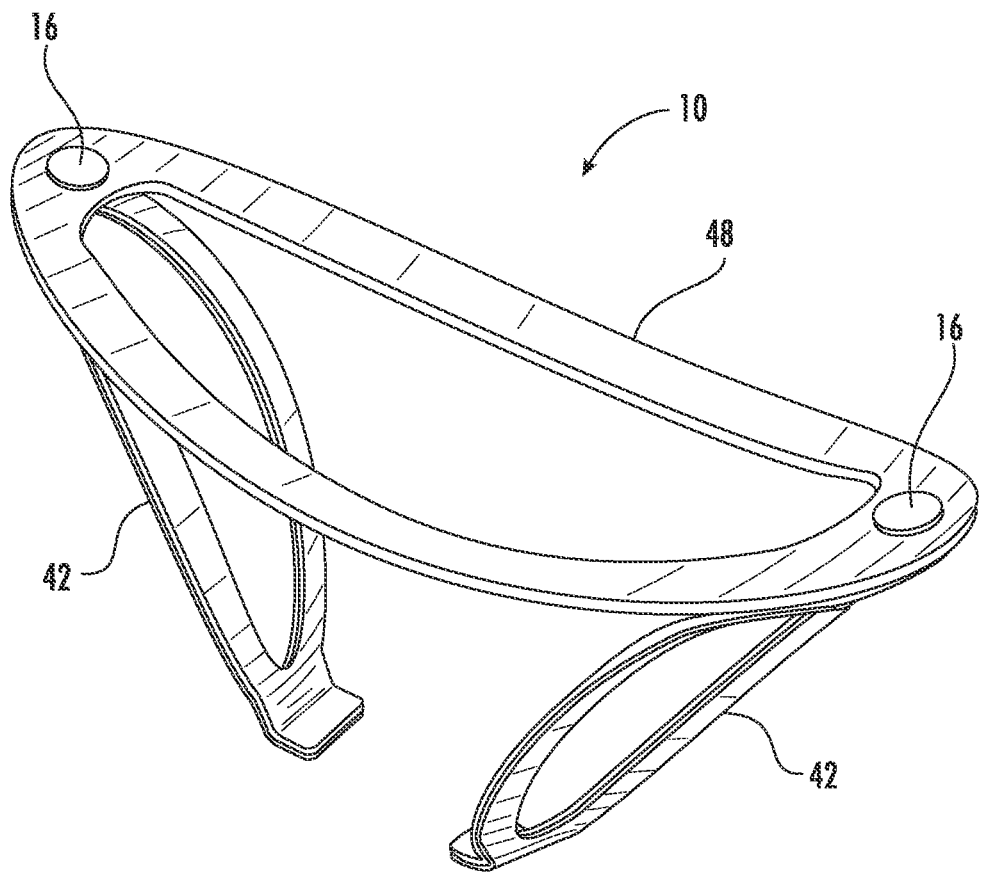
FIG. 87 is a top perspective view of a multistable tissue bridge in its extended stable equilibrium configuration in accordance with an embodiment of this disclosure.
Figure 88:
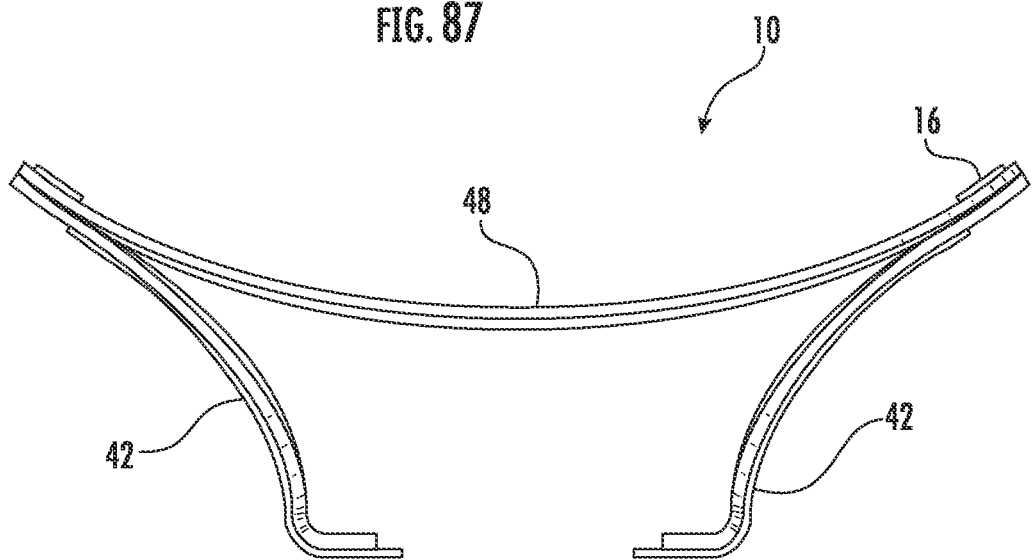
FIG. 88 is a front view of the configuration of FIG. 87.
Figure 89:
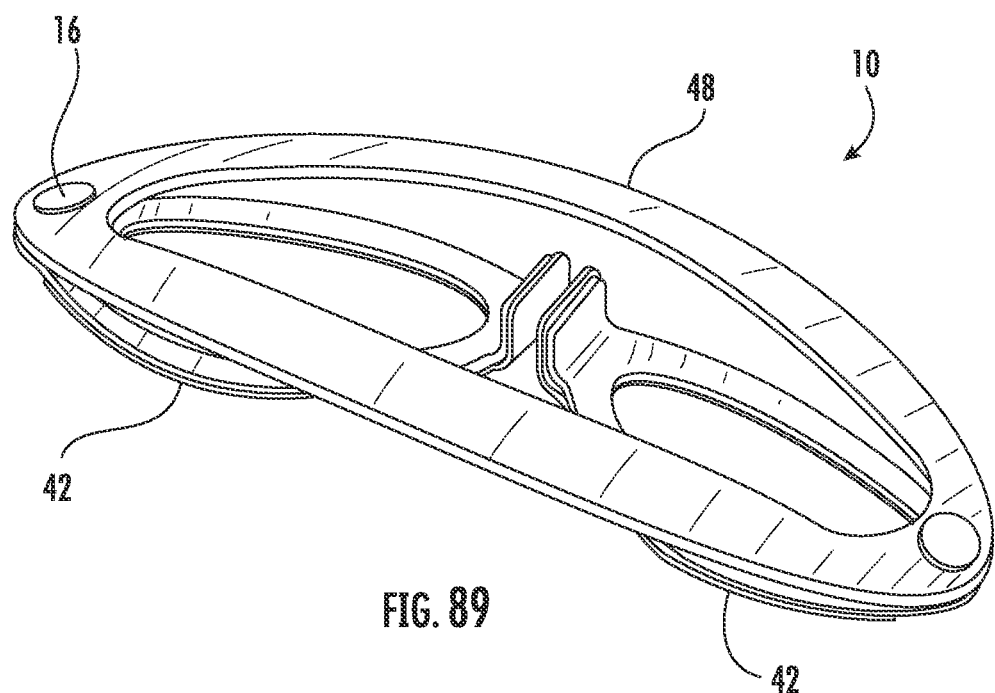
FIG. 89 is a top perspective view of the tissue bridge of FIG. 87 in its retracted stable equilibrium configuration.

FIGS. 87 and 88 depict a multistable tissue bridge 10 in its extended stable equilibrium configuration, wherein the flexible multistable spanning structure 48 is in its concave-up stable equilibrium configuration, and the flexible, multistable struts 42 are in their concave-down stable equilibrium configurations. In contrast, FIGS. 89 and 90 depicted the tissue bridge 10 of FIGS. 87 and 88 in its retracted stable equilibrium configuration, wherein the multistable spanning structure 48 is in its concave-down stable equilibrium configuration, and the struts 42 are in their concave-up stable equilibrium configurations.

Figure 90:
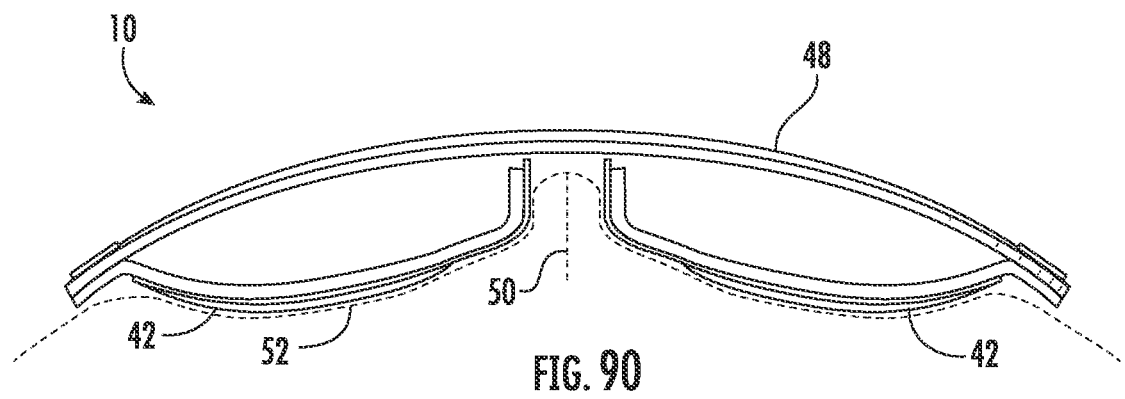
FIG. 90 is a front view of the configuration of FIG. 89, wherein an everted wound is schematically depicted with dashed lines, in accordance with an embodiment of this disclosure.

As the tissue bridge 10 of FIGS. 87-90 is being forced into closer contact with tissue 52 during mounting, the transition of the multistable spanning structure 48 from its concave-up stable equilibrium configuration to its concave-down stable equilibrium configuration can occur simultaneously or substantially simultaneously with the transition of the struts 42 from their concave-down stable equilibrium configurations to their concave-up stable equilibrium configurations. In FIG. 90, everted tissue 52 associated with a scar or wound 50 is schematically depicted with dashed lines.

At least partially reiterating from above, the multistable spanning structure 48 and one or more multistable struts 42 of the same tissue bridge 10 can be configured to operate independently (e.g., substantially or at least somewhat independently) from one another with regard to transitioning between their stable equilibrium configurations. For example and with regard to stable equilibrium configurations, a multistable tissue bridge 10 can have multistable (e.g., symmetrically bistable or asymmetrically bistable) struts 42 that at least sometimes operate independently of its multistable (e.g., symmetrically bistable or asymmetrically bistable) spanning structure 48, so that the struts may not always undergo a change between stable equilibrium configurations when the spanning structure reconfigures between stable equilibrium configurations.

Figure 91:
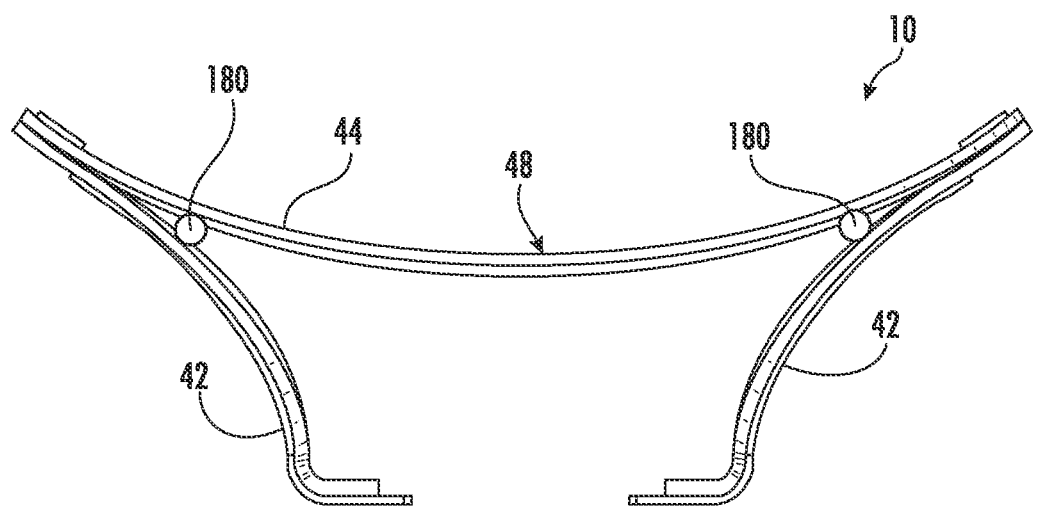
FIG. 91 is a front view of a multistable tissue bridge in its extended stable equilibrium configuration in accordance with an embodiment of this disclosure.
Figure 92:
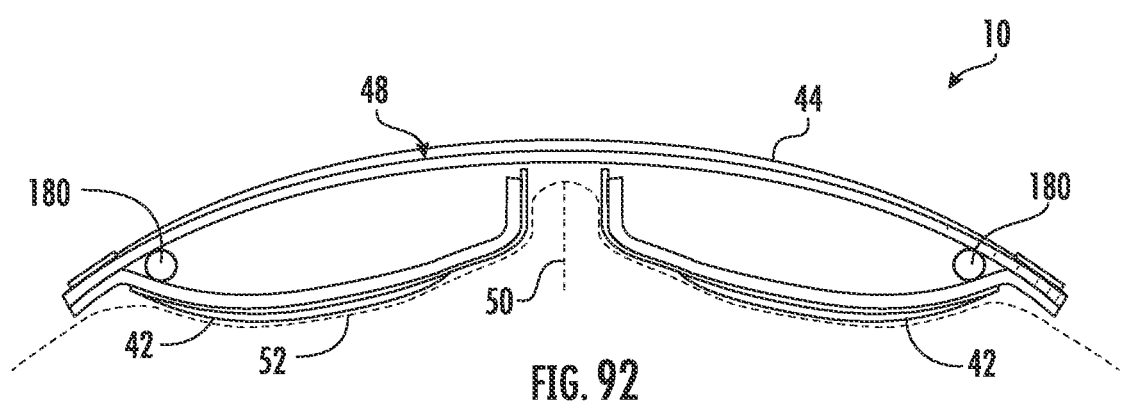
FIG. 92 is a front view of the tissue bridge of FIG. 91 in its retracted stable equilibrium configuration, wherein an everted wound is schematically depicted with dashed lines, in accordance with an embodiment of this disclosure.

FIGS. 91 and 92 are respectively similar to FIGS. 88 and 90 except, for example, for depicting that the multistable tissue bridge 10 can further include one or more additional structural features 180. The additional structural features 180 can be configured to assist in at least the transition from the extended stable equilibrium configuration to the retracted stable equilibrium configuration. For example, the transition assist structures 180 can be in the form of cylindrical or any other suitably configured fulcrums 180 or fulcrum-like structures mounted between the multistable spanning structure 48 (e.g., arms 44) and corresponding arms of the flexible, multistable struts 42. As a more specific example, during mounting of the tissue bridge 10 onto tissue, as the tissue bridge 10 is being forced into closer contact with the tissue, the respective portions of the struts 42 can pivot about the fulcrums 180 in a manner that seeks to at least partially cause the struts to transition from their concave-down stable equilibrium configurations (FIG. 91) to their concave-up stable equilibrium configurations (FIG. 92).

Figure 93:
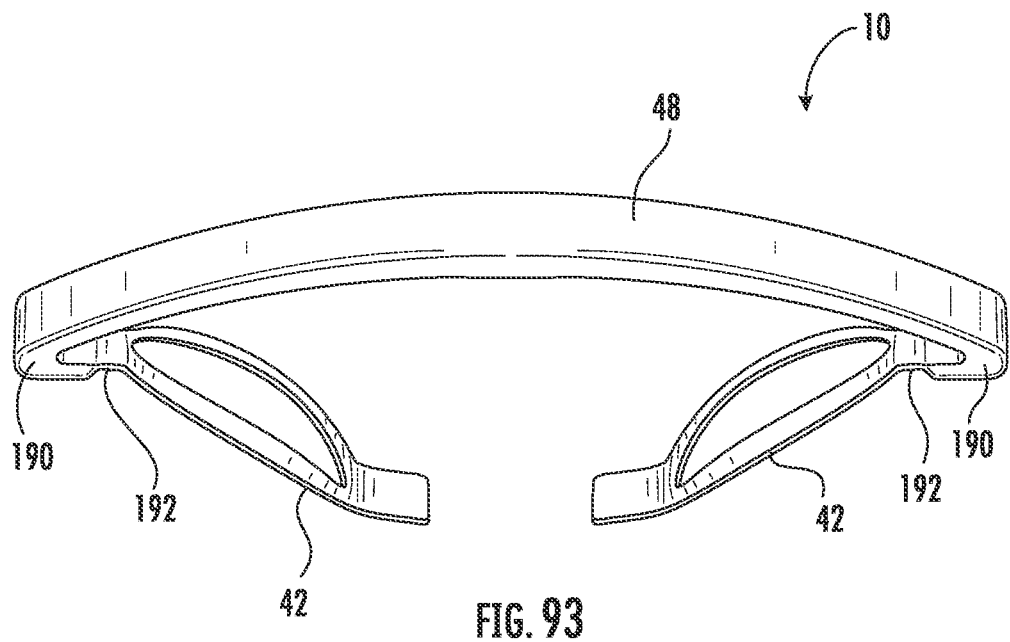
FIG. 93 is a perspective view of a multistable tissue bridge in an extended stable equilibrium configuration in accordance with an embodiment of this disclosure.
Figure 94:
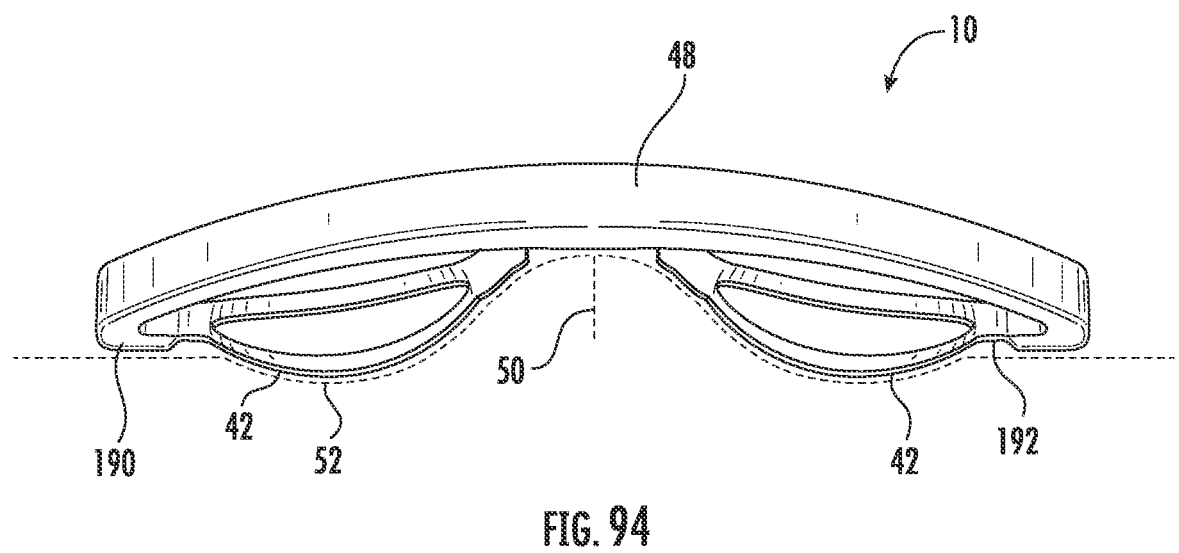
FIG. 94 is a perspective view of the tissue bridge of FIG. 93 in a retracted configuration, wherein an everted wound is schematically depicted with dashed lines, in accordance with an embodiment of this disclosure.

The tissue bridge embodiment of FIGS. 93 and 94 can be like the tissue bridge embodiment of FIGS. 87-90 (e.g., including both structures and associated methods) except, for example, the spanning structure 48 of FIGS. 93 and 94 can be relatively rigid and, thus, not multistable. FIG. 93 depicts the multistable tissue bridge 10 in its extended stable equilibrium configuration, wherein the spanning structure 48 is in its concave-down stable configuration, and the flexible, multistable struts 42 are in their concave-down stable equilibrium configurations. In contrast, FIG. 94 depicts the tissue bridge 10 of FIG. 93 in a retracted configuration, wherein the relatively rigid spanning structure 48 remains in its concave-down stable configuration, and the struts 42 are in their concave-up stable equilibrium configurations. In FIG. 94, everted tissue 52 associated with a scar or wound 50 is schematically depicted with dashed lines.

More specifically referring to the embodiment of the tissue bridge 10 depicted in FIGS. 93 and 94, the relatively rigid spanning structure 48 can be in the form of an arch or any other suitable shape. Upper ends of underturned flanges 190 can be connected to opposite end portions of the arch or relatively rigid spanning structure 48, outer ends of hinges 192 can be connected to inner ends of the underturned flanges 190, and outer or proximal ends of the struts 42 can be connected to inner ends of the hinges 192. The underturned flanges 190 may alternatively be configured as, or referred to as, underturned end portions of the relatively rigid spanning structure 48.

The hinges 192 can be living hinges formed of flexible material and/or areas of relatively reduced thickness or volume, or other suitable hinges. The entire tissue bridge 10 of FIGS. 93 and 94 can be formed of the same flexible material, for example as a single piece of the material, with the thickness and/or volume of the flexible material being varied in a manner that causes the hinges 192 and struts 42 to be relatively flexible and the spanning structure 48 to be relatively rigid. For example, the living hinges 192 may be at least partially defined by an area of relatively reduced thickness in the tissue bridge 10. The thickness, width, and/or other features (e.g. holes) can produce varied areas of flexibility along the length and width of the strut(s) 42 or other portion of the tissue bridge 10.

The bodies 12 and tissue bridges 10 can be formed from laminated structures and other suitable materials.

Figure 95:
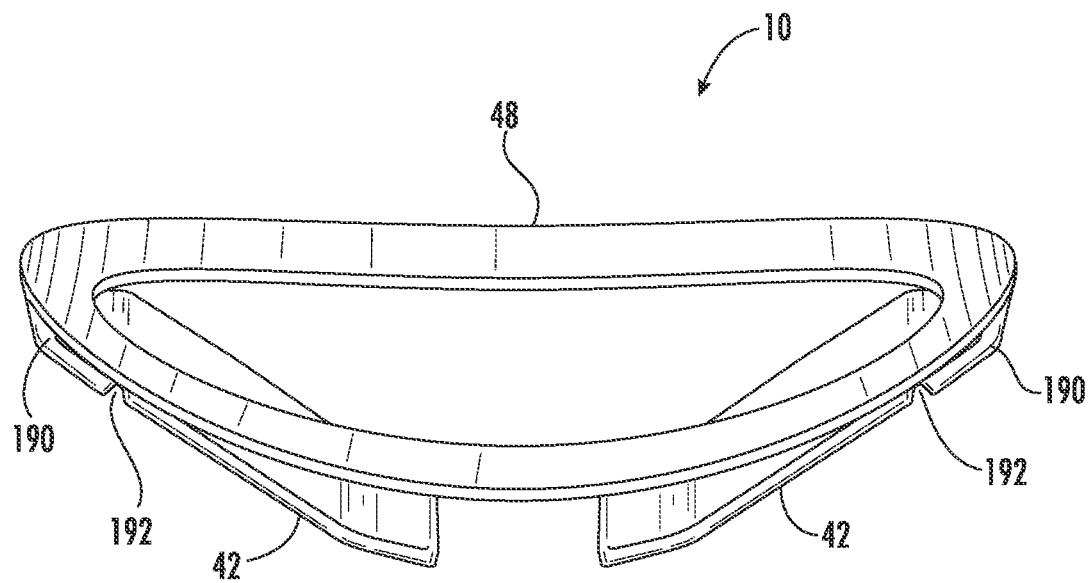
FIG. 95 is a perspective view of a multistable tissue bridge in an extended stable equilibrium configuration in accordance with an embodiment of this disclosure.
Figure 96:
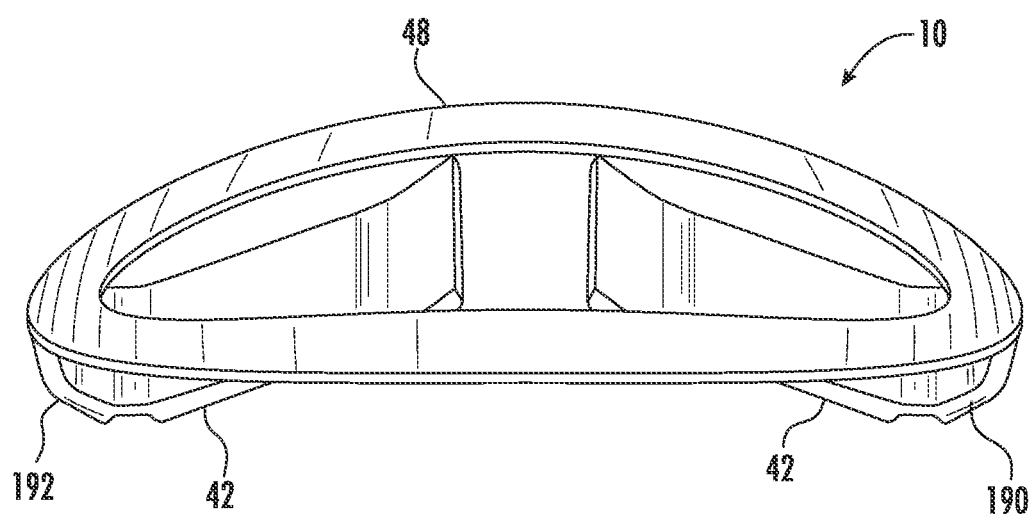
FIG. 96 is a perspective view of the tissue bridge of FIG. 95 in a retracted configuration.

The tissue bridge embodiment of FIGS. 95 and 96 can be like the tissue bridge embodiment of FIGS. 87-90 (e.g., including both structures and associated methods) except, for example, the struts 42 of FIGS. 95 and 96 can be relatively rigid and, thus, not multistable. FIG. 95 depicts the multistable tissue bridge 10 in its extended stable equilibrium configuration, wherein the multistable spanning structure 48 is in its concave-up stable equilibrium configuration, and the inner or distal end portions of the relatively rigid struts 42 extend (e.g., are inclined) outwardly (e.g., downwardly) away from the multistable spanning structure 48. In contrast, FIG. 96 depicts the multistable tissue bridge 10 in a retracted configuration, wherein the multistable spanning structure 48 is in its concave-down stable equilibrium configuration, and the distal end portions of the relatively rigid struts 42 are relatively retracted with respect to the spanning structure 48, so that at least portions of (e.g., the distal end portions of) the struts are closer to one another.

More specifically referring to the embodiment of the tissue bridge 10 depicted in FIGS. 95 and 96, the multistable spanning structure 48 can at least sometimes be in the form of an arch or other suitable shape. Upper ends of underturned flanges 190 can be connected to opposite end portions of the spanning structure 48, outer ends of living hinges 192 can be connected to inner ends of the underturned flanges 190, and outer or proximal ends of the rigid struts 42 can be connected to inner ends of the hinges 192. The underturned flanges 190 may alternatively be configured as or referred to as underturned end portions of the spanning structure 48.

The hinges 192 can be living hinges formed of flexible material or other suitable hinges may be used. The entire tissue bridge 10 of FIGS. 95 and 96 can be formed of the same flexible material, for example as a single piece of the material, with the thickness and/or volume of the flexible material being varied in a manner that causes the hinges 192 to be relatively flexible and the struts 42 to be relatively rigid. For example, the living hinges 192 may be at least partially defined by an area of relatively reduced thickness in the tissue bridge 10. The bodies 12 and tissue bridges 10 can be formed from laminated structures and other suitable materials.

As examples, the tissue bridges 10 of FIGS. 93-96 can be unitary devices formed by thermoforming, injection molding, 3D printing, or in any other suitable manner. As another example, each tissue bridge 10 can be assembled from multiple separately formed pieces, by respectively connecting the pieces to one another.

Figure 97:
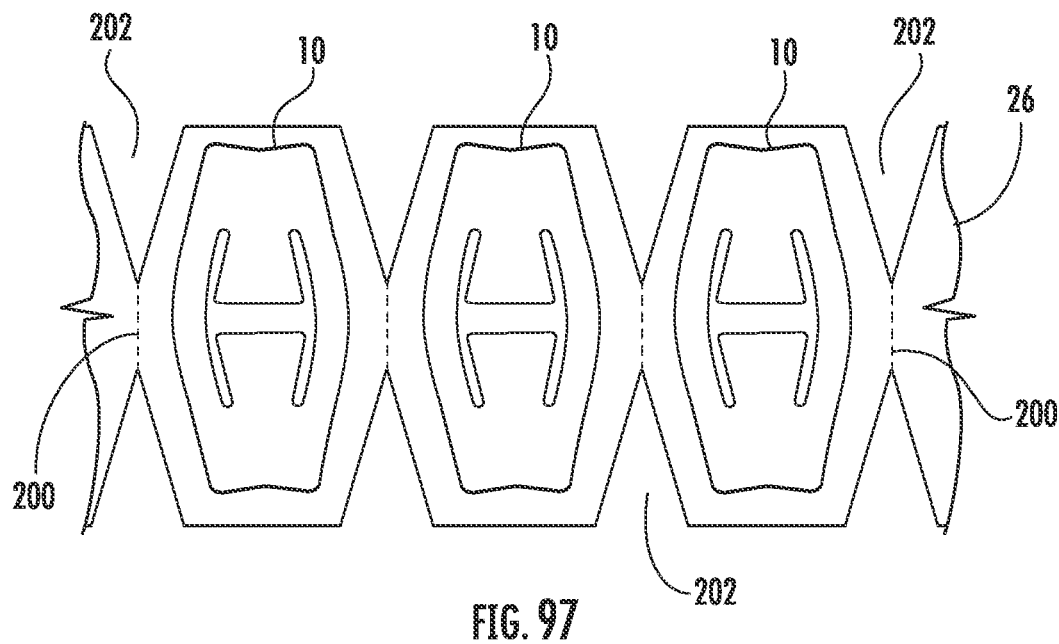
FIG. 97 is a schematic top view of several of the above-discussed tissue bridges connected in series by way of a patient-contact carrier sheet and/or other suitable material, in accordance with an embodiment of this disclosure.

FIG. 97 is a view from above depicting an embodiment of a system wherein several of the above-discussed tissue bridges 10 are positioned above and connected in series to the same continuous piece of patient-contact carrier 26 and/or other suitable material, so that a series of the tissue bridges can be applied to a patient (e.g., to a single elongate wound of the patient) simultaneously or substantially simultaneously while remaining attached to the same piece of patient-contact carrier, or the like. The patient-contact carrier 26 can include lines of disruption 200 (e.g., tear lines formed of perforations or in any other suitable manner) and/or holes 202 in a manner that seeks to allow the series of the tissue bridges to be applied to a patient (e.g., to a single elongate, serpentine-shaped wound of the patient) simultaneously or substantially simultaneously while remaining attached to the same piece of serpentine-shaped patient-contact carrier. As another example, pieces of the patient-contact carrier 26 can be fully separated from one another along the lines of disruption 200 (e.g., tear lines formed of perforations or in any other suitable manner) and/or holes 202 so that the tissue bridges 10 can be individually applied to patients.

Figure 98:
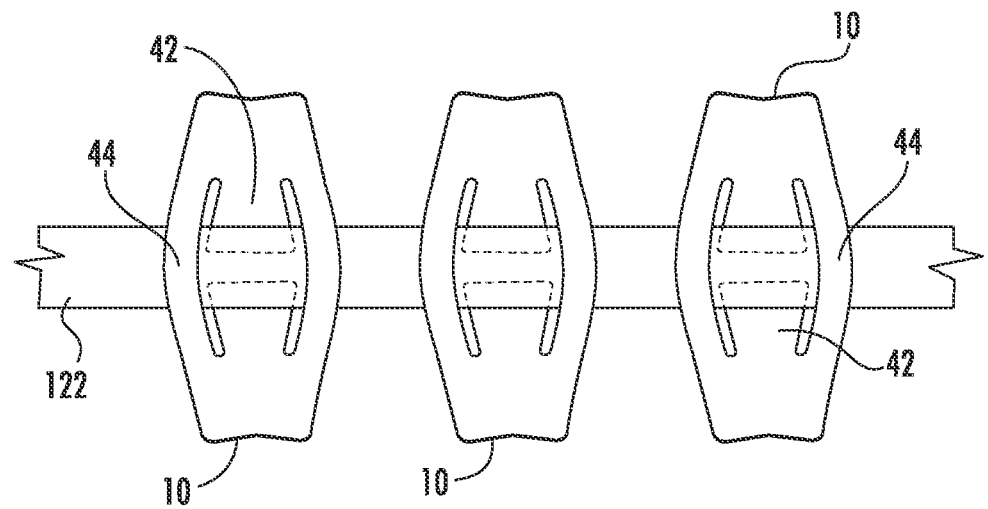
FIG. 98 is a schematic top view of several of the above-discussed tissue bridges connected in series by way of a strip of padding material and/or other suitable material, in accordance with an embodiment of this disclosure.

FIG. 98 is a view from above depicting an embodiment of a system wherein several the above-discussed tissue bridges 10 are connected in series to the same continuous piece or strip of padding 122 and/or other suitable material, so that a series of the tissue bridges can be applied to a patient (e.g., to a single elongate wound of the patient) simultaneously or substantially simultaneously while remaining attached to the same piece of padding, or the like. In the example of FIG. 98, the arms 44 of the tissue bridges 10 are positioned above and connected to the strip of padding 122 and/or other suitable material, and the inner ends of the struts 42 are positioned beneath the padding strip 122. In FIG. 98, the inner ends of the struts 42 are hidden from view beneath the padding strip 122 and, thus, the inner ends of the struts are schematically depicted by dashed lines. The lower surfaces of the tissue bridge arms 44 can be connected to the padding strip 122 by way of respective portions of one or more suitable adhesive layers (see, e.g., FIG. 1, adhesive layers 28, 30) and/or other suitable fastening mechanisms.

Figure 99:
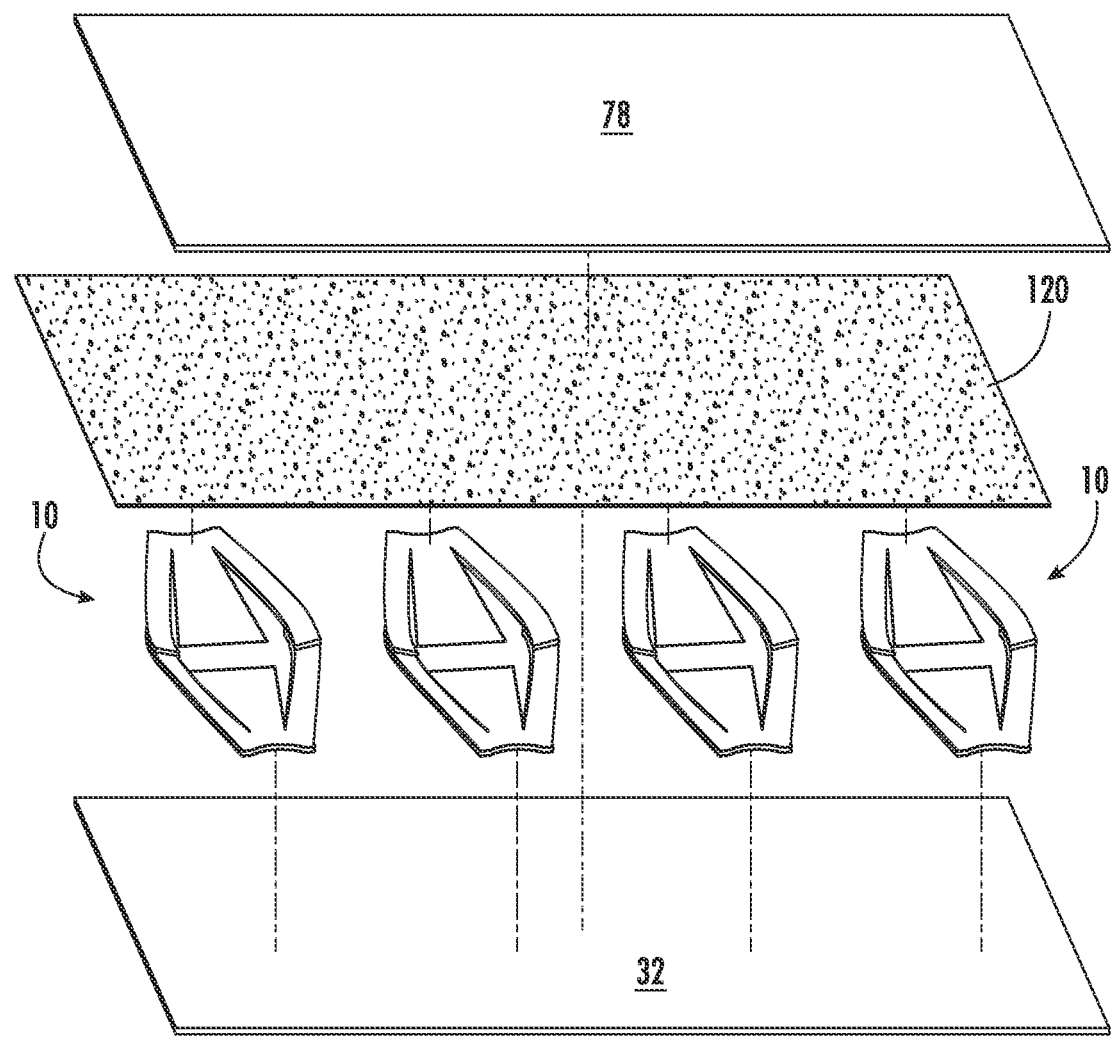
FIG. 99 is a schematic, partially exploded, top perspective view of a system of several of the above-discussed tissue bridges connected in series by way of a release liner and carrier sheet, in accordance with an embodiment of this disclosure.

As an alternative to the configuration depicted in FIG. 98, the padding 122 and/or other suitable material can be connected to upper surfaces of the tissue bridges 10. For example, FIG. 99 is a schematic, partially exploded top perspective view of an embodiment of a system in which several of the above-discussed tissue bridges 10 arranged in series are mounted between the same cover strip or sheet 78 and the same release liner 32. The lower surfaces of the tissue bridges 10 can be connected to the release liner 32 by way of one or more suitable adhesive layers (see, e.g., FIG. 1, adhesive layers 28, 30) and/or other suitable fastening mechanisms. The upper surfaces of the tissue bridges 10 can be connected to the cover sheet 78 by an upper adhesive layer 120.

As an example of a method of mounting the tissue bridges of the system of FIG. 99 to a patient, the connected-together series of the tissue bridges 10 can be applied to the patient (e.g., to a single elongate wound of the patient) simultaneously or substantially simultaneously while remaining attached to the same piece of cover sheet 78, after removal of the release liner 32. In one version, the cover sheet 78 can remain attached directly to the patient by way of the adhesive layer 120 for as long as the tissue bridges 10 remain attached to the patient. As a contrasting version, the cover sheet 78 and adhesive layer 120 can be removed from the tissue bridges 10 and the patient while the tissue bridges 10 remain attached to the patient by way of the patient-contact adhesive 30 (FIG. 1). In such a contrasting example, the adhesive layer 120 would typically have a lower adhesive strength than the other adhesive layer(s) (see, e.g., FIG. 1, adhesive layers 28, 30). In such a contrasting example, the tissue bridges 10 mounted on the patient can be covered with conventional wound dressings (e.g., non-adherent dressings) that can be periodically removed and replaced (e.g., to facilitate inspection of the underlying scar or wound 50).

Figure 100:
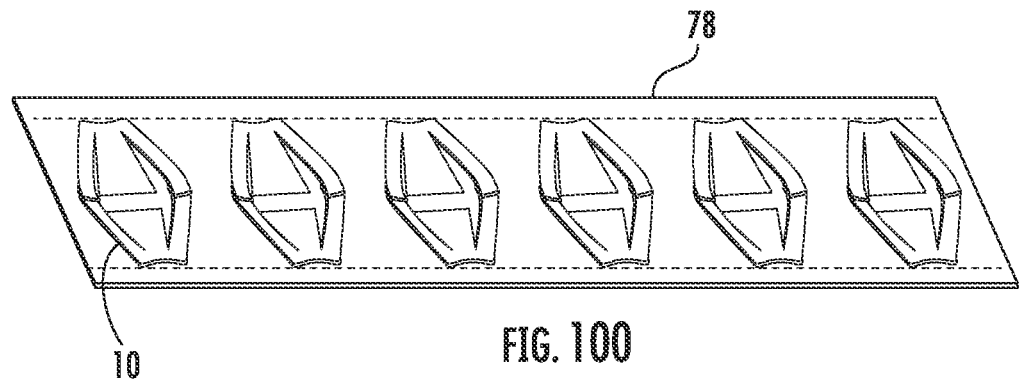
FIG. 100 is a schematic, bottom perspective view of the assembled system of FIG. 99 without the release liner, in accordance with an embodiment of this disclosure.

FIG. 100 is a schematic bottom perspective view of the assembled system of FIG. 99 without the release liner 32. Opposite marginal portions of the cover sheet 78 are schematically identified with dashed lines in FIG. 100. Referring to FIGS. 99 and 100, the width or crosswise dimension, or the like, of the release and cover sheets 32, 78 can be wider than the width or crosswise dimension, or the like, of the adhesive layer 120 so that marginal portions of the release and cover sheets 32, 78 are not adhered to one another in a manner that facilitates initiation of manual removal of the release liner 32 from the tissue bridges 10 and cover sheet 78.

Other embodiments can be like the embodiment of FIGS. 99 and 100 (e.g., including both structures and associated methods), except for variations noted and variations that will be apparent to those of ordinary skill in the art. For example, the bottom view of FIG. 101 is similar to the bottom view of FIG. 100 except, for example, in FIG. 101 opposite surfaces of a padding strip 122 like that of FIG. 98, or the like, are respectively connected (e.g., by way of suitable adhesive material) to the tissue bridges 10 and cover sheet 78 (e.g., by way of the adhesive layer 120 (FIG. 99)).

Figure 101:
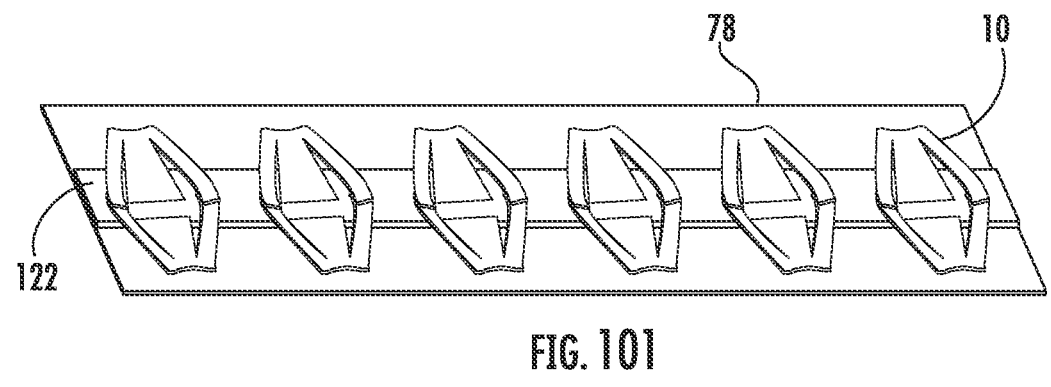
FIG. 101 is a bottom perspective view like FIG. 100 except for further depicting a strip of padding, in accordance with an embodiment of this disclosure.
Figure 102:
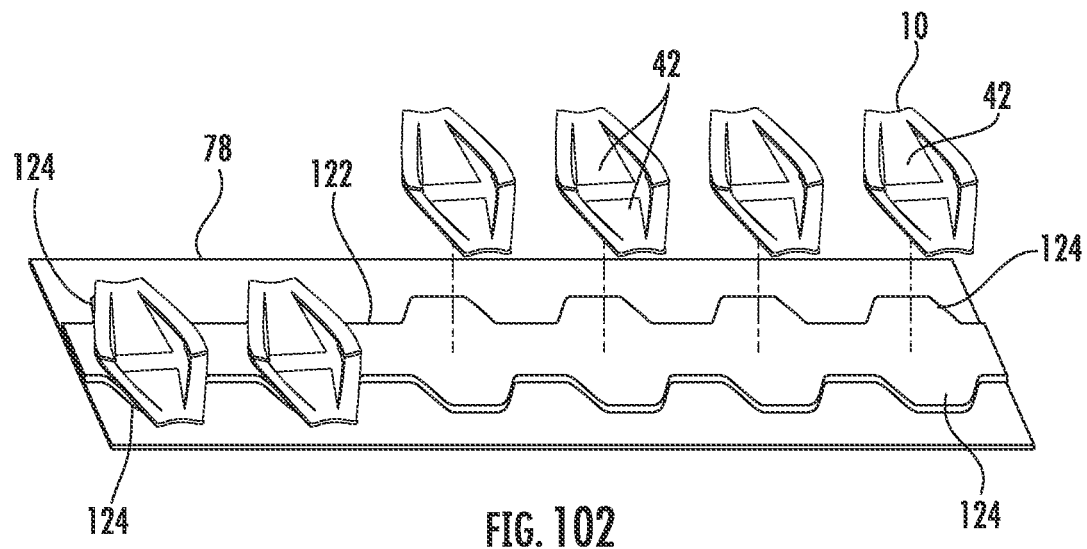
FIGS. 102 through 104 are partially exploded, bottom perspective views similar to FIG. 100, except for showing the padding in different configurations.
Figure 103:
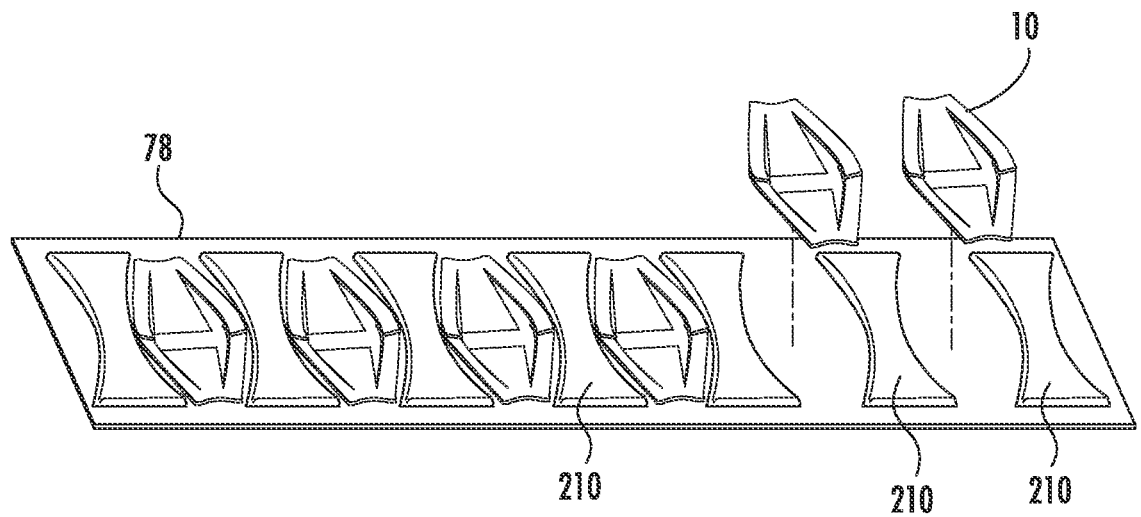
Figure 104:
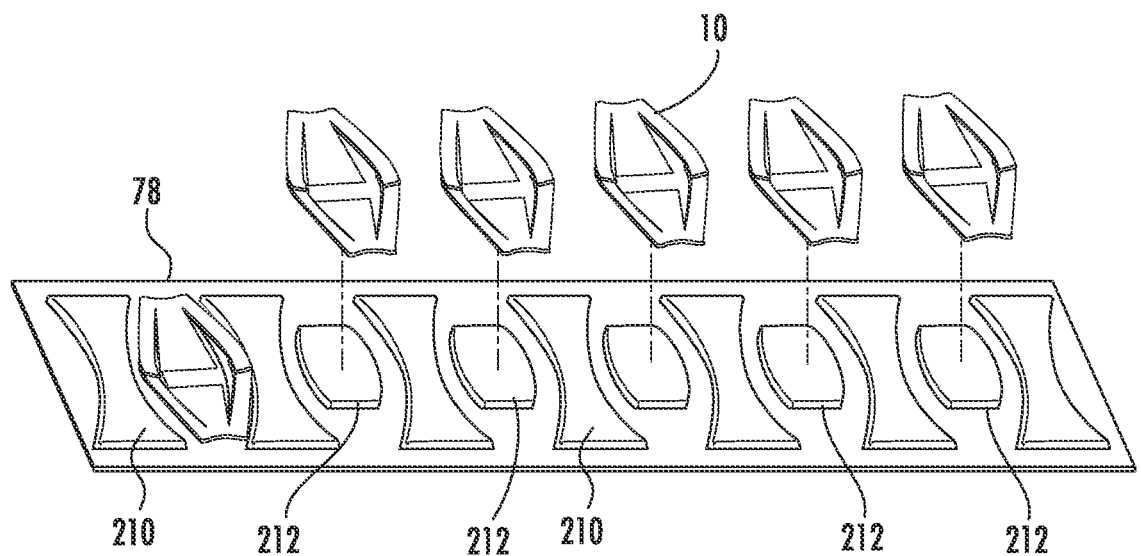

As another example, FIG. 102 is similar to FIG. 101 except, for example, that the padding strip 122 includes lateral extensions 124 configured for at least partially covering the struts 42. As further examples, FIGS. 103 and 104 are similar to FIG. 101 except, for example, that the padding strip 122 has been replaced with pads 210 configured for being positioned between the tissue bridges 10 and pads 212 configured for at least partially covering the struts 42. Throughout the Detailed Description section of this disclosure, the pads or padding 122 can be non-adherent, multilayer, medicated, drug-eluting, wicking, and/or have other suitable characteristics.

The tissue bridges 10 can include differently configured layers. For example, FIG. 105 can be described as depicting another embodiment of a multistable (e.g., symmetrically bistable or asymmetrically bistable) tissue bridge 10, wherein a single patient-contact carrier 26 has spaced apart reinforcing sheets 220 mounted thereto by way of spaced apart intermediate adhesive layers 222. Upper surfaces of the reinforcing sheets 220 can be respectively connected to the lower surfaces of the strut portions 20 by the inner adhesive 28. Optionally, a pad, silicone, and/or other suitable medicinal substance can be mounted, for example, to the central area of the patient-contact carrier 26.

In accordance with an embodiment of this disclosure, FIGS. 105-109 depict an embodiment of a system or multistable medical device 218 in which the multistable (e.g., symmetrically bistable or asymmetrically bistable) body 12 is configured to function as an applicator for use in carrying and applying a reinforced elastic wound covering 228. The reinforced elastic wound covering 228 can be more generally referred to as a flexible web, and it can include: an elastic patient-contact carrier 26; patient-contact adhesive 30; any associated pad, silicone, and/or other suitable medicinal substance mounted, for example, to the central area of the lower surface of the patient-contact carrier 26; the reinforcing sheets 220 and associated intermediate adhesive layers 222; and/or one or more release liners 32.

Two different versions of the multistable medical device 218 are described in the following. First, a version is discussed in the context of the multistable medical device 218 having stable equilibrium configurations that are utilized in a method of applying the wound covering 228 to a scar or wound 50 (e.g., the elastic patient-contact carrier 26 may be relatively weak (e.g., have a relatively low resistance to being stretched) as compared to forces associated with changing between the stable equilibrium configurations of the body 12). Thereafter, a version is discussed in which one or more of any stable equilibrium configurations of the multistable medical device 218 may not be utilized in a method of applying the wound covering 228 to a scar or wound 50 (e.g., the elastic patient-contact carrier 26 may be relatively strong (e.g., have a relatively high resistance to being stretched) as compared to forces associated with changing between any stable equilibrium configurations of the body 12)

Figure 105:
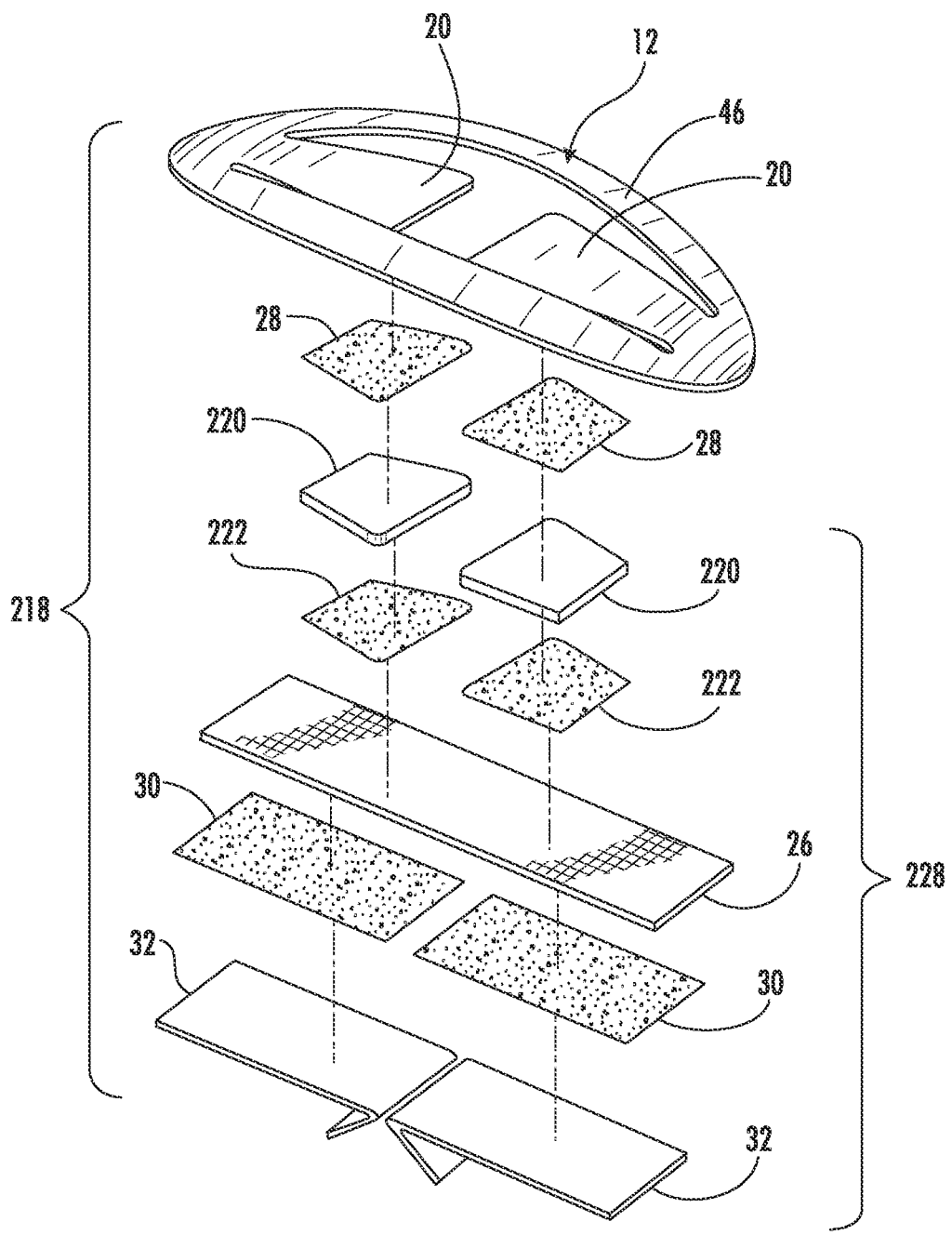
FIG. 105 is an exploded, top perspective view of a device including a multistable body (e.g., an applicator) and a reinforced elastic wound covering (e.g., for being applied using the applicator), in accordance with an embodiment of this disclosure.
Figure 106:
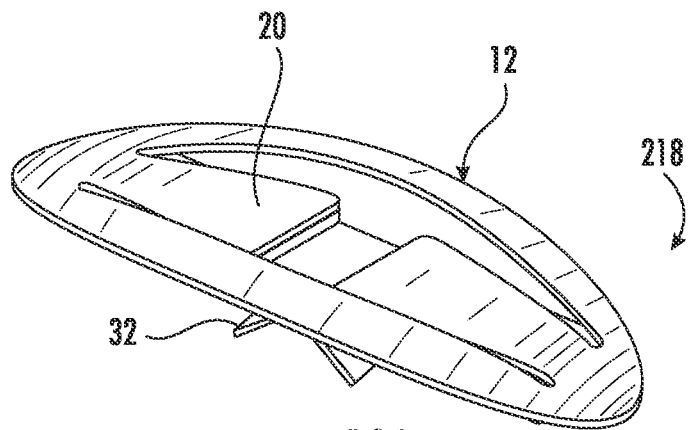
FIG. 106 is an assembled, top perspective view of the device of FIG. 105 in its retracted stable equilibrium configuration.
Figure 107:
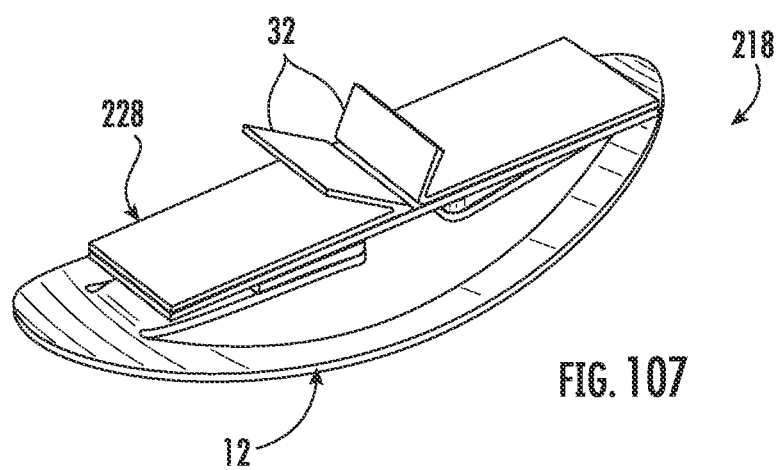
FIG. 107 is a bottom perspective view of the configuration of FIG. 106.
Figure 108:
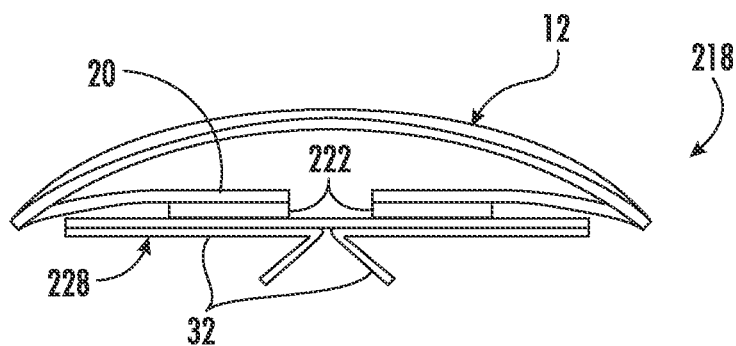
FIG. 108 is a front view of the configuration of FIG. 106.
Figure 109:
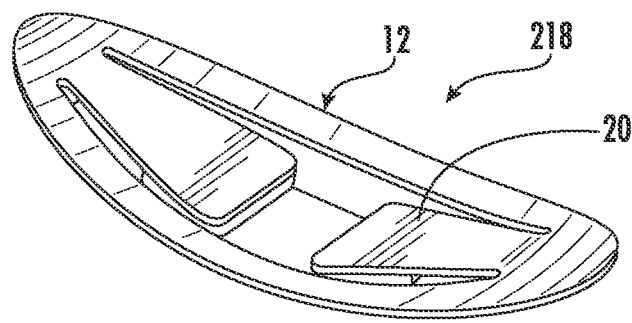
FIG. 109 is a top perspective view of the device of FIG. 106 in its extended stable equilibrium configuration or a further extended configuration.

As best understood with reference to FIG. 105, a specific multistable body 12 considered in isolation can have at least one unstable equilibrium configuration between stable equilibrium configurations. The medical device 218 that includes the specific multistable body 12 can have equilibrium configurations that are different from the equilibrium configurations of the specific multistable body 12 in isolation. That is and for example, the equilibrium configurations (e.g., the asymmetrical stable equilibrium configurations) of the medical device 218 can be at least partially defined by characteristics (e.g., stiffness, flexibility, and/or elasticity) of one or more of its components (e.g., the span of the elastic patient-contact carrier 26 between the struts 20). In this regard, the multistable medical device 218 is in its retracted stable equilibrium configuration in FIGS. 106-108, and the multistable medical device 218 is in its extended stable equilibrium configuration in FIGS. 109 and 110. For example, the elastic stretching of the span of (e.g., medial portion of) the elastic patient-contact carrier 26 between the struts 20 can be greater in the extended stable equilibrium configuration than any elastic stretching of the span of the elastic patient-contact carrier between the struts in the retracted stable equilibrium configuration. Accordingly, the medial portion of the carrier sheet 26 can be configured (e.g., can be elastic) in a manner that at least partially biases the medical device 218 toward its retracted configuration (e.g., retracted stable equilibrium configuration).

Figure 110:
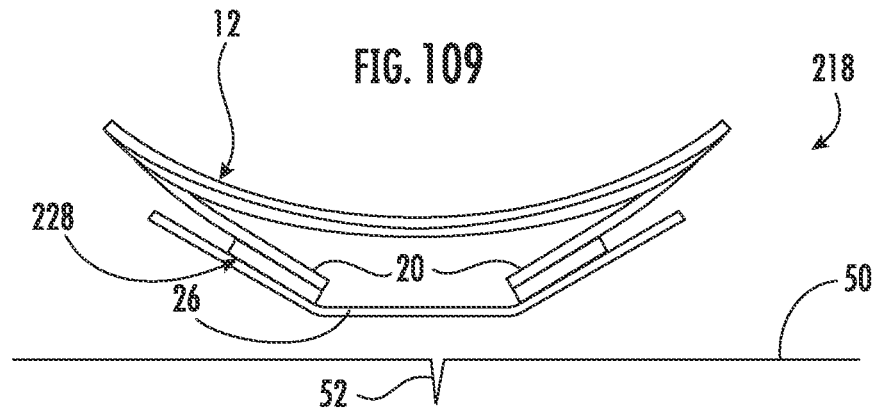
FIGS. 110 through 112 are front views that schematically depict a sequence of steps of a method of applying the reinforced elastic wound covering portion of FIGS. 105 through 109 to a scar or wound, wherein in FIG. 112 the reinforced elastic wound covering has been installed to the wound and separated from the multistable body, in accordance with an embodiment of this disclosure.
Figure 111:
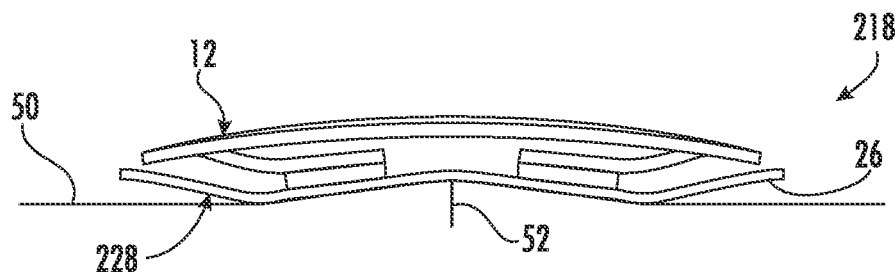
Figure 112:
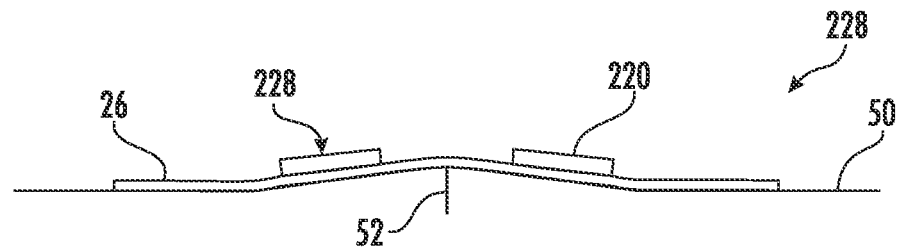

FIGS. 110-112 schematically depict an example of a sequence of steps of first and second methods of applying the wound covering 228 to a scar or wound 50 after the release liners 32 (FIGS. 105-108) have been removed, or the release liners 32 may be partially removed and then farther removed during the mounting process (see, e.g., FIGS. 63-68). In accordance with the first method, the medical device 218 is in its extended stable equilibrium configuration in FIG. 110, and in, or proximate, its retracted stable equilibrium configuration in FIG. 111.

Referring to FIG. 110, the medical device 218 in its extended stable equilibrium configuration can be manually held so that the length of the medical device 218 extends crosswise to, or more specifically substantially perpendicular to, the length of the scar, cut, or wound 50. Then, the patient-contact adhesive 30 (FIG. 105) on the lower or outer surfaces of the patient-contact carrier 26 can be engaged against the patient's tissue or skin 52 on either side of the scar, cut, or wound 50. Then, the device 218 can continue to be forced or pushed closer to the tissue 52 so that the patient-contact carrier 26 becomes further adhered to the patient's tissue 52 by the patient-contact adhesive 30.

Referring to FIG. 111 and in an example, after the medical device 218 is forced or pushed past its intermediate or maximally unstable equilibrium configuration, the body automatically transitions at least proximate to the retracted stable equilibrium configuration to further adhere the patient-contact carrier 26 to the tissue 52. In the process, the struts 42 become closer together and push the portions of the tissue 52 on opposite sides of the scar or wound 50 toward one another to relieve tension.

Referring to FIG. 112, after the medical device 218 reaches or is proximate its retracted stable equilibrium configuration, the body 12, along with the adhesive 28 directly connected to the body, can be removed from the wound covering 228. The adhesive 28 can have less adhesive strength than the adhesives 30, 222 in a manner that seeks to facilitate manual removal of the body 12 from the wound covering 228 while the wound covering remains adhered to the tissue 52. Alternatively, the body 12 may optionally remain mounted to the wound covering 228 while the wound covering remains adhered to the tissue 52, wherein the contracting elasticity of the span of (e.g., medial portion of) the elastic patient-contact carrier 26 and the biasing of the body 12 toward the retracted configuration can work together in a manner that seeks to enhance the tension reduction and/or eversion of the scar or wound 50.

In another version of the medical device 218, it may not be multistable or one or more of any multistable configurations of the multistable body 12 or medical device may not play a significant role in a method of applying the wound covering 228 to a scar or wound 50. For example, the force provided by the stretched span of the elastic patient-contact carrier 26 between the struts 20 may function as an arrestation mechanism that restricts the medical device 218 from reaching any relatively widely extended stable equilibrium configuration. In this version, one or more of the above-discussed configurations of the medical device 218 may be provided manually, or in another suitable manner, without reliance upon any tendency of the body 12 or medical device 218 to be biased toward any stable equilibrium configuration. For example, the configuration depicted in FIG. 110 may be achieved by manually grasping the opposite end portions of the laminate 228, or the like, that includes the elastic patient-contact carrier 26, patient-contact adhesive 30, and optionally one or more release liners 32, and pulling those opposite end portions away from one another in a manner that stretches the elastic patient-contact carrier and deforms the body 12. Reiterating from above, the release liners 32 may be partially removed and then further removed during the mounting process (see, e.g., FIGS. 63-68). Any arrestation feature provided by the stretched span of the elastic patient-contact carrier 26 between the struts 20 may be adjusted or tuned by changing the length and/or elasticity of the span of the elastic patient-contact carrier 26 between the struts 20.

Throughout the Detailed Description section of this disclosure, the adhesive layers 28, 30, 120, 222 can be continuous, discontinuous, and/or patterned. Also, one or more of the adhesives 28, 30, 120, 222 may be replaced with other suitable bonding or attaching features. For example, in addition to or as an alternative to the reinforced elastic wound covering 228 being connected to the body 12 by the adhesive, other features may be used to connect the reinforced elastic wound covering to the body either temporarily (e.g., the body is removed from the reinforced elastic wound covering after application to tissue) or permanently (e.g., the body remains connected to the reinforced elastic wound covering after application to tissue). Examples of such other features that may be used to connect the reinforced elastic wound covering 228 to the body 12 include hook and loop fasteners, slot and tab fasteners, hooks, pins, and/or other suitable features.

At least partially reiterating from above for multistable tissue bridges 10, at least lower or outer surfaces of the inner or distal end portions of the struts 42 typically include engagement or connection zones configured to move respective portions of patient tissue 52 toward one another in response to the struts becoming closer to one another. The engagement or connection zones of the struts 42 can be at least partially defined by or comprise respective portions of the adhesive material 30 and/or other suitable features. For example and referring to FIGS. 113 and 114, the engagement or connection zones of the struts 42 can be at least partially defined by or comprise pins, hooks, barbs, prongs 240, and/or other suitable features.

Figure 113:
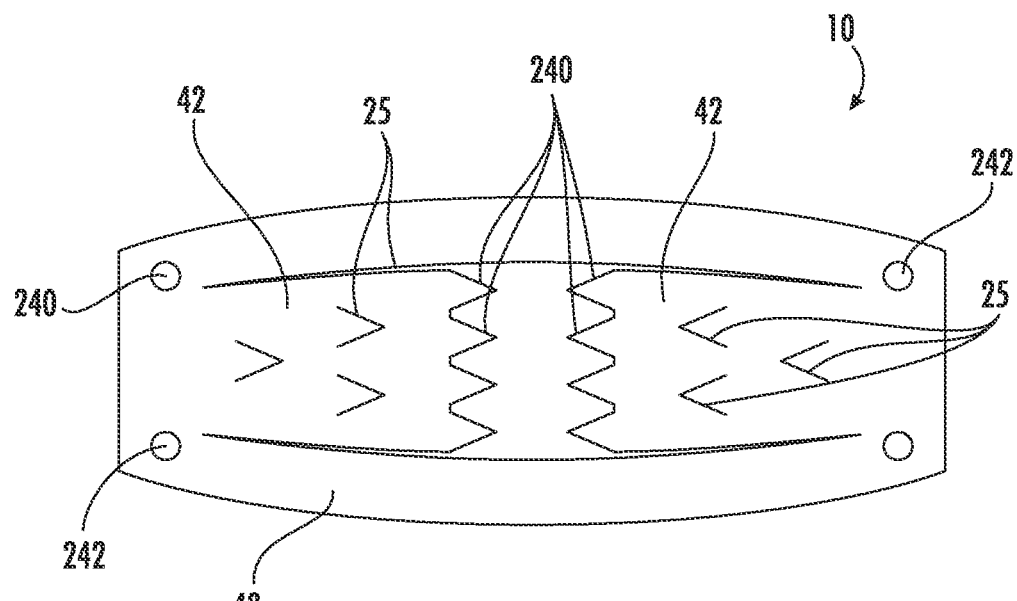
FIG. 113 is a schematic top view of a multistable tissue bridge in its extended stable equilibrium configuration, in accordance with an embodiment of this disclosure.
Figure 114:
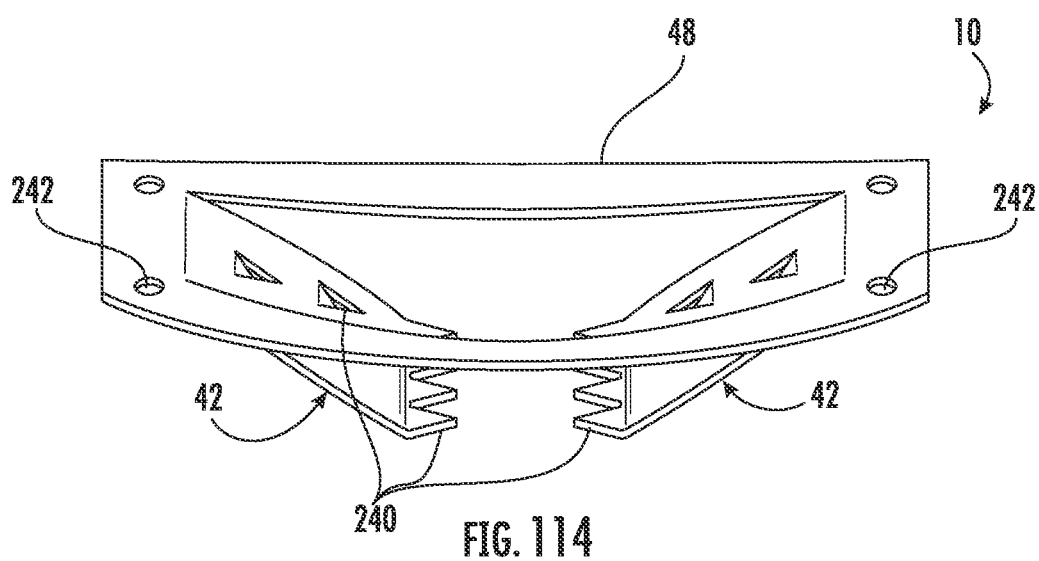
FIG. 114 is a top perspective view of the configuration of FIG. 113.

FIGS. 113 and 114 depict a multistable (e.g., symmetrically bistable or asymmetrically bistable) tissue bridge 10 that may be constructed of metallic or other suitable material (e.g., bioabsorbable material and/or polymeric material) by way of bending, thermoforming, stamping, injection molding, and/or in any other suitable manner. The cuts 25 or other suitable discontinuities in the tissue bridge 10 can at least partially define the prongs 240 at least in the struts 42. The tissue bridge 10 can optionally further include one or more mounting holes 242 configured for receiving attachment mechanisms such as, but not limited to, liquid adhesive material, fasteners, staples, threaded fasteners (e.g., screws, bolts, or the like), sutures, and/or suitable mechanisms for at least partially attaching the tissue bridge to tissue. A variety of differently configured materials and attachment features (e.g., hooks, pins or prongs 240, ingrowth holes, and mounting holes 242) are within the scope of this disclosure, as discussed in greater detail below.

The tissue bridge embodiment depicted in FIGS. 113-115D may be constructed of a flexible material configured so that the tissue bridge is multistable (e.g., symmetrically bistable or asymmetrically bistable) by virtue of having an extended stable equilibrium configuration, a retracted stable equilibrium configuration, and at least one unstable equilibrium configuration (e.g., a maximally unstable equilibrium configuration) between the stable equilibrium configurations. In this regard, FIGS. 113-115A depict the tissue bridge 10 in its extended stable equilibrium configuration, wherein the multistable spanning structure 48 is in its concave-up stable equilibrium configuration.

FIGS. 115A-115D schematically depict an example of a sequence of steps of a method of applying the tissue bridge 10 of FIGS. 113 and 114 to a scar or wound 50. The tissue bridge 10 is in its extended stable equilibrium configuration in FIGS. 115A and 115B; in or proximate its intermediate or maximally unstable equilibrium configuration in FIG. 115C; and in, or proximate, its retracted stable equilibrium configuration in FIG. 115D.

Figure 115A:
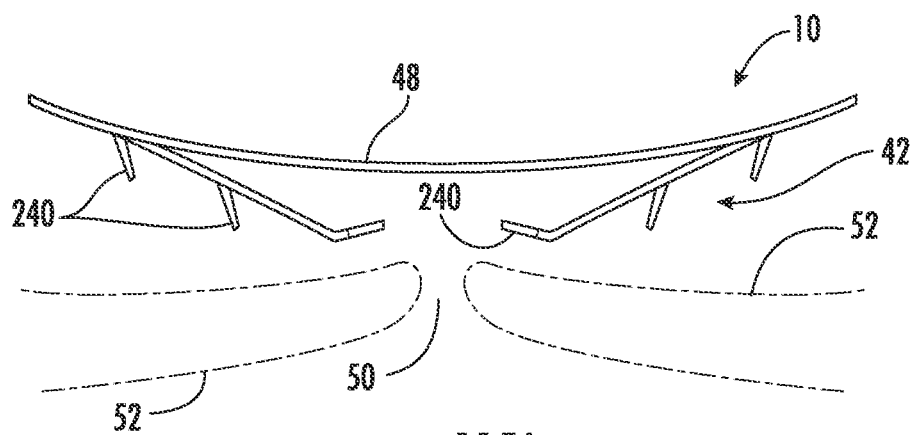
FIGS. 115A through 115D are front views that schematically depict an example of a sequence of steps of a method of applying the tissue bridge of FIGS. 113 and 114 to tissue (e.g., fascia), in accordance with an embodiment of this disclosure.
Figure 115B:
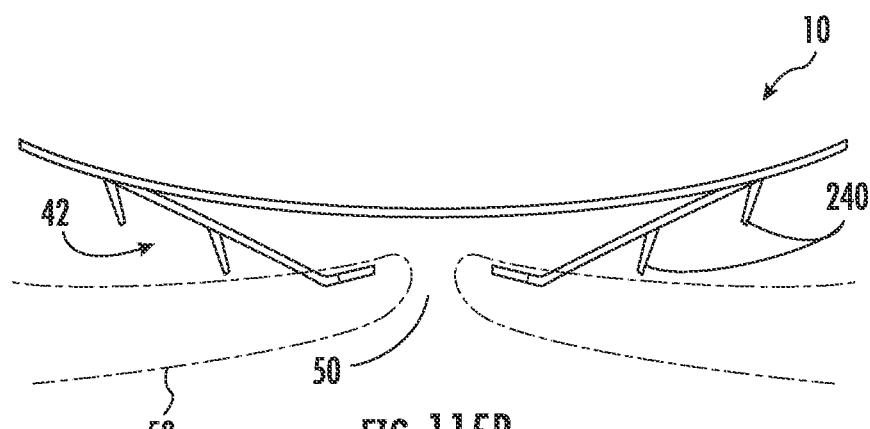
Figure 115C:
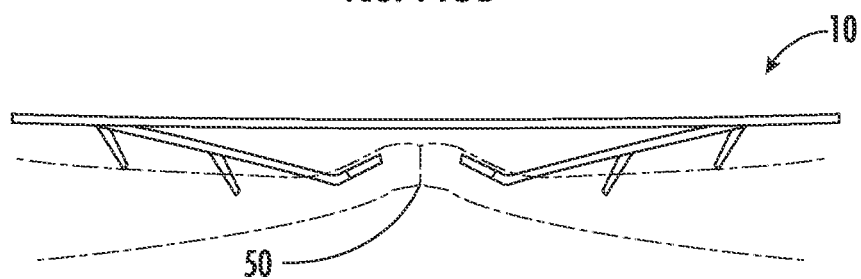
Figure 115D:
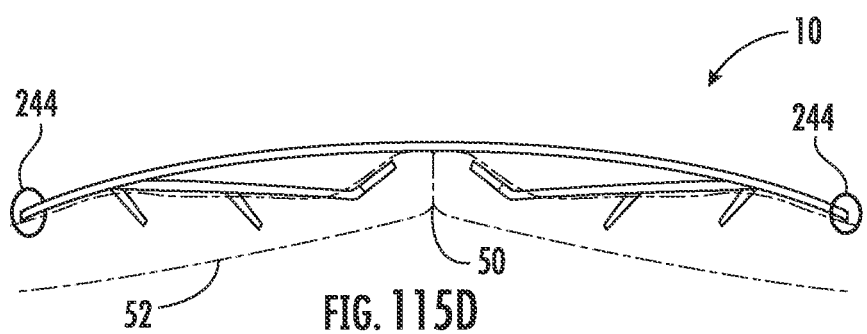

Referring to FIG. 115A, the tissue bridge 10 in its extended stable equilibrium configuration can be manually held so that the length of the tissue bridge extends across the cut, wound, or gap 50 in the tissue 52 (e.g., fascia). In the extended stable equilibrium configuration, the tips of the inner prongs 240 can be inserted into the tissue 52 by way of suitable relative movement between the tissue and the inner prongs. Referring to FIGS. 115B and 115C, the tissue bridge 10 can be forced or pushed closer to the tissue 52 so that at least the tips of the intermediate prongs 240, and optionally then the tips of outer prongs 240, become inserted into the tissue 52. Referring to FIG. 115D, in an example, after the tissue bridge 10 is forced or pushed past (e.g., beyond) its intermediate or maximally unstable equilibrium configuration (e.g., FIG. 115C), the tissue bridge automatically transitions at least proximate to the retracted stable equilibrium configuration (FIG. 115D) to further attach the tissue bridge to the tissue 52. In the process, the struts 42 become closer together and push the portions of the tissue 52 to which they are attached farther toward one another. Referring to FIG. 115D, one or more attachment mechanisms 244 schematically depicted as sutures 244 can extend through respective mounting holes 242 (FIGS. 113 and 114) and into the tissue 52 for at least partially further mounting the tissue bridge 10 to the tissue.

As another example, the tissue bridge 10 of FIGS. 113 and 114 can be mounted to an internal defect positioned in a tissue cavity or otherwise located so that the tissue bridge is at least partially enveloped by the tissue. The prongs 240 and mounting holes 242 can be configured differently than depicted in FIGS. 113 and 114. For example, the prongs 240 and mounting holes 242 can be defined in any of the portions of the tissue bridges 10.

Figure 116:
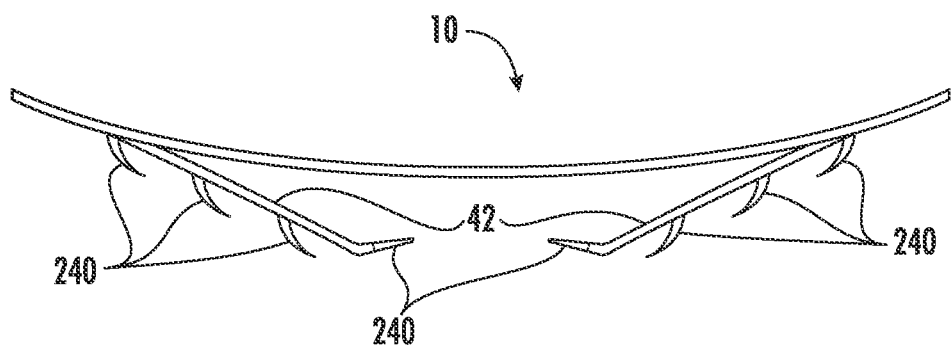
FIG. 116 is a side view of a version of the tissue bridge of FIGS. 113 and 114 wherein at least some of the prongs or hooks are curved and point medially.
Figure 117:
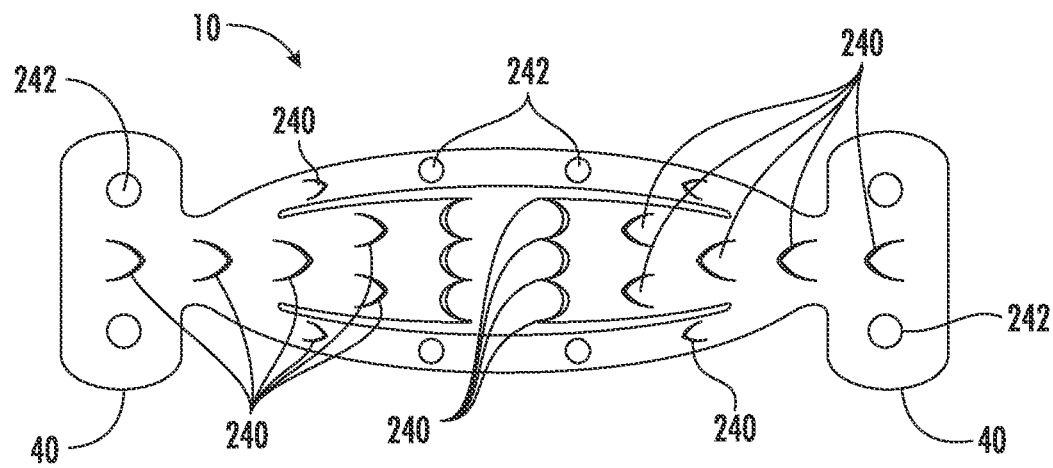
FIG. 117 is a top view of a version of the tissue bridge of FIGS. 113 and 114.

FIG. 116 is a side view of a version of the tissue bridge 10 of FIGS. 113 and 114, wherein at least some of the pins, hooks, barbs, or prongs 240 are curved and point medially. FIG. 117 is a top view of a version of the tissue bridge 10 of FIGS. 113 and 114 wherein the opposite end portions 40 of the tissue are extended and/or tab-like as compared to FIGS. 113 and 114. As also depicted in FIG. 117, lateral edges of the struts 42 can at least partially define (e.g., extend to the tips of) respective prongs 240 at the inner ends of the struts. As further examples, the edges extending between the tips of the prongs 240 at the inner ends of the struts 42 can be arcuate, rounded, and/or flattened in a manner that seeks to prevent those edges from cutting the tissue against which they are engaged.

Figure 118:
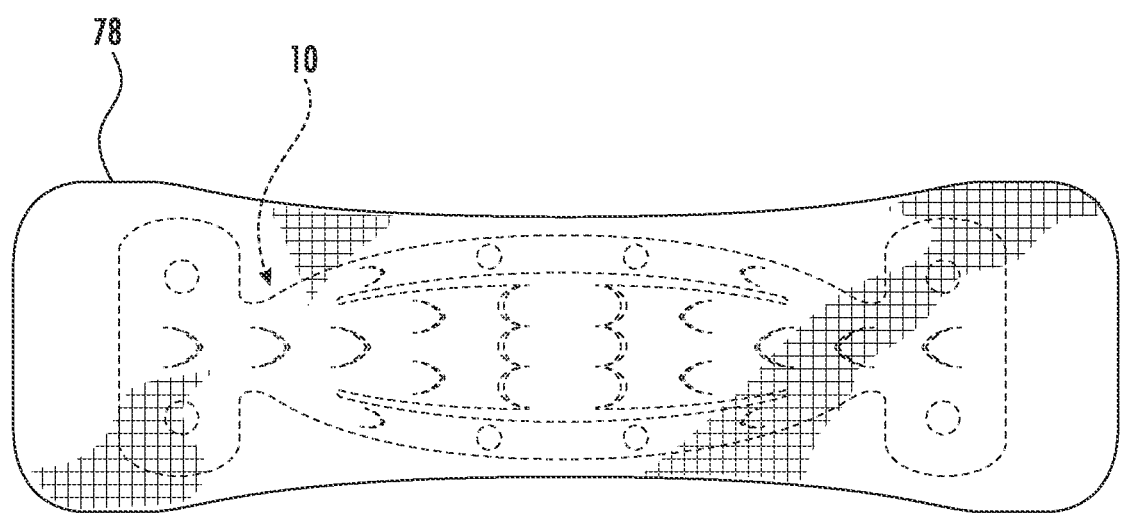
FIG. 118 is a top view of a version of the tissue bridge of FIGS. 113 and 114 including surgical mesh.

The end portions 40 can be configured to supplement fixation of the tissue bridge 10 to tissue, for example by including prongs 240 and/or mounting holes 242 (e.g., for receiving sutures). As another example, the end portions 40, or other suitable portions of the tissue bridge 10, can be formed of, can cover, be covered by, or otherwise be associated with surgical mesh material or other suitable perforated or mesh material (e.g., material configured (e.g., defining holes) for allowing tissue ingrowth). Alternatively, FIG. 118 depicts that the entire tissue bridge 10 can cover, be covered by, or otherwise be associated with a sheet 78 of surgical mesh material, or the like.

The tissue bridge 10 and/or one or more covers 78 (e.g., surgical mesh material 78) associated with the tissue bridge can include holes for promoting ingrowth of tissue. The tissue bridge 10 and/or one or more covers 78 (e.g., surgical mesh material 78) associated with the tissue bridge can be configured to be absorbed in the tissue over time. In one example, the non-absorbable cover 78 can span across the midline of the multistable tissue bridge 10, and the multistable tissue bridge can be absorbable, so that the non-absorbable cover can provide long-term strength after absorption of the tissue bridge. Alternatively, the cover 78 can be absorbable in the tissue and the tissue bridge 10 can be nonabsorbable. Alternatively, both the cover 78 and the tissue bridge 10 can be absorbable in the tissue. Additionally, the materials and/or thicknesses of the cover 78 and tissue bridge 10 can differ from one another so that their rates of absorption (e.g., into the tissue) differ from one another.

As discussed above, the engagement zones of the struts 42 can be defined by and/or comprise a variety of different suitable features configured to move respective portions of patient tissue 52 toward one another in response to the struts becoming closer to one another. For example and referring to FIGS. 119-121, the engagement zones of the struts 42 can be inner or distal end portions of the struts that are configured to extend into receptacles 250 (e.g., bore holes) defined in the tissue 52 (e.g., bone) on opposite sides of the wound, gap, break 50, and/or the like. As one example of possible contrast, tissue bridges 10 to be mounted to bone may be constructed of a material (e.g., metallic material) that is relatively rigid as compared to the flexible material (e.g., polymeric material) from which tissue bridges 10 to be mounted to skin are constructed.

Figure 120:
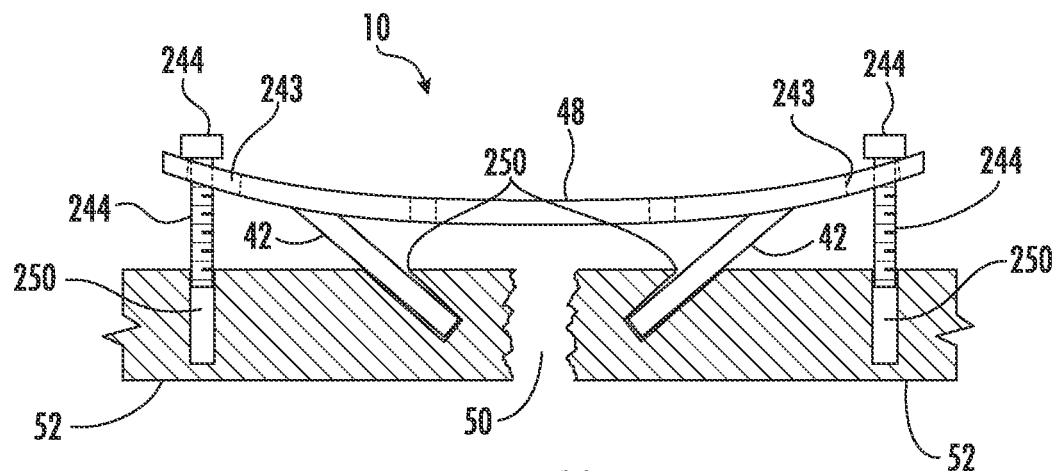
FIGS. 120 and 121 are front views that schematically depict an example of a sequence of steps of a method of applying a multistable tissue bridge to the broken bone of FIG. 119, in accordance with an embodiment of this disclosure.
Figure 121:
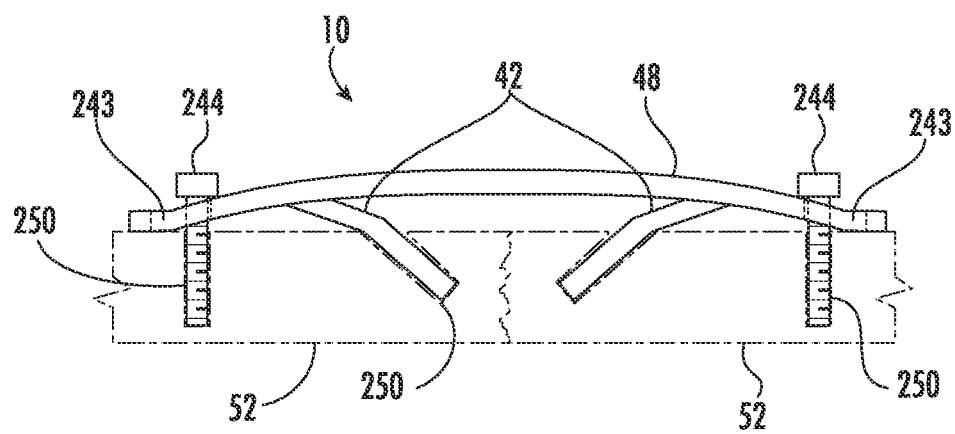

Referring to FIG. 120, the multistable (e.g., symmetrically bistable or asymmetrically bistable) tissue bridge 10 in its extended stable equilibrium configuration can be manually held so that the length of the tissue bridge extends across the wound, gap, or break 50 in the tissue 52 (e.g., bone). In the extended stable equilibrium configuration, the inner ends of the struts 42 can be inserted into the tissue 52 (e.g., into the receptacles 250 that may have been drilled, bored, and/or otherwise formed in the tissue) by way of suitable relative movement between the tissue and the inner ends of the struts. Referring to FIG. 121, in an example, the tissue bridge 10 can be forced or pushed closer to the tissue 52 so that the tissue bridge is forced or pushed past its intermediate or maximally unstable equilibrium configuration, and the tissue bridge automatically transitions at least proximate to the retracted stable equilibrium configuration to cause the struts 42 to become closer together and push the portions of the tissue 52 to which they are attached toward one another.

At least partially reiterating from above, the force for flattening out the concavity of the multistable spanning structure 48 can be provided by way of attachment mechanisms 244 (e.g., bone anchors and/or threaded fasteners such as screws and bolts) and tools (e.g., hand tools). For example and referring to FIGS. 120 and 121 regarding the tissue bridge 10 being forced toward and against the tissue 52, this relative movement between the tissue bridge and the tissue can be at least partially provided by the fasteners 244 being forced or driven a predetermined distance into the tissue. For example, the heads of the fasteners 244 and/or a washer or other suitable mechanism associated with the fasteners 244 can engage and push the tissue bridge closer to the tissue 52 in response to the fasteners 244 being forced or driven (e.g., screwed) a predetermined distance into the tissue. Additionally and/or alternatively, the heads of the fasteners 244 and/or a washer or other suitable mechanism associated with the fastener 244 can engage the respective outer surface portion of the tissue bridge body 12 to at least further securely mount the tissue bridge (in or proximate its retracted stable equilibrium configuration) to the tissue 52.

In FIGS. 120 and 121, guideways (e.g., guideway slots 243 (see, e.g., FIG. 122) that can also function as guide slots) that are hidden from view and located in the tissue bridge 10 end portions 40 are schematically depicted with dashed lines. Attachment mechanisms, for example fasteners 244 (e.g., bone anchors, screws, and/or bolts) can extend through the guideway slots 243 and into the tissue 52 for at least partially guiding movement of the tissue bridge and/or at least partially mounting the tissue bridge 10 to the tissue.

As apparent from comparing and contrasting FIGS. 120 and 121, each of the fasteners 244 can move in two directions relative to the guideway slots 243. Regarding the relative movement between the guideway slots 243 and fasteners 244 in a first direction, for forcing the tissue bridge 10 toward the tissue 52, the threaded fastener shafts extend through the guide slots and travel crosswise to the lengths of the guide slots in response to the fasteners 244 being tightened (e.g., rotatably driven into the tissue 52).

Regarding the relative movement between the guideway slots 243 and fasteners 244 in a second direction that is crosswise, or more specifically perpendicular, to the first direction, the threaded fastener shafts can move within and along the lengths of the guide slots, from at or proximate the outer ends of the guide slots to or proximate the inner ends of the guide slots. Further regarding the fasteners 244 traveling within and along the lengths of the guide slots 243, the lengths of one or more of the guide slots may not be perpendicular to the axis or axes of rotation of the associated strut(s) 42, or the like. It is believed that this can advantageously result in the application of predetermined torsional forces, for example torsional forces that may adjust alignment between the pieces of bone 52 separated by the break 50.

Figure 119:
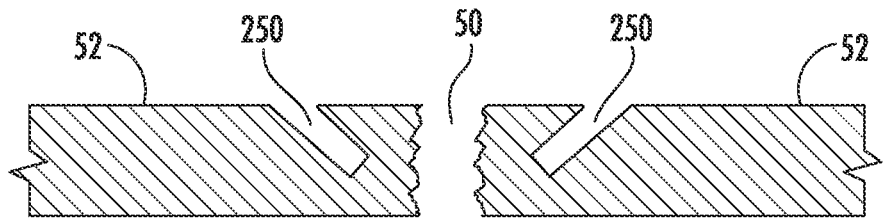
FIG. 119 is a side cross-sectional view depicting a broken piece of tissue (e.g., bone) with a bore hole in each piece, in accordance with an embodiment of this disclosure.

Whereas the receptacles 250 are angled (e.g., inclined) in FIGS. 119-121, the receptacles can extend more vertically or in any other suitable configuration. For example, structures and methods associated with the embodiment depicted in FIGS. 119-121 can be like structures and methods associated with embodiments depicted in FIGS. 122-133, except for variations noted and variations that will be apparent to those of ordinary skill in the art. For example, FIGS. 122-125 depict a tissue bridge 10 wherein pivotable inner portions of the struts 42 are angled or inclined relative to the central and outer end portions of the struts, for example so that the strut inner end portions can remain coaxial (e.g., substantially coaxial) with the vertical tissue receptacles 250 into which the strut inner end portions extend. The changeable inclination or angle of the inner end portions of the struts 42 can be provided, for example, by hinges 192 (e.g., a hinge including a hinge pin and associated bearing structure(s), a living hinge, and/or a hinge defined by malleable material (e.g., metallic material)).

Figure 122:
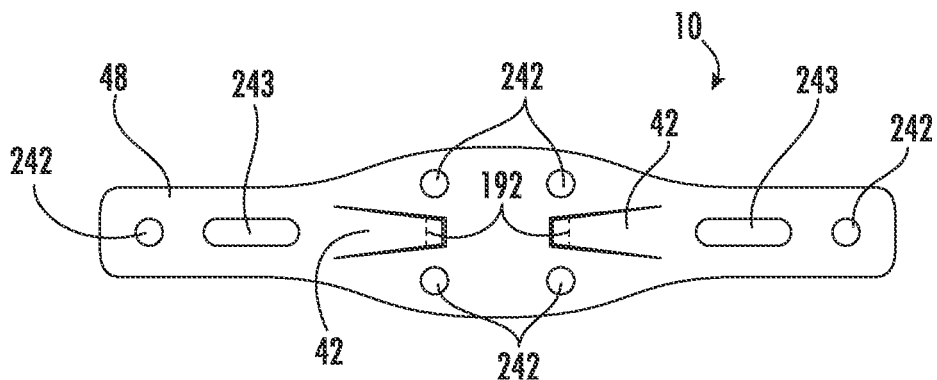
FIG. 122 is a top view of a multistable tissue bridge in accordance with an embodiment of this disclosure.
Figure 123:
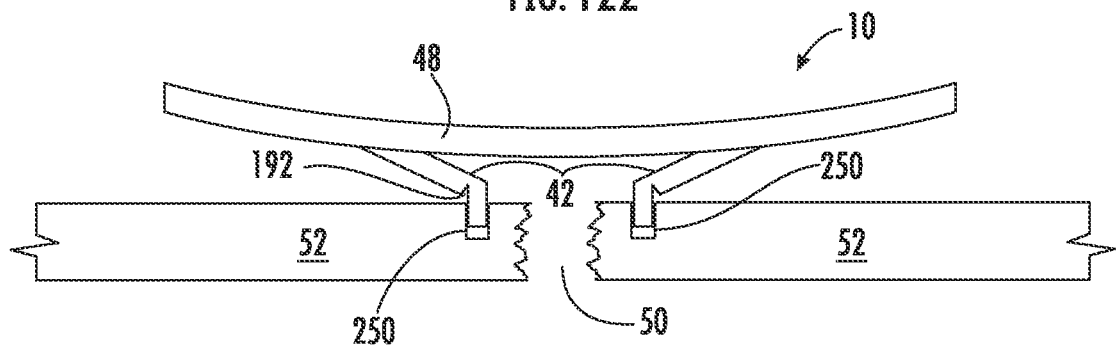
FIGS. 123 through 125 are front views that schematically depict an example of a sequence of steps of a method of applying the multistable tissue bridge of FIG. 122 to a broken bone, in accordance with an embodiment of this disclosure.
Figure 124:
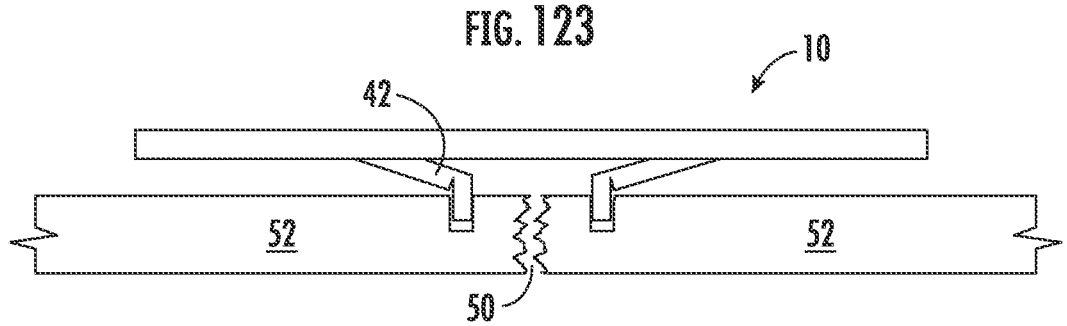
Figure 125:
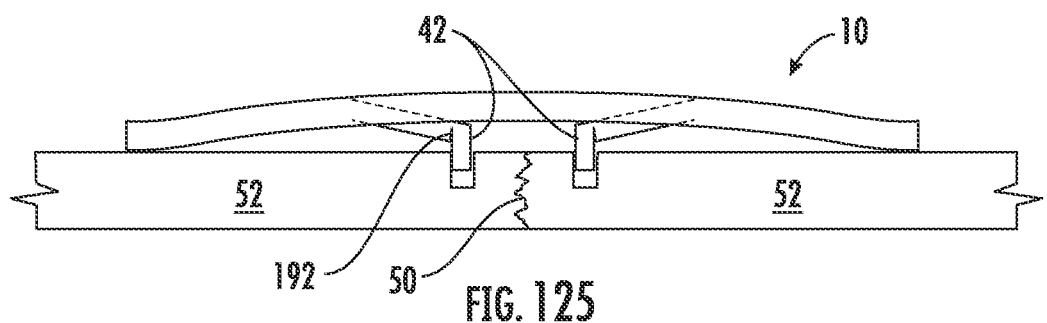

FIGS. 123-125 schematically depict an example of a sequence of steps of a method of applying the tissue bridge 10 of FIG. 122 to a scar or wound 50. The tissue bridge 10 is in its extended stable equilibrium configuration in FIG. 123; in or proximate its intermediate or maximally unstable equilibrium configuration in FIG. 124; and in, or proximate, its retracted stable equilibrium configuration in FIG. 125.

Referring to FIG. 123, the tissue bridge 10 in its extended stable equilibrium configuration can be manually held so that the length of the tissue bridge extends across the wound, gap, or break 50 in the tissue 52. In the extended stable equilibrium configuration, the inner ends of the struts 42 can be inserted into the receptacles 250. Referring to FIG. 124, the tissue bridge 10 can be forced or pushed closer to the tissue 52 so that the tissue bridge is transitioned to its intermediate or maximally unstable equilibrium configuration. Referring to FIG. 125, in an example, the tissue bridge 10 can be forced or pushed closer to the tissue 52 so that the tissue bridge automatically transitions at least proximate to its retracted stable equilibrium configuration to cause the struts 42 to become closer together and push the portions of the tissue 52 to which they are attached toward one another. Fasteners 244 (see, e.g., FIGS. 120 and 121) can extend through the guideway slots 243 (FIG. 122) in the tissue bridge end portions 40 and into the tissue 52 for at least partially forcing the tissue bridge 10 toward the tissue 52 and mounting the tissue bridge 10 to the tissue. As discussed above with reference to FIGS. 120 and 121, the fasteners 244 are driven farther into the tissue 52, the shafts of the fasteners 244 can move within and along the lengths of the guideway slots 243, from at or proximate the outer ends of the guide slots to or proximate the inner ends of the guide slots. Thereafter, one or more fasteners 244 can be applied through the one or more mounting holes 242 (FIG. 122) and into the tissue 52 for at least further mounting the tissue bridge 10 to the tissue.

Referring to FIG. 125, even after the tissue bridge 10 is fully mounted to the tissue 52, the tissue bridge can be maintained in or proximate retracted stable equilibrium configuration so that the central arch of the tissue bridge can be spaced apart from the break 50 while lateral portions of the tissue bridge are in closure proximity and/or intimately engaged and attached to the bone 52. It is believed that the gap between the central portion of the tissue bridge 10 and the break 50 seeks to avoid damaging the bone 52 (e.g. periosteum) near the fracture 50. It is also believed that the central arch of the tissue bridge 10 can contribute the strength of the spanning structure or plate 48 of the tissue bridge.

Figure 126:
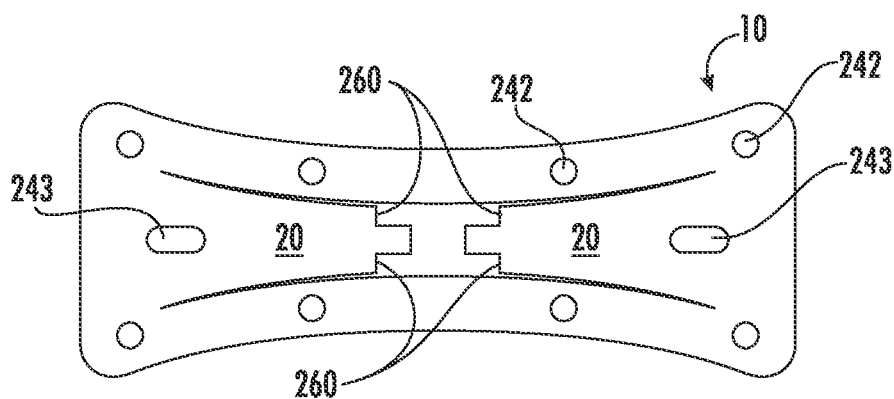
FIG. 126 is a top view of a multistable tissue bridge in accordance with an embodiment of this disclosure.
Figure 127:
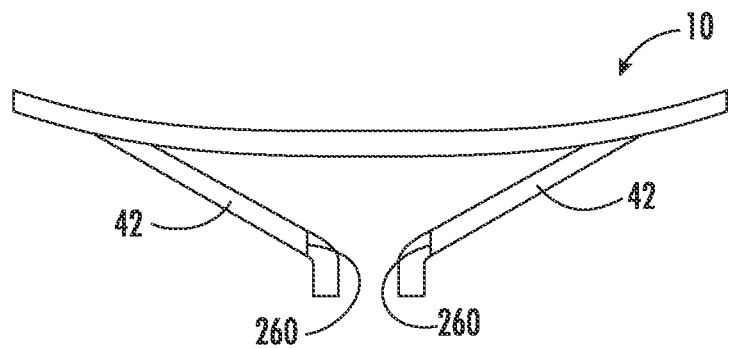
FIG. 127 is a schematic front view of the multistable tissue bridge of FIG. 126 in its extended stable equilibrium configuration.

Referring back to FIG. 122, the angled inner ends of the struts 42 can be reduced in size as compared to outer portions of the struts by virtue of the struts being tapered or configured in any other suitable manner. For example, FIG. 126 depicts a multistable (e.g., symmetrically bistable or asymmetrically bistable) tissue bridge 10, wherein the angled inner ends of the struts 42 can be reduced in size as compared to outer portions of the struts by virtue of shoulders 260 extending crosswise to, or more specifically perpendicular to, the length of the struts. FIG. 127 depicts the tissue bridge 10 of FIG. 126 in its extended stable equilibrium configuration.

Figure 128:
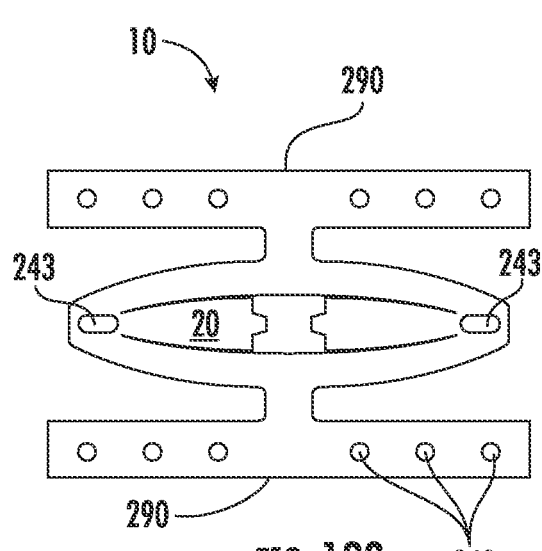
FIG. 128 is a top view of another embodiment of a multistable tissue bridge.
Figure 129:
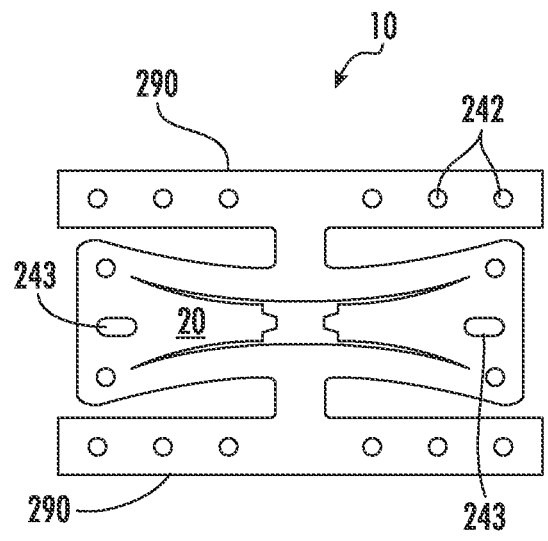
FIG. 129 is a top view of another embodiment of a multistable tissue bridge.

FIGS. 128 and 129 depict other examples of multistable (e.g., symmetrically bistable or asymmetrically bistable) tissue bridges 10, wherein the tissue bridges include integral lateral mounting plate portions 290 with mounting holes 242 for receiving fasteners 244 for further facilitating mounting of the tissue bridges to the tissue (e.g., bone).

Figure 130:
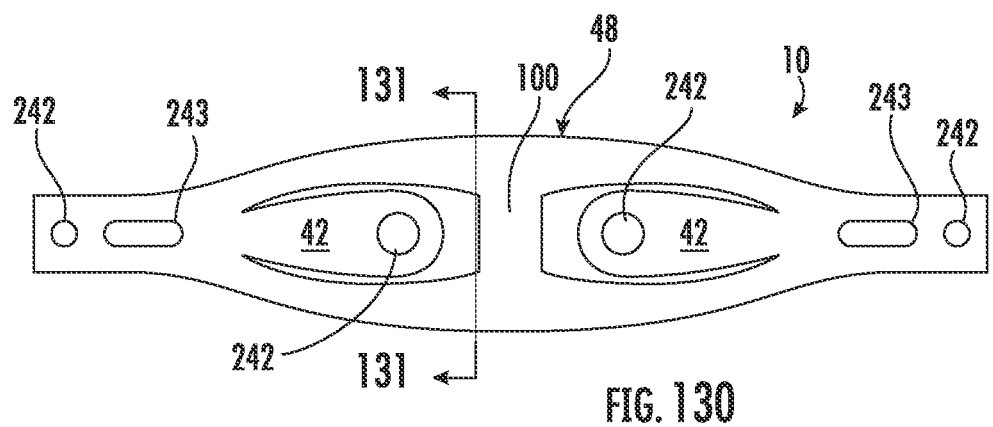
FIG. 130 is a top view of a multistable tissue bridge in its retracted stable equilibrium configuration, in accordance with an embodiment of this disclosure.
Figure 131:
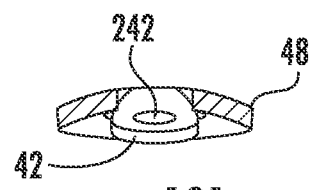
FIG. 131 is a cross-sectional view taken along line 131-131 of FIG. 130.
Figure 132:
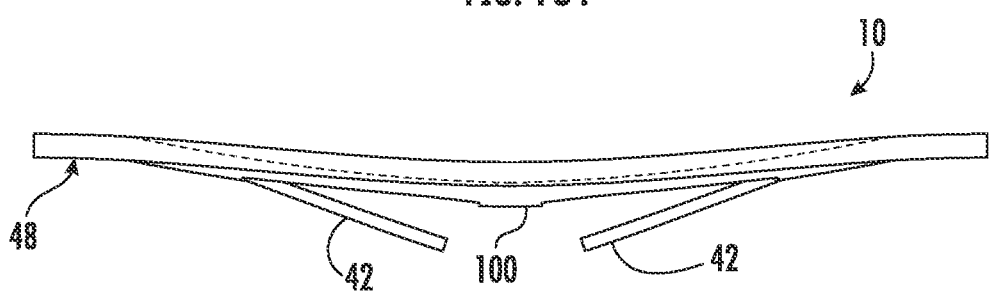
FIGS. 132 and 133 are front views that schematically depict an example of a sequence of steps of a method of applying the tissue bridge of FIG. 130 to a broken bone, in accordance with an embodiment of this disclosure.
Figure 133:
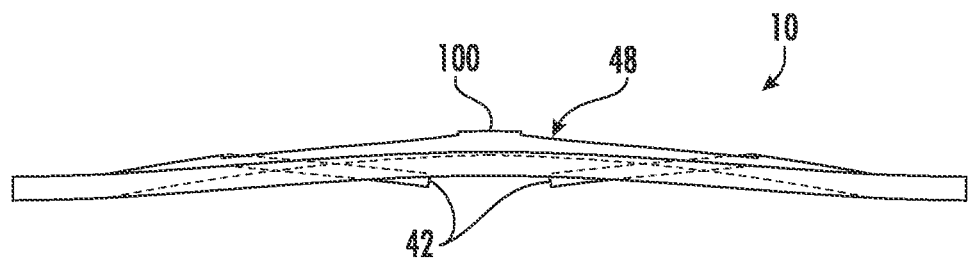

FIGS. 130-133 depict another embodiment of a multistable (e.g., symmetrically bistable or asymmetrically bistable) tissue bridge 10, wherein the tissue bridge is in its retracted stable equilibrium configuration in FIGS. 130, 131 and 133, and in its extended stable equilibrium configuration in FIG. 132. In the example depicted in FIGS. 130 and 131, the strut engagement or connection zones, which are configured to participate in moving respective portions of patient tissue 52 toward one another in response to the tissue bridge 10 reconfiguring toward the retracted stable equilibrium configuration, include mounting holes 242. The mounting holes 242 that extend through inner or distal end portions of the struts 42 are configured to receive attachment mechanisms 244 such as, but not limited to, fasteners 244 (see, e.g., FIGS. 120, 122, 141, and 142) and/or suitable mechanisms for at least partially attaching the tissue bridge to tissue 52.

FIGS. 132 and 133 schematically depict an example of a sequence of steps of a method of applying the tissue bridge 10 to a wound 50. Referring to FIG. 132, initially the inner or distal end portions of the struts 42 can be attached to the tissue 52 (see, e.g., the bone 52 of FIGS. 120 and 121) by way of fasteners 244 that extend through the strut mounting holes 242 (FIGS. 130 and 131) and into the tissue while the tissue bridge is in or proximate its extended stable equilibrium configuration. Referring to FIG. 133, then the multistable spanning structure 48 can be driven toward the tissue 52 (e.g., bone) by way of fasteners 244 that extend through the guideway slots 243 (FIG. 130) and into the tissue 52 to cause the tissue bridge 10 to transition to proximate its retracted stable equilibrium configuration. As the fasteners 244 in the guideway slots 243 are driven farther into the tissue 52, the shafts of the fasteners 244 can move within and along the lengths of the guideway slots 243, from at or proximate the outer ends of the guide slots to or proximate the inner ends of the guide slots. Then, the tissue bridge 10 can be further attached to the tissue 52 (e.g., bone) by way of one or more attachment mechanisms 244 (e.g., bone anchors, screws, and/or other suitable helically threaded fasteners) that extend through the one or more mounting holes 242 in the multistable spanning structure 48 and into the tissue 52.

At least partially reiterating from above, the tissue bridges 10 described above with reference to FIGS. 1-133 may be configured to be multistable by virtue of including at least one portion having, for example, at least one unstable equilibrium configuration (e.g., a maximally unstable configuration) between, for example, an extended stable equilibrium configuration, and a retracted stable equilibrium configuration. The multistable tissue bridges 10 can be configured, for example so that the stable equilibrium configurations of the spanning structures 46, 48 are symmetrical or asymmetrical. For example, for a given tissue bridge 10, the stable equilibrium configurations of the spanning structures 46, 48 may not be mirror images of one another.

An embodiment of an asymmetrical multistable tissue bridge 10 can be formed by injection thermoforming, or in any other suitable manner (e.g., stamping, injection molding, 3D printing, casting, machining, and/or the like), so that the curvature of the spanning structure 48 is different in the concave-up stable equilibrium configuration as compared to the concave-down stable equilibrium configuration. In this regard, it is believed that the multistable tissue bridges 10 can be configured to both fit different curvatures of the body and have different degrees of angle between the spanning structure 48 and strut(s) 42. For increasing central movement of the tissues, a tissue bridge 10 can be tuned, for example, by increasing the angle between the proximal end portion of the strut 42 and the body end portion 40 to which the strut proximal end portion is attached. Such a tissue bridge 10 with a relatively large angle between the strut proximal end portion and the body end portion can be tuned for being mounted on a relatively flat portion of tissue, for example by adjusting the side arm angles so that the retracted stable equilibrium configuration is relatively flat and the extended stable equilibrium configuration is more curved.

The tissue bridges 10 may be configured so that they do not include an unstable equilibrium configuration between stable equilibrium configurations. As a more specific example, equilibrium configurations may not be included, so that the tissue bridges 10 are not biased by strain or elastic potential energy toward either of the extended or retracted configurations. For example, in the embodiment of the tissue bridge 10 depicted in FIGS. 134-135, the spanning structure 48 can be a relatively thick, rigid plate 48 of material (e.g., metallic material, alloys, stainless steel, titanium, or other suitable material) configured so that throughout the usage of the tissue bridge the spanning structure or plate 48 may not deflect (e.g., may maintain its substantially planar or other substantially non-changing configuration), or more generally any deflection of the spanning structure or plate 48 may be relatively small (e.g., a relatively rigid spanning structure). In contrast, the one or more struts 42 can be pivotable relative to the spanning structure or plate 48, for providing the retracted configuration depicted in FIG. 135 and the extended configuration depicted in FIG. 136A.

Figure 134:
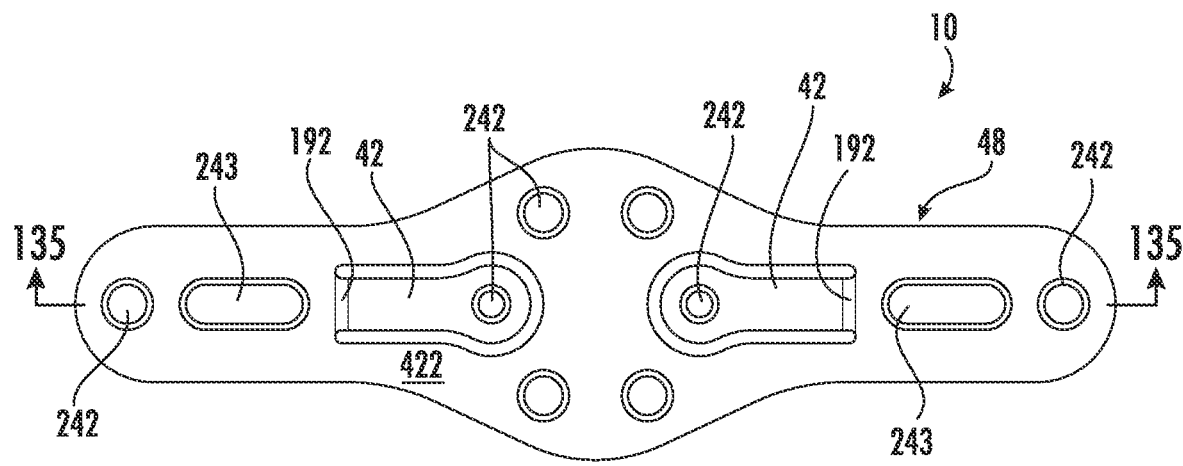
FIG. 134 is a top view of a tissue bridge in accordance with an embodiment of this disclosure.
Figure 135:
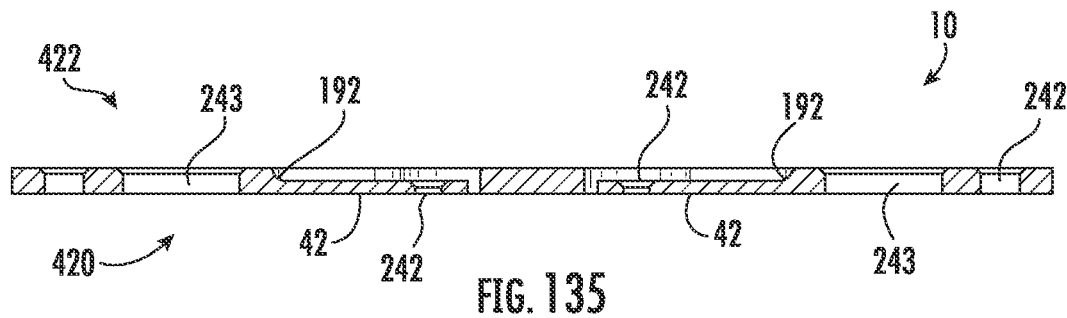
FIG. 135 is a cross-sectional view taken along line 135-135 of FIG. 134.
Figure 136A:
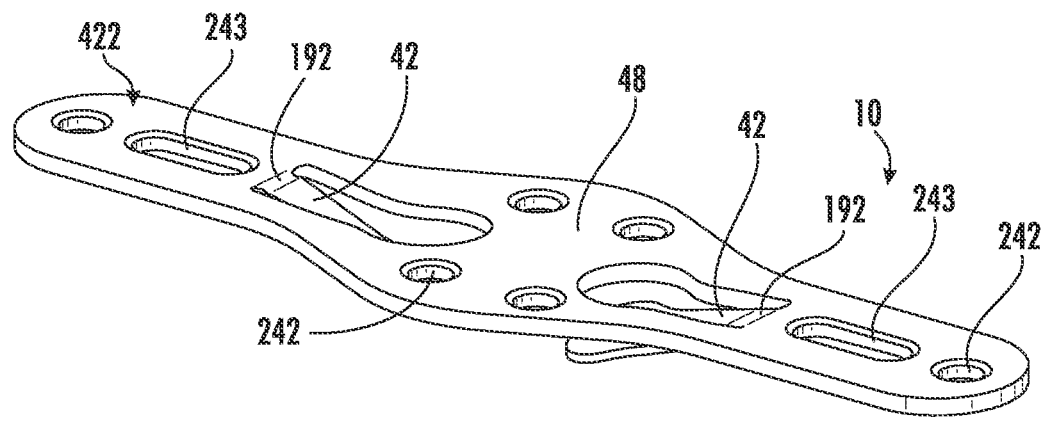
FIG. 136A is a top perspective view of the tissue bridge of FIG. 134 in its extended configuration.

The one or more struts 42 can be pivotable relative to the spanning structure or plate 48 by virtue of one or more hinges 192 (e.g., a hinge including a hinge pin and associated bearing structure(s), a living hinge, and/or a hinge defined by malleable material (e.g., metallic material)) being positioned or defined between the proximal end or end portion of the strut and the spanning plate 48, as will be discussed in greater detail below. The angle defined between the strut proximal end portions and the spanning plate 48 at the respective hinges, or the like, can vary between an acute angle in the tissue bridge extended configuration (FIG. 136A) to a zero or near zero angle in the tissue bridge retracted configuration (FIGS. 134 and 135). As a more specific example, in the retracted configuration of the tissue bridge 10 depicted in FIGS. 134 and 135, the struts 42 can be both coplanar with the spanning plate 48 and positioned in respective strut-receiving holes in the spanning plate. Conversely and as depicted in FIG. 136A, in the extended configuration, the struts 42 can extend obliquely outwardly from the respective strut-receiving holes in the spanning plate 48.

In the embodiment depicted in FIGS. 134-136A, the spanning plate 48 has opposite first and second sides 420, 422, the struts 42 are configured to pivot at least outwardly from holes in the spanning plate and away from the first side 420, and the first side 420 is for being in opposing face-to-face relation or contact with the tissue 52 (e.g., bone) to which the tissue bridge 10 is mounted. In this instance, the first side 420 of the tissue bridge 10 would typically be oriented toward the bone tissue 52 at least because the counterbored or countersunk openings of the holes 242, 243 are located at the second side 422. Alternatively, the tissue bridge 10 can be configured for having the second side 422 be in opposing face-to-face relation or contact with the bone tissue 52.

An example of a sequence of steps of a method of applying the tissue bridge 10 of FIGS. 134 and 135 is described in the following with reference to FIGS. 136A-136C. Initially or after pivoting of the struts 42, the tissue bridge 10 can be in the extended configuration depicted in FIG. 136A, so that the struts 42 extend outwardly from the respective holes in the spanning plate 48, and obliquely away from the first side 420 of the tissue bridge. Then, and as best understood with reference to FIG. 136B, through relative movement between the tissue bridge 10 and the tissue 52 (e.g., bone), the distal end portions of the struts 42 can be engaged against the tissue. The distal end portions of the struts 42 can be attached to the bone tissue 52 by way of attachment mechanisms 244 (e.g., bone anchors, screws, and/or other suitable helically threaded fasteners) that extend through the strut mounting holes 242 and into the tissue 52.

Then, the tissue bridge spanning structure 48 can be at least partially attached to the tissue 52 (e.g., bone) by way of attachment mechanisms 244 (e.g., bone anchors, screws, and/or other suitable helically threaded fasteners) that extend through the guideway holes or slots 243 in the tissue bridge spanning structure 48 and into the tissue 52. Then, and referring to FIG. 136C, the relatively rigid spanning structure or plate 48 can be driven toward the tissue 52 by way of the fasteners 244 that extend through the guideway slots 243 to both cause the tissue bridge 10 to transition to, or at least closer to, its retracted configuration (by way of convergent relative pivoting between the struts 42 and spanning structure 48), and cause the first side 420 of the tissue bridge 10 engage the tissue. As the tissue bridge transitions from its extended configuration toward its retracted configuration, the fasteners 244 extending through the strut mounting holes 242 apply force against the patient's tissue 52 so that the wound 50 is at least partially closed.

As the shafts of the fasteners 244 extending through the guideway slots 243 are driven farther into the tissue 52, the shafts of the fasteners 244 can move within and along the lengths of the guideway slots 243, from at or proximate the outer ends of the guide slots to or proximate the inner ends of the guide slots. Then, the spanning plate 48 can be further attached to the tissue 52 (e.g., bone) by way of one or more attachment mechanisms 244 (e.g., bone anchors, screws, and/or other suitable helically threaded fasteners) that extend through the one or more mounting holes 242 in the plate 48 and into the tissue 52.

Figure 136D:
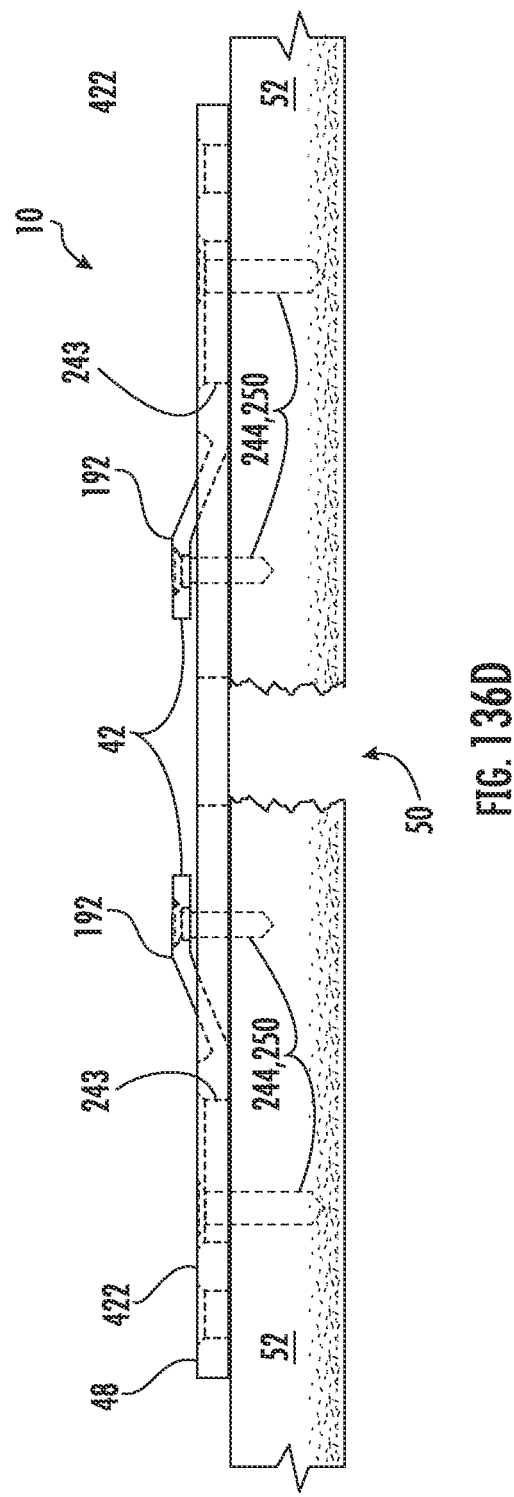
FIG. 136D depicts one of a sequence of steps of a method of applying the tissue bridge of FIGS. 134 and 135 to a broken bone, in accordance with an embodiment of this disclosure.

Another example of a sequence of steps of a method of applying the tissue bridge 10 of FIGS. 134 and 135 is described in the following with reference to FIGS. 136C and 136D. Initially or after pivoting of the struts 42, the tissue bridge 10 can be in the extended configuration depicted in FIG. 136D, so that the struts 42 extend outwardly from the respective holes in the spanning plate 48, and obliquely away from the second side 422 of the tissue bridge.

Then, through relative movement between the tissue bridge 10 and the tissue 52 (e.g., bone), the first side 420 of the tissue bridge 10 can be engaged against the tissue. Then, the tissue bridge spanning structure 48 can be at least partially attached to the tissue 52 by way of attachment mechanisms 244 (e.g., bone anchors, screws, and/or other suitable helically threaded fasteners) that extend through the guideway holes or slots 243 in the tissue bridge spanning structure 48 and into the tissue 52. The fasteners 244 extending through the guideway slots 243 can be tightened until each of their heads engage or become closely proximate to the second side 422 of the tissue bridge 10, the first side 420 of the tissue bridge engages or becomes proximate the tissue, and any torque loading in the attachment mechanisms in the guideway slots 243 is relatively small so that there can be predetermined relative movement. The predetermined relative movement comprises relative movement between the first side 420 of the tissue bridge and the tissue 52, and movement between the fasteners 244 in the guideway slots 243 along the length of the guideway slots.

Then, the distal end portions of the struts 42 can be at least partially attached to the bone tissue 52 by way of attachment mechanisms 244 (e.g., bone anchors, screws, and/or other suitable helically threaded fasteners) that extend through the strut mounting holes 242 and into the tissue 52. Then, and referring to FIG. 136C, the distal ends of the struts 42 can be driven toward, and into engagement with, the tissue 52 by way of the fasteners 244 that extend through the strut mounting holes 242 to cause the tissue bridge 10 to transition to, or at least closer to, its retracted configuration (by way of convergent relative pivoting between the struts 42 and spanning structure 48). Then, the fasteners 244 that extend through the guideways 243 can be further tightened, and the spanning plate 48 can be further attached to the tissue 52 by way of one or more attachment mechanisms 244 (e.g., bone anchors, screws, and/or other suitable helically threaded fasteners) that extend through the one or more mounting holes 242 in the plate 48 and into the tissue 52. As the tissue bridge transitions from its extended configuration toward its retracted configuration, the fasteners 244 extending through the strut mounting holes 242 apply force against the patient's tissue 52 so that the wound 50 is at least partially closed In the examples depicted in FIGS. 136B and 136D, for seeking to avoid any potential misalignment of the fasteners 244, the distal end portions of the struts 42 are angled to extend crosswise (e.g., substantially perpendicular) to the axes of the fasteners extending through the strut mounting holes 242 so that the strut mounting holes are substantially coaxial with the shafts of the fasteners extending therethrough. The angle defined between the strut distal end portions and the remainder of the struts 42 can vary between an acute angle in the tissue bridge extended configuration to a zero or near zero angle in the tissue bridge retracted configuration. The change in the angle defined between the strut distal end portions and the remainder of the struts 42 can be at least partially provided by hinges 192 defined between the strut distal end portions and the remainder of the struts 42.

In the embodiments depicted in FIGS. 134-136D, the hinges 192 between the strut distal end portions and the remainder of the struts 42, and the hinges between the proximal end or end portions of the struts and the spanning plate 48 can be at least partially defined by malleability of the material from which the tissue bridge 10 is constructed and the struts being thinner than the spanning plate. Alternatively or in addition, these hinges associated with the struts 42 can be provided in any other suitable manner (e.g., a hinge including a hinge pin and associated bearing structure(s), a living hinge, and/or other suitable structures).

Figure 136E:
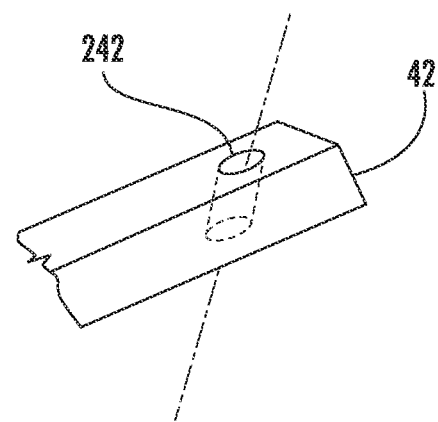
FIGS. 136E through 136H are cutaway views that schematically depict examples of versions of mounting holes extending through distal end portions of struts.
Figure 136F:
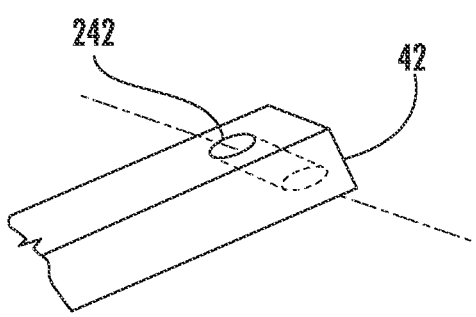
Figure 136G:
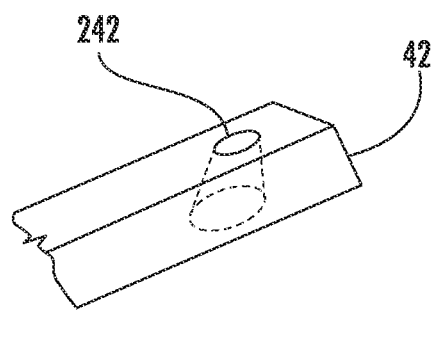
Figure 136H:
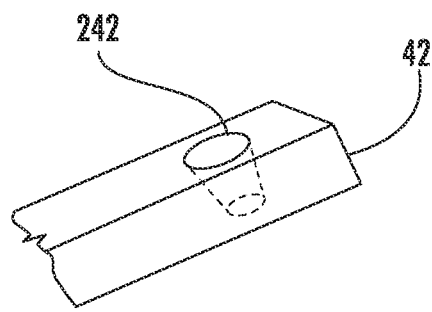

Alternatively or in addition to including the hinges 192 between the strut distal end portions and the remainder of the struts 42, the strut mounting holes 242 can be configured for seeking to avoid fastener misalignment and/or for other reasons (e.g., applying leverage, facilitating relative rotation, or for other suitable reasons). For example, the strut mounting holes 242 can be configured as depicted in FIGS. 136E-136H. FIGS. 136E and 136F depict that the axis of the strut mounting hole 242 can extend obliquely relative to the lengthwise axis of the strut 42. FIGS. 136G and 136H depict that the opposite openings of the mounting hole 242 can be relatively wide or relatively small as compared to one another, and that the mounting hole can be at least partially frustoconical, for example frustoconical or at least partially frustoconical along its entire length.

Figure 137:
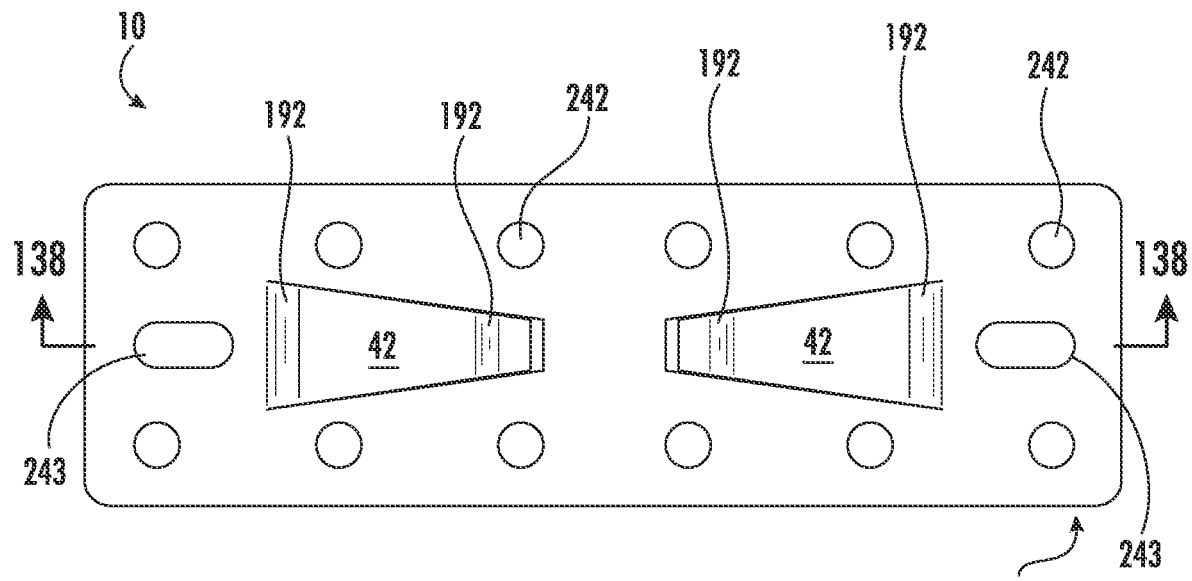
Figure 138:
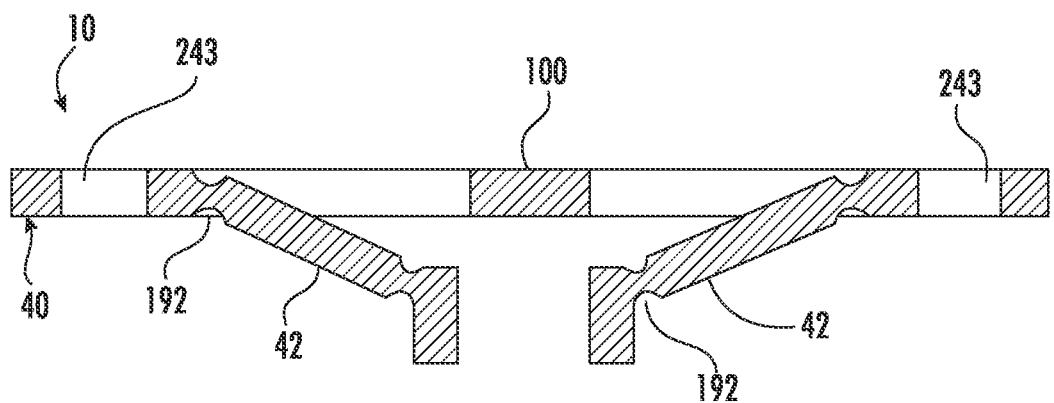

The embodiment of the tissue bridge 10 of FIGS. 134-136C can be like the tissue bridge embodiment of FIGS. 137 and 138 (e.g., including both structures and associated methods), except for variations noted and variations that will be apparent to those of ordinary skill in the art. In the example depicted in FIGS. 137 and 138, the strut engagement or connection zones, which are configured to move respective portions of patient tissue 52 toward one another in response to reconfiguring toward the retracted configuration, are in the form of distal end portions of the struts 42. The distal end portions of the struts 42 can be configured for being inserted into tissue holes 250 (see, e.g., FIGS. 119-121, 123-125, and 136B-136D). In FIG. 137, the inner or distal end portions of the struts 42 are pivotable relative to the other portions of the struts due to hinges 192, and the proximal end portions of the struts are pivotably connected to the tissue bridge end portions 40 by way of hinges 192. The hinges 192 can be living hinges and/or any other suitable hinges.

Figure 139:
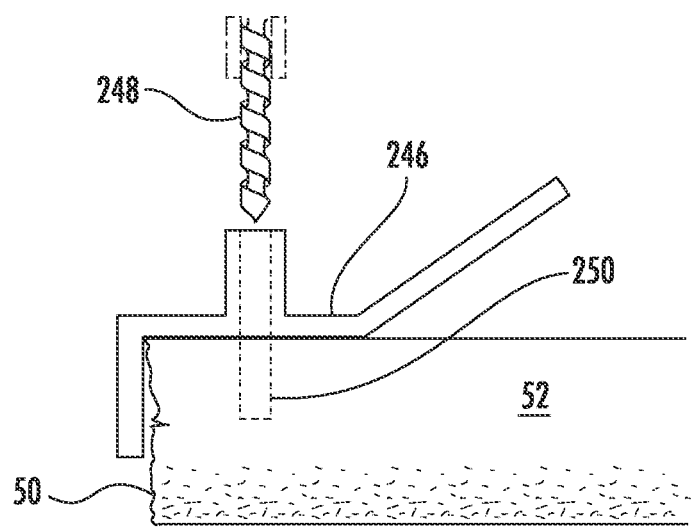

FIG. 139 schematically depicts that, for mounting the inner or distal ends of the struts 42 of a tissue bridge 10, a jig 246 may be used to drill, bore, and/or ream a receptacle hole 250 adjacent the wound or break 50 in the tissue 52 (e.g., bone). The jig 246 can be used in conjunction with a drill bit 248 to at least partially form the receptacle or tissue hole 250. The tissue hole 250 can be configured for receiving the distal end portion of a strut 42, an attachment mechanism 244 (e.g., threaded fastener) extending through a strut mounting hole 242, and/or another suitable strut engagement or connection zone feature.

Figure 140:
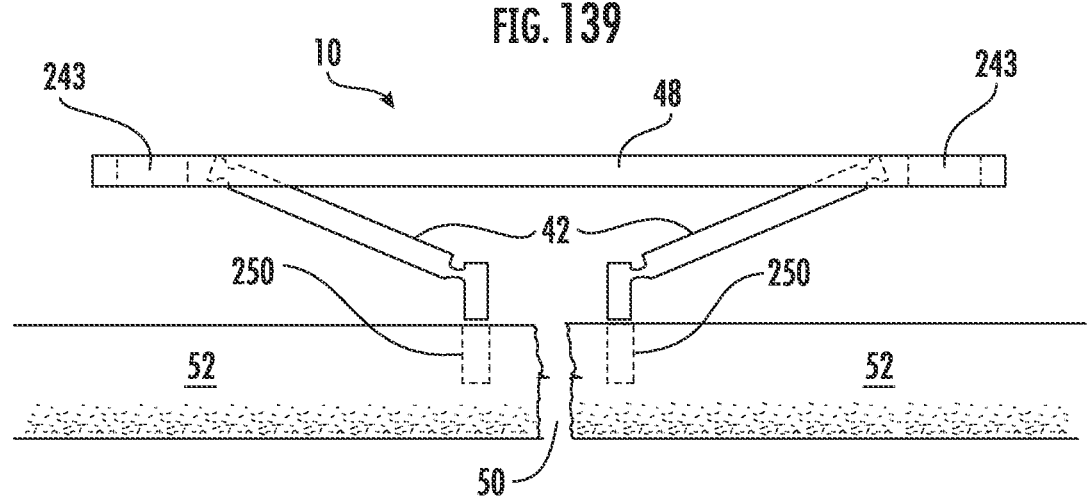
Figure 141:
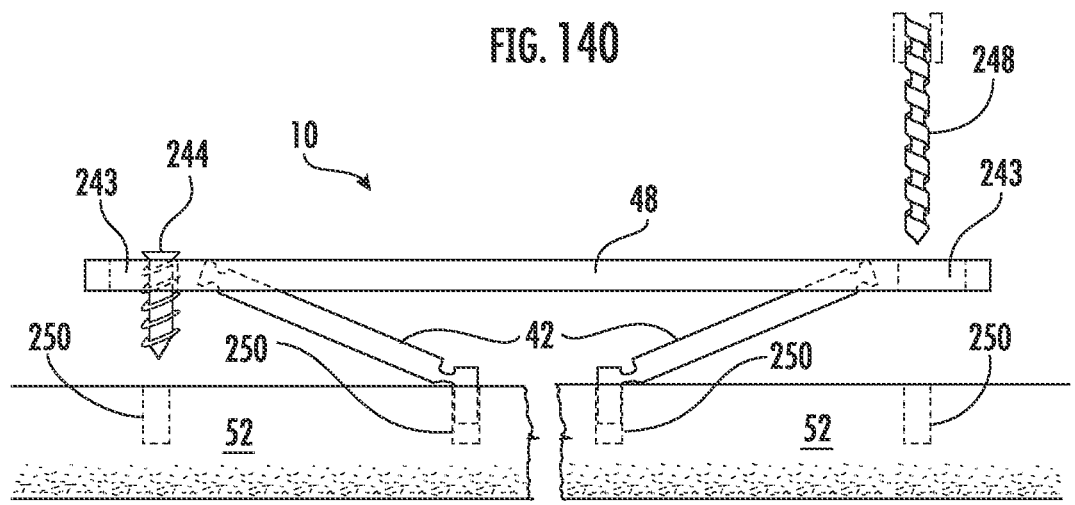

FIG. 140 schematically depicts the inner or distal end portions of the struts 42 being mounted in or to the receptacle holes 250 of the type formed as discussed above with reference to FIG. 139. Referring to FIG. 141, after the struts 42 are mounted as indicated with reference to FIG. 140, the tissue bridge 10 can be sufficiently rigid so that the tissue bridge is self-supporting in its extended configuration, and the outer end portions of the guideway slots 243 can be used as guides for directing the drill bits 248 or other boring devices into the intended locations of the receptacle holes 250 respectively coaxially aligned with the outer end portions of the guideway slots 243.

Figure 142:
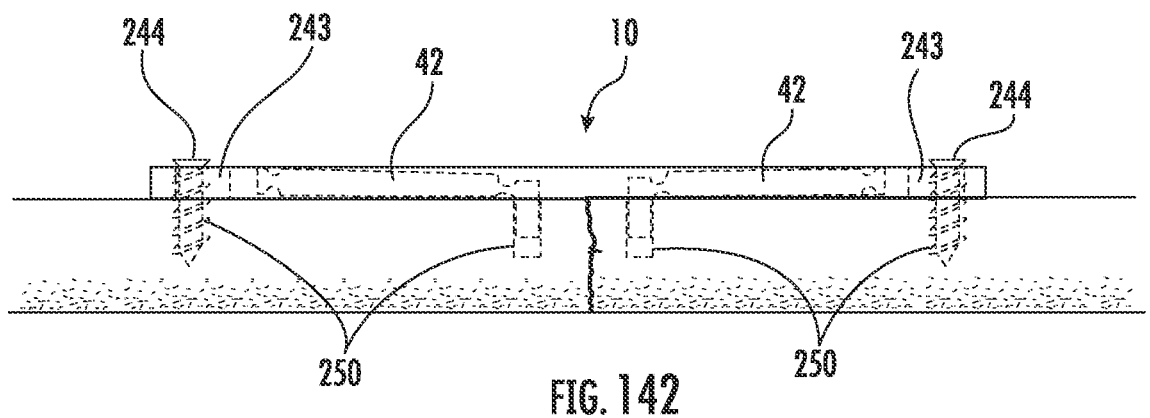
Figure 143:
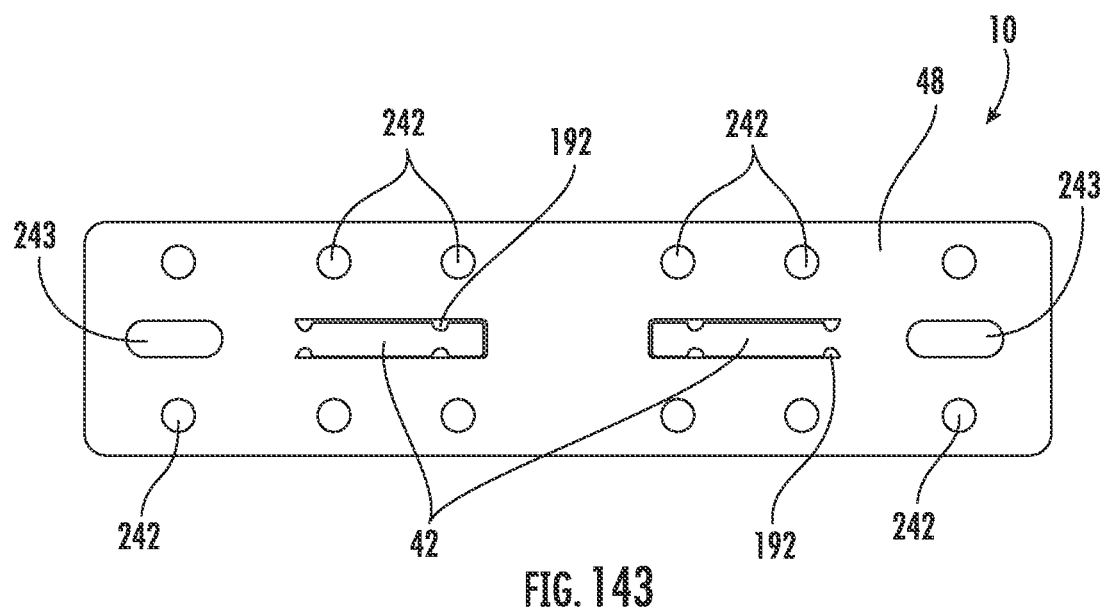
Figure 144:
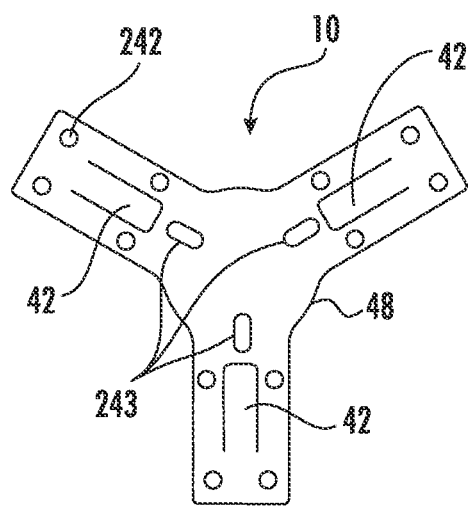
Figure 145:
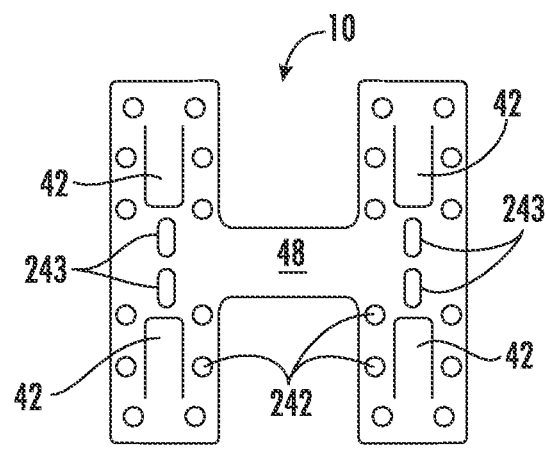
Figure 146:
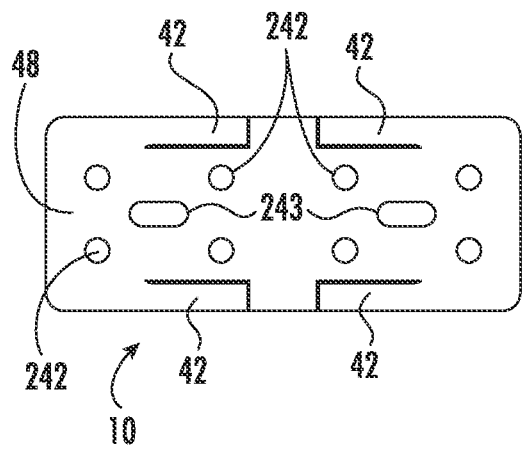

FIG. 142 schematically depicts that the tissue bridge spanning structure 48 has been mounted to the tissue 52 by way of the corresponding guideway slots 243 and attachment mechanisms 244 (e.g., bone anchors, screws, and/or other suitable helically threaded fasteners) to transition the tissue bridge from the extended configuration to the retracted configuration and, thus, move the inner ends of the struts 42 and ends of the broken tissue 52 (e.g., bone) closer to one another, and also move the fasteners 244 from or proximate the outer ends of the guideway slots 243 to or proximate the inner ends of the guideway slots 243.

The tissue bridges 10 can include any suitable number and configurations of struts 42, spanning structures 48 (e.g., plates), mounting holes 242, guideway slots 243, and/or other suitable features. In this regard, FIGS. 143-147A depict additional examples of tissue bridges 10. In the examples depicted in FIGS. 119-147A, each of the tissue bridges 10 can be a unitary structure that is absent of separable parts. Alternatively, the tissue bridges 10 can be formed of separate pieces that are fixedly or removably connected with respect to one another.

FIG. 147B is an exploded view of a multipart tissue bridge 10 in which the strut 42 is pivotably connected to the spanning structure or plate 48 by way of at least one interpositioned portion of the tissue bridge. The interpositioned portion of the tissue bridge can be a body 300 to which the proximal end of the strut 42 is pivotably connected by at least one living hinge 192 or other suitable hinge. The body 300 can be configured for being releasably mounted to the spanning plate 48. The strut 42, spanning plate 48, and body 300 can all be constructed of the same type of material (e.g., metallic material, alloys, stainless steel, titanium, or other suitable material). Alternatively, the strut 42 and body 300 and can be constructed from a different type of material than the spanning plate 48, for example when the strut and body are removed from the spanning plate after the spanning plate has been fully mounted to the associated tissue 52 (e.g., bone), as will be discussed in greater detail below.

In the embodiment depicted in FIG. 147B, the spanning plate 48 includes mounting holes 242 and a guideway in the form of a guideway slot 243. The body 300 can be fixedly or releasably mounted to the spanning plate 48 in any suitable manner, for example by way of welding and/or one or more suitable attachment mechanisms 244 (e.g., undercuts, pins, bone anchors, screws, and/or other suitable helically fasteners 244).

In the example depicted in FIG. 147B, the body 300 defines a lower receptacle or channel 302 between downwardly extending flanges 304. The channel 302 can be configured for receiving a lengthwise portion of the spanning plate 48 so that inner faces of the flanges 304 are in opposing face-to-face configuration or sliding contact with respective portions of the side edges of the spanning plate 48. At least one mounting hole 242 can extend through the body 300.

The at least one mounting hole 242 of the body 300 can be coaxially aligned with a mounting hole 242 of the spanning plate 48 by way of, for example, sliding the body along the spanning plate while the channel 302 is in receipt of a lengthwise portion of the spanning plate 48 so that inner faces of the flanges 304 are in sliding contact with respective portions of the side edges of the spanning plate. The externally threaded shaft of a fastener 244 can extend through the mounting hole 242 of the body 300 and into the mounting hole 242 (e.g., internally threaded) of the spanning plate 48 for releasably mounting the body to the spanning plate. At least initially, the one or more fasteners 244 connecting the body 300 to the spanning plate 48 do not extend into the tissue 52.

As another example, the one or more mounting holes 242 of the spanning plate 48 that are respectively aligned (e.g., coaxially aligned) with the one or more mounting holes 242 of the body 300 may not be internally threaded. In this case, non-threaded pins 244 can extend through the one or more mounting holes 242 of the body 300 and into the corresponding one or more mounting hole 242 of the spanning plate 48 for releasably mounting the body to the spanning plate.

The channel 302 can be referred to as a guiding structure or guideway for guiding relative movement between the spanning plate 48 and the body 300 for aligning the respective mounting holes 242. Alternatively, the channel 302 can be omitted, supplemented with, and/or replaced by any other suitable guiding structure and/or attaching structure. The inclusion of any such guiding structures may be optional.

An example of a sequence of steps of a method of applying the tissue bridge 10 of FIG. 147B to tissue 52 is described in the following with reference to FIGS. 147C and 147D. The body 300 can be mounted to the spanning plate 48 either before or after the spanning plate is partially mounted to tissue 52 (e.g., bone). Referring to FIG. 147C, the tissue bridge spanning structure 48 can be attached to a first portion of the tissue 52 by way of one or more attachment mechanisms 244 (e.g., bone anchors, screws, and/or other suitable helically threaded fasteners) that extend through respective mounting holes 242 in the tissue bridge spanning structure 48 and into the tissue 52, for example as depicted in FIG. 147C.

With continued reference to FIG. 147C, the distal end portion of the strut 42 can be at least partially attached to a second portion of the bone tissue 52 by way of at least one attachment mechanism 244 (e.g., a screw or other suitable helically threaded fasteners) that extends through the strut mounting hole 242, through the guide slot 243, and into the second portion of the tissue 52. Then, and referring to FIG. 147D, the distal end of the strut 42 can be driven toward the second portion of the tissue 52 by way of the fastener 244 that extends through the strut mounting hole 242 and guide slot 243 to cause the tissue bridge 10 to transition to, or at least closer to, its retracted configuration (by way of convergent relative pivoting between the strut 42 and spanning structure 48). Typically the strut 42 is not driven toward the second portion of the tissue 52 by way of the fastener 244 that extends through the strut mounting hole 242 and guide slot 243 until after the tissue bridge spanning structure 48 is securely attached to the first portion of the tissue 52. As a more general example, when a tissue bridge 10 with a single strut 42 is used for mending a broken bone 52, typically at least one fixation point on the side of the break 50 opposite the strut 42 is fixedly secured to the spanning structure or plate 48 prior to the distal end of the strut 42 being driven toward the bone.

With continued reference to FIG. 147D, as the tissue bridge 10 transitions from its extended configuration toward its retracted configuration, the at least one fastener 244 extending through the strut mounting hole 242 and the guideway slot 243, and the one or more fasteners 244 in the first portion of the tissue 52, apply force against the patient's tissue 52 so that the wound 50 is at least partially closed. Additionally, the fastener 244 extending through the strut mounting hole 242 and the guideway slot 243 moves along the length of the guideway slot while the tissue bridge 10 transitions from its extended configuration toward its retracted configuration.

Then, the spanning plate 48 can be further attached to the tissue 52 by way of one or more attachment mechanisms 244 (e.g., bone anchors, screws, and/or other suitable helically threaded fasteners) that extend through respective mounting holes 242 in the plate 48 and into the second portion of the tissue 52, for example as depicted in FIG. 147D. Then, optionally the strut 42 and body 300 can be removed from the plate 48 and tissue 52, for example by removing respective fasteners 244 respectively extending through the body and strut into or through the plate. The spanning plate 48 can be further attached to the tissue 52 by way of one or more attachment mechanisms 244 (e.g., bone anchors, screws, and/or other suitable helically threaded fasteners) that extend into the bone 52 through hole(s) 242, 243 in the plate 48 that are at least further exposed by removal of the body 300 and strut 42.

FIGS. 147E and 147F depict an embodiment that is like the embodiment depicted in FIGS. 147B-147D (e.g., including both structures and associated methods), except for variations noted and variations that will be apparent to those of ordinary skill in the art. For example, in 147E and 147F the proximal end of the strut 42 is directly pivotably connected to the spanning structure or plate 48. Referring to FIG. 147F, when the tissue bridge 10 reaches its retracted configuration, a strut mounting hole 242 (FIG. 147E) can become aligned (e.g., coaxially) with a plate mounting hole 242, and a fastener 277 can be attached through those mounting holes into the tissue 52 (e.g., bone).

FIGS. 147G and 147H depict an embodiment that is like the embodiment depicted in FIGS. 147B-147D (e.g., including both structures and associated methods), except for variations noted and variations that will be apparent to those of ordinary skill in the art. For example, in 147G and 147H the struts 42 (e.g., lateral struts) pivotably connected to the body 300 can be positioned at opposite sides of the body and proximate (e.g., outwardly from) opposite sides or edges of the spanning structure or plate 48. Guide slots 234 (see, e.g., FIG. 147B) may be omitted from the spanning structure or plate 48 since the spanning structure or plate is not positioned beneath the strut mounting holes 242, so that any weakening of the plate by guide slot(s) may optionally be avoided.

Referring to FIG. 147H, the distal ends of the lateral struts 42 can be driven toward the second portion of the tissue 52 by way of driving the fasteners 244 that extend through the strut mounting holes 242 into the tissue 52, to cause the tissue bridge 10 to transition to, or at least closer to, its retracted configuration (by way of convergent relative pivoting between the lateral struts 42 and spanning structure 48). With continued reference to FIG. 147H, as the tissue bridge 10 transitions from its extended configuration toward its retracted configuration, the fasteners 244 extending through the strut mounting holes 242 and the one or more fasteners 244 in the first portion of the tissue 52 apply force against the patient's tissue 52 so that the wound 50 is at least partially closed. Additionally, one of the lateral struts 42 may be caused to pivot farther than the other of the lateral struts in a manner that adjusts alignment between the first and second portions of the bone tissue 52.

FIGS. 147I-147O schematically depict that tissue bridges 10 of either the multipart or single-piece type can include a variety of differently configured lateral struts 42. For tuning purposes, the lengths and angles (see, e.g., FIG. 140O) of the one or more struts 42 (e.g., lateral struts) can be varied.

Reiterating from above, a tissue bridge 10 can include a single strut 42. As another example, FIG. 147P depicts an embodiment that is like the embodiment depicted in FIGS. 147E and 147F (e.g., including both structures and associated methods), except for variations noted and variations that will be apparent to those of ordinary skill in the art. In the retracted configuration of the tissue bridge 10 depicted in FIG. 147P, the entire strut 42 can be both coplanar with the spanning plate 48 and positioned in a strut-receiving hole in the spanning plate. In the extended configuration of the tissue bridge 10 depicted in FIG. 147P, the entire strut 42 can extend obliquely outwardly from the strut-receiving hole in the spanning plate 48.

Reiterating from above, a tissue bridge 10 can include more than two struts 42. For example, FIG. 147Q schematically depicts an embodiment that is like the embodiment depicted in FIG. 136D (e.g., including both structures and associated methods), except for variations noted and variations that will be apparent to those of ordinary skill in the art. In the tissue bridge 10 depicted in FIG. 147Q, four struts 42 are pivotably connected to a single spanning structure or plate 48. It is believed that the tissue bridge 10 of FIG. 147Q may be used for connecting an intervening segment of bone 52 (e.g., a bone graft).

Similarly to the embodiments of FIGS. 51, 52 and 147O, FIGS. 147R-147T depict examples in which forces provided by the struts 42 of a tissue bridge 10 onto or into the tissue 52 can extend crosswise to one another. The directions in which the struts 42 of a tissue bridge 10 direct forces onto or into tissue 52 can be varied (e.g., tuned) based upon the directional forces that may be of most benefit to the tissue (e.g., multi-vector reduction requirements). For example, it is believed that one or more of the tissue bridges 10 of FIGS. 147R-147T may be used for repairing fractures involving major secondary fracture segments of multiple bones (e.g., the radius and ulna). As a more specific example, it is believed that the tissue bridge 10 of FIG. 147R may be used for repairing fractures of the proximal tibia or distal radius, or the like.

As another example, FIG. 147T depicts that at least the spanning structure 48 can be formed of surgical mesh material configured for reinforcing bone, for example during craniofacial surgery. Such surgical mesh may be a mesh made of, for example, metallic material, alloys, stainless steel, titanium, or other suitable material, that includes numerous holes that may be used for fixation of the spanning mesh 48 to the bone. As another example, it is believed that one or more struts 42 may be formed in a piece of such surgical mesh by using a stamping mechanism, so that a user may be able to custom fabricate such a tissue bridge 10 and bend the struts to provide a desired amount of compression when the tissue bridge is mounted and configured in its retracted configuration.

The struts 42 of the embodiments of FIGS. 144-147T can be configured differently, for example by being as depicted in FIGS. 136D-136H and/or in any other suitable manner.

Referring to FIG. 147U and at least partially reiterating from above, the one or more struts 42 can be pivotably connected to the spanning structure or plate 48 by way of at least one interpositioned portion of the tissue bridge 10. The interpositioned portion of the tissue bridge can be a body 300 to which the proximal end of the at least one strut 42 is pivotably connected by at least one living hinge 192 or other suitable hinge.

In the embodiment of FIGS. 147U and 147V, the body 300 comprises an articulated arm 300.

The articulated arm 300 can include a series of links or arm portions that are respectively movably connected to one another. For example, the arm 300 can include a proximal portion 600 (e.g., a mounting bracket or base 600) fixedly connected to the spanning structure or plate 48, or the base 600 can be part of the spanning plate. The arm 300 can further include an arm intermediate portion 602 pivotably connected to the arm proximal portion 600 by at least one living hinge 192 or other suitable hinge. The arm 300 can further include an arm distal portion 604 pivotably connected to the arm intermediate portion 602 by at least one living hinge 192 or other suitable hinge.

With continued reference to the embodiment depicted in FIGS. 147U and 147V, the strut 42 can include link or strut portions that are movably connected to one another. For example, the strut 42 can include a strut proximal portion 606 pivotably connected to the arm distal portion 604 by at least one living hinge 192 or other suitable hinge, and a strut distal portion 608 pivotably connected to the strut proximal portion by at least one living hinge 192 or other suitable hinge An example of a sequence of steps of a method of applying the tissue bridge 10 of FIGS. 147U and 147V is described in the following, including using the frame of reference depicted in these figures (e.g., "right", "left", and "upper") for convenience and not for the purpose of limiting the scope of this disclosure. Referring to FIG. 147U, the tissue bridge spanning structure 48 can be attached to a first portion of the tissue 52 (e.g., bone) by way of one or more attachment mechanisms 244 (e.g., bone anchors, screws, and/or other suitable helically threaded fasteners) that extend through respective mounting holes 242 in the tissue bridge spanning structure 48 and into the first portion of the tissue 52, for example as depicted in FIG. 147U.

An attachment mechanism 244 (e.g., bone anchors, screws, and/or other suitable helically threaded fasteners) can be inserted through a mounting hole 242 in the strut distal portion 608 and a left portion of a guideway opening or slot 243 in the spanning plate 48, and be at least partially attached to the tissue 52. The fastener 244 extending through the mounting hole 242 in the strut distal portion 608 and the guideway slot 243 in the plate 48 can be tightened until its head engages or becomes closely proximate to the upper side of the strut distal portion, and any torque loading in this fastener is relatively small so that there can be predetermined relative movement. The predetermined relative movement comprises relative movement between the lower side of the plate 48 and the tissue 52, relative movement between the upper side of the plate 48 and the lower surface of the strut distal portion 608, and movement of the fastener 244 in, and along the length of, the guideway slot 243 in plate 48.

Referring to FIG. 147U, an attachment mechanism 244 (e.g., screw or other suitable helically threaded fastener) can be inserted through a right portion of a guideway opening or slot 243 in the arm intermediate portion 602 and into an internally threaded mounting hole 242 in the spanning plate 48. Then, referring to FIG. 147V, the arm intermediate portion 602 can be driven toward the plate 48 by way of the fastener 244 that extends through the guideway slot 243 in the arm intermediate portion 602 and internally threaded mounting hole 242 in the spanning plate 48 to cause the tissue bridge 10 to transition to, or at least closer to, its retracted configuration (e.g., by way of convergent relative pivoting between the strut 42 and spanning structure 48).

As the tissue bridge 10 transitions from its extended configuration (FIG. 146U) toward its retracted configuration (FIG. 147V), the fasteners 244 extending through the guideway slots 243 move along the lengths of the guideway slots in opposite directions relative to one another, and the respective fasteners 244 apply force against the patient's tissue 52 so that the wound 50 is at least partially closed. Then, the fastener 244 that extends through the mounting hole 242 in the strut distal portion 608 and the guideway slot 243 in the plate 48 can be further tightened, and the spanning plate 48 can be further attached to the tissue 52 by way of one or more attachment mechanisms 244 (e.g., bone anchors, screws, and/or other suitable helically threaded fasteners) that extend through the one or more mounting holes 242 in the plate 48 and into a second portion of the bone tissue 52.

With continued reference to the embodiment depicted in FIGS. 147U and 147V, one or more of the portions 600, 602, 604, 606, 608 can be omitted or configured differently. For example, the strut 42 may be configured as depicted in FIGS. 13E-136H and/or in any other suitable manner. Whereas respective portions 600, 602, 604, 606, 608 have been identified as arm portions or strut portions for ease of understanding, each of the portions 600, 602, 604, 606, 608 may be referred to differently. For example, each of the portions 600, 602, 604, 606, 608 may be referred to as a link of an articulated linkage, as a portion of an articulated strut, as a portion of an articulated arm, and/or in any other suitable manner.

The embodiment of the tissue bridge depicted in FIGS. 148 and 149 includes a spanning structure 48 and struts 42 that are relatively rigid. The spanning structure can be in the form of an arch or any other suitable shape. Upper ends of underturned flanges 190 can be connected to opposite end portions of the arch or spanning structure 48. The underturned flanges 190 may alternatively be configured as, or referred to as, underturned end portions of the spanning structure 48. Outer ends of hinges 192 can be connected to inner ends of the underturned flanges 190, and outer ends of the struts 42 can be connected to inner ends of the hinges 192. The hinges 192 can be living hinges formed of flexible material, or any other suitable hinges.

The entire body 12 of the tissue bridge 10 of FIGS. 148 and 149 can be formed of the same flexible material, for example as a single piece of the material, with the thickness and/or volume of the flexible material being varied in a manner that causes the hinges 192 to be relatively flexible and the strut and spanning structures 42, 48 to be relatively rigid. For example, the living hinges 192 may be at least partially defined by an area of relatively reduced thickness in the tissue bridge 10. The bodies 12 and tissue bridges 10 can be formed from laminated structures and other suitable materials.

In FIG. 149, the tissue bridge 10 is depicted in its extended configuration. The tissue bridge embodiment of FIGS. 148-152 can be sufficiently rigid so that the tissue bridge is self-supporting in its extended configuration.

Referring to FIGS. 148 and 149, the tissue bridge 10 can also include one or more engagement or connecting mechanisms configured to at least partially stably secure the tissue bridge 10 in its retracted configuration. Each of the connecting mechanisms can be an interlocking flexible fastener 400 (FIG. 152) including elongate flange fastener parts 402 respectively mounted to a central portion of the spanning structure 48 and an inner or distal end portion of a strut 42 so that hooked portions of the fastener parts mate with one another and secure the tissue bridge 10 in its retracted configuration. Optionally, the fasteners 400 can releasably secure the tissue bridge 10 in its retracted configuration. That is, the fasteners 400 can permanently or releasably secure the tissue bridge 10 in its retracted configuration. Alternatively, the fasteners 400 can be or comprise locking mechanisms, hook and loop fasteners, pin fastener, ratchets, adhesive material, and/or other suitable connecting features.

FIGS. 150-152 schematically depict an example of a sequence of steps of a method of applying the tissue bridge 10 of FIGS. 148 and 149 to a wound 50 after the release liners 32 have been removed. The tissue bridge 10 is in the extended configuration in FIG. 150, in an intermediate configuration in FIG. 151, and in its retracted configuration in FIG. 152.

As shown in FIG. 152, the fastener parts 402 become fastened together in response to the tissue bridge 10 becoming configured in its retracted configuration, and the resulting fasteners 400 can secure the tissue bridge 10 in its retracted configuration. The patient-contact adhesive 30 secures the tissue bridge 10 to the tissue 52 in FIGS. 150-152. Referring to FIG. 153, the tissue bridge 10 can be further secured to the tissue 52 by way of an adhesive-backed cover sheet 78 that extends beyond opposite ends of the tissue bridge. Alternatively or additionally, the opposite end portions of the cover sheet can be attached to the tissue by way of one or more suitable non-adhesive attachment mechanisms (e.g., pins, needles, sutures, staples, and/or the like).

A variety of different configurations of the tissue bridges 10 are within the scope of this disclosure. For example, the embodiment of FIGS. 148-152 can be like the embodiment of FIG. 154 (e.g., including both structures and associated methods), except for variations noted and variations that will be apparent to those of ordinary skill in the art. In FIG. 154, the tissue bridge is tapered so that central portions are relatively wide and outer ends are relatively narrow, although other configurations are within the scope of this disclosure.

In the embodiment of FIGS. 155-159, the opposite ends of the spanning structure 48 are connected by hinges 192 to midportions of the struts 42. The retracted configuration can be at least partially defined by, or secured by, fastener parts 402 in the form of adhesive 402 (e.g., one or more layers of pressure-sensitive adhesive) mounted on one or both of the surfaces of the struts 42 and spanning structure 48 that are substantially in opposing face-to-face relation or contact with one another when the tissue bridge 10 is in the retracted configuration (FIG. 159). For example, the adhesive 402 may be a two-part adhesive (e.g., epoxy resin and the hardener), wherein the respective parts are initially separate from one another (e.g., relegated to different ones of the surfaces of the struts 42 and spanning structure 48) and come into contact with one another to create an adhesive bond when the tissue bridge 10 transitions into the retracted configuration. As another example, there may be an elevated or protruding portion of the distal end portions of the struts 42 that engages the underside of the spanning structure 48 at a contact zone, wherein the adhesive is in the contact zone. As a further example, the adhesive 402 can be part of a double-sided adhesive tape (e.g., a film with pressure-sensitive adhesive on both sides), wherein the adhesive on one side (first adhesive) is adhered to one of the strut 42 and the spanning structure 48, and the adhesive on the other side (second adhesive) is covered by a release liner that is removed shortly before it is desired for the second adhesive to become adhered to the other of the strut 42 and the spanning structure 48 to secure the tissue bridge 10 in its retracted configuration.

The hinges 192 can include hinge pins 500 that each extend into one or more bearing structure(s) 502. Midportions of the hinge pins 500 can respectively be fixedly connected to opposite ends of the spanning structure 48. Opposite end portions of each hinge pin 500 can be rotatably journaled in bearing structure(s) 502 fixedly connected to respective struts 42. The positions, connections, or other characteristics of the hinge pins 500 and bearings 502 can be interchanged, and the hinges 192 can be replaced with other suitable hinges or pivotable mechanisms.

The tissue bridge 10 depicted in FIGS. 155-159 includes one or more connecting or engagement mechanisms 520 configured in a manner that at least partially secures the tissue bridge 10 in its extended configuration. The engagement mechanisms 520 can be arrestation mechanisms, for example structural mechanical stops 520 fixedly connected to the bearings 502 for engaging against the opposite end portions of the spanning structure 48 when the tissue bridge 10 reaches its extended configuration, so that relative movement between the struts 42 and spanning structure 48 can be ceased in at least one direction when the tissue bridge is in its extended configuration.

FIGS. 157-159 schematically depict an example of a sequence of steps of a method of applying the tissue bridge 10 of FIGS. 155 and 156 to a wound 50 after the release liners 32 have been removed. The tissue bridge 10 is in the extended configuration in FIG. 157, in an intermediate configuration in FIG. 158, and in its retracted configuration in FIG. 159. The patient-contact adhesive 30 secures the tissue bridge 10 to the tissue 52 in FIGS. 158 and 159.

The connecting mechanisms 400, fastener parts or adhesive 402, and arresting structures or engagement mechanisms 520 can be replaced with other suitable features configured to at least partially secure the tissue bridges 10 in one or more of their configurations (e.g., extended and/or retracted configurations). Examples of features 40, 402, 520 configured to at least partially secure the tissue bridges 10 in one or more of their configurations may include locking mechanisms, a variety of fasteners, snap fasteners including protruding parts for extending into respective receptacles, hook and loop fasteners, pins, ratchets, hinge springs, and/or other suitable features. Such features configured to at least partially secure the tissue bridges 10 in one or more of their configurations or at least partially define one or more of the tissue bridge configurations may help to accommodate different tissue curvatures, for example by securing the tissue bridges in their desired applied positions (e.g. by securing the lateral section(s) in a manner that encourages eversion).

For each of the above-described tissue bridge embodiments that are described as being multistable and, thus, have a plurality of stable equilibrium configurations, it is believed that in an alternative variation of the embodiment the number of stable equilibrium configurations that are included or utilized can be reduced. For example, for each of the above-described tissue bridge embodiments that are described as being bistable by virtue of having both a retracted stable equilibrium configuration and an extended stable equilibrium configuration, in an alternative variation of the embodiment it is believed that the extended stable equilibrium configuration may be replaced with an extended configuration that is not a stable equilibrium configuration (e.g., the alternative variation of the tissue bridge may be monostable). As a further example of variations to the above-described embodiments having retracted stable equilibrium configurations (e.g., symmetrical or asymmetrical), in addition to or rather than being biased toward their retracted configurations, they may be at least partially secured in their retracted configurations by connecting mechanisms 400 (FIGS. 150-159), fastener parts or adhesive 402 (FIGS. 150-159), and/or other suitable features.

FIGS. 160-164 depict a flexible, multiconfigurable medical device or tissue bridge 10 in accordance with an embodiment that may optionally be referred to as a preferred embodiment. For example, this embodiment is being identified as the preferred embodiment, and the tissue bridge 10 of the preferred embodiment may be referred to as the preferred tissue bridge, for ease or understandability and readability, and not to limit the scope of this disclosure. The tissue bridge 10 of the preferred embodiment can be like the tissue bridges of the other embodiments of this disclosure, and vice versa, except for variations noted and variations that will be apparent to those of ordinary skill in the art. For example, the preferred tissue bridge 10 typically has at least one stable equilibrium configuration that can be referred to as a retracted stable equilibrium configuration. In this regard, it is believed that the preferred embodiment of the tissue bridge 10 may have different variations or implementations, one of which is multistable (e.g., symmetrically bistable or asymmetrically bistable) by being configured to provide both (e.g., be biased toward both) a retracted stable equilibrium configuration and an extended stable equilibrium configuration, and another variation that is monostable by being configured to provide a retracted stable equilibrium configuration and an extended configuration that is not a stable equilibrium configuration, as discussed further below.

As best understood with reference to FIG. 161, the tissue bridge 10 can be described as including a multi-part body 12 having struts 20 mounted to at least one spanning structure 48 of the body. In different versions of the preferred embodiment, the at least one spanning structure 48 can be multistable (e.g., symmetrically bistable or asymmetrically bistable) and monostable, respectively. The preferred tissue bridge 10 further includes a flexible web or multilayer sheet 700 mounted to the struts 20 by inner adhesive layers 28. The multilayer sheet 700 (e.g., flexible web) can include a flexible web or patient-contact structure (carrier sheet 26 and patient-contact adhesive 30) and an outer release sheet or liner 32 (e.g., removable backing) mounted to the patient-contact structure by the patient-contact adhesive 30. The carrier sheet 26 can be elastomeric or non-elastomeric.

In the preferred embodiment, the inner adhesive layers 28 fixedly connect the struts 20 to the carrier sheet 26, the patient-contact adhesive 30 is fixedly connected to the carrier sheet 26, and the release liner 32 is removably connected to the patient-contact adhesive 30. The patient-contact structure (carrier sheet 26 and patient-contact adhesive 30), optionally together with the release liner 32, can be recessed relative to, or extend outwardly past, respective edges of the struts 20. For example, the release liner 32 can be larger than the carrier sheet 26 so that the release liner includes a pull-tab portion 701 that protrudes outwardly beyond an associated edge of the carrier sheet for facilitating manual removal of the release liner from the remainder of the tissue bridge 10. As best understood with reference to FIG. 164, the struts 20 can include lines of disruption 722 (e.g., score lines, kiss cuts, a series of holes, and/or other suitable disruptions) along which bending may occur, for example to at least partially facilitate bending that defines the angle or inclination of the inner or distal end portions of the struts 20. The lines of disruption 722 may be omitted and/or configured differently, as further discussed below.

At least partially reiterating from above with reference to FIG. 161, as one example the tissue bridge 10 can be described as including a body 12, which includes the struts 20 and spanning structure 48, mounted to the multilayer sheet 700 (e.g., flexible web). In another example, the tissue bridge 10 can be described as being formed by mounting the spanning structure 48 to a subassembly 702, wherein the subassembly includes the struts 20 mounted to the multilayer sheet 700, as discussed further below.

Referring to FIGS. 160, 162 and 163, the multilayer sheet 700 (e.g., flexible web) can be described as including a medial section or portion 704 positioned between end or lateral sections or portions 706. Similarly, and as best understood by also referring to FIG. 161, each of the carrier sheet layer 26, patient-contact adhesive layer 30, and release liner layer 32 has a medial portion between end or lateral portions of the layer. In the example depicted in FIG. 161, pairs of lines of disruption in the form of fold lines 708 identify the boundaries between the medial and lateral portions of the layers 26, 30, 32. In FIG. 161, the medial portion of each of the carrier sheet layer 26, patient-contact adhesive layer 30, and release liner layer 32 is depicted in the form of an elongated protrusion resembling an inverted channel. In the preferred embodiment, the medial portion of the carrier sheet 26 spans between the inner ends of the struts 20 and may optionally function as an arrestation mechanism that restricts, for example, how far the struts can move away from one another, for example in a manner that seeks to restrict the tissue bridge 10 from being transitioned beyond, or too far beyond, a predetermined, desired extended configuration of the tissue bridge. When the carrier sheet 26 is non-elastic, any arrestation provided thereby may be instantaneous as a result of occurring at one specific distance between the inner ends of the struts 20 that is equal to the length of the medial portion of the carrier sheet 26 that is between the inner ends of the struts 20. When the carrier sheet 26 is elastic, any arrestation provided thereby may occur over a period of time during which the medial portion of the carrier sheet 26 stretches between the inner ends of the struts 20, as further discussed below. Variations are within the scope of this disclosure. For example, any arrestation feature provided by the stretched span of the elastic patient-contact carrier 26 between the struts 20 may be adjusted or tuned by changing the length and/or elasticity of the span of the elastic patient-contact carrier 26 between the struts 20. As another example, any arrestation feature provided by the carrier sheet 26 may be supplemented by, or replaced with, other suitable arrestation mechanism(s). As another, it is believed that the medial portion of the patient-contact adhesive 30 may be omitted in some implementations of the preferred embodiment. As other examples, for facilitating or modifying bending and/or folding, the disruption 722 in the struts 20 can be varied or omitted, and disruptions can be included in other layers or portions of the tissue bridge 10, at least some examples of which are further discussed below.

In the preferred embodiment, the inner adhesive layers 28 fixedly connect the struts 20 of the body 12 to the lateral portions of the carrier sheet 26. The body's struts 20 respectively together with the lateral portions of the inner adhesive layers 28, the lateral portions of the carrier sheet 26, and the lateral portions of the patient-contact adhesive 30 can be referred to as struts or strut assemblies 42 (FIG. 161) of the tissue bridge 10.

FIGS. 160-163 depict the tissue bridge 10 in its retracted stable equilibrium configuration (e.g., a second configuration), and FIG. 164 depicts the tissue bridge in an extended configuration (e.g., a first configuration). Generally described, at least a portion of the body 12 of the preferred tissue bridge 10 is flexible so that it is reconfigurable between the retracted and extended configurations, inner ends of the struts 20 are closer to one another in the retracted stable equilibrium configuration than in the extended configuration, and the inner ends of the struts 20 are closer to the medial portion of the spanning structure 48 in the retracted stable equilibrium configuration than in the extended configuration.

In the example of the extended depicted in FIG. 164, the length of the portion of the multilayer sheet 700 (e.g., flexible web) extending between the inner tips of the struts 20 (i.e., the length of the multilayer sheet's medial section 704) is the same as the distance between the inner tips of the struts 20. In contrast for the examples depicted in FIGS. 160-163, in the retracted stable equilibrium configuration, the length of the multilayer sheet's medial section 704 is greater than the distance between the inner tips of the struts 20, so the multilayer sheet's medial section 704 is in the form of at least one elongate protrusion. The arcuate protruding shape of the multilayer sheet's medial section 704 may optionally be at least partially defined by one or more folds 708 (FIGS. 160, 162, and 163), or the like. The protruding medial portion 700 of the multilayer sheet 700 can be in the form of, or at least partially in the form of, at least one arcuate channel, U-shaped channel, rectangular channel (e.g., defined by four of the folds 708), pleat, loose pleat-like structure, fold, bend, and/or doubled over portion of the multilayer sheet 700. Referring to FIG. 162, the protruding medial portion 700 of the multilayer sheet 700 can extend inwardly or outwardly, wherein the outward configuration is schematically depicted with dashed lines. Other characteristics (e.g., variations in length and optional elasticity) of the multilayer sheet's medial section 704 are further discussed below.

Referring to FIGS. 160-163, the spanning structure 48 of the preferred embodiment includes a medial portion in the form side arm portions 22 extending between end or lateral portions 18 of the spanning structure. In the preferred embodiment, at least the side arm portions 22 form a central arch. Each lateral portion 18 can include an intermediate section 714 positioned between end sections 716 of the lateral portion 18. In the preferred embodiment, the end sections 716 are respectively connected to the side arms 22. As best understood with reference to FIG. 163, the intermediate section 714 may be referred to as an upwardly open mounting channel or bracket 714 (e.g., weld channel). The mounting channel 714 can have spaced apart triangular sidewalls 718 extending downwardly respectively from the end sections 716, and a mounting platform or wall 720 extending crosswise between lower edges of the sidewalls 718. In the preferred embodiment, the mounting walls 720 are connected to respective portions of the struts 20, as discussed further below.

The configurations of the lateral portions 18 of the spanning structure 48 can vary. For example, the mounting channels 714 can be wider and, thus, extend farther into the end sections 716. As another example, each mounting channel 714 can extend for a different width (e.g., the entire width) of its end portion 18. As a further example, each end portion 18 can include multiple side-by-side mounting channels 714, or other suitable portions or features, connected directly or indirectly to respective portions of the respective strut 20. The mounting channels 714 can be replaced with, or supplemented with, other suitable features for mounting the struts 20 to the spanning structure 48, the struts 20 may be integrally formed as parts of the spanning structure 48, and other variations are within the scope of this disclosure.

In the preferred embodiment, both the struts 20 and the flexible spanning structure 48 are stiffer than the patient-contact carrier 26, for example as a result of the spanning structure 48 and the struts 20 being thicker than the patient-contact carrier 26. More generally, the spanning structure 48 and the struts 20 can be stiffer than the patient-contact carrier 26 because of a variety of factors, such as being larger, thicker, comprising material having a higher modulus of elasticity and/or being constructed to have a relatively high apparent modulus of elasticity.

In one example of a suitable manufacturing method for the preferred tissue bridge 10, the spanning structure 48 and struts 20 are formed of polycarbonate, the precursor of the spanning structure 48 is flat, and the spanning structure's curved nature (see, e.g., FIGS. 5-8) is provided by thermoforming the precursor of the spanning structure. In the example depicted in FIG. 163, the thermoforming causes the arms 22 to be twisted in opposite directions (e.g., asymmetrically) from one another, and further causes central portions of the arms to extend convergently toward one another. In other examples, variable twists and/or curves may be imparted upon one or more of the side arms 22, end section 18, or any other portions of the spanning structure 48 to alter the function, for example to "tune" the structure to be more or less asymmetrically bistable, both in structural form between the bistable states (e.g., the stable retracted configuration could have a smaller radius on the undersurface than the radius of the upper surface in the extended stable configuration, or vice-versa), in the amount of deformation which must be imparted upon the device to move from either bistable configuration to the maximally unstable configuration, or in the amount of force which must be applied to deform from either stable configuration to the maximally unstable configuration. In addition, other modifications can be imparted to the same effect, e.g. changing the dimensions or configuration of the mounting portion 714 or the connection between the mounting portion 714 and the strut 20, by altering the direction or slope of the sidewalls 718, by altering the radii of the junction 716 between the arms 22 and mounting portions, or other modifications. More generally, the spanning structure 48 and struts 20 may be constructed of polymeric films or laminates (e.g., polyethylene, polyethylene terephthalate, or any other suitable materials), metallic sheets, alloys, and/or other suitable materials. In the preferred embodiment, the mounting walls 720 are directly connected to respective portions of the struts 20 by sonic welding. More generally, these connections can be formed using adhesive material, heat sealing, welding, and/or using any other suitable fastening mechanisms. As another example, the mounting walls 720 may be indirectly connected to respective portions of the struts 20 due to there being one or more intervening layers or structures therebetween. Other examples of methods of manufacturing the preferred tissue bridge 10 may include cold pressing, injection molding, and/or other suitable manufacturing techniques. The struts 20 can be integrally formed with the spanning structure 48 by, for example, injection molding the body 12 as a single component, in which case the struts may still be described as being connected to the spanning structure 48.

Reiterating from above, the preferred embodiment tissue bridge's struts 42 (FIG. 161) include the body's struts 20, the inner adhesive layers 28, the lateral portions of the carrier sheet 26, and the lateral portions of the patient-contact adhesive 30. The lateral portions of the patient-contact adhesive 30 can be referred to as engagement zones of the struts 42. Reiterating from above, in addition to or as an alternative to the patient-contact adhesive 30 on the body's struts 20 being or defining the engagement zones, the engagement zones can comprise pins, needles, sutures, staples, barbs, prongs, and/or other suitable fasteners or the like. Other variations are within the scope of this disclosure. For example, the patient-contact adhesive 30 can be recessed inwardly from the opposite ends of the spanning structure 48, as further discussed below.

FIG. 164 depicts an example of the tissue bridge 10 in its extended configuration after the release liner 32 has been removed. Reiterating from above, it is believed that the preferred tissue bridge 10 can be configured to be multi-stable (e.g., symmetrically bistable or asymmetrically bistable) or monostable. In both bistable and monostable versions of the preferred tissue bridge 10, the tissue bridge can be configured to have the retracted stable equilibrium configuration depicted in FIGS. 160-163. Bistable versions of the preferred tissue bridge 10 can be symmetrically bistable or asymmetrically bistable.

FIGS. 165-167 depict curves (i.e., readily-available elastic potential energy versus displacement curves) respectively for examples of a symmetrically bistable version of the preferred tissue bridge 10 (FIG. 165), an asymmetrically bistable version of the preferred tissue bridge (FIG. 166), and another asymmetrically bistable version of the preferred tissue bridge (FIG. 167). The vertical axes represent readily-available elastic potential energy (e.g., stored energy, bending-based potential energy, strain potential energy, or the like) for each tissue bridge as a whole. The horizontal axes represent displacement (e.g., bending-based displacement for each tissue bridge as a whole). For the examples depicted in FIGS. 165-167, the horizontal axes tic marks designated by numeral 724 identify the retracted stable equilibrium configurations for which the readily-available elastic potential energy typically is zero or near zero for each tissue bridge as a whole (e.g., a minimum potential energy configuration or state). For the examples depicted in FIGS. 165-167, the horizontal axes tic marks designated by numeral 725 identify maximally unstable equilibrium configurations for which the readily-available elastic potential energy typically is significantly greater than zero for each tissue bridge as a whole. For the examples depicted in FIGS. 165 and 166, the horizontal axes tic marks designated by numeral 726 identify the extended stable equilibrium configurations for which the readily-available elastic potential energy typically is zero or near zero for each tissue bridge as a whole (e.g., a minimum potential energy configuration or state). In FIG. 167, the horizontal axis tic mark designated by numeral 727 identifies the extended stable equilibrium configuration for which (for each tissue bridge as a whole) the readily-available elastic potential energy typically is greater than zero and less than that of the maximally unstable equilibrium configuration 725.

Referring to FIG. 165, for the symmetrically bistable preferred tissue bridge 10, the maximally unstable equilibrium configuration 725 is midway along the horizontal axis between the stable equilibrium configurations 724, 726, and the amount of applied force required to transition from the stable equilibrium configuration 724 to the stable equilibrium configuration 726 is believed to be the same as the amount of applied force required to transition from the stable equilibrium configuration 726 to the stable equilibrium configuration 724. Referring to FIG. 166, for the asymmetrically bistable preferred tissue bridge 10, the maximally unstable equilibrium configuration 725 is not midway along the horizontal axis between the stable equilibrium configurations 724, 726; along the horizontal axis, the maximally unstable equilibrium configuration 725 can be closer to the stable equilibrium configuration 726 than to the stable equilibrium configuration 724, or the maximally unstable equilibrium configuration 725 can be closer to the stable equilibrium configuration 724 than to the stable equilibrium configuration 726; and the amount of applied force required to transition from the stable equilibrium configuration 724 to the stable equilibrium configuration 726 is believed to be different from the amount of applied force required to transition from the stable equilibrium configuration 726 to the stable equilibrium configuration 724.

Further referring to FIGS. 165-167, in some versions of the tissue bridges 10, they can be deformed past the extended stable equilibrium configurations 726, 727 to, for example, one or more further extended, unstable configurations designated by numeral 728 in FIGS. 165-167. When in a further extended, unstable configuration 728, a tissue bridge 10 is typically biased toward the respective stable equilibrium configuration 726, 727.

In the above discussions of FIGS. 165-167, the depicted curves have been described as being for the tissues bridges 10 in their entirety (i.e., as a whole, e.g., including their patient-contact carriers 26). Alternatively, the curves of FIGS. 165-167 may be for bistable spanning structures 48 in isolation (e.g., without the other components of the tissue bridges 10). When such bistable spanning structures 48 defining the curves of FIGS. 165-167 are included in tissue bridges 10 in which the patient-contact carrier 26 is elastic and becomes stretched as the tissue bridge is transitioned from its stable retracted equilibrium configuration 724 or unstable equilibrium configuration 725 toward its extended configuration 726, 727, the elastic contracting force provided by the stretched medial portion of the patient-contact carrier 26 can cause the curves for the tissues bridges 10 to differ from those of FIGS. 165-167. For example, when a bistable spanning structure 48 which, in isolation, has a curve as depicted in FIG. 167 is included in a tissue bridge having a patient-contact carrier 26 with a medial portion that is elastic and becomes stretched as the tissue bridge is transitioned from its stable retracted equilibrium configuration 724 toward its unstable equilibrium configuration 725 or extended configuration 727, the elastic contracting force of the medial portion of patient-contact carrier 26 can be large enough so that the tissue bridge functions in a monostable manner (e.g., at least in its reasonably functional range of operation). For example, the medial portion of the patient-contact carrier 26 may prevent the tissue bridge 10 from being transitioned all the way from the stable retracted equilibrium configuration 724 to the unstable equilibrium configuration 725.

Reiterating from above, in the extended configuration of the preferred tissue bridges 10, the length of multilayer sheet's medial section 704 may be the same as, or about the same as, the distance between the inner tips of the struts 20, and the medial section 704 may be elastic (e.g., the patient-contact carrier 26 may be elastic). The non-stretched length of the elastic medial section 704 can be varied in a predetermined manner for tuning operability of the tissue bridges 10, for example by establishing whether or not the medial section 704 is stretched, or how much the medial section 704 is stretched. For example, in the extended configuration, the length of the unstretched medial section 704 extending between the inner tips of the struts 20 can be the same as or greater than the distance between the inner tips of the struts 20. As another example, in the extended configuration, the length of the unstretched medial section 704 extending between the inner tips of the struts 20 can be the same as the distance between the inner tips of the struts 20. As a further example, in the extended configuration, the medial section 704 can be stretched so that the length of the medial section 704 is the same as the distance between the inner tips of the struts 20.

More generally, operability of the tissue bridges 10 that are the subject of FIGS. 160-167 can be varied (e.g., tuned) for example, by adjusting characteristics (e.g., shape, stiffness, flexibility, and/or elasticity) of one or more of the various components of the tissue bridges. For example, in different versions of the tissue bridges 10, the spanning structure 48 can be more rectangular, more elliptical, or in other shapes that vary from the general hour-glass shape depicted in FIGS. 160 and 161. As another example, in different versions of the spanning structure 48, a wide variety of differently configured bends can be imparted into the arms 22 along different axes of the arms in a manner that affects the biased nature of the arms and, thus, affects the monostable or multistable characteristics of the tissue bridges 10. Similarly, a wide variety of differently configured bends can be imparted into the spanning structure's ends or lateral portions 18 along different axes of the lateral portions in a manner that affects the biased nature of the lateral portions and, thus, affects the monostable or multistable characteristics of the tissue bridges 10. These bends and/or other features of the tissue bridges 10 may be symmetrical or asymmetrical, and otherwise variously configured for a wide variety of tuning purposes. These bends may be imparted via thermoforming and/or any other suitable manufacturing or tuning techniques. As further examples and as at least partially alluded to above, in variations of the preferred tissue bridges 10, in addition to or rather than being biased toward their retracted configurations, they may be at least partially secured in their retracted configurations by connecting mechanisms, fastener parts, adhesives 400, 402 (see, e.g., FIGS. 150-159), and/or other suitable features.

FIGS. 168 and 169 depict the tissue bridge 10 after the release liner 32 has been removed therefrom. Referring to FIGS. 168 and 169, aspects of an example of a sequence of steps of a method of applying the preferred embodiment tissue bridge 10 to a scar or closed wound 50 after the release liner 32 has been removed is described in the following. Referring to FIG. 168, the tissue bridge 10 in, or proximate, an extended configuration (see, e.g., FIGS. 156-167, extended configurations 726, 727, 228, or the like) can be manually held between a user's finger 54 and thumb 56, or in any other suitable manner, so that the length of the tissue bridge extends crosswise to, or more specifically substantially perpendicular to, the length of a scar, cut, or wound 50 in a patient's tissue 52. Optionally, the patient-contact adhesive 30 can be recessed inwardly from the opposite ends of the spanning structure 48 in a manner that inhibits the patient-contact adhesive 30 from inadvertently becoming adhered to the finger 54 or thumb 56, any covering materials over the finger 54 or thumb 56 (e.g. sterile or unsterile gloves, a finger cot, etc.), or the like.

While the preferred tissue bridge 10 is in an extended configuration, the patient-contact adhesive 30 on the lower or outer surfaces of the inner or distal ends of the struts 20, and medial portion of the patient-contact adhesive 30 extending between the inner or distal end portions of the struts 20, can be engaged against the patient's tissue or skin 52. Alternatively, the patient-contact adhesive 30 extending between the inner or distal ends of the struts 42 can be omitted.

For the bistable versions of the preferred tissue bridge 10 (see, e.g., FIGS. 165-167), after at least the patient-contact adhesive 30 on the lower or outer surfaces of the inner or distal end portions of the struts 20 has been engaged against the patient's tissue or skin 52, the user can continue to manually force or push the tissue bridge 10 closer to the tissue 52. The action forces applied by the user's finger 54 and thumb 56 at the opposite ends or other suitable locations on the spanning structure 48 urge the preferred bistable tissue bridge 10 more closely against the tissue 52. The tissue 52 provides resisting or reaction forces so that the struts 42 of the preferred bistable tissue bridge 10 apply spaced apart reaction forces against respective portions of the spanning structure 48. When sufficiently large, the action and reaction forces and resulting torque cause the preferred bistable tissue bridge 10 to reconfigure from its extended configuration toward and past its intermediate or maximally unstable equilibrium configuration 725. In an example, after the preferred bistable tissue bridge 10 is forced or pushed past its maximally unstable equilibrium configuration 725, the tissue bridge is operative to automatically transition (e.g., bend itself in response to its elastic potential energy) at least proximate to its retracted stable equilibrium configuration 724 to further adhere the one or more struts 42 to the tissue 52. In the process, distal end portions of the struts 42 become closer to one another, and closer to the medial portion of the spanning structure 48, so that the struts push the portions of the tissue 52 to which they are adhered toward one another in a manner that approximates the wound and/or scar tissue 50 and reduces tension associated with the wound and/or scar tissue 50 (e.g., which may evert the tissue adjacent the scar or wound). Additionally and optionally, the patient-contact carrier 26 can be elastomeric, and it can be stretched during the application process, e.g. if the user overbends the tissue bridge 10 past the stable extended configuration prior to adherence of the tissue bridge to the skin surface, then the elastic recoil of the patient-contact carrier 26 upon transition of the tissue bridge from the extended configuration to the retracted configuration further contributes to tension reduction associated with the wound and/or scar tissue 50.

For a monostable version of the preferred tissue bridge 10, the extended configuration may be manually achieved by manually holding the tissue bridge between a user's finger 54 and thumb 56, or in any other suitable manner, while manually increasing force applied to the tissue bridge, until the desired extended configuration is achieved, and then continuing to apply manual force to the tissue bridge to temporarily maintain it in an extended configuration. Then, in an example, after at least the patient-contact adhesive 30 on the lower or outer surfaces of the inner or distal end portions of the struts 20 has been engaged against the patient's tissue or skin 52, the user can allow the bias of the monostable version of the preferred tissue bridge 10 to automatically at least partially transition the tissue bridge at least proximate to its retracted stable equilibrium configuration 724 to further adhere the one or more struts 42 to the tissue 52. In the process, distal end portions of the struts 42 become closer to one another, and closer to the medial portion of the spanning structure 48, so that the struts push the portions of the tissue 52 to which they are adhered toward one another in a manner that reduces tension associated with the wound and/or scar tissue 50 (e.g., which may evert the tissue adjacent the scar or wound). As an example, the user may optionally manually assist with (e.g., apply manual force throughout) the transitioning of the tissue bridge 10 toward its retracted stable equilibrium configuration 724.

Further regarding the monostable version of the preferred tissue bridge 10, the medial portion of the carrier sheet 26, which spans between the inner ends of the struts 20, can be configured to function as an arrestation mechanism that restricts, for example, how far the struts can move away from one another and, thus, at least partially defines the tissue bridge's extended configuration 727. Similarly regarding the bistable versions of the preferred tissue bridge 10 (see, e.g., FIGS. 165-167), the medial portion of the carrier sheet 26 can be configured to function as an arrestation mechanism that restricts, for example, how far the struts 20 can move away from one another and, thus, at least partially defines the tissue bridge's extended stable equilibrium configuration 726. As further examples, optionally the medial portion of the carrier sheet 26 can be elastic (e.g., can be polyurethane or another suitable elastic material) so that the carrier sheet at least partially biases, temporarily biases, or only partially biases the preferred tissue bridges 10 toward their retracted configurations 724 (e.g., retracted stable equilibrium configurations). That said, in the preferred embodiment, the majority of the forces that bias the tissue bridge 10 toward its retracted configuration 724 are provided by the spanning structure 48. More generally and for example, 0%, or at least about 2%, 5%, 10%, 20%, 30%, 40%, 50%, 60%, 70%, 80%, 90%, 95%, 98%, or 100% (or any values or subranges therebetween) of the forces that bias the preferred tissue bridge 10 toward its retracted configuration can be provided by the spanning structure 48.

In the examples depicted in FIGS. 168 and 169, respective portions of the struts 20 are depicted as being planar. In other examples, one or more of those respective portions may not be planar, depending upon the rigidity of the struts 20 and other factors. For example and referring to FIG. 168, for each strut 20, the portion of the strut between the line of disruption 722 and the mounting channel 714 may be arcuately bent with its concavity facing upward. For facilitating predetermined bending of the struts, in addition to and/or alternatively to the lines of disruption 722, the struts 20 can include a variety of different types of features (see, e.g., disruptions 76, 722 in FIGS. 171-176) that are configured to vary rigidity of respective portions of the struts in a manner that promotes predetermined bending of the struts, as further discussed below.

An example of what is believed to be a suitable method of assembling tissues bridges 10 is described in the following, in accordance with the preferred embodiment. Partially reiterating from above, and as best understood with reference to FIGS. 161 and 170, a series of tissue bridges 10 may be formed by respectively mounting spanning structure 48 to subassemblies 702. In FIG. 170, the flat subassemblies 702 are part of a precursor web 730 including a continuous, or substantially continuous, sheet of release liner material 32'. Reiterating from above and as best understood with reference to FIG. 161 for the preferred embodiment, each subassembly 702 includes the struts 20 mounted to the multilayer sheet 700 (e.g., flexible web) by the inner adhesive 28. In FIG. 170, dashed lines 732 partially depict the boundaries between the individual release liners 32 and the remainder of the release liner material 32', wherein these boundaries may be defined by lines of disruption 732, for example perforated tear lines, a series of slits or cuts, kiss cuts, and/or other suitable features for allowing removal of the tissue bridges 10 from scrap portions of the release liner material 32'. In a manufacturing machine, multiple of the precursor webs 730 may extend in the machine direction and be positioned side-by-side. As another example, a single precursory web may include multiple rows of the subassemblies 702 extending in the machine direction and positioned side-by-side. As another example, the liner material 32' with one or more (e.g., multiple) of the tissue bridges 10 connected thereto can be considered to be, or can be included as part of, a kit. The liner material 32' with one or more (e.g., multiple) of the tissue bridges 10 connected thereto may be formed into a roll.

While the subassemblies 702 are part of the precursor web 730 as depicted in FIG. 170, the elongate protrusions (see, e.g., FIGS. 160 and 162) may be formed in the medial sections 704 of the multilayer sheets 700 (e.g., flexible web) of the precursor web 730 prior to mounting the spanning structures 48 to the subassemblies 702. For example, it is believed that the elongate protrusions may be formed in the medial sections 704 by pushing opposite edges of the multilayer sheet 700 toward one another. As another example, it is believed that the precursor web 730 may be drawn into engagement with, and relative to, a folding plow or other suitable structure in a manner that forms the elongate protrusion in the medial sections 704 of the multilayer sheets 700 of the precursor web 730. While the elongate protrusion is defined by the medial sections 704 of a multilayer sheet 700 of the precursor web 730, the mounting walls 720 of a spanning structure 48 may be respectively connected to struts 20, as discussed above.

Figure 176:
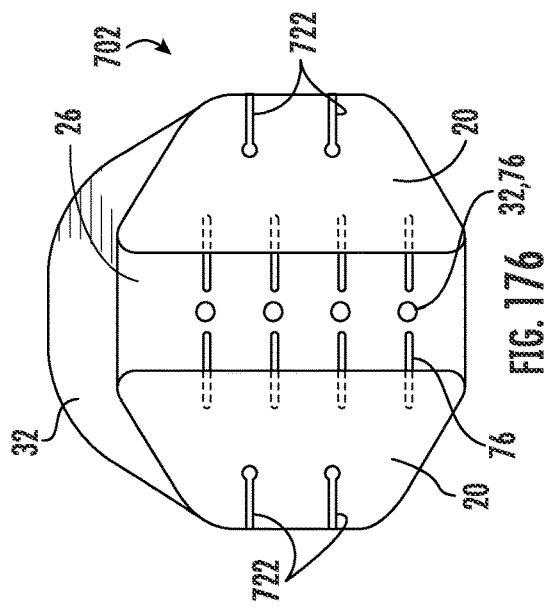
Figure 172:
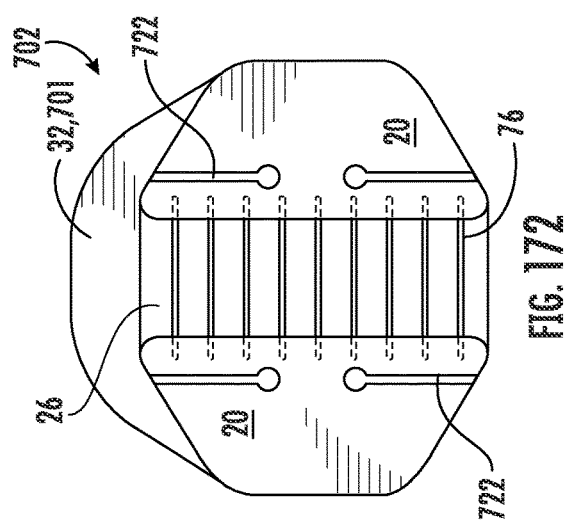
Figure 175:
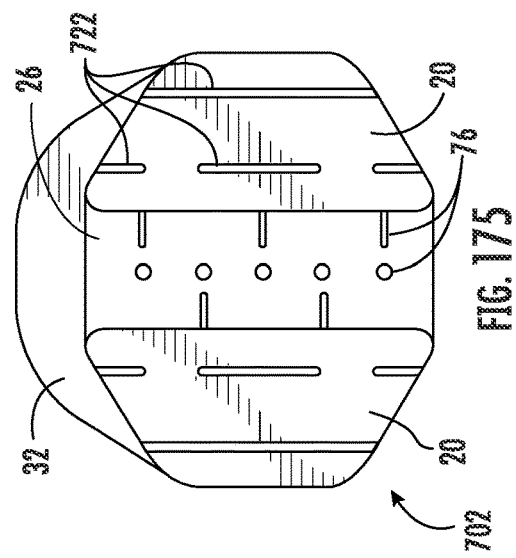
Figure 171:
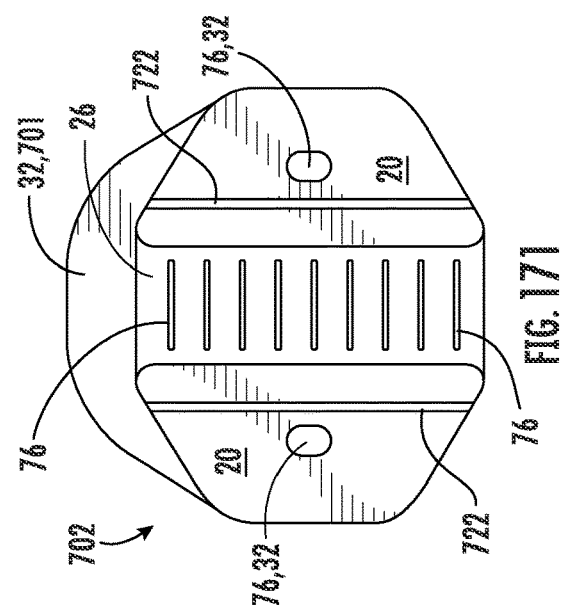
Figure 174:
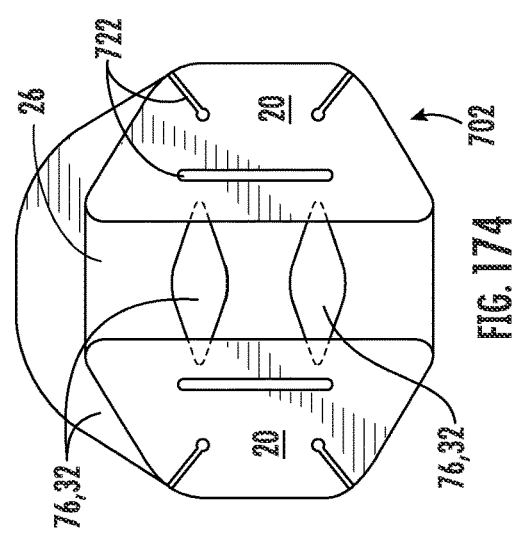

FIGS. 171-176 depict isolated top plan views of flat tissue bridge subassemblies 702 similar to the subassemblies of FIG. 170, except for including differently configured lines of disruption 722 in the struts 20; and including disruptions 76 (e.g., holes, cuts, slits, scores, and/or other suitable features) in the patient-contact structure 26, 30, and optionally also in the struts 20, in accordance with other versions of the preferred embodiment. In FIGS. 172, 175 and 176, portions of the disruptions 76 that are hidden from view are schematically depicted with dashed lines. In the examples of FIGS. 174 and 176, the mounting wall 720 (FIGS. 160 and 163) may be mounted to (e.g., solely to) the portion of the respective strut 20 that is positioned between the lines of disruption 722. The configurations of the disruptions 722 in the struts 20 can vary in a manner that helps to at least partially define rigidity and bending characteristics of the struts, wherein the bending can be responsive to transitioning of the associated tissue bridge 10 between extended and retracted configurations and/or contours of the tissue 52 to which the tissue bridge is mounted. For example, bending of a strut 20 typically occurs more easily along a line of disruption 722. The inclusion and configurations of the disruptions 76 in the patient-contact structure 26, 30, and optionally also in the struts 20, can vary in a manner that helps to define how much fluid or gas can pass in either direction through the structure, helps to control any expansion of the structure, and/or helps to at least partially define bending characteristics of the structure. More generally, the one or more slits or holes 76 (e.g., circular holes, elongate holes, and/or any other suitable configured holes) can extend through respective portions of the preferred tissue bridge 10 and be configured for providing ventilation, for allowing the application of medicinal substances, for facilitating supplementary fixation (e.g., using pins, needles, sutures, staples, and/or the like), and/or for defining a line of disruption along which bending may occur.

FIG. 177 is an isolated top plan view of another flat tissue bridge subassembly 702, in accordance with another version of the preferred embodiment. FIG. 178 is an isolated top view of the flat release liner 32 of the subassembly 702 of FIG. 177. In FIG. 178, holes 740 extend through the pull tab 701, and cuts in the form of slits 742 extend through both the pull tab 701 and adjacent portions of the release liner 32. The one or more disruptions 740, 742 (e.g., holes 740, and cuts or slits 742) are configured in a manner that seeks to help facilitate manual removal of the release liner 32 from the remainder of the tissue bridge 10 (FIG. 179), for example while the tissue bridges are in the retracted configuration.

Any of the above embodiments of the tissue bridges 10 can be packaged or kitted in multiple combinations. Tissue bridges 10 may be packaged in formed and lidded trays, wrappers, or other acceptable packaging materials. They may be packaged individually or in multiple units, with the multiple unit packaging containing either a plurality of individual tissue bridges, an array of tissue bridges (e.g. as in FIG. 170), or any combination thereof. The tissue bridge(s) 10 may be packaged in an extended stable configuration, a retracted stable configuration, or any other configuration. Packages may include single or multiple tissue bridges 10 as above kitted in any combination with other medications, solutions, tackifiers, ointments, dressings, surgical or other tools, or other items or materials which may be utilized in application of the tissue bridge 10, preparation of the wound for closure, treatment of the wound and or scar, or general treatment of the recipient to which the tissue bridge is applied. Within such kits the tissue bridge may be supplied in a sterile or unsterile manner and the associated items within the kit may be sterile or unsterile, in any combination, and the entire kit may be sterile or unsterile. Sterilization of the tissue bridge(s) 10 and associated packaging may be completed via gamma radiation, ethylene oxide exposure, or any other accepted means of medical device sterilization. Different components within a kit may be sterilized by different methods and/or at different points of time, or the kits may be sterilized as a single unit. A kit can be in the form of a package including a conventional container containing one or more of the tissue bridges 10 of this disclosure, and further containing any other suitable components or materials.

Any of the embodiments of a tissue bridge 10 herein described can be utilized in conjunction with additional therapeutic interventions of a wound or scar as a therapeutic system. For example, a tissue bridge could be applied proximate (either before, during, or after) injection or application of a medication (e.g. steroid, 5-florouracil, etc.), biologic (e.g. growth factors, growth factor analogs or inhibitors), topical interventions (e.g. silicone, humectant moisturizers, emollient moisturizers, occlusive moisturizers, etc.) or other materials. In addition, the application of lasers, other energy-based devices, or temperature modulation (e.g. the application of heat of cooling) to the wound and/or scar can be combined with the application of a tissue bridge. The use of tissue bridges can also be incorporated into a treatment system or protocol utilizing general therapeutic interventions such as oxygen therapy; oral, intravenous, intramuscular, or other routes of pharmacologic or biologic medication, physical therapy or other physical activities and interventions (e.g. therapeutic massage, lymphatic drainage, etc.). Any combination of such interventions may be incorporated into a therapeutic system in conjunction with tissue bridge therapy.

Whereas the tissue bridges 10 have typically been described in the foregoing in the context of interaction with biological tissue, the tissue bridges 10 and/or variations thereof can be more generally referred to as devices 10 configured for urging workpieces toward one another and/or devices configured for urging portions of a workpiece toward one another. For example, each of the devices 10 can be configured to span/cover one or more portions of one or more workpieces, modify the relationship between portion(s) of workpiece(s), and/or modifying the force environment of portion(s) of workpiece(s). For example, it is believed that there can be non-medical uses of the devices (e.g., to fix together pieces of wood while adhesive material positioned at joints between the pieces cures (e.g., dries)). Very generally described, the present invention relates to devices for urging workpieces toward one another and/or devices for urging portions of a workpiece toward one another.

To supplement the present disclosure, this application incorporates entirely by reference commonly assigned U.S. Patent Application Publication Numbers 2014/0128819, 2014/0227483, and 2019/0133582.

Reiterating from above, it is within the scope of this disclosure for one or more of the terms "substantially," "about," "approximately," and/or the like, to qualify each of the adjectives and adverbs of the foregoing disclosure, for the purpose of providing a broad disclosure. As an example, it is believed that those of ordinary skill in the art will readily understand that, in different implementations of the features of this disclosure, reasonably different engineering tolerances, precision, and/or accuracy may be applicable and suitable for obtaining the desired result. Accordingly, it is believed that those of ordinary skill will readily understand usage herein of the terms such as "substantially," "about," "approximately," and the like.

In the above description and drawings, examples of embodiments have been disclosed. The present invention is not limited to such exemplary embodiments. Unless otherwise noted, specific terms have been used in a generic and descriptive sense and not for purposes of limitation. The use of the term "and/or" includes any and all combinations of one or more of the associated listed items.

The invention claimed is:

1. A medical device for at least partially covering and applying force on tissue, the medical device comprising:
   a body comprising:
      at least one spanning structure, and
      first and second struts connected to the spanning structure;
   at least a portion of the medical device being flexible and multistable so that:
      the medical device is reconfigurable between at least first and second stable equilibrium configurations, and
      the medical device has at least one unstable equilibrium configuration between the first and second stable equilibrium configurations; and
   the medical device being configured so that inner ends of the first and second struts are closer to one another in the second stable equilibrium configuration than in the first stable equilibrium configuration,
   wherein the flexible, multistable portion of the medical device is configured to:
      define a first concavity comprising curved arcs that extend crosswise to one another in the first stable equilibrium configuration, and
      define a second concavity comprising curved arcs that extend crosswise to one another in the second stable equilibrium configuration.

2. The medical device according to claim 1, wherein:
   the first stable equilibrium configuration comprises a curved concave-up stable equilibrium configuration, and
   the second stable equilibrium configuration comprises a curved concave-down stable equilibrium configuration.

3. The medical device according to claim 1, wherein:
   the medical device is biased toward the first stable equilibrium configuration at least when in configurations between the at least one unstable equilibrium configuration and the first stable equilibrium configuration, and
   the medical device is biased toward the second stable equilibrium configuration at least when in configurations between the at least one unstable equilibrium configuration and the second stable equilibrium configuration.

4. The medical device according to claim 3, wherein:
   the first stable equilibrium configuration comprises a curved concave-up stable equilibrium configuration, and
   the second stable equilibrium configuration comprises a curved concave-down stable equilibrium configuration.

5. The medical device according to claim 1, wherein the first and second struts are integrally formed with the at least one spanning structure.

6. The medical device according to claim 1, wherein:
   the at least one spanning structure comprises opposite end portions that are spaced apart from one another; and
   the first and second struts respectively extend inwardly from the opposite end portions.

7. The medical device according to claim 1, wherein:
   the at least one spanning structure comprises a medial portion positioned between lateral portions;
   the first and second struts are connected to the lateral portions, respectively;
   the medial portion extends over an area; and
   the inner ends of the first and second struts extend into the area.

8. The medical device according to claim 1, wherein:
the at least one spanning structure comprises opposite side arms; and
at least portions of the side arms are spaced apart from one another so that at least one hole extending through the at least one spanning structure is defined between the side arms.

9. The medical device according to claim 1, comprising a third strut, wherein the medical device is configured so that the inner ends of the first and second struts and an inner end of the third strut are closer to one another in the second stable equilibrium configuration than in the first stable equilibrium configuration.

10. The medical device according to claim 1, wherein:
an inner end portion of the first strut is angled relative to an outer end portion of the first strut; and
an inner end portion of the second strut is angled relative to an outer end portion of the second strut.

11. The medical device according to claim 1, wherein the medical device is configured so that the first and second struts are inclined downwardly in the first stable equilibrium configuration.

12. The medical device according to claim 11, wherein the medical device is configured so that any inclination of the first and second struts in the second stable equilibrium configuration is less than the inclination of the first and second struts in the first stable equilibrium configuration.

13. The medical device according to claim 1, wherein:
each of the first and second struts comprises an engagement zone configured to engage and apply force on tissue; and
the medical device is configured so that the engagement zones of the first and second struts are closer to one another in the second stable equilibrium configuration than in the first stable equilibrium configuration.

14. The medical device according to claim 13, wherein the engagement zones of the first and second struts are configured to move respective portions of tissue toward one another in response to the first and second struts becoming closer to one another.

15. The medical device according to claim 13, wherein the engagement zones comprise adhesive material supported by the first and second struts and configured to be adhered to and move with respective portions of tissue toward one another at least in response to the first and second struts becoming closer to one another.

16. The medical device according to claim 13, wherein:
the first strut comprises opposite first and second sides;
the first side is positioned between the at least one spanning structure and the second side; and
the second side comprises the engagement zone of the first strut.

17. The medical device according to claim 1, further comprising adhesive material and a flexible web connected by the adhesive material to the first and second struts, wherein:
a central portion of the flexible web is spaced apart from the spanning structure,
the central portion of the flexible web is suspended along a gap defined between the inner ends of the first and second struts,
the first and second struts are positioned between the flexible web and the spanning structure, and
at least a portion of the flexible web is configured to engage and apply force on tissue.

18. The medical device according to claim 17, further comprising a release liner, wherein:
the flexible web comprises adhesive configured to adhere the medical device to tissue; and
the release liner is adhered to the adhesive of the flexible web.

19. The medical device according to claim 17, wherein the flexible web comprises a bend suspended between, and spaced apart from each of, the inner ends of the first and second struts.

20. The medical device according to claim 17, wherein:
the flexible web comprises a sheet having opposite inner and outer sides, and adhesive on the outer side;
the adhesive of the flexible web is configured for being adhered to tissue; and
the inner side of the sheet is connected to the first and second struts.

21. The medical device according to claim 17, wherein at least a portion of the flexible web is configured to restrict how far the first and second struts can move away from one another.

22. The medical device according to claim 17, wherein:
for each of the first and second struts, the strut comprises opposite first and second sides, and the first side is positioned between the at least one spanning structure and the second side;
the flexible web includes a medial portion positioned between first and second lateral portions of the flexible web;
the medial portion of the flexible web spans between the inner ends of the first and second struts;
a first strut assembly comprises the first lateral portion of the flexible web and the first strut, wherein the first lateral portion of the flexible web is mounted on the second side of the first strut, and the first strut assembly is configured to engage and apply force on tissue; and
a second strut assembly comprises the second lateral portion of the flexible web and the second strut, wherein the second lateral portion of the flexible web is mounted on the second side of the second strut, and the second strut assembly is configured to engage and apply force on tissue.

23. The medical device according to claim 1, wherein the first strut is configured to:
have the at least one unstable equilibrium configuration, the first stable equilibrium configuration, and the second stable equilibrium configuration;
define the first concavity in the first stable equilibrium configuration; and
define the second concavity in the second stable equilibrium configuration.

24. The medical device according to claim 1, wherein the flexible, multistable portion of the medical device comprises first and second sides that are opposite from one another, and the flexible, multistable portion is configured so that:
the first side of the flexible, multistable portion defines the first concavity in the first stable equilibrium configuration, and
the second side of the flexible, multistable portion defines the second concavity in the second stable equilibrium configuration.

25. The medical device according to claim 1, wherein:
the first concavity's curved arcs comprise a length-wise arc and a width-wise arc; and
the second concavity's curved arcs comprise a length-wise arc and a width-wise arc.

26. A medical device for at least partially covering and applying force on tissue, the medical device comprising:
a body comprising:
at least one spanning structure, and
first and second struts connected to the spanning structure;
at least a portion of the medical device being flexible and multistable so that:
the medical device is reconfigurable between at least first and second stable equilibrium configurations, and
the medical device has at least one unstable equilibrium configuration between the first and second stable equilibrium configurations; and
the medical device being configured so that inner ends of the first and second struts are closer to one another in the second stable equilibrium configuration than in the first stable equilibrium configuration;
wherein a first portion of the medical device is configured to have the at least one unstable equilibrium configuration, the first stable equilibrium configuration, and the second stable equilibrium configuration, and
wherein a second portion of the medical device is configured to have a plurality of configurations comprising a second unstable equilibrium configuration between third and fourth stable equilibrium configurations, and the second portion of the medical device is configured to be:
biased toward the third stable equilibrium configuration at least when in configurations between the second unstable equilibrium configuration and the third stable equilibrium configuration, and
biased toward the fourth stable equilibrium configuration at least when in configurations between the second unstable equilibrium configuration and the fourth stable equilibrium configuration.

27. A medical device for at least partially covering and applying force on tissue, the medical device comprising:
a body comprising:
at least one spanning structure, and
first and second struts connected to the spanning structure;
at least a portion of the medical device being flexible and multistable so that:
the medical device is reconfigurable between at least first and second stable equilibrium configurations, and
the medical device has at least one unstable equilibrium configuration between the first and second stable equilibrium configurations; and
the medical device being configured so that inner ends of the first and second struts are closer to one another in the second stable equilibrium configuration than in the first stable equilibrium configuration,
wherein the first strut is configured to have the at least one unstable equilibrium configuration, the first stable equilibrium configuration, and the second stable equilibrium configuration,
wherein the second strut is flexible and configured to have a plurality of configurations comprising a second unstable equilibrium configuration between third and fourth stable equilibrium configurations, and the second strut is configured to be:
biased toward the third stable equilibrium configuration at least when in configurations between the second unstable equilibrium configuration and the third stable equilibrium configuration, and
biased toward the fourth stable equilibrium configuration at least when in configurations between the second unstable equilibrium configuration and the fourth stable equilibrium configuration, and
the at least one spanning structure, the first strut, and the second strut are cooperatively configured so that the inner end portions of the first and second struts become closer to one another at least in response to the second strut being transitioned from the third stable equilibrium configuration to past the second unstable equilibrium configuration and toward the fourth stable equilibrium configuration.

28. A medical device for at least partially covering and applying force on tissue, the medical device comprising:
a body comprising:
at least one spanning structure comprising a polymeric film, and
first and second struts connected to the spanning structure, wherein the first strut comprises a polymeric film and adhesive material, and the second strut comprises a polymeric film and adhesive material;
the spanning structure being flexible and multistable so that:
the spanning structure is reconfigurable between at least first and second stable equilibrium configurations, and
the spanning structure has at least one unstable equilibrium configuration between the first and second stable equilibrium configurations; and
the medical device being configured so that inner ends of the first and second struts are closer to one another in the second stable equilibrium configuration than in the first stable equilibrium configuration,
wherein the spanning structure is configured to:
be biased toward the first stable equilibrium configuration at least when in configurations between the at least one unstable equilibrium configuration and the first stable equilibrium configuration,
be biased toward the second stable equilibrium configuration at least when in configurations between the at least one unstable equilibrium configuration and the second stable equilibrium configuration,
define a first concavity comprising curved arcs that extend crosswise to one another in the first stable equilibrium configuration, and
define a second concavity comprising curved arcs that extend crosswise to one another in the second stable equilibrium configuration.

29. The medical device according to claim 28, comprising:
a weld connecting the first strut to the spanning structure, and
a weld connecting the second strut to the spanning structure.

30. The medical device according to claim 28, comprising:
a flexible web connected to the first and second struts by adhesive material, wherein:
a central portion of the flexible web is spaced apart from the spanning structure,
the central portion of the flexible web is suspended along a gap defined between the inner ends of the first and second struts,
the first and second struts are positioned between the flexible web and the spanning structure, the flexible web comprises adhesive material configured to adhere the medical device to tissue; and a release liner adhered to the adhesive material of the flexible web.

\* \* \* \* \*